(12) United States Patent
Pattabiraman et al.

(10) Patent No.: US 12,383,631 B2
(45) Date of Patent: *Aug. 12, 2025

(54) IMMUNE ANTIGEN SPECIFIC IL-18 IMMUNOCYTOKINES AND USES THEREOF

(71) Applicant: Bright Peak Therapeutics AG, Basel (CH)

(72) Inventors: Vijaya Raghavan Pattabiraman, Volketswil (CH); Bertolt Kreft, Kleinmachow (DE); Jean-Philippe Carralot, Saint-Louis (FR); Arnaud Goepfert, Sierentz (FR); Kea Martin, Istein (DE); Andrew Chi, San Diego, CA (US)

(73) Assignee: Bright Peak Therapeutics AG, Basel (CH)

( * ) Notice: Subject to any disclaimer, the term of this patent is extended or adjusted under 35 U.S.C. 154(b) by 150 days.

This patent is subject to a terminal disclaimer.

(21) Appl. No.: 18/113,413

(22) Filed: Feb. 23, 2023

(65) Prior Publication Data

US 2023/0355795 A1 Nov. 9, 2023

Related U.S. Application Data

(60) Provisional application No. 63/479,529, filed on Jan. 11, 2023, provisional application No. 63/313,222, filed on Feb. 23, 2022.

(51) Int. Cl.
*A61K 47/68* (2017.01)

(52) U.S. Cl.
CPC ...... *A61K 47/6849* (2017.08); *A61K 47/6813* (2017.08)

(58) Field of Classification Search
CPC .......... A61K 47/6849; A61K 47/6813
See application file for complete search history.

(56) References Cited

U.S. PATENT DOCUMENTS

| | | |
|---|---|---|
| 7,253,260 B2 | 8/2007 | Janson et al. |
| 7,311,902 B2 | 12/2007 | Bam et al. |
| 7,442,526 B2 | 10/2008 | Johanson et al. |
| 7,524,488 B2 | 4/2009 | Dinarello et al. |
| 7,595,039 B2 | 9/2009 | Dede et al. |
| 7,667,076 B2 | 2/2010 | Bode et al. |
| 7,736,639 B2 * | 6/2010 | Bam .............. A61P 35/02 514/19.3 |
| 7,875,709 B2 | 1/2011 | Dinarello et al. |
| 8,216,805 B2 | 7/2012 | Carter et al. |
| 8,679,471 B2 | 3/2014 | Carroll et al. |
| 9,764,038 B2 | 9/2017 | Dennler et al. |
| 9,862,779 B2 | 1/2018 | Beck et al. |
| 10,081,684 B2 | 9/2018 | Ploegh et al. |
| 10,227,383 B2 * | 3/2019 | Ito ................. C07K 7/08 |
| 10,266,502 B2 | 4/2019 | Louis van Delft et al. |
| 10,434,180 B2 | 10/2019 | Bregeon et al. |
| 10,676,516 B2 | 6/2020 | Viney et al. |
| 10,815,303 B2 | 10/2020 | Yue et al. |
| 10,864,277 B2 | 12/2020 | Grawunder et al. |
| 11,053,293 B2 | 7/2021 | Krupnick et al. |
| 11,168,111 B2 | 11/2021 | Davis et al. |
| 11,219,672 B2 | 1/2022 | Okamura et al. |
| 11,291,721 B2 | 4/2022 | Loew et al. |
| 11,413,331 B2 | 8/2022 | Deak et al. |
| 11,421,022 B2 | 8/2022 | Fenn et al. |
| 12,173,062 B2 | 12/2024 | Kreft et al. |
| 2002/0169291 A1 | 11/2002 | Dinarello et al. |
| 2005/0008615 A1 | 1/2005 | Bam et al. |
| 2009/0286855 A1 | 11/2009 | Dinarello et al. |
| 2010/0291088 A1 | 11/2010 | Ghayur et al. |
| 2016/0107999 A1 | 4/2016 | Debets et al. |
| 2018/0200338 A1 | 7/2018 | Umana et al. |
| 2019/0023760 A1 | 1/2019 | Bode et al. |
| 2019/0062395 A1 | 2/2019 | Merchant et al. |
| 2019/0070262 A1 | 3/2019 | Ring et al. |
| 2019/0194641 A1 | 6/2019 | Spycher et al. |
| 2019/0204330 A1 | 7/2019 | Kelly et al. |
| 2019/0338032 A1 | 11/2019 | Campbell et al. |
| 2019/0352405 A1 | 11/2019 | Fang et al. |
| 2020/0019165 A1 | 1/2020 | Levandowski et al. |
| 2020/0190165 A1 | 6/2020 | Yamada et al. |
| 2020/0308242 A1 * | 10/2020 | Lowe .............. A61P 35/00 |

(Continued)

FOREIGN PATENT DOCUMENTS

| | | |
|---|---|---|
| EP | 2970486 B1 | 1/2016 |
| WO | WO-9958572 A1 | 11/1999 |

(Continued)

OTHER PUBLICATIONS

Kim, SH, Azam T, Yoon DY et al. 2001. Site-specific mutations in the mature form of human IL-18 with enhanced biological activity and decreased neutralization by IL-18 binding protein. Proceedings of the National Academy of Sciences of the US 98:3304_3309 DOI 10.1073/pnas.051634098. (Year: 2001).*

Yamamoto Y, Kato Z, Matsukuma E, Li A, Omoya K, Hashimoto K, Ohnishi H, Kondo N. 2004. Generation of highly stable IL-18 based on a ligand receptor complex structure. Biochemical and Biophysical Research Communications 317:181_186 DOI 10.1016/j.bbrc.2004.03.024. (Year: 2004).*

(Continued)

*Primary Examiner* — Daniel E Kolker
*Assistant Examiner* — Julia A Rossi
(74) *Attorney, Agent, or Firm* — WILSON SONSINI GOODRICH & ROSATI

(57) ABSTRACT

The present disclosure relates to modified immunocytokine compositions comprising antibodies or antigen binding fragments specific for immune cell antigens and IL-18 polypeptides. Also provided herein are methods of treatment with and methods of manufacture of immunocytokine compositions.

20 Claims, 39 Drawing Sheets

Specification includes a Sequence Listing.

(56) References Cited

U.S. PATENT DOCUMENTS

| | | |
|---|---|---|
| 2020/0317787 A1 | 10/2020 | Li et al. |
| 2020/0330557 A1 | 10/2020 | Hadden, II et al. |
| 2021/0128743 A1 | 5/2021 | Spycher et al. |
| 2021/0139541 A1 | 5/2021 | Matsuda et al. |
| 2021/0139549 A1 | 5/2021 | Yamada et al. |
| 2021/0252157 A1 | 8/2021 | Pattabiraman et al. |
| 2021/0300972 A1 | 9/2021 | Yamada et al. |
| 2021/0388049 A1 | 12/2021 | Li et al. |
| 2022/0023395 A1 | 1/2022 | Bishai et al. |
| 2022/0041713 A1 | 2/2022 | Viney et al. |
| 2022/0056091 A1 | 2/2022 | Pattabiraman et al. |
| 2022/0112258 A1 | 4/2022 | Cui et al. |
| 2022/0133904 A1 | 5/2022 | Schibli et al. |
| 2023/0071889 A1 | 3/2023 | Poirier et al. |
| 2023/0181754 A1 | 6/2023 | Pattabiraman et al. |
| 2023/0201364 A1 | 6/2023 | Pattabiraman et al. |
| 2023/0201365 A1 | 6/2023 | Kreft et al. |
| 2023/0250181 A1 | 8/2023 | Pattabiraman et al. |
| 2023/0357342 A1 | 11/2023 | Pattabiraman et al. |
| 2024/0116997 A1 | 4/2024 | Pattabiraman et al. |
| 2024/0132563 A1 | 4/2024 | Pattabiraman et al. |
| 2024/0158537 A1 | 5/2024 | Pattabiraman et al. |
| 2024/0417436 A1 | 12/2024 | Pattabiraman et al. |
| 2024/0424127 A1 | 12/2024 | Pattabiraman et al. |

FOREIGN PATENT DOCUMENTS

| | | |
|---|---|---|
| WO | WO-02085923 A2 | 10/2002 |
| WO | WO-2004091517 A2 | 10/2004 |
| WO | WO-2004096238 A1 | 11/2004 |
| WO | WO-2005003294 A2 | 1/2005 |
| WO | WO-2005019415 A2 | 3/2005 |
| WO | WO-2006069246 A2 | 6/2006 |
| WO | WO-2007079130 A2 | 7/2007 |
| WO | WO-2014036492 A1 | 3/2014 |
| WO | WO-2015054658 A1 | 4/2015 |
| WO | WO-2016115168 | 7/2016 |
| WO | WO-2016115168 A1 | 7/2016 |
| WO | WO-2017201352 A1 | 11/2017 |
| WO | WO-2018199337 A1 | 11/2018 |
| WO | WO-2019051015 A1 | 3/2019 |
| WO | WO-2019057772 A1 | 3/2019 |
| WO | WO-2019185792 A1 | 10/2019 |
| WO | WO-2019240287 A1 | 12/2019 |
| WO | WO-2019240288 A1 | 12/2019 |
| WO | WO-2020090979 A1 | 5/2020 |
| WO | WO-2020127369 A1 | 6/2020 |
| WO | WO-2020163715 A1 | 8/2020 |
| WO | WO-2020188061 A1 | 9/2020 |
| WO | WO-2021122866 A1 | 6/2021 |
| WO | WO-2021133839 A1 | 7/2021 |
| WO | WO-2022038417 A2 | 2/2022 |
| WO | WO-2022094473 A1 | 5/2022 |
| WO | WO-2022172944 A1 | 8/2022 |
| WO | WO-2022214653 A1 | 10/2022 |
| WO | WO-2023281479 A1 | 1/2023 |
| WO | WO-2023281482 A1 | 1/2023 |
| WO | WO-2023281484 A1 | 1/2023 |
| WO | WO-2023010021 A1 | 2/2023 |
| WO | WO-2023013763 A1 | 2/2023 |
| WO | WO-2023056193 A2 | 4/2023 |
| WO | WO-2023114829 A1 | 6/2023 |
| WO | WO-2023118497 A1 | 6/2023 |
| WO | WO-2023161854 A1 | 8/2023 |
| WO | WO-2023161856 A1 | 8/2023 |
| WO | WO-2023225602 A1 | 11/2023 |
| WO | WO-2024031046 A2 | 2/2024 |
| WO | WO-2024044780 A1 | 2/2024 |
| WO | WO-2024051728 A1 | 3/2024 |
| WO | WO-2024086191 A2 | 4/2024 |
| WO | WO-2024031046 A3 | 5/2024 |
| WO | WO-2024086191 A3 | 5/2024 |
| WO | WO-2024102587 A2 | 5/2024 |
| WO | WO-2024102693 A2 | 5/2024 |
| WO | WO-2024051728 A9 | 6/2024 |
| WO | WO-2024102693 A3 | 6/2024 |
| WO | WO-2024102587 A3 | 7/2024 |
| WO | WO-2024153183 A1 | 7/2024 |
| WO | WO-2024158838 A2 | 8/2024 |
| WO | WO-2024158840 A2 | 8/2024 |
| WO | WO-2024158838 A3 | 10/2024 |
| WO | WO-2024158840 A3 | 10/2024 |

OTHER PUBLICATIONS

Swencki-Underwood, B., Cunningham, M., Heavner, G., Blasie, C., McCarthy, S., Dougherty, T., Brigham-Burke, M., Gunn, G., Goletz, T., & Snyder, L. (2006). Engineering human IL-18 with increased bioactivity and bioavailability. Cytokine. 34. 114-24. 10.1016/j.cyto.2006.04.004 (Year: 2006).*

Saetang, J., Puseenam, A., Roongsawang, N., Voravuthikunchai, S.P., Sangkhathat, S., & Tipmanee, V. Immunologic function and molecular insight of recombinant Interleukin-18. PLoS One 11(8): e0160321. https://doi.org/10.1371/journal.pone.0160321 (Year: 2016).*

Krumm, B., Meng, X., Xiang, Y. et al. Identification of small molecule inhibitors of Interleukin-18. Sci Rep 7, 483 (2017). https://doi.org/10.1038/s41598-017-00532-x (Year: 2017).*

Zheng, Xiaohu, et al., "The use of supercytokines, immunocytokines, engager cytokines, and other synthetic cytokines in immunotherapy." *Cellular & molecular immunology* 19.2 (2022): 192-209.

Holder, Patrick G., et al., "Engineering interferons and interleukins for cancer immunotherapy." *Advanced drug delivery reviews* 182 (2022): 114112.

Matsuda, Yutaka, et al., "Chemical Site-Specific Conjugation Platform to Improve the Pharmacokinetics and Therapeutic Index of Antibody-Drug Conjugates." *Molecular Pharmaceutics* 18.11 (2021): 4058-4066.

Biophamara Peg, "PEGs Conjugate a Versatile Approach of Antibody Drug," retrieved from https://www.biochempeg.com/article/85.html , Dec. 12, 2019.

Kang, Min Sun, et al., "Recent developments in chemical conjugation strategies targeting native amino acids in proteins and their applications in antibody-drug conjugates." *Chemical Science* 12.41 (2021): 13613-13647.

Carralot, Jean, et al. "Using Site-Specific Chemical Conjugation to Generate Superior Half-Life Extended or PD1-Targeted Formats of a Potent IL-18 Variant Resistant to IL-18 Binding Protein," *Journal for ImmunoTherapy of Cancer*. vol. 10. British Med Assoc House, Tavistock Square, London WC1H 9Jr, England, 2022.

Creative Biolabs: "Anti-PD-LI Antibody-Cytokine Fusion Protein, IgG (84G09)-IL18 CAT#:ACFP-CQ3407", May 10, 2023 (May 10, 2023), XP093045580, Retrieved from the Internet: URL:https://www.creativebiolabs.net/anti-pd-ll-immunocytokine-igg-84g09-1118-99433.html.

Kim, Soo-Hyun M., et al. "Site-specific mutations in the mature form of human IL-18 with enhanced biological activity and decreased neutralization by IL-18 binding protein." *Proceedings of the National Academy of Sciences* 98.6 (2001): 3304-3309.

International Search Report and Written Opinion for PCT Application PCT/IB2023/051688, mailed Jun. 15, 2023, 21 pages. (English).

International Search Report and Written Opinion for PCT Application PCT/IB2023/051690, mailed Jun. 20, 2023, 22 pages. (English).

Harmand, Thibault J., et al., "Protein chemical synthesis by α-ketoacid-hydroxylamine ligation," *Nature protocols* vol. 11, No. 6, May 26, 2016: 1130-1147.

Hein, Christopher D., et al., "Click chemistry, a powerful tool for pharmaceutical sciences," *Pharmaceutical Research*, vol. 25, No. 10, May 29, 2008: 2216-2230.

Kim, Soo-Hyun, et al., "Structural requirements of six naturally occurring isoforms of the IL-18 binding protein to inhibit IL-18," *Proceedings of the National Academy of Sciences*, vol. 97, No. 3, Feb. 1, 2000: 1190-1195.

Kim, Soo-Hyun, et al., "Identification of Amino Acid Residues Critical for Biological Activity in Human Interleukin-18," The Journal of Biological Chemistry vol. 277, No. 13, Mar. 29, 2002: 10998-11003.

(56) References Cited

OTHER PUBLICATIONS

Krumm, Brian, et al., "Structural basis for antagonism of human interleukin 18 by poxvirus interleukin 18-binding protein," *Proceedings of the National Academy of Sciences* 105.52 (2008): 20711-20715.

Thirumurugan, Prakasam, et al., "Click chemistry for drug development and diverse chemical-biology applications," *Chemical reviews* 113.7 (2013): 4905-4979.

Meng, Xiangzhi, et al., "Variola virus IL-18 binding protein interacts with three human IL-18 residues that are part of a binding site for human IL-18 receptor alpha subunit," *Virology* 358.1 (2007): 211-220.

Swencki-Underwood, Bethany, et al., "Engineering human IL-18 with increased bioactivity and bioavailability," *Cytokine* 34.1-2 (2006): 114-124.

Tsutsumi, Naotaka, et al., "The structural basis for receptor recognition of human interleukin-18," *Nature communications* 5.1 (2014): 1-13.

PCT/IB2021/000574 Written Opinion and International Search Report mailed Mar. 15, 2022, (10 Pages).

Al-Lazikani, Bissan et al. Standard Conformations for the Canonical Structures of Immunoglobulins. Journal of Molecular Biology 273(4):927-948 (1997).

CAS Accession No. 1380723-44-3. Retrieved from: https://scifinder-n.cas.org/searchDetail/substance/67913b1e16ad7c155548c573/substanceDetails Accessed Jan. 22, 2025. 36 pages.

CAS Accession No. 1428935-60-7. Retrieved from: https://scifinder-n.cas.org/searchDetail/substance/67913a1016ad7c155548b4a2/substanceDetails. Accessed Jan. 22, 2025. 32 pages.

CAS Accession No. 1537032-82-8. Retrieved from: scifinder-n.cas.org/searchDetail/substance/67913614416ad7c1555488a31/substanceDetails. Accessed Jan. 22, 2025. 28 pages.

CAS Accession No. 1918149-01-5. Retrieved from: https://scifinder-n.cas.org/searchDetail/substance/67913dc216ad7c155548e42f/substanceDetails. Accessed Jan. 22, 2025. 5 pages.

CAS Accession No. 2102192-68-5. Retrieved from: https://scifinder-n.cas.org/searchDetail/substance/67913ceb16ad7c155548dc8a/substanceDetails. Accessed Jan. 22, 2025. 6 pages.

CAS Accession No. 2118349-31-6. Retrieved from: https://scifinder-n.cas.org/searchDetail/substance/67913e8816ad7c155548ec22/substanceDetails. Accessed Jan. 22, 2025. 5 pages.

CAS Accession No. 2216751-26-5. Retrieved from: https://scifinder-n.cas.org/searchDetail/substance/67913f7c16ad7c155548f65d/substanceDetails. Accessed Jan. 22, 2025. 5 pages.

CAS Accession No. 2256084-03-2. Retrieved from: https://scifinder-n.cas.org/searchDetail/substance/67913bfe16ad7c155548d22a/substanceDetails. Accessed Jan. 22, 2025. 3 pages.

CAS Accession No. 857064-38-1. Retrieved from: https://scifinder-n.cas.org/searchDetail/substance/6791409616ad7c1555490514/substanceDetails. Accessed Jan. 22, 2025. 4 pages.

Chemical Abstracts Service. CAS Registry: 1415800-37-1. Bromoacetamido-PEG5-azide: pp. 1-9. STN Entry Date Sep. 5, 2014. Retrieved Nov. 12, 2024. Retrieved from: https://pubchem.ncbi.nlm.nih.gov/compound/77078486.

Chothia, Cyrus, and Arthur M. Lesk. Canonical Structures for the Hypervariable Regions of Immunoglobulins. Journal of Molecular Biology 196(4):901-917 (1987).

Co-pending U.S. Appl. No. 18/813,104, inventors Pattabiraman; Vijaya Raghavan et al., filed Aug. 23, 2024.

Co-pending U.S. Appl. No. 18/813,286, inventors Pattabiraman; Vijaya Raghavan et al., filed Aug. 23, 2024.

Co-pending U.S. Appl. No. 18/813,358, inventors Kreft; Bertolt et al., filed Aug. 23, 2024.

Correspondence between C numberings (https://imgt.org/IMGTScientificChart/Numbering/Hu_IGHGnber.html).

EBI Accession No. AXT 13707. Coding: AXT13707.1. Bacillus Velezensis PucR Family Transcriptional Regulator. EMBL-EBI: pp. 1-3. Record created Dec. 2017. Retrieved Nov. 12, 2024. Retrieved from: https://www.ebi.ac.uk/ena/browser/view/AXT13707.

EBI Accession No. AXT 13710. Coding: AXT13710.1. Bacillus Velezensis Hypothetical Protein. EMBL-EBI: pp. 1-3. Record created Dec. 2017. Retrieved Nov. 12, 2024. Retrieved from: https://www.ebi.ac.uk/ena/browser/view/AXT13710.

Fujii, Tomohiro et al. AJICAP second generation: improved chemical site-specific conjugation technology for antibody-drug conjugate production. Bioconjugate Chemistry 34(4):728-738 (2023).

Kabat, Elvin A. et al. Sequences of Proteins of Immunological Interest, Fifth Edition. Public Health Service, National Institutes of Health 1:647-669 (1991).

Liu, Hongyan et al. Fc Engineering for Developing Therapeutic Bispecific Antibodies and Novel Scaffolds. Frontiers in Immunology 8(38):1-15 (2017).

PCT/IB2021/000574 International Preliminary Report on Patentability dated Mar. 2, 2023.

PCT/IB2021/000574 Invitation to Pay Additional Fees dated Jan. 25, 2022.

PCT/IB2023/051688 International Preliminary Report on Patentability dated Sep. 6, 2024.

PCT/IB2023/051690 International Preliminary Report on Patentability dated Sep. 6, 2024.

Remington's Pharmaceutical Sciences, 17th edition (Mack Publishing Company, Easton, Pa, pp. 1418 (1985).

Saunders, Kevin O. Conceptual Approaches to Modulating Antibody Effector Functions and Circulation Half-Life. Frontiers in Immunology 10:1296, 1-20 (2019).

U.S. Appl. No. 17/406,847 Office Action dated Feb. 1, 2024.

U.S. Appl. No. 17/406,847 Office Action dated Nov. 6, 2024.

Yamada, Kei et al. AJICAP: Affinity Peptide Mediated Regiodivergent Functionalization of Native Antibodies. Angewandte Chemie 58(17):5592-5597 (2019).

Co-pending U.S. Appl. No. 18/813,101, inventors Vijaya; Raghavan Pattabiraman et al., filed Aug. 23, 2024.

Kim, E.J. et al. Efficient induction of T helper type 1-mediated immune responses in antigen-primed mice by anti-CD3 single-chain Fv/interleukin-18 fusion DNA. Immunology 111(1):27-34 (2004).

PCT/IB2024/058220 International Search Report and Written opinion dated Mar. 21, 2025.

PCT/IB2024/058220 Invitation to Pay Additional Fees dated Jan. 24, 2025.

PCT/IB2024/058222 International Search Report and Written Opinion dated Jan. 20, 2025.

PCT/IB2024/058236 International Search Report and Written Opinion dated Jan. 20, 2025.

U.S. Appl. No. 17/406,847 Non-Final Office Action dated Apr. 24, 2025.

* cited by examiner

Simultaneous activation of 2 receptors

IMMUNE ANTIGEN SPECIFIC IL-18 IMMUNOCYTOKINES AND USES THEREOF

CROSS REFERENCE

This application claims the benefit of U.S. Provisional Application No. 63/313,222 filed Feb. 23, 2022, and U.S. Provisional Application No. 63/479,529 filed Jan. 11, 2023, which applications are incorporated herein by reference in their entirety.

CROSS REFERENCE

The instant application contains a Sequence Listing which has been submitted electronically in XML file format and is hereby incorporated by references in its entirety. Said XML copy, created on Apr. 6, 2023, is named 94917-0082_725201US_SL.xml and is 52,712 bytes in size.

SEQUENCE LISTING

The instant application contains a Sequence Listing which has been submitted electronically in XML file format and is hereby incorporated by reference in its entirety. Said XML copy, created on Apr. 6, 2023, is named 94917-0082_725201US_SL.xml and is 252,712 bytes in size.

BACKGROUND

In 2022, an estimated 1.8 million new cases of cancer will be diagnosed in the United States, and over 600,000 people will die from the disease. Immunotherapies utilize the immune system of a subject to aid in the treatment of ailments. Immunotherapies can be designed to either activate or suppress the immune system depending on the nature of the disease being treated. A goal of various immunotherapies for the treatment of cancer is to stimulate the immune system so that it recognizes and destroys tumors or other cancerous tissue.

Immune cells implicated in response to various cancers express certain proteins that are implicated in the regulation of the immune response. These proteins, such as programmed cell death protein 1 (PD-1), programmed death-ligand 1 (PD-L1), and others, can downregulate the immune system and promote self-tolerance by suppressing T cell inflammatory activity. In light of these mechanisms, antibodies or antigen binding fragments which target these proteins have been identified as potential therapeutics. However, in some cases single mechanism therapies targeting these proteins alone are insufficient for treating cancer. Thus, there is a need for improved tools for cancer therapy.

BRIEF SUMMARY

Described herein are immunocytokine compositions which contain an immune cell associated antigen specific antibody or antigen binding fragment thereof and an interleukin 18 (IL-18) polypeptide.

In one aspect, provided herein, is an immunocytokine composition, comprising: an IL-18 polypeptide; and an antibody or an antigen binding fragment thereof specific for an immune cell associated antigen; and a linker, wherein the linker comprises: a first point of attachment to the IL-18 polypeptide; and a second point of attachment to the antibody or antigen binding fragment thereof.

In some embodiments, the linker comprises a polymer. In some embodiments, the polymer comprises a water-soluble polymer. In some embodiments, the water-soluble polymer comprises poly(alkylene oxide), polysaccharide, poly(vinyl pyrrolidone), poly(vinyl alcohol), polyoxazoline, poly(acryloylmorpholine), or a combination thereof. In some embodiments, the polymer has a weight average molecular weight of at least about 0.1 kDa, at least about 0.5 kDa, at least about 1 kDa, at least about 5 kDa, at least about 10 kDa, at least about 20 kDa, at least about 30 kDa, at least 40 kDa, at least 50 kDa, at least 60 kDa, at least 70 kDa, at least 80 kDa, at least 90 kDa, at least 100 kDa, at least 120 kDa, at least 130 kDa, at least 140 kDa, at least 150 kDa, or more.

In some embodiments, the first point of attachment is at a residue which is not the N-terminus or the C-terminus of the IL-18 polypeptide. In some embodiments, the first point of attachment is to a residue in the region of residues 2-156 of the IL-18 polypeptide, wherein residue position numbering is based on SEQ ID NO: 1. In some embodiments, the first point of attachment is to a residue in the region of residues 38-144 of the IL-18 polypeptide. In some embodiments, the first point of attachment is at residue 38, 68, 69, 70, 76, 78, 85, 86, 95, 98, 121, 127, or 144 of the IL-18 polypeptide. In some embodiments, the first point of attachment is at residue 68, 69, 70, 85, 86, 95, or 98 of the IL-18 polypeptide. In some embodiments, the first point of attachment is at residue 68 of the IL-18 polypeptide. In some embodiments, the IL-18 polypeptide comprises an amino acid substitution at the first point of attachment. In some embodiments, the amino acid substitution at the first point of attachment is for an unnatural amino acid. In some embodiments, the amino acid substitution at the first point of attachment is for a natural amino acid. In some embodiments, the amino acid substitution at the first point of attachment is E69C, K70C, E85C, M86C, T95C, or D98C.

In some embodiments, the second point of attachment is at an amino acid residue in an Fc region of the antibody or antigen binding fragment. In some embodiments, the Fc region comprises an amino acid sequence having 90% or more identity to the amino acid sequence of SEQ ID NO: 260. In some embodiments, the second point of attachment is (a) an amino acid residue at positions 16 to 18 of SEQ ID NO: 260, (b) an amino acid residue at positions 58 to 60 of SEQ ID NO: 260, or (c) amino acid residue 87 of SEQ ID NO: 260. In some embodiments, the second point of attachment is to a lysine residue on the antibody or antigen binding fragment. In some embodiments, the IL-18 polypeptide displays reduced binding to IL-18 binding protein (IL-18BP) compared to a wild type IL-18 polypeptide of SEQ ID NO: 1. In some embodiments, the IL-18 polypeptide contains one or more amino acid substitutions that are located at residue positions selected from Y01, F02, E06, V11, C38, K53, D54, S55, T63, C76, and C127, wherein residue position numbering of the IL-18 polypeptides are based on SEQ ID NO: 1 as a reference sequence. In some embodiments, the one or more amino acid substitutions in the IL-18 polypeptide are selected from Y01G, F02A, E06K, V11, C38S, C38A, K53A, D54A, S55A, T63A, C68S, C68A, C76S, C76A, C127S, and C127A. In some embodiments, the IL-18 polypeptide contains E06K and K53A amino acid substitutions. In some embodiments, the IL-18 polypeptides contains a T63A amino acid substitution. In some embodiments, the IL-18 polypeptide is synthetic. In some embodiments, the IL-18 polypeptide comprises one or more amino acid substitutions selected from: (a) a homoserine residue located at any one of residues 26-36; (b) a homoserine residue located at any one of residues 45-67; (c) a homoserine residue located any one of residues 70-80; (d) a homoserine residue located at any one of residues 110-130; (e) a norleucine or O-methyl-homoserine residue located at any one of residues 28-38; (f) a norleucine or O-methyl-homoserine residue located at any one of residues 46-56; g) a norleucine or O-methyl-homoserine residue located at any one of residues 54-64; (h) a norleucine or O-methyl-homoserine residue located at any one of residues 80-90; (i) a norleucine or O-methyl-homoserine residue located at any one of residues 108-118; and (j) a norleucine or O-methyl-homoserine residue located at any one of residues 145-155; wherein residue position numbering of the IL-18 polypeptide is based on SEQ ID NO: 1 as a reference sequence. In some embodiments, the IL-18 polypeptide comprises one or more amino acid substitutions selected from homoserine (Hse) 31, norleucine (Nle) 33, O-methyl-homoserine (Omh) 33, Hse50, Nle51, Omh51, Hse57, Nle60, Omh60, Hse63, Hse67, Hse75, Nle86, Omh86, Hse106, Nle113, Omh113, Hse116, Hse 121, Nle150, and Omh150.

In some embodiments, the antibody or antigen binding fragment thereof is a monoclonal antibody, a humanized antibody, a grafted antibody, a chimeric antibody, a human antibody, a de-immunized antibody, or a bispecific antibody. In some embodiments, the antibody or antigen binding fragment thereof an antigen binding fragment, wherein the antigen binding fragment comprises a Fab, a Fab", a F(ab')$_2$, a bispecific F(ab')$_2$, a trispecific F(ab')$_2$, a variable fragment (Fv), a single chain variable fragment (scFv), a dsFv, a bispecific scFv, a variable heavy domain, a variable light domain, a variable NAR domain, bispecific scFv, a minibody, a diabody, a bispecific diabody, triabody, a tetrabody, a minibody, a maxibody, a camelid, a VHH, a minibody, an intrabody, fusion proteins comprising an antibody portion (a domain antibody), a single chain binding polypeptide, a scFv-Fc, a Fab-Fc, a bispecific T cell engager (BiTE), a tetravalent tandem diabody (TandAb), a Dual-Affinity Re-targeting Antibody (DART), a bispecific antibody (bscAb), a single domain antibody (sdAb), a fusion protein, or a bispecific disulfide-stabilized Fv antibody fragment (dsFv-dsFv'). In some embodiments, the antibody or antigen binding fragment thereof comprises an IgG, an IgM, an IgE, an IgA, an IgD, or is derived therefrom. In some embodiments, the antibody or antigen binding fragment thereof comprises the IgG, and wherein the IgG is an IgG1, an IgG4, or is derived therefrom. In some embodiments, the immune cell associated antigen is 4-1BB, B7-H3, B7-H4, BTLA, CD3, CCR8, CD8A, CD8B, CD16A, CD27, CD28, CD33, CD38, CD39, CD40, CD47, CD70, CD80, CD86, CD96, CD163, CLEC-1, CLEVER-1, CTLA-4, D40, GITR, ICOS, ILT2/3/4, LAG-3, MHCI, MHCII, NKG2A, NKG2D, NKp30, NKp44, NKp46, OX40, PD-1, PD-L1, PD-L2, PSGL-1, SIGLEC-9, SIGLEC-15, SIRP-α, TCR, TIGIT, TIM-3, VISTA, or VSIG4.

In some embodiments, the immune cell associated antigen is PD-1. In some embodiments, the antibody or antigen binding fragment thereof comprises tislelizumab, baizean, 0KVO411B3N, BGB-A317, hu317-1/IgG4mt2, sintilimab, tyvyt, IBI-308, toripalimab, TeRuiPuLi, terepril, tuoyi, JS-001, TAB-001, tamrelizumab, HR-301210, INCSHR-01210, SHR-1210, temiplimab, cemiplimab-rwlc, 6QVL057INT, H4H7798N, REGN-2810, SAR-439684, lambrolizumab, pembrolizumab, MK-3475, SCH-900475, h409A11, nivolumab, nivolumab BMS, BMS-936558, MDX-1106, ONO-4538, prolgolimab, forteca, BCD-100, penpulimab, AK-105, zimberelimab, AB-122, GLS-010, WBP-3055, balstilimab, 1Q2QT5M7EO, AGEN-2034, AGEN-2034w, genolimzumab, geptanolimab, APL-501, CBT-501, GB-226, dostarlimab, ANB-011, GSK-4057190A, P0GVQ9A4S5, TSR-042, WBP-285, serplulimab, HLX-10, CS-1003, retifanlimab, 2Y3T5IF01Z, INCMGA-00012, INCMGA-0012, MGA-012, sasanlimab, LZZ0IC2EWP, PF-06801591, RN-888, spartalizumab, PDR-001, QOG25L6Z8Z, relatlimab/nivolumab, BMS-986213, cetrelimab, JNJ-3283, JNJ-63723283, LYK98WP91F, tebotelimab, MGD-013, BCD-217, BAT-1306, HX-008, MEDI-5752, JTX-4014, cadonilimab, AK-104, BI-754091, pidilizumab, CT-011, MDV-9300, YBL-006, AMG-256, RG-6279, RO-7284755, BH-2950, IBI-315, RG-6139, RO-7247669, ONO-4685, AK-112, 609-A, LY-3434172, T-3011, AMG-404, IBI-318, MGD-019, ONCR-177, LY-3462817, RG-7769, RO-7121661, F-520, XmAb-23104, Pd-1-pik, SG-001, S-95016, Sym-021, LZM-009, budigalimab, 6VDO4TY3OO, ABBV-181, PR-1648817, CC-90006, XmAb-20717, 2661380, AMP-224, B7-DCIg, EMB-02, ANB-030, PRS-332, [89Zr]Deferoxamide-pembrolizumab, 89Zr-Df-Pembrolizumab, [89Zr]Df-Pembrolizumab, STI-1110, STI-A1110, CX-188, mPD-1, MCLA-134, 244C8, ENUM 224C8, ENUM C8, 388D4, ENUM 388D4, ENUM D4, MEDIO680, NVP-LZV-184, or AMP-514, or a modified version thereof. In some embodiments, the antibody or antigen binding fragment thereof comprises nivolumab, pembrolizumab, LZM-009, or cemiplimab, or a modified version thereof.

In some embodiments, the immune cell associated antigen is PD-L1. In some embodiments, the antibody is Avelumab (Bavencio, 451238, KXG2PJ551I, MSB-0010682, MSB-0010718C, PF-06834635, CAS 1537032-82-8), Durvalumab (Imfinzi, 28×28×90 KV (UNII code), MEDI-4736, CAS 1428935-60-7), Atezolizumab (Tecentriq, 52CMI0WC3Y, MPDL-3280A, RG-7446, RO-5541267, CAS 1380723-44-3), Sugemalimab (CS-1001, WBP-3155), KN-046 (CAS 2256084-03-2), APL-502 (CBT-502, TQB-2450), Envafolimab (3D-025, ASC-22, KN-035, hu56V1-Fc-m1, CAS 2102192-68-5), Bintrafusp alfa (M-7824, MSB-0011359C, NW9K8C1JN3, CAS 1918149-01-5), STI-1014 (STI-A1014, ZKAB-001), PD-L1 t-haNK, A-167 (HBM-9167, KL-A167), IMC-001 (STI-3031, STI-A-1015, STI-A1015, s), HTI-1088 (SHR-1316), IO-103, CX-072 (CytomX Therapeutics), AUPM-170 (CA-170), GS-4224, ND-021 (NM21-1480, PRO-1480), BNT-311 (DuoBody-PD-L1x4-1BB, GEN-1046), BGB-A333, IBI-322, NM-01, LY-3434172, LDP, CDX-527, IBI-318, 89Zr-DFO-REGN3504, ALPN-202 (CD80 vIgD-Fc), INCB-086550, LY-3415244, SHR-1701, JS-003 (JS003-30, JS003-SD), HLX-20 (PL2 #3), ES-101 (INBRX-105, INBRX-105-1), MSB-2311, PD-1-Fc-OX40L (SL-279252, TAK-252), FS-118, FS118 mAb2, LAG-3/PD-L1 mAb2), FAZ-053 (LAE-005), Lodapolimab (LY-3300054, NR4MAD6PPB, CAS 2118349-31-6), MCLA-145, BMS-189, Cosibelimab (CK-301, TG-1501, CAS 2216751-26-5), IL-15Ralpha-SD/IL-15 (KD-033), WP-1066 (CAS 857064-38-1), BMS-936559 (MDX-1105), BMS-986192, RC-98, CD-200AR-L (CD200AR-L), ATA-3271, IBC-Ab002, BMX-101, AVA-04-VbP, ACE-1708, KY-1043, ACE-05 (YBL-013), ONC-0055 (ONC0055, PRS-344 S-095012), TLJ-1-CK, GR-1405, PD1ACR-T, N-809 (N-IL15/PDL1), CB-201, MEDI-1109, AVA-004 (AVA-04), CA-327, ALN-PDL, KY-1003, CD22(aPD-L1)CAR-T cells (SL-22P), ATA-2271 (M28z1XXPD1DNR CAR T cells), or a modified version thereof. In some embodiments, the antibody is durvalumab, atezolizumab, or avelumab, or a modified version thereof.

In some embodiments, the antibody or antigen binding fragment thereof comprises an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of Table 1.

In some embodiments, the IL-18 polypeptide comprises an amino acid sequence having at least 80%, 85%, 90%, 91%, 92%, 93%, 94%, 95%, 96%, 97%, 98%, or 99% sequence identity to the sequence set forth in SEQ ID NO: 1. In some embodiments, the IL-18 polypeptide of the immunocytokine provided herein comprises an amino acid sequence of any one of SEQ ID NOs: 2-67. In some embodiments, the IL-18 polypeptide comprises an amino acid sequence of SEQ ID NO: 30. In some embodiments, the IL-18 polypeptide comprises an amino acid sequence of SEQ ID NO: 68-72.

In some embodiments, the immunocytokine composition exhibits a binding affinity ($K_D$) to at least one Fc receptor which is within 10-fold of the binding affinity of the antibody not attached to the IL-18 polypeptide. In some embodiments, the immunocytokine composition exhibits binding affinity ($K_D$) to the antigen of the antibody which is within 5-fold of the binding affinity of the antibody not attached to the IL-18 polypeptide. In some embodiments, the immunocytokine composition exhibits an ability to induce IFNγ production in a cell as measured by half-maximal effective concentration ($EC_{50}$) which is within about 100-fold of the corresponding IL-18 polypeptide not comprised in the immunocytokine composition, and wherein the immunocytokine composition exhibits a lower $EC_{50}$ than WT IL-18. In some embodiments, the immunocytokine composition exhibits enhanced anti-tumor growth inhibition compared to the antibody alone. In some embodiments, the immunocytokine composition exhibits enhanced anti-tumor growth inhibition compared to the antibody and the IL-18 polypeptide administered in combination.

In some embodiments, the immunocytokine composition provided herein, further comprising a second linker, wherein the second linker comprises a third point of attachment to the antibody or antigen binding fragment thereof, and a fourth point of attachment to an additional cytokine. In some embodiments, the additional cytokine is selected from a second IL-18 polypeptide, an IL-7 polypeptide, or an IL-2 polypeptide. In some embodiments, the additional cytokine is a second IL-18 polypeptide. In some embodiments, the second IL-18 polypeptide is substantially identical to the IL-18 polypeptide. In some embodiments, the third point of attachment is to a different heavy chain of the antibody or antigen binding fragment thereof from the second point of attachment.

In one aspect, provided herein, is a pharmaceutical composition comprising: an immunocytokine composition as provided herein, and one or more pharmaceutically acceptable carriers or excipients. In some embodiments, the pharmaceutical composition is formulated for parenteral or enteral administration. In some embodiments, the pharmaceutical composition is formulated for intravenous or subcutaneous administration. In some embodiments, the pharmaceutical composition is in a lyophilized form. In some embodiments, the one or more pharmaceutically acceptable carriers or excipients comprises one or more of each of: a carbohydrate, an inorganic salt, an antioxidant, a surfactant, a buffer, or any combination thereof. In some embodiments, the pharmaceutical composition comprises one, two, three, four, five, six, seven, eight, nine, ten, or more excipients.

In one aspect, provided herein, is a method of treating cancer in a subject in need thereof, comprising administering to the subject an effective amount of the immunocytokine composition as provided herein, or a pharmaceutical composition as provided herein. In some embodiments, the cancer is a melanoma, a lung cancer, a bladder cancer (BC), a microsatellite instability high (MSI-H)/mismatch repair-deficient (dMMR) solid tumor, a tumor mutation burden high (TMB-H) solid tumor, a triple-negative breast cancer (TNBC), a gastric cancer (GC), a cervical cancer (CC), a pleural mesothelioma (PM), classical Hodgkin's lymphoma (cHL), a primary mediastinal large B cell lymphoma (PMBCL), or a combination thereof. In some embodiments, the cancer is a solid cancer consisting of bladder and ureteral cancer, bone cancer, brain and spinal cord cancer, breast cancer, cervical cancer, colorectal cancer, esophageal cancer, eye cancer, gallbladder or bile duct cancer, germ cell tumor, head and neck cancer, kidney cancer, liver cancer, lung cancer, metastatic brain tumor, ovarian cancer, pancreatic cancer, pediatric cancer, peripheral nerve sheath tumor, pituitary cancer, prostate cancer, skin cancer, stomach or gastric cancer, soft tissue cancer, testicular cancer, thyroid cancer, uterine cancer. In some embodiments, the cancer is a carcinoma, and wherein the carcinoma comprises a cutaneous squamous cell carcinoma (CSCC), a urothelial carcinoma (UC), a renal cell carcinoma (RCC), a hepatocellular carcinoma (HCC), a head and neck squamous cell carcinoma (HNSCC), an esophageal squamous cell carcinoma (ESCC), a gastroesophageal junction (GEJ) carcinoma, an endometrial carcinoma (EC), a Merkel cell carcinoma (MCC), or a combination thereof. In some embodiments, the cancer is a leukemia, lymphoma, myeloma, or a combination thereof. In some embodiments, the cancer is leukemia and the leukemia comprises, acute lymphoblastic leukemia, acute myeloid leukemia, chronic lymphocytic leukemia, small lymphocytic lymphoma, or chronic myeloid leukemia. In some embodiments, the cancer is lymphoma and the lymphoma comprises Burkitt lymphoma, chronic lymphocytic leukemia/small lymphocytic lymphoma, cutaneous lymphoma, diffuse large B cell lymphoma, follicular lymphoma, Hodgkin lymphoma, peripheral T cell lymphoma, Waldenstrom macroglobulinemia, lymphoplamacytic lymphoma, marginal zone lymphoma, B cell cutaneous lymphoma, extranodal natural killer T cell lymphoma, T cell lymphoblastic lymphoma, peripheral T cell lymphoma, or T cell cutaneous lymphoma.

In some embodiments, the method of making an immunocytokine composition comprises a) covalently attaching a reactive group to a specific residue of the antibody or antigen binding fragment thereof, b) contacting the reactive group with a complementary reactive group attached to the IL-18 polypeptide; and c) forming the composition.

In one aspect, provided herein is a method of creating a composition comprising: an IL-18 polypeptide; and an antibody or an antigen binding fragment thereof specific for an immune cell antigen; and a linker, wherein the linker comprises: a first point of attachment to the IL-18 polypeptide; and a second point of attachment to the antibody or antigen binding fragment thereof, the method comprising: a) providing the antibody or antigen binding fragment, wherein the antibody or antigen binding fragment comprises at least one acceptor amino acid residue that is reactive with the linker in the presence of a coupling enzyme; and b) reacting said antibody or antigen binding fragment with the linker comprising a primary amine, wherein the linker comprises a reactive group (R), in the presence of an enzyme capable of causing the formation of a covalent bond between the at least one acceptor amino acid residue and the linker, wherein the covalent bond is not at the R moiety, and wherein the method is performed under conditions sufficient to cause the at least one acceptor amino acid residue to form a covalent bond to the reactive group via the linker, wherein the covalent bond comprises the second point of attachment of the linker. In some embodiments, the enzyme comprises a transaminase. In some embodiments, the enzyme comprises a transglutaminase.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

FIG. 14A Shows the unconjugated reference antibodies. Tested in this figure are Pembrolizumab, LZM-009, Nivolumab, Atezolizumab, Durvalumab, and Avelumab.

FIG. 14B Shows the conjugated antibodies. Tested in this figure are compositions A and composition B.

FIG. 15A shows the unconjugated reference antibodies. Tested in this figure are Pembrolizumab, LZM-009, Nivolumab, Atezolizumab, Durvalumab, and Avelumab.

FIG. 15B shows the conjugated antibodies. Tested in this figure are compositions A and composition B.

FIG. 17A shows the unconjugated reference antibodies are Pembrolizumab, LZM-009, Nivolumab, Atezolizumab, Durvalumab, and Avelumab.

FIG. 17B shows the conjugated antibodies tested. Tested in this figure are compositions A and composition B.

DETAILED DESCRIPTION

Disclosed herein are antibodies or antigen binding fragments specific for immune cell associated antigens linked to IL-18 polypeptides in immunocytokine compositions. In some instances, the immunocytokine compositions provided herein are useful as potent stimulators of one or more immune cell types (e.g., T cells, macrophages, etc.). In some embodiments, the immunocytokine compositions can act by one or more modes of action.

In some embodiments, the antibody of the immunocytokine composition allows for targeting of the immunocytokine composition to an immune cell. In some embodiments, the immunocytokine composition can inhibit an activity of the immune cell associated antigen (e.g., inhibiting a checkpoint interaction such as a PD-1/PD-L1 interaction) through binding to the immune cell associated antigen. In some embodiments, the immunocytokine compositions induce IFNγ production in immune cells (e.g., T cells or NK cells). The antibody or antigen binding fragment-IL-18 immunocytokine compositions of the disclosure can have synergistic efficacy and improved tolerability by a subject. In some embodiments, the antibody or antigen binding fragment-IL-18 immunocytokine compositions can significantly reduce the therapeutic dose of the antibody or antigen binding fragment, the IL-18 polypeptide, or both for a subject with a disease, such as a cancer, as compared to a treatment with one or both entities individually or in combination. In some embodiments, the immunocytokine compositions provided herein are associated with fewer side effects than administration of one or both entities individually or in combination, potentially due to the targeting nature of the antibodies for an immune cell.

Figure 1A:
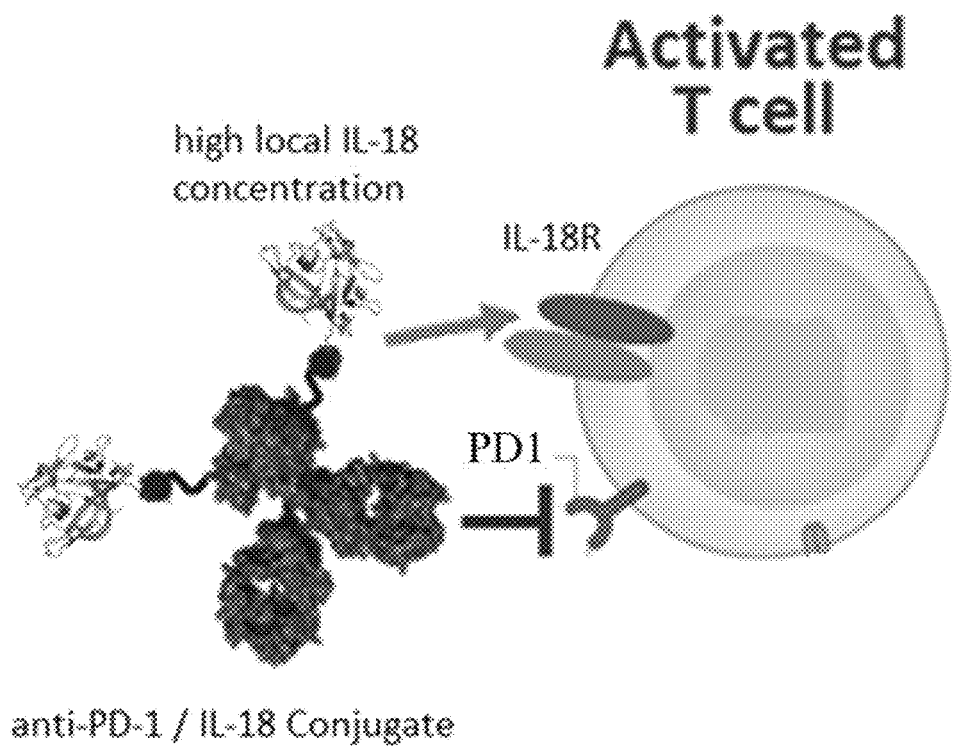
FIG. 1A illustrates a non-limiting mechanism of action of an anti-PD-1 antibody/IL-18 immunocytokine provided herein, wherein an activated T cell shows enhanced activation through concurrent blockade of PD-1 and stimulation by IL-18.

An exemplary, non-limiting mechanism of action of an immunocytokine provided herein is shown in FIG. 1A. In the exemplary embodiment, the immunocytokine composition comprises an anti-PD-1 antibody as the antibody or antigen binding fragment of the immunocytokine composition. In this embodiment, the anti-PD-1 antibody portion of the immunocytokine selectively binds to PD-1 present on the surface of an activated T cell (e.g., a $CD8^+$ T cell). This binding prevents the checkpoint interaction of PD-1 and PD-L1/2, thus preventing attenuation of activity of the T cell. Concomitantly, the IL-18 portion of the immunocytokine, which is effectively in a high local concentration near the T-cell due to the linkage, further activates the T cell through IL-18R signaling. While the exemplary embodiment shows the mechanism of action of an anti-PD-1 antibody, antibodies or antigen binding fragments specific for other immune antigens provided herein can function according to a similar mechanism.

Figure 1B:
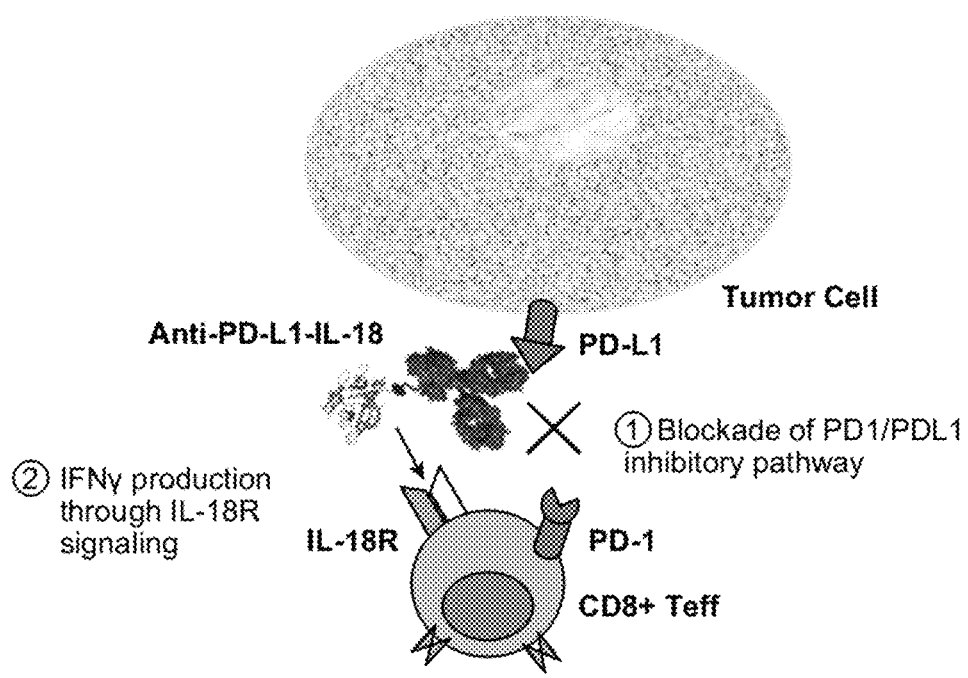
FIG. 1B illustrates a non-limiting mechanism of action of an anti-PD-L1 antibody/IL-18 immunocytokine provided herein, wherein the immunocytokine disrupts PD-L1/PD-1 interaction and effectuates IL-18R signaling.
Figure 1C:
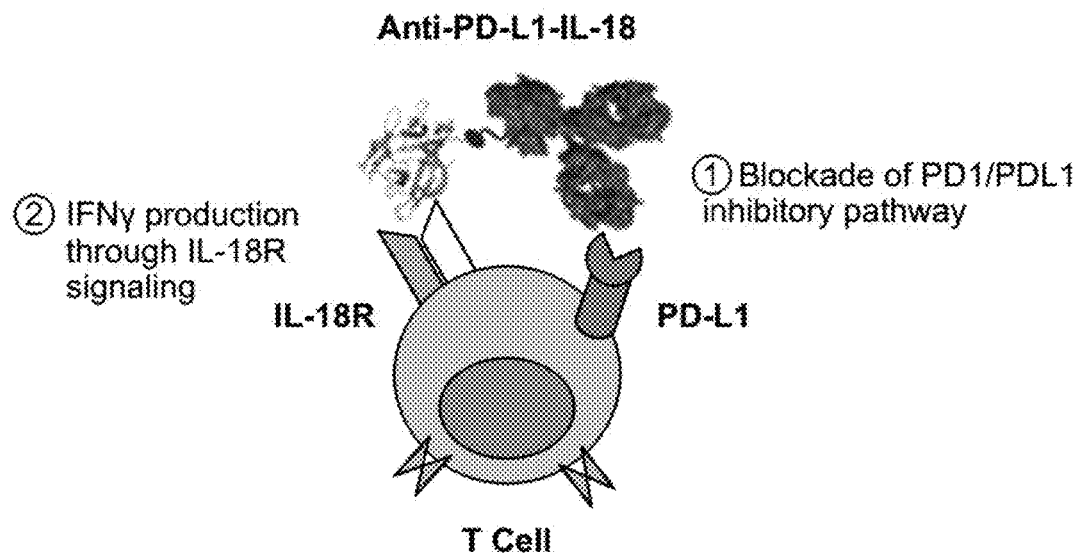
FIG. 1C illustrates a non-limiting mechanism of action of an anti-PD-L1 antibody/IL-18 immunocytokine acting on an immune cell expressing both IL-18R and PD-L1.
Figure 1D:
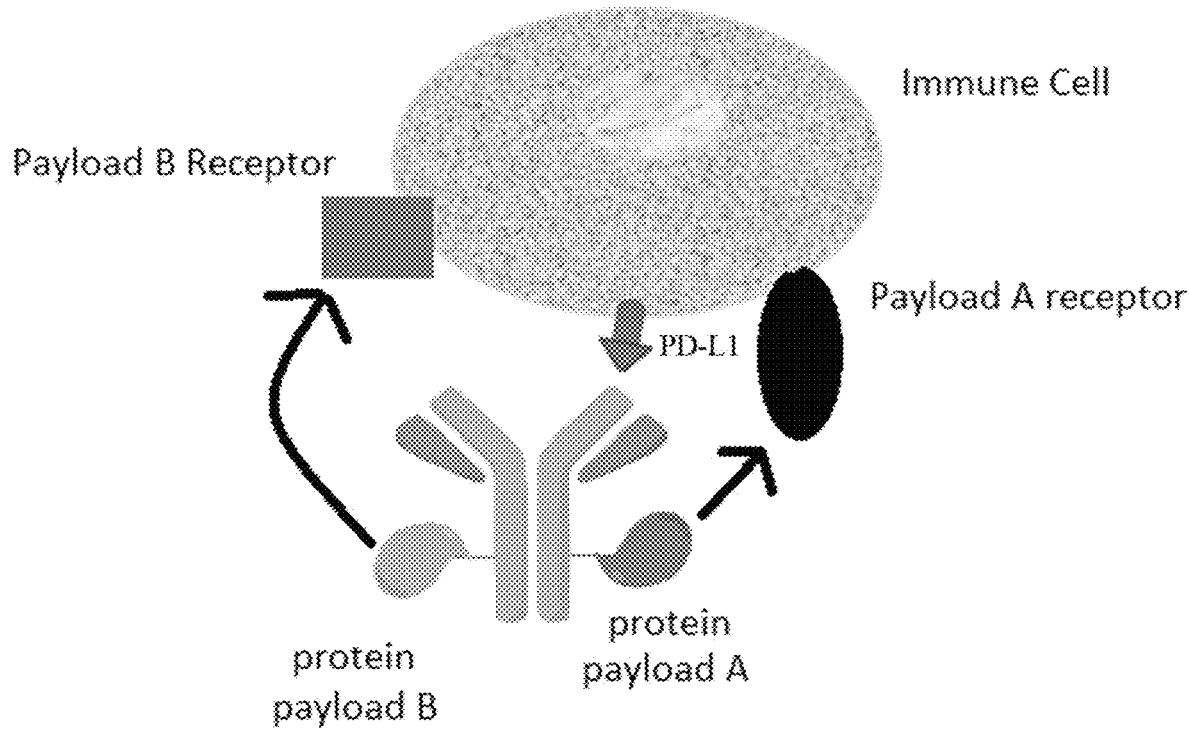
FIG. 1D illustrates an immunocytokine composition provided herein with two different protein payloads (e.g., IL-18 and IL-2) linked to an antibody (e.g., PD-L1 antibody) acting on an immune cell with simultaneous activation of two different receptors (e.g., IL-18R and IL-2R).

Another exemplary, non-limiting mechanism of action of an anti-PD-L1 antibody/IL-18 immunocytokine is shown in FIG. 1B. In the exemplary embodiment, the anti-PD-L1 antibody portion of the immunocytokine binds to PD-L1 expressed on the surface of a tumor cell. When a T cell comes into contact with the tumor cell, an interaction between PD-1 on the T cell and PD-L1 on the cell is blocked, preventing attenuation of the activity of the T cell. Additionally, the IL-18 portion of the immunocytokine is free to signal through IL-18R on the immune cell, thereby inducing production of IFNγ and further activation of the immune cell. Though this exemplary embodiment is demonstrated for PD-L1, other immune antigens provided herein in immunocytokines may display similar mechanisms of action.

Figure 2:
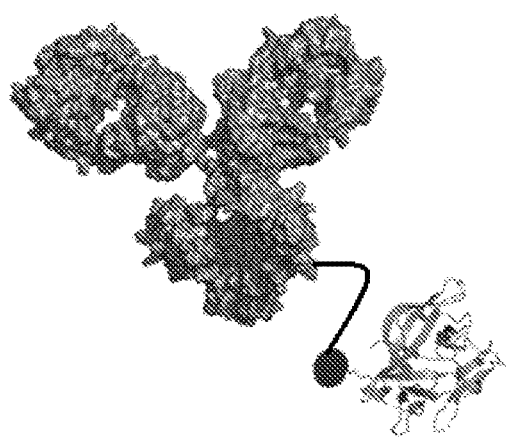
FIG. 2 shows a representative immunocytokine composition with a drug antibody ratio of 1 (DAR1).

Also disclosed herein are methods of manufacturing the immunocytokine compositions provided herein. In some embodiments, the immunocytokine compositions are prepared using chemical linkers which can attach the two moieties of immunocytokine composition to each other at pre-selected sites of each moiety with high fidelity. In some embodiments, the methods provided herein can be used on a wide variety of antibodies or antigen binding fragments in order to rapidly and easily generate a wide variety of immune antigen specific antibody or antigen binding fragments linked to IL-18 polypeptides as immunocytokines. In some embodiments, the methods can be used on readily commercially available antibodies to allow for rapid linking with IL-18 polypeptides provided herein. One non-limiting illustration of an immunocytokine as provided herein is shown in FIG. 2, which depicts an IL-18 polypeptide linked to an antibody as provided herein with a point of attachment of the linker to the IL-18 polypeptide at a side chain of a residue and to a side chain of a residue in the Fc region.

The following description and examples illustrate embodiments of the present disclosure in detail. It is to be understood that this present disclosure is not limited to the particular embodiments described herein and as such can vary. Those of skill in the art will recognize that there are numerous variations and modifications of this present disclosure, which are encompassed within its scope.

Although various features of the present disclosure may be described in the context of a single embodiment, the features may also be provided separately or in any suitable combination. Conversely, although the present disclosure may be described herein in the context of separate embodiments for clarity, the present disclosure may also be implemented in a single embodiment.

The section headings used herein are for organizational purposes only and are not to be construed as limiting the subject matter described.

Immune Antigen Specific Antibodies Linked to IL-18 Polypeptides as Immunocytokines Provided herein are antibodies and antigen binding fragments which binds to immune cell associated antigens linked to IL-18 polypeptides as immunocytokine compositions. The immunocytokine compositions provided herein are effective for simultaneously delivering the IL-18 polypeptide and the antibody or antigen binding fragment to a target cell, such as an immune cell. This simultaneous delivery of both agents to the same cell has numerous benefits, including improved IL-18 polypeptide selectivity, enhanced therapeutic potential of the IL-18 polypeptide, and minimized risk of side effects from administering IL-18 therapies. In some embodiments, the immunocytokine compositions act through multiple modes of action, including without limitation disrupting an activity of the immune cell associated antigen (e.g., immune checkpoint evasion) and/or enhanced activation of immune cells in or around a tumor microenvironment.

The immunocytokine compositions provided herein utilize linkers to attach the antibody or antigen binding fragment to the IL-18 polypeptide. In some embodiments, the linkers are attached to each moiety (i.e., the antibody or antigen binding fragment and the IL-18 polypeptide) at specific residues or a specific subset of residues. In some embodiments, the linkers are attached to each moiety in a site-selective manner, such that a population of the immunocytokine compositions is substantially uniform. This can be accomplished in a variety of ways as provided herein, including by site-selectively adding reagents for a conjugation reaction to a moiety to be conjugated, synthesizing or otherwise preparing a moiety to be conjugated with a desired reagent for a conjugation reaction, or a combination of these two approaches. Using these approaches, the sites of attachment (such as specific amino acid residues) of the linker to each moiety can be selected with precision.

Additionally, these approaches allow a variety of linkers to be employed for the composition which are not limited to amino acid residues as is required for fusion proteins. This combination of linker choice and precision attachment to the moieties allows the linker to also, in some embodiments, perform the function of modulating the activity of one of the moieties, for example if the linker is attached to the IL-18 polypeptide at a position that interacts with a protein which binds to the IL-18 polypeptide (e.g., IL-18 binding protein).

In one aspect, provided herein, is an immunocytokine composition, comprising: an IL-18 polypeptide and an antibody or an antigen binding fragment thereof specific for an immune cell associated antigen. In some embodiments, the immunocytokine composition comprises a linker. In some embodiments, the linker comprises a first point of attachment to the IL-18 polypeptide. In some embodiments, the linker comprises a second point of attachment to the antibody or antigen binding fragment thereof.

Immune Cell Specific Antibodies

In some embodiments, an antibody or an antigen binding fragment of the disclosure specifically binds to an immune cell associated antigen. An immune cell associated antigen provided herein is an antigen expressed at elevated levels in cells of an immune cell relative to other cells. In some embodiments, the immune cell associated antigen is expressed at a level of at least 25% greater, at least 30% greater, at least 40% greater, at least 50% greater, at least 60% greater, at least 70% greater, at least 80% greater, at least 90% greater, or at least 100% greater in the immune cell than another cell. In some embodiments, the immune cell associated antigen is expressed at a level of at least 2-fold greater, at least 4-fold greater, at least 6-fold greater, at least 8-fold greater, or at least 10-fold greater in the immune cell than another cell.

An antibody selectively binds or preferentially binds to a target if it binds with greater affinity, avidity, more readily, and/or with greater duration than it binds to other substances. As such, "specific binding" or "preferential binding" does not necessarily require (although it can include) exclusive binding. Generally, but not necessarily, reference to specific binding means preferential binding where the affinity of the antibody, or antigen binding fragment thereof, is at least at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody for unrelated amino acid sequences. In some embodiments, an antibody or an antigen binding fragment of the disclosure can inhibit the action/activity of the substance to which it binds. In some embodiments, an antibody or antigen binding fragment of the disclosure can agonize the action/activity of the substance to which it binds (e.g., an immune cell agonist antibody or antigen binding fragment such as one specific for CD16A, NKG2D, NKp30, or other targets).

As used herein, the term "antibody" refers to an immunoglobulin (Ig), polypeptide, or a protein having a binding domain which is, or is homologous to, an antigen binding domain. The term further includes "antigen binding fragments" and other interchangeable terms for similar binding fragments as described below. Native antibodies and native immunoglobulins (Igs) are generally heterotetrameric glycoproteins of about 150,000 Daltons, composed of two identical light chains and two identical heavy chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$") followed by a number of constant domains ("$C_H$"). Each light chain has a variable domain at one end ("$V_L$") and a constant domain ("$C_L$") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

In some instances, an antibody or an antigen binding fragment comprises an isolated antibody or antigen binding fragment, a purified antibody or antigen binding fragment, a recombinant antibody or antigen binding fragment, a modified antibody or antigen binding fragment, or a synthetic antibody or antigen binding fragment.

Antibodies and antigen binding fragments herein can be partly or wholly synthetically produced. An antibody or antigen binding fragment can be a polypeptide or protein having a binding domain which can be, or can be homologous to, an antigen binding domain. In one instance, an antibody or an antigen binding fragment can be produced in an appropriate in vivo animal model and then isolated and/or purified.

Depending on the amino acid sequence of the constant domain of its heavy chains, immunoglobulins (Igs) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. An Ig or portion thereof can, in some cases, be a human Ig. In some instances, a $C_H3$ domain can be from an immunoglobulin. In some cases, a chain or a part of an antibody or antigen binding fragment, a modified antibody or antigen binding fragment, or a binding agent can be from an Ig. In such cases, an Ig can be IgG, an IgA, an IgD, an IgE, or an IgM, or is derived therefrom. In cases where the Ig is an IgG, it can be a subtype of IgG, wherein subtypes of IgG can include IgG1, an IgG2a, an IgG2b, an IgG3, or an IgG4. In some cases, a $C_H3$ domain can be from an immunoglobulin selected from the group consisting of an IgG, an IgA, an IgD, an IgE, and an IgM, or is derived therefrom. In some embodiments, an antibody or antigen binding fragment described herein comprises an IgG or is derived therefrom. In some instances, an antibody or antigen binding fragment comprises an IgG1 or is derived therefrom. In some instances, an antibody or antigen binding fragment comprises an IgG4 or is derived therefrom. In some instances, an antibody or antigen binding fragment comprises an IgG2 or is derived therefrom. In some embodiments, an antibody or antigen binding fragment described herein comprises an IgM, is derived therefrom, or is a monomeric form of IgM. In some embodiments, an antibody or antigen binding fragment described herein comprises an IgE or is derived therefrom. In some embodiments, an antibody or antigen binding fragment described herein comprises an IgD or is derived therefrom. In some embodiments, an antibody or antigen binding fragment described herein comprises an IgA or is derived therefrom.

The "light chains" of antibodies (immunoglobulins) from any vertebrate species can be assigned to one of two clearly distinct types, called kappa ("κ" or "K") or lambda ("λ"), based on the amino acid sequences of their constant domains.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (Kabat et al., Sequences of Proteins of Immunological Interest, 5th Ed., 1991, National Institutes of Health, Bethesda Md., pages 647-669; hereafter "Kabat"); and (2) an approach based on crystallographic studies of antigen-antibody complexes (Al-Iazikani et al. (1997) J. Molec. Biol. 273:927-948)). As used herein, a CDR may refer to CDRs defined by either approach or by a combination of both approaches.

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3, and FR4), largely adopting a β-sheet configuration interspersed with three CDRs which form loops connecting and, in some cases, part of the j-sheet structure. The CDRs in each chain are held together in close proximity by the FRs and, with the CDRs from the other chain, contribute to the formation of the antigen binding site of antibodies (see, Kabat).

The terms "hypervariable region" and "CDR" when used herein, refer to the amino acid residues of an antibody which are responsible for antigen binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2), and 89-97 (CDRL3), and in the heavy chain variable domain the CDRs typically correspond to approximately residues 31-35 (CDRH1), 50-65 (CDRH2), and 95-102 (CDRH3) according to Kabat et al., Id. It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2), and 91-96 (CDRL3), and in the heavy chain variable domain, the CDRs typically correspond to approximately residues 26-32 (CDRH1), 53-55 (CDRH2), and 96-101 (CDRH3) according to Chothia and Lesk (J. Mol. Biol., 196: 901-917 (1987)).

As used herein, "framework region," "FW," or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Id. As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, Id. The loop amino acids of a FR can be assessed and determined by inspection of the three-dimensional structure of an antibody heavy chain and/or antibody light chain. The three-dimensional structure can be analyzed for solvent accessible amino acid positions as such positions are likely to form a loop and/or provide antigen contact in an antibody variable domain. Some of the solvent accessible positions can tolerate amino acid sequence diversity and others (e.g., structural positions) are, generally, less diversified. The three-dimensional structure of the antibody variable domain can be derived from a crystal structure or protein modeling.

In the present disclosure, the following abbreviations (in the parentheses) are used in accordance with the customs, as necessary: heavy chain (H chain), light chain (L chain), heavy chain variable region (VH), light chain variable region (VL), complementarity determining region (CDR), first complementarity determining region (CDR1), second complementarity determining region (CDR2), third complementarity determining region (CDR3), heavy chain first complementarity determining region (VH CDR1), heavy chain second complementarity determining region (VH CDR2), heavy chain third complementarity determining region (VH CDR3), light chain first complementarity determining region (VL CDR1), light chain second complementarity determining region (VL CDR2), and light chain third complementarity determining region (VL CDR3).

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is generally defined to stretch from an amino acid residue at position Cys226, or from Pro230, to the carboxyl-terminus thereof. The numbering of the residues in the Fc region is that of the EU index as in Kabat. The Fc region of an immunoglobulin generally comprises two constant domains, $C_H2$ and $C_H3$.

"Antibodies" useful in the present disclosure encompass, but are not limited to, monoclonal antibodies, polyclonal antibodies, chimeric antibodies, bispecific antibodies, grafted antibodies, multispecific antibodies, heteroconjugate antibodies, humanized antibodies, human antibodies, deimmunized antibodies, mutants thereof, fusions thereof, immunoconjugates thereof, antigen binding fragments thereof, and/or any other modified configuration of the immunoglobulin molecule that comprises an antigen recognition site of the required specificity, including glycosylation variants of antibodies, amino acid sequence variants of antibodies, and covalently modified antibodies. In certain embodiments of the methods and conjugates provided herein, the antibody requires an Fc region to enable attachment of a linker between the antibody and the protein (e.g., attachment of the linker using an affinity peptide, such as in AJICAP™ technology).

In some instances, an antibody is a monoclonal antibody. As used herein, a "monoclonal antibody" refers to an antibody obtained from a population of substantially homogeneous antibodies, i.e., the individual antibodies comprising the population are identical except for possible naturally-occurring mutations that may be present in minor amounts. In contrast to polyclonal antibody preparations, which typically include different antibodies directed against different determinants (epitopes), each monoclonal antibody is directed against a single determinant on the antigen (epitope). The modifier "monoclonal" indicates the character of the antibody as being obtained from a substantially homogeneous population of antibodies and is not to be construed as requiring production of the antibody by any particular method.

In some instances, an antibody is a humanized antibody. As used herein, "humanized" antibodies refer to forms of non-human (e.g., murine) antibodies that are specific chimeric immunoglobulins, immunoglobulin chains, or fragments thereof that contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and biological activity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences but are included to further refine and optimize antibody performance. In general, a humanized antibody comprises substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in, for example, WO 99/58572. Other forms of humanized antibodies have one or more CDRs (one, two, three, four, five, or six) which are altered with respect to the original antibody, which are also termed one or more CDRs "derived from" one or more CDRs from the original antibody.

If needed, an antibody or an antigen binding fragment described herein can be assessed for immunogenicity and, as needed, be deimmunized (i.e., the antibody is made less immunoreactive by altering one or more T cell epitopes). As used herein, a "deimmunized antibody" means that one or more T cell epitopes in an antibody sequence have been modified such that a T cell response after administration of the antibody to a subject is reduced compared to an antibody that has not been deimmunized. Analysis of immunogenicity and T-cell epitopes present in the antibodies and antigen binding fragments described herein can be carried out via the use of software and specific databases. Exemplary software and databases include iTope™ developed by Antitope of Cambridge, England. iTope™, is an in silico technology for analysis of peptide binding to human MHC class II alleles. The iTope™ software predicts peptide binding to human MHC class II alleles and thereby provides an initial screen for the location of such "potential T cell epitopes." iTope™ software predicts favorable interactions between amino acid side chains of a peptide and specific binding pockets within the binding grooves of 34 human MHC class II alleles. The location of key binding residues is achieved by the in silico generation of 9mer peptides that overlap by one amino acid spanning the test antibody variable region sequence. Each 9mer peptide can be tested against each of the 34 MHC class II allotypes and scored based on their potential "fit" and interactions with the MHC class II binding groove. Peptides that produce a high mean binding score (>0.55 in the iTope™ scoring function) against >50% of the MHC class II alleles are considered as potential T cell epitopes. In such regions, the core 9 amino acid sequence for peptide binding within the MHC class II groove is analyzed to determine the MHC class II pocket residues (P1, P4, P6, P7, and P9) and the possible T cell receptor (TCR) contact residues (P-1, P2, P3, P5, P8). After identification of any T-cell epitopes, amino acid residue changes, substitutions, additions, and/or deletions can be introduced to remove the identified T-cell epitope. Such changes can be made so as to preserve antibody structure and function while still removing the identified epitope. Exemplary changes can include, but are not limited to, conservative amino acid changes.

An antibody can be a human antibody. As used herein, a "human antibody" means an antibody having an amino acid sequence corresponding to that of an antibody produced by a human and/or that has been made using any suitable technique for making human antibodies. This definition of a human antibody includes antibodies comprising at least one human heavy chain polypeptide or at least one human light chain polypeptide. One such example is an antibody comprising murine light chain and human heavy chain polypeptides. In one embodiment, the human antibody is selected from a phage library, where that phage library expresses human antibodies. Human antibodies can also be made by introducing human immunoglobulin loci into transgenic animals, e.g., mice in which the endogenous immunoglobulin genes have been partially or completely inactivated. Alternatively, the human antibody may be prepared by immortalizing human B lymphocytes that produce an antibody directed against a target antigen (such B lymphocytes may be recovered from an individual or may have been immunized in vitro).

Any of the antibodies herein can be bispecific. Bispecific antibodies are antibodies that have binding specificities for at least two different antigens and can be prepared using the antibodies disclosed herein. Traditionally, the recombinant production of bispecific antibodies was based on the co-expression of two immunoglobulin heavy chain-light chain pairs, with the two heavy chains having different specificities. Bispecific antibodies can be composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations.

According to one approach to making bispecific antibodies, antibody variable domains with the desired binding specificities (antibody-antigen combining sites) are fused to immunoglobulin constant domain sequences. The fusion can be with an immunoglobulin heavy chain constant domain, comprising at least part of the hinge, CH2 and CH3 regions. The first heavy chain constant region (CH1), containing the site necessary for light chain binding, can be present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some instances, an antibody herein is a chimeric antibody. "Chimeric" forms of non-human (e.g., murine) antibodies include chimeric antibodies which contain minimal sequence derived from a non-human Ig. For the most part, chimeric antibodies are murine antibodies in which at least a portion of an immunoglobulin constant region (Fc), typically that of a human immunoglobulin, is inserted in place of the murine Fc. Chimeric or hybrid antibodies also may be prepared in vitro using suitable methods of synthetic protein chemistry, including those involving cross-linking agents.

Provided herein are antibodies and antigen binding fragments thereof, modified antibodies and antigen binding fragments thereof, and binding agents that specifically bind to one or more epitopes on one or more target antigens. In one instance, a binding agent selectively binds to an epitope on a single antigen. In another instance, a binding agent is bivalent and either selectively binds to two distinct epitopes on a single antigen or binds to two distinct epitopes on two distinct antigens. In another instance, a binding agent is multivalent (i.e., trivalent, quatravalent, etc.) and the binding agent binds to three or more distinct epitopes on a single antigen or binds to three or more distinct epitopes on two or more (multiple) antigens.

Antigen binding fragments of any of the antibodies herein are also contemplated. The terms "antigen binding portion of an antibody," "antigen binding domain," "antibody fragment," or a "functional fragment of an antibody" are used interchangeably herein to refer to one or more fragments of an antibody that retain the ability to specifically bind to an antigen. Representative antigen binding fragments include, but are not limited to, a Fab, a Fab', a F(ab')$_2$, a bispecific F(ab')$_2$, a trispecific F(ab')$_2$, a variable fragment (Fv), a single chain variable fragment (scFv), a dsFv, a bispecific scFv, a variable heavy domain, a variable light domain, a variable NAR domain, bispecific scFv, a minibody, a diabody, a bispecific diabody, triabody, a tetrabody, a minibody, a maxibody, a camelid, a VHH, a minibody, an intrabody, fusion proteins comprising an antibody portion (e.g., a domain antibody), a single chain binding polypeptide, a scFv-Fc, a Fab-Fc, a bispecific T cell engager (BiTE; two scFvs produced as a single polypeptide chain, where each scFv comprises an amino acid sequences a combination of CDRs or a combination of VL/VL described herein), a tetravalent tandem diabody (TandAb; an antibody fragment that is produced as a non-covalent homodimer folder in a head-to-tail arrangement, e.g., a TandAb comprising an scFv, where the scFv comprises an amino acid sequences a combination of CDRs or a combination of VL/VL described herein), a Dual-Affinity Re-targeting Antibody (DART; different scFvs joined by a stabilizing interchain disulphide bond), a bispecific antibody (bscAb; two single-chain Fv fragments joined via a glycine-serine linker), a single domain antibody (sdAb), a fusion protein, a bispecific disulfide-stabilized Fv antibody fragment (dsFv-dsFv'; two different disulfide-stabilized Fv antibody fragments connected by flexible linker peptides). In certain embodiments of the invention, a full length antibody (e.g., an antigen binding fragment and an Fc region) are preferred.

Heteroconjugate polypeptides comprising two covalently joined antibodies or antigen binding fragments of antibodies are also within the scope of the disclosure. Suitable linkers may be used to multimerize binding agents. Non-limiting examples of linking peptides include, but are not limited to, $(GS)_n$ (SEQ ID NO: 224), $(GGS)_n$ (SEQ ID NO: 225), $(GGGS)_n$ (SEQ ID NO: 226), $(GGSG)_n$ (SEQ ID NO: 227), or $(GGSGG)_n$ (SEQ ID NO: 228), $(GGGGS)_n$ (SEQ ID NO: 229), wherein n is 1, 2, 3, 4, 5, 6, 7, 8, 9, or 10. For example, a linking peptide can be $(GGGGS)_3$ (SEQ ID NO: 230) or $(GGGGS)_4$ (SEQ ID NO: 231). In some embodiments, a linking peptide bridges approximately 3.5 nm between the carboxy terminus of one variable region and the amino terminus of the other variable region. Linkers of other sequences have been designed and used. Linkers can in turn be modified for additional functions, such as attachment of drugs or attachment to solid supports.

As used herein, the term "avidity" refers to the resistance of a complex of two or more agents to dissociation after dilution. Apparent affinities can be determined by methods such as an enzyme-linked immunosorbent assay (ELISA) or any other suitable technique. Avidities can be determined by methods such as a Scatchard analysis or any other suitable technique.

As used herein, the term "affinity" refers to the equilibrium constant for the reversible binding of two agents and is expressed as $K_D$. The binding affinity ($K_D$) of an antibody or antigen binding fragment herein can be less than 500 nM, 475 nM, 450 nM, 425 nM, 400 nM, 375 nM, 350 nM, 325 nM, 300 nM, 275 nM, 250 nM, 225 nM, 200 nM, 175 nM, 150 nM, 125 nM, 100 nM, 90 nM, 80 nM, 70 nM, 50 nM, 50 nM, 49 nM, 48 nM, 47 nM, 46 nM, 45 nM, 44 nM, 43 nM, 42 nM, 41 nM, 40 nM, 39 nM, 38 nM, 37 nM, 36 nM, 35 nM, 34 nM, 33 nM, 32 nM, 31 nM, 30 nM, 29 nM, 28 nM, 27 nM, 26 nM, 25 nM, 24 nM, 23 nM, 22 nM, 21 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, 1 nM, 990 pM, 980 pM, 970 pM, 960 pM, 950 pM, 940 pM, 930 pM, 920 pM, 910 pM, 900 pM, 890 pM, 880 pM, 870 pM, 860 pM, 850 pM, 840 pM, 830 pM, 820 pM, 810 pM, 800 pM, 790 pM, 780 pM, 770 pM, 760 pM, 750 pM, 740 pM, 730 pM, 720 pM, 710 pM, 700 pM, 690 pM, 680 pM, 670 pM, 660 pM, 650 pM, 640 pM, 630 pM, 620 pM, 610 pM, 600 pM, 590 pM, 580 pM, 570 pM, 560 pM, 550 pM, 540 pM, 530 pM, 520 pM, 510 pM, 500 pM, 490 pM, 480 pM, 470 pM, 460 pM, 450 pM, 440 pM, 430 pM, 420 pM, 410 pM, 400 pM, 390 pM, 380 pM, 370 pM, 360 pM, 350 pM, 340 pM, 330 pM, 320 pM, 310 pM, 300 pM, 290 pM, 280 pM, 270 pM, 260 pM, 250 pM, 240 pM, 230 pM, 220 pM, 210 pM, 200 pM, 190 pM, 180 pM, 170 pM, or any integer therebetween. Binding affinity may be determined using surface plasmon resonance (SPR), KINEXA® Biosensor, scintillation proximity assays, enzyme linked immunosorbent assay (ELISA), ORIGEN immunoassay (IGEN), fluorescence quenching, fluorescence transfer, yeast display, or any combination thereof. Binding affinity may also be screened using a suitable bioassay.

Also provided herein are affinity matured antibodies. The following methods may be used for adjusting the affinity of an antibody and for characterizing a CDR. One way of characterizing a CDR of an antibody and/or altering (such as improving) the binding affinity of a polypeptide, such as an antibody, is termed "library scanning mutagenesis." Generally, library scanning mutagenesis works as follows. One or more amino acid position in the CDR is replaced with two or more (such as 3, 4, 5, 6, 7, 8, 9, 10, 11, 12, 13, 14, 15, 16, 17, 18, 19, or 20) amino acids. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, for example, about 20-80 clones (depending on the complexity of the library), from each library can be screened for binding specificity or affinity to the target polypeptide (or other binding target), and candidates with increased, the same, decreased, or no binding are identified. Binding affinity may be determined using Biacore surface plasmon resonance analysis, which detects differences in binding affinity of about 2-fold or greater.

In some instances, an antibody or antigen binding fragment is bispecific or multispecific and can specifically bind to more than one antigen. In some cases, such a bispecific or multispecific antibody or antigen binding fragment can specifically bind to 2 or more different antigens. In some cases, a bispecific antibody or antigen binding fragment can be a bivalent antibody or antigen binding fragment. In some cases, a multi specific antibody or antigen binding fragment can be a bivalent antibody or antigen binding fragment, a trivalent antibody or antigen binding fragment, or a quatravalent antibody or antigen binding fragment.

An antibody or antigen binding fragment described herein can be isolated, purified, recombinant, or synthetic.

It is contemplated that generic or biosimilar versions of the named antibodies herein which share the same amino acid sequence as the indicated antibodies are also encompassed when the name of the antibody is used.

The antibodies described herein may be made by any suitable method. Antibodies can often be produced in large quantities, particularly when utilizing high level expression vectors.

In one embodiment, an antibody or an antigen binding fragment of the disclosure comprises a fusion protein or a peptide immunotherapeutic agent.

Immune Cell Associated Antigen Specific Antibodies

In some embodiments, the antibody or antigen binding fragment thereof is specific for an immune cell associated antigen. In some embodiments, the immune cell associated antigen is associated with an immune cell subtype (e.g., lymphocyte, neutrophil, macrophage, etc.). In some embodiments, the immune cell associated antigen is associated with a T cell, a monocyte, and/or a natural killer (NK) cell. In embodiments, the immune cell antigen is associated with a T cell. In some embodiments, the immune cell antigen is associated with an effector T cell, a cytotoxic T cell, a helper T cell, a regulatory T cell, and/or a memory T cell.

In some embodiments, the immune cell associated antigen is an immune checkpoint molecule. In some embodiments, the immune cell associated antigen is a costimulatory antigen. In some embodiments, the immune cell associated antigen is a macrophage cell surface antigen. In some embodiments, the immune cell associated antigen is an NK cell surface antigen. In some embodiments, the immune cell associated antigen is a T cell surface antigen (e.g., CD8A, CD8B).

In some embodiments, the immune cell associated antigen is 4-1BB, B7-H3, B7-H4, BTLA, CD3, CCR8, CD8A, CD8B, CD16A, CD27, CD28, CD33, CD38, CD39, CD40, CD47, CD70, CD80, CD86, CD96, CD163, CLEC-1, CLEVER-1, CTLA-4, D40, GITR, ICOS, ILT2/3/4, LAG-3, MHCI, MHCII, NKG2A, NKG2D, NKp30, NKp44, NKp46, OX40, PD-1, PD-L1, PD-L2, PSGL-1, SIGLEC-9, SIGLEC-15, SIRP-α, TCR, TIGIT, TIM-3, VISTA, or VSIG4. In some embodiments, the immune cell associated antigen is PD-1. In some embodiments, the immune cell associated antigen is CCR8, CD8A, CD8B, CD16A, CD96, CD226, CTLA-4, ICOS, LAG-3, NKG2A, NKG2D, NKp30, NKp44, NKp46, PD-1, PD-L1, TIGIT, or TIM-3.

In some embodiments, the immune cell associated antigen is 4-1BB. In some embodiments, the immune cell associated antigen is B7-H3. In some embodiments, the immune cell associated antigen is B7-H4. In some embodiments, the immune cell associated antigen is BTLA. In some embodiments, the immune cell associated antigen is CD3. In some embodiments, the immune cell associated antigen is CCR8. In some embodiments, the immune cell associated antigen is CD8A. In some embodiments, the immune cell associated antigen is CD8B. In some embodiments, the immune cell associated antigen is CD16A. In some embodiments, the immune cell associated antigen is CD27. In some embodiments, the immune cell associated antigen is CD33. In some embodiments, the immune cell associated antigen is CD38. In some embodiments, the immune cell associated antigen is CD39. In some embodiments, the immune cell associated antigen is CD40. In some embodiments, the immune cell associated antigen is CD47. In some embodiments, the immune cell associated antigen is CD80. In some embodiments, the immune cell associated antigen is CD86. In some embodiments, the immune cell associated antigen is CD96. In some embodiments, the immune cell associated antigen is CD163. In some embodiments, the immune cell associated antigen is CLEC-1. In some embodiments, the immune cell associated antigen is CLEVER-1. In some embodiments, the immune cell associated antigen is CTLA4. In some embodiments, the immune cell associated antigen is D40. In some embodiments, the immune cell associated antigen is GITR. In some embodiments, the immune cell associated antigen is ICOS. In some embodiments, the immune cell associated antigen is ILT2/3/4. In some embodiments, the immune cell associated antigen is LAG-3. In some embodiments, the immune cell associated antigen is MHCI. In some embodiments, the immune cell associated antigen is MHCII. In some embodiments, the immune cell associated antigen is NKG2A. In some embodiments, the immune cell associated antigen is NKp30. In some embodiments, the immune cell associated antigen is NKp44. In some embodiments, the immune cell associated antigen is NKp46. In some embodiments, the immune cell associated antigen is OX40. In some embodiments, the immune cell associated antigen is PD-1. In some embodiments, the immune cell associated antigen is PD-L1. In some embodiments, the immune cell associated antigen is PD-L2. In some embodiments, the immune cell associated antigen is PSGL-1. In some embodiments, the immune cell associated antigen is SIGLEC-9. In some embodiments, the immune cell associated antigen is SIGLEC-15. In some embodiments, the immune cell associated antigen is SIRP-□. In some embodiments, the immune cell associated antigen is TCR. In some embodiments, the immune cell associated antigen is TIGIT. In some embodiments, the immune cell associated antigen is TIM-3. In some embodiments, the immune cell associated antigen is VISTA. In some embodiments, the immune cell associated antigen is VSIG4.

In some embodiments, the antibody or antigen binding fragment thereof is an anti-PD-1 antibody or antigen binding fragment. Programmed cell death protein 1 (also known as PD-1 and CD279), is a cell surface receptor that plays a role in down-regulating the immune system and promoting self-tolerance by suppressing T cell inflammatory activity. PD-1 is an immune cell inhibitory molecule that is expressed on activated B cells, T cells, and myeloid cells. PD-1 represents an immune checkpoint and guards against autoimmunity via a dual mechanism of promoting apoptosis (programmed cell death) in antigen-specific T-cells in lymph nodes while reducing apoptosis in regulatory T cells. PD-1 is a member of the CD28/CTLA-4/ICOS costimulatory receptor family that delivers negative signals that affect T and B cell immunity. PD-1 is monomeric both in solution as well as on cell surface, in contrast to CTLA-4 and other family members that are all disulfide-linked homodimers. Signaling through the PD-1 inhibitory receptor upon binding its ligand, PD-L1, suppresses immune responses against autoantigens and tumors and plays a role in the maintenance of peripheral immune tolerance. The interaction between PD-1 and PD-L1 results in a decrease in tumor infiltrating lymphocytes, a decrease in T cell receptor mediated proliferation, and immune evasion by the cancerous cells. A non-limiting, exemplary, human PD-1 amino acid sequence is MQIPQAPWPVVWAVLQLGWRPGWFLDSPDRPWNPPTFSPALLVVTEGDNATFTCSFSNTSESFVLNWYRMSPSNQTDKLAAFPEDRSQPGQDCRFRVTQLPNGRDFHMSVVRARRN DSGTYLCGAISLAPKAQIKESLRAELRVTERRAEVPTAHPSPSPRPAGQFQTLVVGVVGGLLGSLVLLVWVLAVICSRAARGTIGARRTGQPLKEDPSAVPVF SVDYGELDFQWREKTPEPPVPCVPEQTEYATIVFPSGMGTSSPARRGSADGPRSAQPLRPEDGHCSWPL (SEQ ID NO: 331).

In one embodiment, an anti-PD-1 antibody or an anti-PD-1 antigen binding fragment of the disclosure comprises a combination of a heavy chain variable region (VH) and a light chain variable region (VL) described herein. In another embodiment, an anti-PD-1 antibody or an anti-PD-1 antigen binding fragment of the disclosure comprises a combination of complementarity determining regions (VH CDR1, VH CDR2, VH CDR3, VL CDR1, VL CDR2, and VL CDR3) described herein. In one embodiment, an anti-PD-1 antibody or an anti-PD-1 antigen binding fragment of the disclosure comprises a modified Tislelizumab, Baizean, 0KVO411B3N, BGB-A317, hu317-1/IgG4mt2, Sintilimab, Tyvyt, IBI-308, Toripalimab, TeRuiPuLi, Terepril, Tuoyi, JS-001, TAB-001, Camrelizumab, HR-301210, INCSHR-01210, SHR-1210, Cemiplimab, Cemiplimab-rwlc, LIBTAYO®, 6QVL057INT, H4H7798N, REGN-2810, SAR-439684, Avelumab, BAVENCIO®, 451238, KXG2PJ551I, MSB-0010682, MSB-0010718C, PF-06834635, Durvalumab, IMFINZI®, 28×28×90 KV, MEDI-4736, Lambrolizumab, Pembrolizumab, KEYTRUDA®, MK-3475, SCH-900475, h409A11, Nivolumab, Nivolumab BMS, OPDIVO®, BMS-936558, MDX-1106, ONO-4538, Prolgolimab, Forteca, BCD-100, Penpulimab, AK-105, Zimberelimab, AB-122, GLS-010, WBP-3055, Balstilimab, 1Q2QT5M7EO, AGEN-2034, AGEN-2034w, Genolimzumab, Geptanolimab, APL-501, CBT-501, GB-226, Dostarlimab, ANB-011, GSK-4057190A, P0GVQ9A4S5, TSR-042, WBP-285, Serplulimab, HLX-10, CS-1003, Retifanlimab, 2Y3T5IF0IZ, INCMGA-00012, INCMGA-0012, MGA-012, Sasanlimab, LZZOIC2EWP, PF-06801591, RN-888, Spartalizumab, NVP-LZV-184, PDR-001, QOG25L6Z8Z, Relatlimab/nivolumab, BMS-986213, Cetrelimab, JNJ-3283, JNJ-63723283, LYK98WP91F, Tebotelimab, MGD-013, BCD-217, BAT-1306, HX-008, MEDI-5752, JTX-4014, Cadonilimab, AK-104, BI-754091, Pidilizumab, CT-011, MDV-9300, YBL-006, AMG-256, RG-6279, RO-7284755, BH-2950, IBI-315, RG-6139, RO-7247669, ONO-4685, AK-112, 609-A, LY-3434172, T-3011, MAX-10181, AMG-404, IBI-318, MGD-019, INCB-086550, ONCR-177, LY-3462817, RG-7769, RO-7121661, F-520, XmAb-23104, Pd-1-pik, SG-001, S-95016, Sym-021, LZM-009, Budigalimab, 6VDO4TY3OO, ABBV-181, PR-1648817, CC-90006, XmAb-20717, 2661380, AMP-224, B7-DCIg, EMB-02, ANB-030, PRS-332, [89Zr]Deferoxamide-pembrolizumab, 89Zr-Df-Pembrolizumab, [89Zr]Df-Pembrolizumab, STI-1110, STI-A1110, CX-188, mPD-1 Pb-Tx, MCLA-134, 244C8, ENUM 224C8, ENUM C8, 388D4, ENUM 388D4, ENUM D4, MEDIO680, or AMP-514.

In some embodiments, an anti-PD-1 antibody or an anti-PD-1 antigen binding fragment of the disclosure comprises a Tislelizumab, Sintilimab, Toripalimab, Terepril, Camrelizumab, Cemiplimab, Pembrolizumab Nivolumab, Prolgolimab, Penpulimab, Zimberelimab, Balstilimab, Genolimzumab, Geptanolimab, Dostarlimab, Serplulimab, Retifanlimab, Sasanlimab, Spartalizumab, Cetrelimab, Tebotelimab, Cadonilimab, A Pidilizumab, LZM-009, or Budigalimab. In one embodiment, an anti-PD-1 antibody or an anti-PD-1 antigen binding fragment of the disclosure comprises a modified Tislelizumab, Sintilimab, Toripalimab, Terepril, Camrelizumab, Cemiplimab, Pembrolizumab Nivolumab, Prolgolimab, Penpulimab, Zimberelimab, Balstilimab, Genolimzumab, Geptanolimab, Dostarlimab, Serplulimab, Retifanlimab, Sasanlimab, Spartalizumab, Cetrelimab, Tebotelimab, Cadonilimab, A Pidilizumab, LZM-009, or Budigalimab.

In some embodiments, the anti-PD-1 polypeptide is Nivolumab, Pembrolizumab, LZM-009, Dostarlimab, Sintilimab, Spartalizumab, Tislelizumab, or Cemiplimab. In some embodiment, the anti-PD-1 polypeptide is Dostarlimab, Sintilimab, Spartalizumab, or Tislelizumab. In some embodiments, the anti-PD-1 polypeptide is Nivolumab, Pembrolizumab, LZM-009, or Cemiplimab.

In some embodiments, the anti-PD-1 antibody is Pembrolizumab. In some embodiments, the anti-PD-1 antibody is modified Pembrolizumab.

In some embodiments, the anti-PD-1 antibody is a biosimilar of Tislelizumab, Sintilimab, Toripalimab, Terepril, Camrelizumab, Cemiplimab, Pembrolizumab Nivolumab, Prolgolimab, Penpulimab, Zimberelimab, Balstilimab, Genolimzumab, Geptanolimab, Dostarlimab, Serplulimab, Retifanlimab, Sasanlimab, Spartalizumab, Cetrelimab, Tebotelimab, Cadonilimab, A Pidilizumab, LZM-009, or Budigalimab. In some embodiments, the anti-PD-1 antibody is a biosimilar of any one of the antibodies provided herein.

TABLE 1 provides the sequences of exemplary anti-PD-1 antibodies and anti-PD-1 antigen binding fragments that can be modified to prepare anti-PD-1 immunoconjugates. TABLE 1 also shows provides combinations of CDRs that can be utilized in a modified anti-PD-1 immunoconjugate. Reference to an anti-PD-1 antibody herein may alternatively refer to an anti-PD-1 antigen binding fragment.

In some instances, the SEQ ID NOs listed in Table 1 contain full-length heavy or light chains of the indicated antibodies with the VH or VL respectively indicated in bold. Where there is a reference herein to a VH or VL of a SEQ ID NO in Table 1 which contains a full-length heavy or light chain, it is intended to reference the bolded portion of the sequence. For example, reference to "a VH having an amino acid sequence shown in SEQ ID NO: 332" refers to the bolded portion of SEQ ID NO: 332 in Table 1.

An anti-PD-1 antibody or an anti-PD-1 antigen binding fragment can comprise a VH having an amino acid sequence of any one of SEQ ID NOS: 332, 334, 336, 338, 340, 346, 348, 350, 352, 354, 356, 358, 360, 362, 364, 366, 368, 370, 372, 374, 376, and 378. An anti-PD-1 antibody or an anti-PD-1 antigen binding fragment can comprise a VL having an amino acid sequence of any one of SEQ ID NOS: 333, 335, 337, 339, 341, 347, 349, 351, 353, 355, 357, 359, 361, 363, 365, 367, 369, 371, 373, 375, 377, and 379.

An anti-PD-1 antibody or an anti-PD-1 antigen binding fragment can comprise a heavy chain or VH having an amino acid sequence of any one of SEQ ID NOS: 332, 334, 336, 338, 340, 346, 348, 350, 352, 354, 356, 358, 360, 362, 364, 366, 368, 370, 372, 374, 376, and 378, or a portion corresponding to a VH thereof. An anti-PD-1 antibody or an anti-PD-1 antigen binding fragment can comprise a light chain or VL having an amino acid sequence of any one of SEQ ID NOS: 333, 335, 337, 339, 341, 347, 349, 351, 353, 355, 357, 359, 361, 363, 365, 367, 369, 371, 373, 375, 377, and 379, or a portion corresponding to a VL thereof.

In one instance, an anti-PD-1 antibody or an anti-PD-1 antigen binding fragment comprises a VH having an amino acid sequence shown in SEQ ID NO: 332, and a VL having an amino acid sequence shown in SEQ ID NO: 333. In another instance, an anti-PD-1 antibody or an anti-PD-1 antigen binding fragment comprises a VH having an amino acid sequence shown in SEQ ID NO: 334, and a VL having an amino acid sequence shown in SEQ ID NO: 335. In another instance, an anti-PD-1 antibody or an anti-PD-1 antigen binding fragment comprises a VH having an amino acid sequence shown in SEQ ID NO: 336, and a VL having an amino acid sequence shown in SEQ ID NO: 337. In another instance, an anti-PD-1 antibody or an anti-PD-1 antigen binding fragment comprises a VH having an amino acid sequence shown in SEQ ID NO: 338, and a VL having an amino acid sequence shown in SEQ ID NO: 339. In another instance, an anti-PD-1 antibody or an anti-PD-1 antigen binding fragment comprises a VH having an amino acid sequence shown in SEQ ID NO: 340, and a VL having an amino acid sequence shown in SEQ ID NO: 341. In another instance, an anti-PD-1 antibody or an anti-PD-1 antigen binding fragment comprises a VH having an amino acid sequence shown in SEQ ID NO: 346, and a VL having an amino acid sequence shown in SEQ ID NO: 347. In another instance, an anti-PD-1 antibody or an anti-PD-1 antigen binding fragment comprises a VH having an amino acid sequence shown in SEQ ID NO: 348, and a VL having an amino acid sequence shown in SEQ ID NO: 349. In another instance, an anti-PD-1 antibody or an anti-PD-1 antigen binding fragment comprises a VH having an amino acid sequence shown in SEQ ID NO: 350, and a VL having an amino acid sequence shown in SEQ ID NO: 351. In another instance, an anti-PD-1 antibody or an anti-PD-1 antigen binding fragment comprises a VH having an amino acid sequence shown in SEQ ID NO: 352, and a VL having an amino acid sequence shown in SEQ ID NO: 353. In another instance, an anti-PD-1 antibody or an anti-PD-1 antigen binding fragment comprises a VH having an amino acid sequence shown in SEQ ID NO: 354, and a VL having an amino acid sequence shown in SEQ ID NO: 355. In another instance, an anti-PD-1 antibody or an anti-PD-1 antigen binding fragment comprises a VH having an amino acid sequence shown in SEQ ID NO: 356, and a VL having an amino acid sequence shown in SEQ ID NO: 357. In another instance, an anti-PD-1 antibody or an anti-PD-1 antigen binding fragment comprises a VH having an amino acid sequence shown in SEQ ID NO: 358, and a VL having an amino acid sequence shown in SEQ ID NO: 359. In another instance, an anti-PD-1 antibody or an anti-PD-1 antigen binding fragment comprises a VH having an amino acid sequence shown in SEQ ID NO: 360, and a VL having an amino acid sequence shown in SEQ ID NO: 361. In another instance, an anti-PD-1 antibody or an anti-PD-1 antigen binding fragment comprises a VH having an amino acid sequence shown in SEQ ID NO: 362, and a VL having an amino acid sequence shown in SEQ ID NO: 363. In another instance, an anti-PD-1 antibody or an anti-PD-1 antigen binding fragment comprises a VH having an amino acid sequence shown in SEQ ID NO: 364, and a VL having an amino acid sequence shown in SEQ ID NO: 365. In another instance, an anti-PD-1 antibody or an anti-PD-1 antigen binding fragment comprises a VH having an amino acid sequence shown in SEQ ID NO: 366, and a VL having an amino acid sequence shown in SEQ ID NO: 367. In another instance, an anti-PD-1 antibody or an anti-PD-1 antigen binding fragment comprises a VH having an amino acid sequence shown in SEQ ID NO: 368, and a VL having an amino acid sequence shown in SEQ ID NO: 369. In another instance, an anti-PD-1 antibody or an anti-PD-1 antigen binding fragment comprises a VH having an amino acid sequence shown in SEQ ID NO: 370, and a VL having an amino acid sequence shown in SEQ ID NO: 371. In another instance, an anti-PD-1 antibody or an anti-PD-1 antigen binding fragment comprises a VH having an amino acid sequence shown in SEQ ID NO: 372, and a VL having an amino acid sequence shown in SEQ ID NO: 373. In another instance, an anti-PD-1 antibody or an anti-PD-1 antigen binding fragment comprises a VH having an amino acid sequence shown in SEQ ID NO: 374, and a VL having an amino acid sequence shown in SEQ ID NO: 375. In another instance, an anti-PD-1 antibody or an anti-PD-1 antigen binding fragment comprises a VH having an amino acid sequence shown in SEQ ID NO: 376, and a VL having an amino acid sequence shown in SEQ ID NO: 377. In another instance, an anti-PD-1 antibody or an anti-PD-1 antigen binding fragment comprises a VH having an amino acid sequence shown in SEQ ID NO: 378, and a VL having an amino acid sequence shown in SEQ ID NO: 379.

In one instance, an anti-PD-1 antibody or an anti-PD-1 antigen binding fragment comprises a VH having an amino acid sequence of SEQ ID NO: 332, and a VL having an amino acid sequence of SEQ ID NO: 333. In another instance, an anti-PD-1 antibody or an anti-PD-1 antigen binding fragment comprises a VH having an amino acid sequence of SEQ ID NO: 334, and a VL having an amino acid sequence of SEQ ID NO: 335. In another instance, an anti-PD-1 antibody or an anti-PD-1 antigen binding fragment comprises a VH having an amino acid sequence of SEQ ID NO: 336, and a VL having an amino acid sequence of SEQ ID NO: 337. In another instance, an anti-PD-1 antibody or an anti-PD-1 antigen binding fragment comprises a VH having an amino acid sequence of SEQ ID NO: 338, and a VL having an amino acid sequence of SEQ ID NO: 339. In another instance, an anti-PD-1 antibody or an anti-PD-1 antigen binding fragment comprises a VH having an amino acid sequence of SEQ ID NO: 340, and a VL having an amino acid sequence of SEQ ID NO: 341. In another instance, an anti-PD-1 antibody or an anti-PD-1 antigen binding fragment comprises a VH having an amino acid sequence of SEQ ID NO: 346, and a VL having an amino acid sequence of SEQ ID NO: 347. In another instance, an anti-PD-1 antibody or an anti-PD-1 antigen binding fragment comprises a VH having an amino acid sequence of SEQ ID NO: 348, and a VL having an amino acid sequence of SEQ ID NO: 349. In another instance, an anti-PD-1 antibody or an anti-PD-1 antigen binding fragment comprises a VH having an amino acid sequence of SEQ ID NO: 350, and a VL having an amino acid sequence of SEQ ID NO: 351. In another instance, an anti-PD-1 antibody or an anti-PD-1 antigen binding fragment comprises a VH having an amino acid sequence of SEQ ID NO: 352, and a VL having an amino acid sequence of SEQ ID NO: 353. In another instance, an anti-PD-1 antibody or an anti-PD-1 antigen binding fragment comprises a VH having an amino acid sequence of SEQ ID NO: 354, and a VL having an amino acid sequence of SEQ ID NO: 355. In another instance, an anti-PD-1 antibody or an anti-PD-1 antigen binding fragment comprises a VH having an amino acid sequence of SEQ ID NO: 356, and a VL having an amino acid sequence of SEQ ID NO: 357. In another instance, an anti-PD-1 antibody or an anti-PD-1 antigen binding fragment comprises a VH having an amino acid sequence of SEQ ID NO: 358, and a VL having an amino acid sequence of SEQ ID NO: 359. In another instance, an anti-PD-1 antibody or an anti-PD-1 antigen binding fragment comprises a VH having an amino acid sequence of SEQ ID NO: 360, and a VL having an amino acid sequence of SEQ ID NO: 361. In another instance, an anti-PD-1 antibody or an anti-PD-1 antigen binding fragment comprises a VH having an amino acid sequence of SEQ ID NO: 362, and a VL having an amino acid sequence of SEQ ID NO: 363. In another instance, an anti-PD-1 antibody or an anti-PD-1 antigen binding fragment comprises a VH having an amino acid sequence of SEQ ID NO: 364, and a VL having an amino acid sequence of SEQ ID NO: 365. In another instance, an anti-PD-1 antibody or an anti-PD-1 antigen binding fragment comprises a VH having an amino acid sequence of SEQ ID NO: 366, and a VL having an amino acid sequence of SEQ ID NO: 367. In another instance, an anti-PD-1 antibody or an anti-PD-1 antigen binding fragment comprises a VH having an amino acid sequence of SEQ ID NO: 368, and a VL having an amino acid sequence of SEQ ID NO: 369. In another instance, an anti-PD-1 antibody or an anti-PD-1 antigen binding fragment comprises a VH having an amino acid sequence of SEQ ID NO: 370, and a VL having an amino acid sequence of SEQ ID NO: 371. In another instance, an anti-PD-1 antibody or an anti-PD-1 antigen binding fragment comprises a VH having an amino acid sequence of SEQ ID NO: 372, and a VL having an amino acid sequence of SEQ ID NO: 373. In another instance, an anti-PD-1 antibody or an anti-PD-1 antigen binding fragment comprises a VH having an amino acid sequence of SEQ ID NO: 374, and a VL having an amino acid sequence of SEQ ID NO: 375. In another instance, an anti-PD-1 antibody or an anti-PD-1 antigen binding fragment comprises a VH having an amino acid sequence of SEQ ID NO: 376, and a VL having an amino acid sequence of SEQ ID NO: 377. In another instance, an anti-PD-1 antibody or an anti-PD-1 antigen binding fragment comprises a VH having an amino acid sequence of SEQ ID NO: 378, and a VL having an amino acid sequence of SEQ ID NO: 379.

In one instance, an anti-PD-1 antibody or an anti-PD-1 antigen binding fragment comprises a VH CDR1 having an amino acid sequence of SEQ ID NO: 380, a VH CDR2 having an amino acid sequence of SEQ ID NO: 381, a VH CDR3 having an amino acid sequence of SEQ ID NO: 382, VL CDR1 having an amino acid sequence of SEQ ID NO: 383, a VL CDR2 having an amino acid sequence of SEQ ID NO: 384, and a VL CDR3 having an amino acid sequence of SEQ ID NO: 385. In one instance, an anti-PD-1 antibody or an anti-PD-1 antigen binding fragment comprises a VH CDR1 having an amino acid sequence of SEQ ID NO: 386, a VH CDR2 having an amino acid sequence of SEQ ID NO: 387, a VH CDR3 having an amino acid sequence of SEQ ID NO: 388, VL CDR1 having an amino acid sequence of SEQ ID NO: 389, a VL CDR2 having an amino acid sequence of SEQ ID NO: 390, and a VL CDR3 having an amino acid sequence of SEQ ID NO: 391. In one instance, an anti-PD-1 antibody or an anti-PD-1 antigen binding fragment comprises a VH CDR1 having an amino acid sequence of SEQ ID NO: 392, a VH CDR2 having an amino acid sequence of SEQ ID NO: 393, a VH CDR3 having an amino acid sequence of SEQ ID NO: 394, VL CDR1 having an amino acid sequence of SEQ ID NO: 395, a VL CDR2 having an amino acid sequence of SEQ ID NO: 396, and a VL CDR3 having an amino acid sequence of SEQ ID NO: 397. In one instance, an anti-PD-1 antibody or an anti-PD-1 antigen binding fragment comprises a VH CDR1 having an amino acid sequence of SEQ ID NO: 398, a VH CDR2 having an amino acid sequence of SEQ ID NO: 399, a VH CDR3 having an amino acid sequence of SEQ ID NO: 400, VL CDR1 having an amino acid sequence of SEQ ID NO: 401, a VL CDR2 having an amino acid sequence of SEQ ID NO: 402, and a VL CDR3 having an amino acid sequence of SEQ ID NO: 403.

In one instance, an anti-PD-1 antibody comprises a fusion protein. Such fusion protein can be, for example, a two-sided Fc fusion protein comprising the extracellular domain (ECD) of programmed cell death 1 (PD-1) and the ECD of tumor necrosis factor (ligand) superfamily member 4 (TNFSF4 or OX40L) fused via hinge-CH2-CH3 Fc domain of human IgG4, expressed in CHO-K1 cells, where the fusion protein has an exemplary amino acid sequence of SEQ ID NO: 104.

In some embodiments, the antibody or antigen binding fragment thereof is an anti-PD-L1 antibody or antigen binding fragment. Programmed death-ligand 1 (PD-L1) is a ligand for an immunosuppressive receptor "programmed death receptor 1 (PD-1)" that is predominantly expressed in activated T and B cells, which can negatively regulate antigen receptor signaling. The ligands (PD-L1 and PD-L2) for PD-1 may be constitutively expressed or may be derived into a number of cell types, including non-hematopoietic cell tissues and various tumor types. PD-L1 is expressed in B cells, T cells, bone marrow cells and dendritic cells (DCs), but also on non-lymphatic organs such as peripheral cells, pseudo-vascular endothelial cells and heart, lungs, etc. A non-limiting, exemplary, human PD-L1 amino acid sequence is MRIFAVFIFMTYWHLLNAFTVTVPKDLY-VVEYGSNMTIECKFPVEKQLDLAALIVYWE MEDKNIIQFVH-GEEDLKVQHSSYRQRARLLKDQLSLG-NAALQITDVKLQDAGVYRCMI SYGGA-DYKRITVKVNAPYNKINQRILVVDPVTSEHELTCQAE-GYPKAEVIWTSSDHQVL SGKTTTTNSKREEKLFNVTSTLRINTTTNEIFYC-TFRRLDPEENHTAELVIPELPLAHPPNE RTHLVIL-GAILLCLGVALTFI-FRLRKGRMMDVKKCGIQDTNSKKQSDTHLEET (SEQ ID NO: 330)

In one embodiment, an anti-PD-L1 antibody or an anti-PD-L1 antigen binding fragment of the disclosure comprises a combination of a heavy chain variable region (VH) and a light chain variable region (VL) described herein. In another embodiment, an anti-PD-L1 antibody or an anti-PD-L1 antigen binding fragment of the disclosure comprises a combination of complementarity determining regions (VH CDR1, VH CDR2, VH CDR3, VL CDR1, VL CDR2, and VL CDR3) described herein. In one embodiment, an anti-PD-L1 antibody or an anti-PD-L1 antigen binding fragment of the disclosure comprises a modified Modified Avelumab (Bavencio, 451238, KXG2PJ551I, MSB-0010682, MSB-0010718C, PF-06834635, CAS 1537032-82-8: EMD Serono, Merck & Co., Merck KGaA, Merck Serono, National Cancer Institute (NCI), Pfizer), Durvalumab (Imfinzi, 28×28×90 KV (UNII code), MEDI-4736, CAS 1428935-60-7: AstraZeneca, Celgene, Children's Hospital Los Angeles (CHLA), City of Hope National Medical Center, MedImmune, Memorial Sloan-Kettering Cancer Center, Mirati Therapeutics, National Cancer Institute (NCI), Samsung Medical Center (SMC), Washington University), Atezolizumab (Tecentriq, 52CMI0WC3Y, MPDL-3280A, RG-7446, RO-5541267, CAS 1380723-44-3: Academisch Medisch Centrum (AMC), Chugai Pharmaceutical, EORTC, Genentech, Immune Design (Merck & Co.), Memorial Sloan-Kettering Cancer Center, National Cancer Institute (NCI), Roche, Roche Center for Medical Genomics), Sugemalimab (CS-1001, WBP-3155: CStone Pharmaceuticals, EQRx, Pfizer), KN-046 (CAS 2256084-03-2: Jiangsu Alphamab Biopharmaceuticals, Sinovent), APL-502 (CBT-502, TQB-2450: Apollomics, Jiangsu Chia Tai Tianqing Pharmaceutical), Envafolimab (3D-025, ASC-22, KN-035, hu56V1-Fc-m1, CAS 2102192-68-5: 3D Medicines, Ascletis, Jiangsu Alphamab Biopharmaceuticals, Suzhou Alphamab, Tracon Pharmaceuticals, Inc.), Bintrafusp alfa (M-7824, MSB-0011359C, NW9K8C1JN3, CAS 1918149-01-5: EMD Serono, GlaxoSmithKline, Merck KGaA, National Cancer Institute (NCI)), STI-1014 (STI-A1014, ZKAB-001: Lee's Pharmaceutical, Sorrento Therapeutics), PD-L1 t-haNK (ImmunityBio, NantKwest), A-167 (HBM-9167, KL-A167: Harbour BioMed, Sichuan Kelun-Biotech Biopharmaceutical), IMC-001 (STI-3031, STI-A-1015, STI-A1015, ImmuneOncia Therapeutics, Sorrento Therapeutics), HTI-1088 (SHR-1316: Atridia, Jiangsu Hengrui), IO-103 (IO Biotech), CX-072 (CytomX Therapeutics), AUPM-170 (CA-170: Aurigene, Curis), GS-4224 (Gilead), ND-021 (NM21-1480, PRO-1480: CStone Pharmaceuticals, Numab Therapeutics), BNT-311 (DuoBody-PD-L1x4-1BB, GEN-1046: BioNTech, Genmab), BGB-A333 (BeiGene), IBI-322 (Innovent Biologics), NM-01 (Nanomab Technology, Shanghai First People's Hospital), LY-3434172 (Eli Lilly), LDP (Dragonboat Biopharmaceutical), CDX-527 (Celldex Therapeutics), IBI-318 (Innovent Biologics, Lilly), 89Zr-DFO-REGN3504 (Regeneron), ALPN-202 (CD80 vIgD-Fc: Alpine Immune Sciences), INCB-086550 (Incyte), LY-3415244 (Eli Lilly), SHR-1701 (Jiangsu Hengrui), JS-003 (JS003-30, JS003-SD: Shanghai Junshi Biosciences), HLX-20 (PL2 #3: Henlix Biotech, Shanghai Henlius Biotech), ES-101 (INBRX-105, INBRX-105-1: Elpiscience BioPharma, Inhibrx), MSB-2311 (MabSpace Biosciences), PD-1-Fc-OX40L (SL-279252, TAK-252: Heat Biologics, Shattuck Labs, Takeda), FS-118, FS118 mAb2, LAG-3/PD-L1 mAb2: F-star Therapeutics, Merck & Co., Merck KGaA), FAZ-053 (LAE-005: Laekna Therapeutics, Novartis), Lodapolimab (LY-3300054, NR4MAD6PPB, CAS 2118349-31-6: Eli Lilly), MCLA-145 (Incyte, Merus), BMS-189 (BMS-986189, PD-L1-Milla from Bristol-Myers Squibb), Cosibelimab (CK-301, TG-1501, CAS 2216751-26-5: Checkpoint Therapeutics, Dana-Farber Cancer Institute, Samsung Biologics, TG Therapeutics), IL-15Ralpha-SD/IL-15 (KD-033: Kadmon), WP-1066 (CAS 857064-38-1: M.D. Anderson Cancer Center, Moleculin Biotech), BMS-936559 (MDX-1105: Bristol-Myers Squibb, Medarex, National Institute Allergy Infect Dis.), BMS-986192 (Bristol-Myers Squibb), RC-98 (RemeGen), CD-200AR-L (CD200AR-L: OX2 Therapeutics, University of Minnesota), ATA-3271 (Atara Biotherapeutics), IBC-Ab002 (ImmunoBrain Checkpoint), BMX-101 (Biomunex Pharmaceuticals), AVA-04-VbP (Avacta), ACE-1708 (Acepodia Biotech), KY-1043 (Kymab, Provenance Biopharmaceuticals), ACE-05 (YBL-013: Y-Biologics), ONC-0055 (ONC0055, PRS-344 S-095012: *Pieris* Pharmaceuticals, Servier), TLJ-1-CK (I-Mab Biopharma), GR-1405 (Chinese Academy of Medical Sciences), PD-1ACR-T (Taipei Medical University), N-809 (N-IL15/PD-L1: ImmunityBio), CB-201 (Crescendo Biologics), MEDI-1109 (MedImmune), AVA-004 (AVA-04: Avacta), CA-327 (Aurigene, Curis), ALN-PDL (Alnylam Pharmaceuticals), KY-1003 (Kymab), CD22(aPD-L1)CAR-T cells (SL-22P: Hebei Senlang Biotechnology), ATA-2271 (M28zlXXPD-1DNR CAR T cells: Atara Biotherapeutics), and Zeushield cytotoxic T lymphocytes (Second Xiangya Hosp Central South Univ.).

In some embodiments, the anti-PD-L1 antibody is Avelumab, Durvalumab, Atezolizumab, Sugemalimab, Envafolimab, Lodapolimab, or Cosibelimab, or a modified version thereof. In some embodiments, the anti-PD-L1 antibody is Avelumab, Durvalumab, Atezolizumab, Sugemalimab, Envafolimab, Lodapolimab, or Cosibelimab. In some embodiments, the antibody is a biosimilar of Avelumab, Durvalumab, Atezolizumab, Sugemalimab, Envafolimab, Lodapolimab, or Cosibelimab.

TABLE 1 provides the sequences of exemplary anti-PD-L1 antibodies and anti-PD-L1 antigen binding fragments that can be modified to prepare anti-PD-L1 immunoconjugates. TABLE 1 also provides exemplary combinations of CDRs that can be utilized in a modified anti-PD-L1 immunoconjugate. Reference to an anti-PD-L1 antibody herein may alternatively refer to an anti-PD-L1 antigen binding fragment.

In some embodiments, an anti-PD-L1 antibody or an anti-PD-L1 antigen binding fragment comprises a heavy chain or VH having an amino acid sequence of any one of SEQ ID NOS: 232, 234, 236, 238, 242, 244, or 248. An anti-PD-L1 antibody or an anti-PD-L1 antigen binding fragment comprises a heavy chain or VH having an amino acid sequence of any one of SEQ ID NOS: 233, 235, 237, 239, 243, 245, or 249. In one instance, an anti-PD-L1 antibody or an anti-PD-L1 antigen binding fragment comprises a heavy chain or VH having an amino acid sequence of SEQ ID NO: 232, and a light chain or VL having an amino acid sequence of SEQ ID NO: 233. In another instance, an anti-PD-L1 antibody or an anti-PD-L1 antigen binding fragment comprises a heavy chain or VH having an amino acid sequence of SEQ ID NO: 234, and a light chain or VL having an amino acid sequence of SEQ ID NO: 235. In another instance, an anti-PD-L1 antibody or an anti-PD-L1 antigen binding fragment comprises a heavy chain or VH having an amino acid sequence of SEQ ID NO: 236, and a light chain or VL having an amino acid sequence of SEQ ID NO: 237. In another instance, an anti-PD-L1 antibody or an anti-PD-L1 antigen binding fragment comprises a heavy chain or VH having an amino acid sequence of SEQ ID NO: 238, and a light chain or VL having an amino acid sequence of SEQ ID NO: 239. In another instance, an anti-PD-L1 antibody or an anti-PD-L1 antigen binding fragment comprises a VH having an amino acid sequence of SEQ ID NO: 242, and a VL having an amino acid sequence of SEQ ID NO: 243. In another instance, an anti-PD-L1 antibody or an anti-PD-L1 antigen binding fragment comprises a VH having an amino acid sequence of SEQ ID NO: 244, and a VL having an amino acid sequence of SEQ ID NO: 245. In another instance, an anti-PD-L1 antibody or an anti-PD-L1 antigen binding fragment comprises a heavy chain or VH having an amino acid sequence of SEQ ID NO: 248, and a light chain or VL having an amino acid sequence of SEQ ID NO: 249.

In some embodiments, an anti-PD-L1 antibody or an anti-PD-L1 antigen binding fragment comprises a heavy chain or VH having an amino acid sequence of any one of SEQ ID NOS: 232, 234, 236, 238, 242, 244, or 248, or a portion corresponding to a VH thereof. An anti-PD-L1 antibody or an anti-PD-L1 antigen binding fragment comprises a light chain or VL having an amino acid sequence of any one of SEQ ID NOS: 233, 235, 237, 239, 243, 245, or 249, or a portion corresponding to a VL thereof. In one instance, an anti-PD-L1 antibody or an anti-PD-L1 antigen binding fragment comprises a heavy chain or VH having an amino acid sequence shown in SEQ ID NO: 232, and a light chain or VL having an amino acid sequence shown in SEQ ID NO: 233. In another instance, an anti-PD-L1 antibody or an anti-PD-L1 antigen binding fragment comprises a heavy chain or VH having an amino acid sequence shown in SEQ ID NO: 234, and a light chain or VL having an amino acid sequence shown in SEQ ID NO: 235. In another instance, an anti-PD-L1 antibody or an anti-PD-L1 antigen binding fragment comprises a heavy chain or VH having an amino acid sequence shown in SEQ ID NO: 236, and a light chain or VL having an amino acid sequence shown in SEQ ID NO: 237. In another instance, an anti-PD-L1 antibody or an anti-PD-L1 antigen binding fragment comprises a heavy chain or VH having an amino acid sequence shown in SEQ ID NO: 238, and a light chain or VL having an amino acid sequence shown in SEQ ID NO: 239. In another instance, an anti- PD-L1 antibody or an anti-PD-L1 antigen binding fragment comprises a VH having an amino acid sequence shown in SEQ ID NO: 242, and a VL having an amino acid sequence shown in SEQ ID NO: 243. In another instance, an anti-PD-L1 antibody or an anti-PD-L1 antigen binding fragment comprises a VH having an amino acid sequence shown in SEQ ID NO: 244, and a VL having an amino acid sequence shown in SEQ ID NO: 245. In another instance, an anti-PD-L1 antibody or an anti-PD-L1 antigen binding fragment comprises a heavy chain or VH having an amino acid sequence shown in SEQ TD NO: 248, and a light chain or VL having an amino acid sequence shown in SEQ TD NO: 249.

In one instance, an anti-PD-L1 antibody or an anti-PD-L1 antigen binding fragment comprises a VH CDR1 having an amino acid sequence of SEQ ID NO: 250, a VH CDR2 having an amino acid sequence of SEQ ID NO: 251, a VH CDR3 having an amino acid sequence of SEQ ID NO: 252, VL CDR1 having an amino acid sequence of SEQ ID NO: 253, a VL CDR2 having an amino acid sequence of SEQ TD NO: 254, and a VL CDR3 having an amino acid sequence of SEQ TD NO: 255.

In one instance, an anti-PD-L1 antibody comprises a single domain binding antibody having an amino acid sequence of SEQ TD NO: 256, a anti-specific fusion single chain antibody construct having an amino acid sequence of SEQ ID NO: 257, or a bispecific tetrameric antibody like engager having an amino acid sequence of SEQ TD NO: 258.

TABLE 1

Exemplary Antibodies for Immune Cell Associated Antigens

| Antibody or Ag-binding fragment | Antigen Bound | Sequence | SEQ ID NO |
|---|---|---|---|
| Tislelizumab, Baizean, 0KVO411B3N, BGB-A317, hu317-1/IgG4mt2 Heavy Chain (VH in Bold) | PD-1 | QVQLQESGPGLVKPSETLSLTCTVSGFSLTSYGVHWIRQPPGK GLEWIGVIYADGSTNYNPSLKSRVTISKDTSKNQVSLKLSSVT AADTAVYYCARAYGNYWYIDVWGQGTTVTVSSASTKGPSVFP LAPCSRSTSESTAALGCLVKDYFPEPVTVSWNSGALTSGVHTFPA VLQSSGLYSLSSVVTVPSSSLGTKTYTCNVDHKPSNTKVDKRVES KYGPPCPPCPAPPVAGGPSVFLFPPKPKDTLMISRTPEVTCVVVAV SQEDPEVQFNWYVDGVEVHNAKTKPREEQFNSTYRVVSVLTVV HQDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSKLTVDKSRWQEGNVFSCSVMHEALHNHYTQKSLS LSLGK | 332 |
| Tislelizumab, Baizean, 0KVO411B3N, BGB-A317, hu317-1/IgG4mt2 Light Chain (VL in Bold) | PD-1 | DIVMTQSPDSLAVSLGERATINCKSSESVSNDVAWYQQKPGQP PKLLINYAFHRFTGVPDRFSGSGYGTDFTLTISSLQAEDVAVY YCHQAYSSPYTFGQGTKLEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC | 333 |
| Sintilimab, Tyvyt, IBI-308 Heavy Chain (VH in Bold) | PD-1 | QVQLVQSGAEVKKPGSSVKVSCKASGGTFSSYAISWVRQAPG QGLEWMGLIIPMFDTAGYAQKFQGRVAITVDESTSTAYMELS SLRSEDTAVYYCARAEHSSTGTFDYWGQGTLVTVSSASTKGPS VFPPLAPCSRSTSESTAALGCLVKDYFPEPVTVSWNSGALTSGVHT FPAVLQSSGLYSLSSVVTVPSSSLGTKTYTCNVDHKPSNTKVDKR VESKYGPPCPPCPAPEFLGGPSVFLFPPKPKDTLMISRTPEVTCVV VDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTTP PVLDSDGSFFLYSRLTVDKSRWQEGNVFSCSVMHEALHNHYTQK SLSLSLGK | 334 |
| Sintilimab, Tyvyt, IBI-308 Light Chain (VL in Bold) | PD-1 | DIQMTQSPSSVSASVGDRVTITCRASQGISSWLAWYQQKPGK APKLLISAASSLQSGVPSRFSGSGSGTDFTLTISSLQPEDFATYY CQQANHLPFTFGGGTKVEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC | 335 |
| Toripalimab, TeRuiPuLi, Terepril, Tuoyi, JS-001, TAB-001 Heavy Chain (VH in Bold) | PD-1 | QGQLVQSGAEVKKPGASVKVSCKASGYTFTDYEMHWVRQA PIHGLEWIGVIESETGGTAYNQKFKGRVTITADKSTSTAYMEL SSLRSEDTAVYYCAREGITTVATTYYWYFDVWGQGTTVTVSS ASTKGPSVFPLAPCSRSTSESTAALGCLVKDYFPEPVTVSWNSGA LTSGVHTFPAVLQSSGLYSLSSVVTVPSSSLGTKTYTCNVDHKPS NTKVDKRVESKYGPPCPPCPAPEFLGGPSVFLFPPKPKDTLMISRT PEVTCVVVDVSQEDPEVQFNWYVDGVEVHNAKTKPREEQFNST YRVVSVLTVLHQDWLNGKEYKCKVSNKGLPSSIEKTISKAKGQP REPQVYTLPPSQEEMTKNQVSLTCLVKGFYPSDIAVEWESNGQPE NNYKTTPPVLDSDGSFFLYSRLTVDKSRWQEGNVFSCSVMHEAL HNHYTQKSLSLSLGK | 336 |

TABLE 1-continued

Exemplary Antibodies for Immune Cell Associated Antigens

| Antibody or Ag-binding fragment | Antigen Bound | Sequence | SEQ ID NO |
|---|---|---|---|
| Toripalimab, TeRuiPuLi, Terepril, Tuoyi, JS-001, TAB-001 Light Chain (VL in Bold) | PD-1 | DVVMTQSPLSLPVTLGQPASISCRSSQSIVHSNGNTYLEWYLQ KPGQSPQLLIYKVSNRFSGVPDRFSGSGSGTDFTLKISRVEAED VGVYYCFQGSHVPLTFGQGTKLEIKRTVAAPSVFIFPPSDEQLK SGTASVVCLLNNFYPREAKVQWKVDNALQSGNSQESVTEQDSK DSTYSLSSTLTLSKADYEKHKVYACEVTHQGLSSPVTKSFNRGEC | 337 |
| Camrelizumab, HR-301210, INCSHR-01210, SHR-1210 Heavy Chain (VH in Bold) | PD-1 | EVQLVESGGGLVQPGGSLRLSCAASGFTFSSYMMSWVRQAP GKGLEWVATISGGGANTYYPDSVKGRFTISRDNAKNSLYLQM NSLRAEDTAVYYCARQLYYFDYWGQGTTVTVSSASTKGPSVF PLAPCSRSTSESTAALGCLVKDYFPEPVTVSWNSGALTSGVHTFP AVLQSSGLYSLSSVVTVPSSSLGTKTYTCNVDHKPSNTKVDKRVE SKYGPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTLPP SQEEMTKNQVSLTCLVKGFYPSDIAVEWESNGQPENNYKTTPPV LDSDGSFFLYSRLTVDKSRWQEGNVFSCSVMHEALHNHYTQKSL SLSLGK | 338 |
| Camrelizumab, HR-301210, INCSHR-01210, SHR-1210 Light Chain (Light Chain in Bold) | PD-1 | DIQMTQSPSSLSASVGDRVTITCLASQTIGTWLTWYQQKPGK APKLLIYTATSLADGVPSRFSGSGSGTDFTLTISSLQPEDFATY YCQQVYSIPWTFGGGTKVEIKRTVAAPSVFIFPPSDEQLKSGTA SVVCLLNNFYPREAKVQWKVDNALQSGNSQESVTEQDSKDSTYS LSSTLTLSKADYEKHKVYACEVTHQGLSSPVTKSFNRGEC | 339 |
| Cemiplimab, Cemiplimab-rwlc, LIBTAYO ®, 6QVL057INT, H4H7798N, REGN-2810, SAR-439684 Heavy Chain (VH in Bold) | PD-1 | EVQLLESGGVLVQPGGSLRLSCAASGFTFSNFGMTWVRQAPG KGLEWVSGISGGGRDTYFADSVKGRFTISRDNSKNTLYLQMN SLKGEDTAVYYCVKWGNIYFDYWGQGTLVTVSSASTKGPSVF PLAPCSRSTSESTAALGCLVKDYFPEPVTVSWNSGALTSGVHTFP AVLQSSGLYSLSSVVTVPSSSLGTKTYTCNVDHKPSNTKVDKRVE SKYGPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTLPP SQEEMTKNQVSLTCLVKGFYPSDIAVEWESNGQPENNYKTTPPV LDSDGSFFLYSRLTVDKSRWQEGNVFSCSVMHEALHNHYTQKSL SLSLGK | 340 |
| Cemiplimab, Cemiplimab-rwlc, LIBTAYO ® 6QVL057INT, H4H7798N, REGN-2810, SAR-439684 Light Chain (VL in Bold) | PD-1 | DIQMTQSPSSLSASVGDSITITCRASLSINTFLNWYQQKPGKAP NLLIYAASSLHGGVPSRFSGSGSGTDFTLTIRTLQPEDFATYYC QQSSNTPFTFGPGTVVDFRRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC (Disulfide bridge) H22-H96, H131-L214, H144-H200, H223-H'223, H226-H'226, H258-H318, H364-H422, H'22-H'96, H'131-L'214, H'114-H'200, H'258-H'318, H'364-H'422, L23-L88, L134-L194, L'23-L'88, L'134-L'194) | 341 |
| Lambrolizumab, Pembrolizumab, 1 KEYTRUDA ®, MK-3475, SCH-900475, h409A11 Heavy Chain (VH in Bold) | PD-1 | QVQLVQSGVEVKKPGASVKVSCKASGYTFTNYYMYWVRQAP GQGLEWMGGINPSNGGTNFNEKFKNRVTLTTDSSTTTAYME LKSLQFDDTAVYYCARRDYRFDMGFDYWGQGTTVTVSSAST KGPSVFPLAPCSRSTSESTAALGCLVKDYFPEPVTVSWNSGALTS GVHTFPAVLQSSGLYSLSSVVTVPSSSLGTKTYTCNVDHKPSNTK VDKRVESKYGPPCPPCPAPEFLGGPSVFLFPPKPKDTLMISRTPEV TCVVVDVSQEDPEVQFNWYVDGVEVHNAKTKPREEQFNSTYRV VSVLTVLHQDWLNGKEYKCKVSNKGLPSSIEKTISKAKGQPREPQ VYTLPPSQEEMTKNQVSLTCLVKGFYPSDIAVEWESNGQPENNY KTTPPVLDSDGSFFLYSRLTVDKSRWQEGNVFSCSVMHEALHNH YTQKSLSLSLGK | 346 |
| Lambrolizumab, Pembrolizumab, KEYTRUDA ®, | PD-1 | EIVLTQSPATLSLSPGERATLSCRASKGVSTSGYSYLHWYQQK PGQAPRLLIYLASYLESGVPARFSGSGSGTDFTLTISSLEPEDF AVYYCQHSRDLPLTFGGGTKVEIKRTVAAPSVFIFPPSDEQLKS | 347 |

TABLE 1-continued

Exemplary Antibodies for Immune Cell Associated Antigens

| Antibody or Ag-binding fragment | Antigen Bound | Sequence | SEQ ID NO |
|---|---|---|---|
| MK-3475, SCH-900475, h409A11 Light Chain (VL in Bold) | | GTASVVCLLNNFYPREAKVQWKVDNALQSGNSQESVTEQDSKD STYSLSSTLTLSKADYEKHKVYACEVTHQGLSSPVTKSFNRGEC | |
| Lambrolizumab, Pembrolizumab, KEYTRUDA ®, MK-3475, SCH-900475, h409A11 VH | PD-1 | QVQLVQSGVEVKKPGASVKVSCKASGYTFTNYYMYWVRQAPG QGLEWMGGFPSNGGTNFNEKFKNRVTLTTDSSTTTAYMELKSLQ FDDTAVYYCARRDYRFDMGFDYWGQGTTVTVSS (Disulfide bridge) H22-H96, H134-L218, H147-H203, H226-H'226, H229-H'229, H261-H321, H367-H425, H'22-H'96, H'134-L'218, H'147-H'203, H'261-H'321, H'367-H'425, L23-L92, L138-L198, L'23-L'92, L'138-L'198) | 348 |
| Lambrolizumab, Pembrolizumab, KEYTRUDA ®, MK-3475, SCH-900475, h409A11 VL | PD-1 | EIVLTQSPATLSLSPGERATLSCRASKGVSTSGYSYLHWYQQKPG QAPRLLIYLASYLESGVPARFSGSGSGTDFTLTISSLEPEDFAVYYC QHSRDLPLTFGGGTKVEIK | 349 |
| Nivolumab, Nivolumab BMS, OPDIVO ®, BMS-936558, MDX-1106, ONO-4538 VH | PD-1 | QVQLVESGGGVVQPGRSLRLDCKASGITFSNSGMHWVRQAPGK GLEWVAVIWYDGSKRYYADSVKGRFTISRDNSKNTLFLQMNSLR AEDTAVYYCATNDDYWGQGTLVTVSS | 350 |
| Nivolumab, Nivolumab BMS, OPDIVO ®, BMS-936558, MDX-1106, ONO-4538 VL | PD-1 | EIVLTQSPATLSLSPGERATLSCRASQSVSSYLAWYQQKPGQAPR LLIYDASNRATGIPARFSGSGSGTDFTLTISSLEPEDFAVYYCQQSS NWPRTFGQGTKVEIK (Disulfide bridge) H22-H96, H127-L214, H140-H196, H219-H'219, H222-H'222, H254-H314, H360-H418, H'22-H'96, H'127-L'214, H'140-H'196, H254-H'314, H'360-H'418, L-23-L88, L134-L194, L'23-L'88, L'134-L'194) | 351 |
| Prolgolimab, Forteca, BCD-100 Heavy Chain (VH in Bold) | PD-1 | QVQLVQSGGGLVQPGGSLRLSCAASGFTFSSYWMYWVRQVP GKGLEWVSAIDTGGGRTYYADSVKGRFAISRVNAKNTMYLQ MNSLRAEDTAVYYCARDEGGGTGWGVLKDWPYGLDAWGQ GTLVTVSSASTKGPSVFPLAPSSKSTSGGTAALGCLVKDYFPEPV TVSWNSGALTSGVHTFPAVLQSSGLYSLSSVVTVPSSSLGTQTYIC NVNHKPSNTKVDKRVEPKSCDKTHTCPPCPAPEAAGGPSVFLFPP KPKDTLMISRTPEVTCVVVDVSHEDPEVKFNWYVDGVEVHNAK TKPREEQYNSTYRVVSVLTVLHQDWLNGKEYKCKVSNKALPAPI EKTISKAKGQPREPQVYTLPPSREEMTKNQVSLTCLVKGFYPSDI AVEWESNGQPENNYKTTPPVLDSDGSFFLYSKLTVDKSRWQQGN VFSCSVMHEALHNHYTQKSLSLSPGK | 352 |
| Prolgolimab, Forteca, BCD-100 Light Chain (VL in Bold) | PD-1 | QPVLTQPLSVSVALGQTARITCGGNNIGSKNVHWYQQKPGQ APVLVIYRDSNRPSGIPERFSGSNSGNTATLTISRAQAGDEADY YCQVWDSSTAVFGTGTKLTVLQRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC | 353 |
| Balstilimab, 1Q2QT5M7EO, AGEN-2034, AGEN-2034w Heavy Chain (VH in Bold) | PD-1 | QVQLVESGGGVVQPGRSLRLSCAASGFTFSSYGMHWVRQAP GKGLEWVAVIWYDGSNKYYADSVKGRFTISRDNSKNTLYLQ MNSLRAEDTAVYYCASNGDHWGQGTLVTVSSASTKGPSVFPL APCSRSTSESTAALGCLVKDYFPEPVTVSWNSGALTSGVHTFPAV LQSSGLYSLSSVVTVPSSSLGTKTYTCNVDHKPSNTKVDKRVESK YGPPCPPCPAPEFLGGPSVFLFPPKPKDTLMISRTPEVTCVVVDVS QEDPEVQFNWYVDGVEVHNAKTKPREEQFNSTYRVVSVLTVLH QDWLNGKEYKCKVSNKGLPSSIEKTISKAKGQPREPQVYTLPPSQ | 354 |

TABLE 1-continued

Exemplary Antibodies for Immune Cell Associated Antigens

| Antibody or Ag-binding fragment | Antigen Bound | Sequence | SEQ ID NO |
|---|---|---|---|
| | | EEMTKNQVSLTCLVKGFYPSDIAVEWESNGQPENNYKTTPPVLD SDGSFFLYSRLTVDKSRWQEGNVFSCSVMHEALHNHYTQKSLSL SLG | |
| Balstilimab, 1Q2QT5M7E0, AGEN-2034, AGEN-2034w Light Chain (VL in Bold) | PD-1 | EIVMTQSPATLSVSPGERATLSCRASQSVSSNLAWYQQKPGQ APRLLIYGASTRATGIPARFSGSGSGTEFTLTISSLQSEDFAVYY CQQYNNWPRTFGQGTKVEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC | 355 |
| Dostarlimab, ANB-011, GSK-4057190A, P0GVQ9A4S5, TSR-042, WBP-285 Heavy Chain (VH in Bold) | PD-1 | EVQLLESGGGLVQPGGSLRLSCAASGFTFSSYDMSWVRQAPG KGLEWVSTISGGGSYTYYQDSVKGRFTISRDNSKNTLYLQMN SLRAEDTAVYYCASPYYAMDYWGQGTTVTVSSASTKGPSVFP LAPCSRSTSESTAALGCLVKDYFPEPVTVSWNSGALTSGVHTFPA VLQSSGLYSLSSVVTVPSSSLGTKTYTCNVDHKPSNTKVDKRVES KYGPPCPPCPAPEFLGGPSVFLFPPKPKDTLMISRTPEVTCVVVDV SQEDPEVQFNWYVDGVEVHNAKTKPREEQFNSTYRVVSVLTVL HQDWLNGKEYKCKVSNKGLPSSIEKTISKAKGQPREPQVYTLPPS QEEMTKNQVSLTCLVKGFYPSDIAVEWESNGQPENNYKTTPPVL DSDGSFFLYSRLTVDKSRWQEGNVFSCSVMHEALHNHYTQKSLS LSLGK | 356 |
| Dostarlimab, ANB-011, GSK-4057190A, P0GVQ9A4S5, TSR-042, WBP-285 Light Chain (VL in Bold) | PD-1 | DIQLTQSPSFLSAYVGDRVTITCKASQDVGTAVAWYQQKPGK APKLLIYWASTLHTGVPSRFSGSGSGTEFTLTISSLQPEDFATY YCQHYSSYPWTFGQGTKLEIKRTVAAPSVFIFPPSDEQLKSGTA SVVCLLNNFYPREAKVQWKVDNALQSGNSQESVTEQDSKDSTYS LSSTLTLSKADYEKHKVYACEVTHQGLSSPVTKSFNRGEC | 357 |
| Serplulimab, HLX-10 Heavy Chain (VH in Bold) | PD-1 | QVQLVESGGGLVKPGGSLRLSCAASGFTFSNYGMSWIRQAPG KGLEWSTISGGGSNIYYADSVKGRFTISRDNAKNSLYLQMNSL RAEDTAVYYCVSYYYGIDFWGQGTSVTVSSASKYGPSVFPLAPC SRSTSESTAALGCLVKDYFPEPVTVSWNSGALTSGVHTFPAVLQS SGLYSLSSVVTVPSSSLGTKTYTCNVDHKPSNTKVDKRVESKYGP PCPPCPAPEFLGGPSVFLFPPKPKDTLMISRTPEVTCVVVDVSQED PEVQFNWYVDGVEVHNAKTKPREEQFNSTYRVVSVVLTVLHQD WLNGKEYKCKVSNKGLPSSIEKTISKAKGQPREPQVYTLPPSQEE MTKNQVSLTCLVKGFYPSDIAVEWESNGQPENNYKTTPPVLDSD GSFFLYSRLTVDKSRWQEGNVFSCSVMHEALHNHYTQKSLSLSL GK | 358 |
| Serplulimab, HLX-10 Light Chain (VL in Bold) | PD-1 | DIQMTQSPSSLSASVGDRVTITCKASQDVTTAVAWYQQKPGK APKLLIYWASTRHTGVPSRFSGSGSGTDFTLTISSLQPEDFATY YCQQHYTIPWTFGGGTKLEIKRTVAAPSVFIFPPSDEQLKSGTA SVVCLLNNFYPREAKVQWKVDNALQSGNSQESVTEQDSKDSTYS LSSTLTLSKADYEKHKVYACEVTHQGLSSPVTKSFNRGEC | 359 |
| Retifanlimab, 2Y3T5IF01Z, INCMGA-00012, INCMGA-0012, MGA-012 Heavy Chain (VH in Bold) | PD-1 | QVQLVQSGAEVKKPGASVKVSCKASGYSFTSYWMNWVRQAP GQGLEWIGVIHPSDSETWLDQKFKDRVTITVDKSTSTAYMEL SSLRSEDTAVYYCAREHYGTSPFAYWGQGTLVTVSSASTKGPS VFPLAPCSRSTSESTAALGCLVKDYFPEPVTVSWNSGALTSGVHT FPAVLQSSGLYSLSSVVTVPSSSLGTKTYTCNVDHKPSNTKVDKR VESKYGPPCPPCPAPEFLGGPSVFLFPPKPKDTLMISRTPEVTCVV VDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTTP PVLDSDGSFFLYSRLTVDKSRWQEGNVFSCSVMHEALHNHYTQK SLSLSLG | 360 |

TABLE 1-continued

Exemplary Antibodies for Immune Cell Associated Antigens

| Antibody or Ag-binding fragment | Antigen Bound | Sequence | SEQ ID NO |
|---|---|---|---|
| Retifanlimab, 2Y3T5IF01Z, INCMGA-00012, INCMGA-0012, MGA-012 Light Chain (VL in Bold) | PD-1 | EIVLTQSPATLSLSPGERATLSCRASESVDNYGMSFMNWFQQ KPGQPPKLLIHAASNQGSGVPSRFSGSGSGTDFTLTISSLEPED FAVYFCQQSKEVPYTFGGGTKVEIKRTVAAPSVFIFPPSDEQLK SGTASVVCLLNNFYPREAKVQWKVDNALQSGNSQESVTEQDSK DSTYSLSSTLTLSKADYEKHKVYACEVTHQGLSSPVTKSFNRGEC | 361 |
| Sasanlimab, LZZ0IC2EWP, PF-06801591, RN-888 Heavy Chain (VH in Bold) | PD-1 | QVQLVQSGAEVKKPGASVKVSCKASGYTFTSYWINWVRQAP GQGLEWMGNIYPGSSLTNYNEKFKNRVTMTRDTSTSTVYME LSSLRSEDTAVYYCARLSTGTFAYWGQGTLVTVSSASTKGPSV FPLAPCSRSTSESTAALGCLVKDYFPEPVTVSWNSGALTSGVHTF PAVLQSSGLYSLSSVVTVPSSSLGTKTYTCNVDHKPSNTKVDKRV ESKYGPPCPPCPAPEFLGGPSVFLFPPKPKDTLMISRTPEVTCVVV DVSQEDPEVQFNWYVDGVEVHNAKTKPREEQFNSTYRVVSVLT VLHQDWLNGKEYKCKVSNKGLPSSIEKTISKAKGQPREPQVYTLP PSQEEMTKNQVSLTCLVKGFYPSDIAVEWESNGQPENNYKTTPP VLDSDGSFFLYSRLTVDKSRWQEGNVFSCSVMHEALHNHYTQKS LSLSLGK | 362 |
| Sasanlimab, LZZ0IC2EWP, PF-06801591, RN-888 Light Chain (VL in Bold) | PD-1 | DIVMTQSPDSLAVSLGERATINCKSSQSLWDSGNQKNFLTWY QQKPGQPPKLLIYWTSYRESGVPDRFSGSGSGTDFTLTISSLQ AEDVAVYYCQNDYFYPHTFGGGTKVEIKRTVAAPSVFIFPPSDE QLKSGTASVVCLLNNFYPREAKVQWKVDNALQSGNSQESVTEQ DSKDSTYSLSSTLTLSKADYEKHKVYACEVTHQGLSSPVTKSFNR GEC | 363 |
| Spartalizumab, NVP-LZV-184, PDR-001, QOG25L6Z8Z Heavy Chain (VH in Bold) | PD-1 | EVQLVQSGAEVKKPGESLRISCKGSGYTFTTYWMHWVRQAT GQGLEWMGNIYPGTGGSNFDEKFKNRVTITADKSTSTAYME LSSLRSEDTAVYYCTRWTTGTGAYWGQGTTVTVSSASTKGPS VFPLAPCSRSTSESTAALGCLVKDYFPEPVTVSWNSGALTSGVHT FPAVLQSSGLYSLSSVVTVPSSSLGTKTYTCNVDHKPSNTKVDKR VESKYGPPCPPCPAPEFLGGPSVFLFPPKPKDTLMISRTPEVTCVV VDVSQEDPEVQFNWYVDGVEVHNAKTKPREEQFNSTYRVVSVL TVLHQDWLNGKEYKCKVSNKGLPSSIEKTISKAKGQPREPQVYT LPPSQEEMTKNQVSLTCLVKGFYPSDIAVEWESNGQPENNYKTTP PVLDSDGSFFLYSRLTVDKSRWQEGNVFSCSVMHEALHNHYTQK SLSLSLG | 364 |
| Spartalizumab, NVP-LZV-184, PDR-001, QOG25L6Z8Z Light Chain (VL in Bold) | PD-1 | EIVLTQSPATLSLSPGERATLSCKSSQSLLDSGNQKNFLTWYQ QKPGQAPRLLIYWASTRESGVPSRFSGSGSGTDFTFTISSLEAE DAATYYCQNDYSYPYTFGQGTKVEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNRGE C | 365 |
| Cetrelimab, JNJ-3283, JNJ-63723283, LYK98WP91F Heavy Chain (VH in Bold) | PD-1 | QVQLVQSGAEVKKPGSSVKVSCKASGGTFSSYAISWVRQAPG QGLEWMGGIIPIFDTANYAQKFQGRVTITADESTSTAYMELSS LRSEDTAVYYCARPGLAAAYDTGSLDYWGQGTLVTVSSASTK GPSVFPLAPCSRSTSESTAALGCLVKDYFPEPVTVSWNSGALTSG VHTFPAVLQSSGLYSLSSVVTVPSSSLGTKTYTCNVDHKPSNTKV DKRVESKYGPPCPPCPAPEFLGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSRLTVDKSRWQEGNVFSCSVMHEALHNHY TQKSLSLSLGK | 366 |
| Cetrelimab, JNJ-3283, JNJ-63723283, LYK98WP91F Light Chain (VL in Bold) | PD-1 | EIVLTQSPATLSLSPGERATLSCRASQSVRSYLAWYQQKPGQA PRLLIYDASNRATGIPARFSGSGSGTDFTLTISSLEPEDFAVYYC QQRNYWPLTFGQGTKVEIKRTVAAPSVFIFPPSDEQLKSGTASV VCLLNNFYPREAKVQWKVDNALQSGNSQESVTEQDSKDSTYSLS STLTLSKADYEKHKVYACEVTHQGLSSPVTKSFNRGEC | 367 |

TABLE 1-continued

Exemplary Antibodies for Immune Cell Associated Antigens

| Antibody or Ag-binding fragment | Antigen Bound | Sequence | SEQ ID NO |
|---|---|---|---|
| Tebotelimab, MGD-013 Heavy Chain (VL in Bold) | PD-1 | DIQMTQSPSSLSASVGDRVTITCRASQDVSSVVAWYQQKPGK APKLLIYSASYRYTGVPSRFSGSGSGTDFTLTISSLQPEDFATY YCQQHYSTPWTFGGGTKLEIKGGGSGGGGQVQLVQSGAEVKK PGASVKVSCKASGYSFTSYWMNWVRQAPGQGLEWIGVIHPSDSE TWLDQKFKDRVTITVDKSTSTAYMELSSLRSEDTAVYYCAREHY GTSPFAYWGQGTLVTVSSGGCGGGEVAACEKEVAALEKEVAAL EKEVAALEKESKYGPPCPPCPAPEFLGGPSVFLFPPKPKDTLYITR EPEVTCVVVDVSQEDPEVQFNWYVDGVEVHNAKTKPREEQFNS TYRVVSVLTVLHQDWLNGKEYKCKVSNKGLPSSIEKTISKAKGQ PREPQVYTLPPSQEEMTKNQVSLTCLVKGFYPSDIAVEWESNGQP ENNYKTTPPVLDSDGSFFLYSRLTVDKSRWQEGNVFSCSVMHEA LHNHYTQKSLSLSLG | 368 |
| Tebotelimab, MGD-013 Light Chain (VL in Bold) | PD-1 | EIVLTQSPATLSLSPGERATLSCRASESVDNYGMSFMNWFQQ KPGQPPKLLIHAASNQGSGVPSRFSGSGSGTDFTLTISSLEPED FAVYFCQQSKEVPYTFGGGTKVEIKGGGSGGGGQVQLVQSGA EVKKPGASVKVSCKASGYTFTDYNMDWVRQAPGQGLEWMGDI NPDNGVTIYNQKFEGRVTMTTDTSTSTAYMELRSLRSDDTAVYY CAREADYFYFDYWGQGTTLTVSSGGCGGGKVAACKEKVAALKE KVAALKEKVAALKE | 369 |
| Pidilizumab, CT-011, MDV-9300 Heavy Chain (VH in Bold) | PD-1 | QVQLVQSGSELKKPGASVKISCKASGYTFTNYGMNWVRQAP GQGLQWMGWINTDSGESTYAEEFKGRFVFSLDTSVNTAYLQI TSLTAEDTGMYFCVRVGYDALDYWGQGTLVTVSSASTKGPSV FPLAPSSKSTSGGTAALGCLVKDYFPEPVTVSWNSGVHTF PAVLQSSGLYSLSSVVTVPSSSLGTQTYICNVNHKPSNTKVDKRV EPKSCDKTHTCPPCPAPELLGGPSVFLFPPKPKDTLMISRTPEVTC VVVDVSHEDPEVKFNWYVDGVEVHNAKTKPREEQYNSTYRVVS VLTVLHQDWLNGKEYKCKVSNKALPAPIEKTISKAKGQPREPQV YTLPPSREEMTKNQVSLTCLVKGFYPSDIAVEWESNGQPENNYK TTPPVLDSDGSFFLYSKLTVDKSRWQQGNVFSCSVMHEALHNHY TQKSLSLSPGK | 370 |
| Pidilizumab, CT-011, MDV-9300 Light Chain (VL in Bold) | PD-1 | EIVLTQSPSSLSASVGDRVTITCSARSSVSYMHWFQQKPGKAP KLWIYRTSNLASGVPSRFSGSGSGTSYCLTINSLQPEDFATYYC QQRSSFPLTFGGGTKLEIKRTVAAPSVFIFPPSDEQLKSGTASVV CLLNNFYPREAKVQWKVDNALQSGNSQESVTEQDSKDSTYSLSS TLTLSKADYEKHKVYACEVTHQGLSSPVTKSFNRGEC | 371 |
| SG-001 VH | PD-1 | QVQLVESGGGVVQPGRSLRLTCKASGLTFSSSGMHWVRQAPGK GLEWVAVIWYDGSKRYYADSVKGRFTISRDNSKNTLFLQMNSLR AEDTAVYYCATNNDYWGQGTLVTVSS | 372 |
| SG-001 VL | PD-1 | EIVLTQSPATLSLSPGERATLSCRASQSVSSYLAWYQQKPGQAPR LLIYTASNRATGIPARFSGSGSGTDFTLTISSLEPEDFAVYYCQQYS NWPRTFGQGTKVEIK | 373 |
| mpLZM-009 VH (Murine Precursor of LZM-009) | PD-1 | EVQLQQSGPVLVKPGASVKMSCKASGYTFTSYYMYWVKQSHGK SLEWIGGVNPSNGGTNFNEKFKSKATLTVDKSSSTAYMELNSLTS EDSAVYYCARRDYRYDMGFDYWGQGTTLTVSS | 374 |
| mpLZM-009 VL (Murine Precursor of LZM-009) | PD-1 | QIVLTQSPAIMSASPGEKVTMTCRASKGVSTSGYSYLHWYQQKP GSSPRLLIYLASYLESGVPVRFSGSGSGTSYSLTISRMEAEDAATY YCQHSRELPLTFGTGTRLEIK | 375 |
| LZM-009 VH | PD-1 | QVQLVQSGAEVKKPGASVKVSCKASGYTFTSYYMYWVRQAPG QGLEWMGGVNPSNGGTNFNEKFKSRVTITADKSTSTAYMELSSL RSEDTAVYYCARRDYRYDMGFDYWGQGTTVTVSS | 376 |
| LZM-009 VL | PD-1 | EIVLTQSPATLSLSPGERATISCRASKGVSTSGYSYLHWYQQKPG QAPRLLIYLASYLESGVPARFSGSGSGTDFTLTISSLEPEDFATYYC QHSRELPLTFGTGTKVEIK | 377 |
| Budigalimab, 6VD04TY3OO, ABBV-181, PR- | PD-1 | EIQLVQSGAEVKKPGSSVKVSCKASGYTFTHYGMNWVRQAP GQGLEWVGWVNTYTGEPTYADDFKGRLTFTLDTSTSTAYME LSSLRSEDTAVYYCTREGEGLGFGDWGQGTTVTVSSASTKGP SVFPLAPSSKSTSGGTAALGCLVKDYFPEPVTVSWNSGALTSGVH | 378 |

TABLE 1-continued

Exemplary Antibodies for Immune Cell Associated Antigens

| Antibody or Ag-binding fragment | Antigen Bound | Sequence | SEQ ID NO |
|---|---|---|---|
| 1648817 Heavy Chain (VH in Bold) | | TFPAVLQSSGLYSLSSVVTVPSSSLGTQTYICNVNHKPSNTKVDK KVEPKSCDKTHTCPPCPAPEAAGGPSVFLFPPKPKDTLMISRTPEV TCVVVDVSHEDPEVKFNWYVDGVEVHNAKTKPREEQYNSTYRV VSVLTVLHQDWLNGKEYKCKVSNKALPAPIEKTISKAKGQPREP QVYTLPPSREEMTKNQVSLTCLVKGFYPSDIAVEWESNGQPENN YKTTPPVLDSDGSFFLYSKLTVDKSRWQQGNVFSCSVMHEALHN HYTQKSLSLSPGK | |
| Budigalimab, 6VD04TY3OO, ABBV-181, PR-1648817 Light Chain (VL in Bold) | PD-1 | DVVMTQSPLSLPVTPGEPASISCRSSQSIVHSHGDTYLEWYLQ KPGQSPQLLIYKVSNRFSGVPDRFSGSGSGTDFTLKISRVEAED VGVYYCFQGSHIPVTFGQGTKLEIKRTVAAPSVFIFPPSDEQLKS GTASVVCLLNNFYPREAKVQWKVDNALQSGNSQESVTEQDSKD STYSLSSTLTLSKADYEKHKVYACEVTHQGLSSPVTKSFNRGEC | 379 |
| Lambrolizumab, Pembrolizumab, KEYTRUDA ®, MK-3475, SCH-900475, h409A11 VH CDR1 | PD-1 | NYYMY | 380 |
| Lambrolizumab, Pembrolizumab, KEYTRUDA ®, MK-3475, SCH-900475, h409A11 VH CDR2 | PD-1 | GINPSNGGTNFNEKFKN | 381 |
| Lambrolizumab, Pembrolizumab, KEYTRUDA ®, MK-3475, SCH-900475, h409A11 VH CDR3 | PD-1 | RDYRFDMGFDY | 382 |
| Lambrolizumab, Pembrolizumab, KEYTRUDA ®, MK-3475, SCH-900475, h409A11 VL CDR1 | PD-1 | RASKGVSTSGYSYLH | 383 |
| Lambrolizumab, Pembrolizumab, KEYTRUDA ®, MK-3475, SCH-900475, h409A11 VL CDR2 | PD-1 | LASYLES | 384 |
| Lambrolizumab, Pembrolizumab, KEYTRUDA ®, MK-3475, SCH-900475, h409A11 VL CDR3 | PD-1 | QHSRDLPLT | 385 |

TABLE 1-continued

Exemplary Antibodies for Immune Cell Associated Antigens

| Antibody or Ag-binding fragment | Antigen Bound | Sequence | SEQ ID NO |
|---|---|---|---|
| Nivolumab, Nivolumab BMS, OPDIVO ®, BMS-936558, MDX-1106, ONO-4538 VH CDR1 | PD-1 | NSGMH | 386 |
| Nivolumab, Nivolumab BMS, OPDIVO ®, BMS-936558, MDX-1106, ONO-4538 VH CDR2 | PD-1 | VIWYDGSKRYYADSVKG | 387 |
| Nivolumab, Nivolumab BMS, OPDIVO ®, BMS-936558, MDX-1106, ONO-4538 VH CDR3 | PD-1 | NDDY | 388 |
| Nivolumab, Nivolumab BMS, OPDIVO ®, BMS-936558, MDX-1106, ONO-4538 VL CDR1 | PD-1 | RASQSVSSYLA | 389 |
| Nivolumab, Nivolumab BMS, OPDIVO ®, BMS 936558, MDX-1106, ONO-4538 VL CDR2 | PD-1 | DASNRAT | 390 |
| Nivolumab, Nivolumab BMS, OPDIVO ®, BMS-936558, MDX-1106, ONO-4538 VL CDR3 | PD-1 | QQSSNWPRT | 391 |
| Serplulimab, HLX-10 VH CDR1 | PD-1 | FTFSNYGMS | 392 |
| Serplulimab, HLX-10 VH CDR2 | PD-1 | TISGGGSNIY | 393 |
| Serplulimab, HLX-10 VH CDR3 | PD-1 | VSYYYGIDF | 394 |

TABLE 1-continued

Exemplary Antibodies for Immune Cell Associated Antigens

| Antibody or Ag-binding fragment | Antigen Bound | Sequence | SEQ ID NO |
|---|---|---|---|
| Serplulimab, HLX-10 VL CDR1 | PD-1 | KASQDVTTAVA | 395 |
| Serplulimab, HLX-10 VL CDR2 | PD-1 | WASTRHT | 396 |
| Serplulimab, HLX-10 VL CDR3 | PD-1 | QQHYTIPWT | 397 |
| SG-001 VH CDR1 | PD-1 | GLTFSSSG | 398 |
| SG-001 VH CDR2 | PD-1 | IWYDGSKR | 399 |
| SG-001 VH CDR3 | PD-1 | ATNNDY | 400 |
| SG-001 VL CDR1 | PD-1 | RASQSVSSYLA | 401 |
| SG-001 VL CDR2 | PD-1 | TASNRAT | 402 |
| SG-001 VL CDR3 | PD-1 | QQYSNWPRT | 403 |
| PD-1-Fc-OX40L (Code), SL-279252 (Code), TAK-252 (Code) | PD-1 | MQIPQAPWPWWAVLQLGWRPGWFLDSPDRPWNPPTFSPALLVV TEGDNATFTCSFSNTSESFVLNWYRMSPSNQTDKLAAFPEDRSQP GQDCRFRVTQLPNGRDFHMSVVRARRNDSGTYLCGAISLAPKAQ IKESLRAELRVTERRAEVPTAHPSPSPRPAGQFQSKYGPPCPSCPA PEFLGGPSVFLFPPKPKDTLMISRTPEVTCVVVDVSQEDPEVQFNW YVDGVEVHNAKTKPREEQFNSTYRVVSVLTVLHQDWLSGKEYK CKVSSKGLPSSIEKTISNATGQPREPQVYTLPPSQEEMTKNQVSLT CLVKGFYPSDIAVEWESNGQPENNYKTTPPVLDSDGSFFLYSRLT VDKSSWQEGNVFSCSVMHEALHNHYTQKSLSLSLGKIEGRMDQ VSHRYPRIQSIKVQFTEYKKEKGFILTSQKEDEIMKVQNNSVIINC DGFYLISLKGYFSQEVNISLHYQKDEEPLFQLKKVRSVNSLMVAS LTYKDKVYLNVTTDNTSLDDFHVNGGELILIHQNPGEFCVLMQIP QAPWPWWAVLQLGWRPGWFLDSPDRPWNPPTFSPALLVVTEGD NATFTCSFSNTSESFVLNWYRMSPSNQTDKLAAFPEDRSQPGQDC RFRVTQLPNGRDFHMSVVRARRNDSGTYLCGAISLAPKAQIKESL RAELRVTERRAEVPTAHPSPSPRPAGQFQQVSHRYPRIQSIKVQFT EYKKEKGFILTSQKEDEIMKVQNNSVIINCDGFYLISLKGYFSQEV NISLHYQKDEEPLFQLKKVRSVNSLMVASLTYKDKVYLNVTTDN TSLDDFHVNGGELILIHQNPGEFCVL | 404 |
| Avelumab (Generic) Bavencio (Brand) 451238 KXG2PJ551I MSB-0010682 MSB-0010718C PF-06834635 Heavy Chain (VH in Bold) | PD-L1 | EVQLLESGGGLVQPGGSLRLSCAASGFTFSSYIMMWVRQAPG KGLEWVSSIYPSGGITFYADTVKGRFTISRDNSKNTLYLQMNS LRAEDTAVYYCARIKLGTVTTVDYWGQGTLVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKK VEPKSCDKTHTCPPCPAPELLGGPSVFLFPPKPKDTLMISRTPEVT CVVVDVSHEDPEVKFNWYVDGVEVHNAKTKPREEQYNSTYRVV SVLTVLHQDWLNGKEYKCKVSNKALPAPIEKTISKAKGQPREPQ VYTLPPSRDELTKNQVSLTCLVKGFYPSDIAVEWESNGQPENNYK TTPPVLDSDGSFFLYSKLTVDKSRWQQGNVFSCSVMHEALHNHY TQKSLSLSPGK | 232 |

TABLE 1-continued

Exemplary Antibodies for Immune Cell Associated Antigens

| Antibody or Ag-binding fragment | Antigen Bound | Sequence | SEQ ID NO |
|---|---|---|---|
| Avelumab (Generic) Bavencio (Brand) 451238 KXG2PJ551I MSB-0010682 MSB-0010718C PF-06834635 Light Chain (VL in Bold) | PD-L1 | QSALTQPASVSGSPGQSITISCTGTSSDVGGYNYVSWYQQHPG KAPKLMIYDVSNRPSGVSNRFSGSKSGNTASLTISGLQAEDEA DYYCSSYTSSSTRVFGTGTKVTVLGQPKANPTVTLFPPSSEELQA NKATLVCLISDFYPGAVTVAWKADGSPVKAGVETTKPSKQSNNK YAASSYLSLTPEQWKSHRSYSCQVTHEGSTVEKTVAPTECS | 233 |
| Durvalumab (Generic) Imfinzi (Brand) 28X28X90KV (UNII code) MEDI-4736 Heavy Chain (VH in Bold) | PD-L1 | EVQLVESGGGLVQPGGSLRLSCAASGFTFSRYWMSWVRQAP GKGLEWVANIKQDGSEKYYVDSVKGRFTISRDNAKNSLYLQ MNSLRAEDTAVYYCAREGGWFGELAFDYWGQGTLVTVSSAS TKGPSVFPLAPSSKSTSGGTAALGCLVKDYFPEPVTVSWNSGALT SGVHTFPAVLQSSGLYSLSSVVTVPSSSLGTQTYICNVNHKPSNTK VDKRVEPKSCDKTHTCPPCPAPEFEGGPSVFLFPPKPKDTLMISRT PEVTCVVVDVSHEDPEVKFNWYVDGVEVHNAKTKPREEQYNST YRVVSVLTVLHQDWLNGKEYKCKVSNKALPASIEKTISKAKGQP REPQVYTLPPSREEMTKNQVSLTCLVKGFYPSDIAVEWESNGQPE NNYKTTPPVLDSDGSFFLYSKLTVDKSRWQQGNVFSCSVMHEAL HNHYTQKSLSLSPGK | 234 |
| Durvalumab (Generic) Imfinzi (Brand) 28X28X90KV (UNII code) MEDI-4736 Light Chain (VL in Bold) | PD-L1 | EIVLTQSPGTLSLSPGERATLSCRASQRVSSSYLAWYQQKPGQ APRLLIYDASSRATGIPDRFSGSGSGTDFTLTISRLEPEDFAVYY CQQYGSLPWTFGQGTKVEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC | 235 |
| Atezolizumab (Generic) Tecentriq (Brand) 52CMI0WC3Y MPDL-3280A RG-7446 RO-5541267 Heavy Chain (VH in Bold) | PD-L1 | EVQLVESGGGLVQPGGSLRLSCAASGFTFSDSWIHWVRQAPG KGLEWVAWISPYGGSTYYADSVKGRFTISADTSKNTAYLQM SLRAEDTAVYYCARRHWPGGFDYWGQGTLVTVSSASTKGPS VFPLAPSSKSTSGGTAALGCLVKDYFPEPVTVSWNSGALTSGVHT FPAVLQSSGLYSLSSVVTVPSSSLGTQTYICNVNHKPSNTKVDKK VEPKSCDKTHTCPPCPAPELLGGPSVFLFPPKPKDTLMISRTPEVT CVVVDVSHEDPEVKFNWYVDGVEVHNAKTKPREEQYASTYRVV SVLTVLHQDWLNGKEYKCKVSNKALPAPIEKTISKAKGQPREPQ VYTLPPSREEMTKNQVSLTCLVKGFYPSDIAVEWESNGQPENNY KTTPPVLDSDGSFFLYSKLTVDKSRWQQGNVFSCSVMHEALHNH YTQKSLSLSPGK | 236 |
| Atezolizumab (Generic) Tecentriq (Brand) 52CMI0WC3Y MPDL-3280A RG-7446 RO-5541267 Light Chain (VL in Bold) | PD-L1 | DIQMTQSPSSLSASVGDRVTITCRASQDVSTAVAWYQQKPGK APKLLIYSASFLYSGVPSRFSGSGSGTDFTLTISSLQPEDFATYY CQQYLYHPATFGQGTKVEIKRTVAAPSVFIFPPSDEQLKSGTAS VVCLLNNFYPREAKVQWKVDNALQSGNSQESVTEQDSKDSTYS LSSTLTLSKADYEKHKVYACEVTHQGLSSPVTKSFNRGEC | 237 |
| Sugemalimab (Generic) CS-1001 WBP-3155 | PD-L1 | EVQLLESGGGLVQPGGSLRLSCAASGFTFSSYAMSWVRQAPG KGLEWVSGISGSGGFTYYADSVKGRFTISRDNSKNTLYLQMN SLRAEDTAVYYCAKPPRGYNYGPFDYWGQGTLVTVSSASTKG PSVFPLAPCSRSTSESTAALGCLVKDYFPEPVTVSWNSGALTSGV | 238 |

TABLE 1-continued

Exemplary Antibodies for Immune Cell Associated Antigens

| Antibody or Ag-binding fragment | Antigen Bound | Sequence | SEQ ID NO |
|---|---|---|---|
| Heavy Chain (VH in Bold) | | HTFPAVLQSSGLYSLSSVVTVPSSSLGTKTYTCNVDHKPSNTKVD KRVESKYGPPCPPCPAPEFLGGPSVFLFPPKPKDTLMISRTPEVTC VVVDVSQEDPEVQFNWYVDGVEVHNAKTKPREEQFNSTYRVVS VLTVLHQDWLNGKEYKCKVSNKGLPSSIEKTISKAKGQPREPQV YTLPPSQEEMTKNQVSLTCLVKGFYPSDIAVEWESNGQPENNYK TTPPVLDSDGSFFLYSRLTVDKSRWQEGNVFSCSVMHEALHNHY TQKSLSLSLGK | |
| Sugemalimab (Generic) CS-1001 WBP-3155 Light Chain (VL in Bold) | PD-L1 | SYVLTQPPSVSVAPGQTARITCGGNNIGSKSVHWYQQKPGQA PVLVVYDDSDRPSGIPERFSGSNSGNTATLTISRVEAGDEADYY CQVWDSSSDHVVFGGGTKLTVLGQPKAAPSVTLFPPSSEELQA NKATLVCLISDFYPGAVTVAWKADSSPVKAGVETTTPSKQSNNK YAASSYLSLTPEQWKSHRSYSCQVTHEGSTVEKTVAPTECS | 239 |
| JS-003 JS003-30 JS003-SD VH | PD-L1 | QGQLQESGPSLVKPSQTLSLTCTVSGDSITRGYWNWIRKHPGKGL EYIGYISYTGSTYSNLSLKSRVTISRDTSKNQYYLKLSSVTAADTA VYYCATSTGWLDPVDYWGQGTLVTVSS | 242 |
| JS-003 JS003-30 JS003-SD VL | PD-L1 | DIVMTQSPDSLAVSLGERATINCKASQNVDTSVAWFQQKPGQPP KALIYSASFRYSGVPDRFSGSGSGTDFTLTISSLQAEDVAVYFCQQ YYGYPFTFGQGTKLEIK | 243 |
| HLX-20 PL2#3 VH | PD-L1 | EVQLVQSGGGLVKPGGSLRLSCAASGFTFSSYTMNWVRQAPGK GLEWVSSISSGSDYLYYADSVKGRFTISRDNAKNSLYLQMNSLRA EDTAVYYCARNELRWYPQAGAFDRWGQGTMVTVSS | 244 |
| HLX-20 PL2#3 VL | PD-L1 | QSVVTQPPSMSAAPGQRVTISCSGSSSYIESSYVGWYQQLPGTAP RLLIYDDDMRPSGIPDRFSGSKSGTSATLAITGLQTGDEADYYCEI WRSGLGGVFGGGTKLTVL | 245 |
| Lodapolimab (Generic) LY-3300054 NR4MAD6 PPB Heavy Chain (VH in Bold) | PD-L1 | QVQLVQSGAEVKKPGSSVKVSCKASGGTFSSYAISWVRQAPG QGLEWMGGIIPIFGTANYAQKFQGRVTITADKSTSTAYMELSS LRSEDTAVYYCARSPDYSPYYYYGMDWGQGTTVTVSSASTK GPSVFPLAPSSKSTSGGTAALGCLVKDYFPEPVTVSWNSGALTSG VHTFPAVLQSSGLYSLSSVVTVPSSSLGTQTYICNVNHKPSNTKV DKRVEPKSCDKTHTCPPCPAPEAEGAPSVFLFPPKPKDTLMISRTP EVTCVVVDVSHEDPEVKFNWYVDGVEVHNAKTKPREEQYNSTY RVVSVLTVLHQDWLNGKEYKCKVSNKALPSSIEKTISKAKGQPR EPQVYTLPPSREEMTKNQVSLTCLVKGFYPSDIAVEWESNGQPEN NYKTTPPVLDSDGSFFLYSKLTVDKSRWQQGNVFSCSVMHEALH NHYTQKSLSLSPGK | 248 |
| Lodapolimab (Generic) LY-3300054 NR4MAD6 PPB Light Chain (VL in Bold) | PD-L1 | QSVLTQPPSASGTPGQRVTISCSGSSSNIGSNTVNWYQQLPGT APKLLIYGNSNRPSGVPDRFSGSKSGTSASLAISGLQSEDEADY YCQSYDSSLSGSVFGGGIKLTVLGQPKAAPSVTLFPPSSEELQAN KATLVCLISDFYPGAVTVAWKADSSPVKAGVETTTPSKQSNNKY AASSYLSLTPEQWKSHRSYSCQVTHEGSTVEKTVAPAECS | 249 |
| HLX-20 PL2#3 VH CDR1 | PD-L1 | SYTMN | 250 |
| HLX-20 PL2#3 VH CDR2 | PD-L1 | SISSGSDYLYYADSVKG | 251 |
| HLX-20 PL2#3 VH CDR3 | PD-L1 | NELRWYPQAGAFDR | 252 |
| HLX-20 PL2#3 VL CDR1 | PD-L1 | SGSSSYIESSYVG | 253 |
| HLX-20 PL2#3 VL CDR2 | PD-L1 | DDDMRPS | 254 |

TABLE 1-continued

Exemplary Antibodies for Immune Cell Associated Antigens

| Antibody or Ag-binding fragment | Antigen Bound | Sequence | SEQ ID NO |
|---|---|---|---|
| HLX-20 PL2#3 VL CDR3 | PD-L1 | EIWRSGLGGV | 255 |
| Envafolimab (Generic) 3D-025 ASC-22 KN-035 hu56V1-Fc-m1 single-domain antibody (VH in Bold) | PD-L1 | QVQLVESGGGLVQPGGSLRLSCAASGKMSSRRCMAWFRQAP GKERERVAKLLTTSGSTYLADSVKGRFTISRDNSKNTVYLQM NSLRAEDTAVYYCAADSFEDPTCTLVTSSGAFQYWGQGTLVT VSSEPKSSDKTHTCPPCPAPELLGGPSVFLFPPKPKDTLMISRTPEV TCVVVAVSHEDPEVKFNWYVDGVEVHNAKTKPREEQYNSTYRV VSVLTVLHQDWLNGKEYKCKVSNKALPAGIEKTISKAKGQPREP QVYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGK | 256 |
| ND-021 NM21-1480 PRO-1480 Tri-specific fusion single-chain antibody construct | PD-L1 | DIQMTQSPASLSASVGDRVTITCQASQSIGTYLAWYQQKPGKPPK LLIYRAFILASGVPSRFSGSGSGTDFTLTISSLQPEDFATYYCQSNF YSDSTTIGPNAFGTGTKVTVLGGGGGSEVQLVESGGGLVQPGGS LRLSCAASGFSFSANYYPCWVRQAPGKGLEWIGCIYGGSSDITYD ANWTKGRFTISRDNSKNTVYLQMNSLRAEDTAVYYCARSAWYS GWGGDLWGQGTLVTVSSGGGGSGGGGSGGGGSGGGGSIQMTQ SPSSLSASVGDRVTITCQASQSISNRLAWYQQKPGKAPKLLIYSAS TLASGVPSRFSGSGSGTDFTLTISSLQPEDFATYYCQSTYYGNDGN AFGTGTKVTVLGGGGGSEVQLVESGGGLVQPGGSLRLSCAASGF SFNSDYWIYWVRQAPGKGLEWIASIYGGSSGNTQYASWAQGRFT ISRDNSKNTVYLQMNSLRAEDTAVYFCARGYVDYGGATDLWGQ GTLVTVSSGGGGSGGGGSIQMTQSPSSLSASVGDRVTITCQSSESV YSNNQLSWYQQKPGQPPKLLIYDASDLASGVPSRFSGSGSGTDFT LTISSLQPEDFATYYCAGGFSSSSDTAFGGGTKLTVLGGGGGSGG GGSGGGGSGGGGSEVQLVESGGGLVQPGGSLRLSCAASGFSLSS NAMGWVRQAPGKGLEYIGIISVGGFTYYASWAKGRFTISRDNSK NTVYLQMNSLRAEDTATYFCARDRHGGDSSGAFYLWGQGTLVT VSS | 257 |
| ACE-05 YBL-013 Bispecific tetrameric antibody-like cell engager (ALICE) comprising two identical light chains (LC) consisting of antigen binding domains (ABDs) targeting programmed cell death-ligand 1 (PD-L1), and two different heavy chain (HC)-like chains (ACE-05-VH and ACE-05-VL) each consisting of an anti-PD-L1 ABD and an anti-CD3 ABD; wherein | PD-L1 | QMQLVQSGAEVKKPGSSVKVSCKASGGTFSSYAISWVRQAPGQG LEWMGRIIPILGIANYAQKFQGRVTITADKSTSTAYMELSSLRSED TAVYYCAKPRDGYNLVAFDIWGQGTMVTVSSASTKGPSVFPLAP SSKSTSGGTAALGCLVKDYFPEPVTVSWNSGALTSGVHTFPAVL QSSGLYSLSSVVTVPSSSLGTQTYICNVNHKPSNTKVDKKVEPKS CDKTHTCPPCPAPELLGGPGGGSEVQLQQSGPELVKPGPSMKIS CKASGYSFTGYTMNWVKQSHGKNLEWMGLINPYKGVSTYNQK FKDKATLTVDKSSSTAYMELLSLTSEDSAVYYCARSGYYGDSDW YFDVWGQGTTLTVFSQMQLVQSGAEVKKPGSSVKVSCKASGGT FSSYAISWVRQAPGQGLEWMGRIIPILGIANYAQKFQGRVTITAD KSTSTAYMELSSLRSEDTAVYYCAKPRDGYNLVAFDIWGQGTM VTVSSASTKGPSVFPLAPSSKSTSGGTAALGCLVKDYFPEPVTVS WNSGALTSGVHTFPAVLQSSGLYSLSSVVTVPSSSLGTQTYICNV NHKPSNTKVDKKVEPKSCDKTHTCPPCPAPELLGGPGGGSDIQ MTQTTSSLSASLGDRVTISCRASQDIRNYLNWYQQKPDGTVKLLI YYTSRLHSGVPSKFSGSGSGTDYSLTISNLEQEDIATYFCQQGNTL PWTFAGGTKLEIKRQLVLTQPPSVSGAPGQRVTISCTGSSSNIGAG YDVHWYQQLPGAAPKLLIYGDINRPSGVPDRFSGSKSGISASLAIT GLQAEDEADYYCQSYDSSLSGGVFGGGTKLTVLRTVAAPSVFIFP PSDEQLKSGTASVVCLLNNFYPREAKVQWKVDNALQSGNSQESV TEQDSKDSTYSLSSTLTLSKADYEKHKVYACEVTHQGLSSPVTKS FNRGEC | 258 |

TABLE 1-continued

Exemplary Antibodies for Immune Cell Associated Antigens

| Antibody or Ag-binding fragment | Antigen Bound | Sequence | SEQ ID NO |
|---|---|---|---|
| each HC comprises a G4S linker between the hinge region and the second ABD | | | |

Modification to Fc Region

Disclosed herein are antibodies or antigen binding fragments thereof that comprise an Fc region, wherein the Fc region comprises at least one covalently linked linker. In some embodiments, the linker is a chemical linker. In some embodiments, the chemical linker is covalently attached to a tyrosine, aspartic acid, glutamic acid, arginine, histidine, or lysine residue. In some embodiments, the chemical linker is covalently attached to a lysine, cysteine, or tyrosine residue. In some embodiments, the chemical linker is covalently attached to a cysteine residue. In some embodiments, the chemical linker is covalently attached to a lysine residue. In some embodiments, the chemical linker is covalently attached to a constant region of the antibody.

In some embodiments, the antibody comprises an Fc region. In some embodiments, the Fc region is an IgG Fc region, an IgA Fc region, an IgD Fc region, an IgM Fc region, or an IgE Fc region. In some embodiments, the Fc region is an IgG Fc region, an IgA Fc region, or an IgD Fc region. In some embodiments, the Fc region is a human Fc region. In some embodiments, the Fc region is a humanized. Fc region. In some embodiments, the Fc region is an IgG Fc region. In some instances, an IgG Fc region is an IgG1 Fc region, an IgG2a Fc region, or an IgG4 Fc region.

One or more mutations may be introduced in an Fc region to reduce Fc-mediated effector functions of an antibody or antigen-binding fragment such as, for example, antibody-dependent cellular cytotoxicity (ADCC) and/or complement function. In some instances, a modified Fc comprises a humanized IgG4 kappa isotype that contains a S229P Fc mutation. In some instances, a modified Fc comprises a human IgG1 kappa where the heavy chain CH2 domain is engineered with a triple mutation such as, for example: (a) L238P, L239E, and P335S; or (2) K248; K288; and K317.

In some embodiments, the Fc region has an amino acid sequence at least 80%, at least 85%, at least 90%, at least 91%, at least 92%, at least 93%, at least 94%, at least 95%, at least 96%, at least 97%, at least 98%, or at least 99% identical to a sequence as set forth in SEQ ID NO: 260 (Pro Lys Ser Cys Asp Lys Thr His Thr Cys Pro Pro Cys Pro Ala Prol Glu Xaa Xaa Gly Xaa Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asp Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Xaa Glu Xaa Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Xaa Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly, where Xaa can be any naturally occurring amino acid). In some embodiments, the Fc region comprises one or more mutations which make the Fc region susceptible to modification or conjugation at a particular residue, such as by incorporation of a cysteine residue at a position which does not contain a cysteine in SEQ ID NO: 260. Alternatively, the Fc region could be modified to incorporate a modified natural amino acid or an unnatural amino acid which comprises a conjugation handle, such as one connected to the modified natural amino acid or unnatural amino acid through a linker. In some embodiments, the Fc region does not comprise any mutations which facilitate the attachment of a linker to an additional cytokine (e.g., an IL-18 polypeptide). In some embodiments, the chemical linker is attached to a native residue as set forth in SEQ ID NO: 260. In some embodiments, the chemical linker is attached to a native lysine residue of SEQ ID NO: 260.

In some embodiments, the chemical linker is attached to the Fc region at an amino acid residue at one of positions 10-90 of SEQ ID NO: 260. In some embodiments, the chemical linker is attached to the Fc region at an amino acid residue at one of positions 10-20, 10-30, 10-40, 10-50, 10-60, 10-70, 1-80, 10-90, 10-100, 10-110, 10-120, 10-130, 10-140, 10-150, 10-160, 10-170, 10-180, 10-190, or 10-200 of SEQ ID NO: 260. In some embodiments, the chemical linker is attached to the Fc region at an amino acid residue at one of positions 10-30, 50-70, or 80-100 of SEQ ID NO: 260. In some embodiments, the chemical linker is attached to the Fc region at an amino acid residue at any one of positions 20-40, 65-85, or 90-110 of SEQ ID NO: 260. In some embodiments, the chemical linker is attached to the Fc region at an amino acid residue at one of positions 15-26, 55-65, or 85-90 of SEQ ID NO: 260. In some embodiments, the chemical linker is attached to the Fc region at an amino acid residue at any one of positions 25-35, 70-80, or 95-105 of SEQ ID NO: 260. In some embodiments, the chemical linker is attached to the Fc region at an amino acid residue at any one of positions 30, 32, 72, 74, or 101 of SEQ ID NO: 260. In some embodiments, the chemical linker is attached to the Fc region at an amino acid residue at any one of positions K30, K32, K72, K74, or K101 of SEQ ID NO: 260. In some embodiments, the chemical linker is attached to the Fc region at amino acid residue 30 of SEQ ID NO: 260. In some embodiments, the chemical linker is attached to the Fc region at amino acid residue 32 of SEQ ID NO: 260. In some embodiments, the chemical linker is attached to the Fc region at amino acid residue 72 of SEQ ID NO: 260. In some embodiments, the chemical linker is attached to the Fc region at amino acid residue 74 of SEQ ID NO: 260. In some embodiments, the chemical linker is attached to the Fc region at amino acid residue 101 of SEQ ID NO: 260.

The chemical linker can be covalently attached to one amino acid residue of an Fc region of the antibody. In some embodiments, the chemical linker is covalently attached to a non-terminal residue of the Fc region. In some embodiments, the non-terminal residue is in the CH1, CH2, or CH3 region of the antibody. In some embodiments, the non-terminal residue is in the CH2 region of the antibody.

In some embodiments, the chemical linker is covalently attached at an amino acid residue of the antibody or antigen binding fragment which selectively binds a immune associated antigen (e.g., an anti-PD-1 antibody) such that the function of the antibody or antigen binding fragment is maintained (e.g., without denaturing the polypeptide). For example, when the antibody or antigen binding fragment is a human IgG (e.g., human IgG1), exposed lysine residues and exposed tyrosine residues are present at the following positions (refer to web site www.imgt.org/IMGTScientific-Chart/Numbering/Hu_IGHGnber.html by EU numbering). Exemplary exposed Lysine Residues: CH2 domain (position 246, position 248, position 274, position 288, position 290, position 317, position 320, position 322, and position 338) CH3 domain (position 360, position 414, and position 439). Exemplary exposed Tyrosine Residues: CH2 domain (position 278, position 296, and position 300) CH3 domain (position 436).

The human IgG, such as human IgG1, may also be modified with a lysine or tyrosine residue at any one of the positions listed above in order provide a residue which is ideally surface exposed for subsequent modification.

In some embodiments, the chemical linker is covalently attached at an amino acid residue in the constant region of an antibody. In some embodiments, the chemical linker is covalently attached at an amino acid residue in the CH1, CH2, or CH3 region. In some embodiments, the chemical inker is covalently attached at an amino acid residue in the CH2 region. In some embodiments, the chemical linker may be covalently attached to one amino acid residue in the following groups of residues following EU numbering in human IgG Fc: amino acid residues 1-478, amino acid residues 2-478, amino acid residues 1-477, amino acid residues 2-477, amino acid residues 10-467, amino acid residues 30-447, amino acid residues 50-427, amino acid residues 100-377, amino acid residues 150-327, amino acid residues 200-327, amino acid residues 240-327, and amino acid residues 240-320.

In some embodiments, the chemical linker is covalently attached to one lysine residue of a human IgG Fc region. In some embodiments, the chemical linker is covalently attached at Lys 246 of an Fc region of the antibody, wherein amino acid residue position number is based on Eu numbering. In some embodiments, the chemical linker is covalently attached at Lys 248 of an Fc region of the antibody, wherein amino acid residue position number is based on Eu numbering. In some embodiments, the chemical linker is covalently attached at Lys 288 of an Fc region of the antibody, wherein amino acid residue position number is based on Eu numbering. In some embodiments, the chemical linker is covalently attached at Lys 290 of an Fc region of the 0 antibody, wherein amino acid residue position number is based on Eu numbering. In some embodiments, the chemical linker is covalently attached at Lys 317 of the antibody, wherein amino acid residue position number is based on Eu numbering.

The chemical linker can be covalently attached to an amino acid residue selected from a subset of amino acid residues. In some embodiments, the subset comprises two three, four, five, six, seven, eight, nine, or ten amino acid residues of an Fc region of the antibody. The chemical linker can be covalently attached to one of two lysine residues of an Fc region of the antibody.

In some embodiments, the antibody will comprise two linkers covalently attached to the Fc region of the antibody. In some embodiments, each of the two linkers will be covalently attached to a different heavy chain of the antibody. In some embodiments, each of the two linkers will be covalently attached to a different heavy chain of the antibody at a residue position which is the same. In some embodiments, each of the two linkers will be covalently attached to a different heavy chain of antibody at a residue position which is different. When the two linkers are covalently attached to residue positions which differ, any combination of the residue positions provided herein may be used in combination.

In some embodiments, a first chemical linker is covalently attached at Lys 248 of a first Fc region of the antibody, and a second chemical linker is covalently attached at Lys 288 of a second Fc region of the antibody, wherein amino acid residue position number is based on Eu numbering. In some embodiments, a first chemical linker is covalently attached at Lys 248 of a first Fc region of the antibody, and a second chemical linker is covalently attached at Lys 317 of a second Fc region of the antibody, wherein residue position number is based on Eu numbering. In some embodiments, a first chemical linker is covalently attached at Lys 288 of a first Fc region of the antibody, and a second chemical linker is covalently attached at Lys 317 of a second Fc region of the antibody, wherein amino acid residue position number is based on Eu numbering.

Method of Modifying an Fc Region

Also provided herein are method of preparing a modified Fc region of an antibody or antigen binding fragment, such as for the attachment of a linker, a conjugation handle, the IL-18 polypeptide, or any combination thereof to the antibody or antigen binding fragment. A variety of methods for site-specific modification of Fc regions of antibodies are known in the art.

Modification with an Affinity Peptide Configured to Site-Specifically Attach Linker to the Antibody In some embodiments, an Fc region is modified to incorporate a linker, a conjugation handle, or a combination thereof. In some embodiments, the modification is performed by contacting the Fc region with an affinity peptide bearing a payload configured to attach a linker or other group to the Fc region, such as at a specific residue of the Fc region. In some embodiments, the linker is attached using a reactive group which forms a bond with a residue of the Fc region. In some embodiments, the affinity peptide comprises a cleavable linker. The cleavable linker is configured on the affinity peptide such that after the linker or other group is attached to the Fc region, the affinity peptide can be removed, leaving behind only the desired linker or other group attached to the Fc region. The linker or other group can then be used further to add attach additional groups, such as a cytokine or a linker attached to a cytokine, to the Fc region.

Non-limiting examples of such affinity peptides can be found at least in PCT Publication No. WO2018199337A1, PCT Publication No. WO2019240288A1, PCT Publication No. WO2019240287A1, and PCT Publication No. WO2020090979A1, each of which is incorporated by reference as if set forth herein in its entirety. In some embodiments, the affinity peptide is a peptide which has been modified to deliver the linker/conjugation handle payload one or more specific residues of the Fc region of the antibody. In some embodiments, the affinity peptide has at least 80%, 85%, 90%, 91%, 92%, 93%, 94%, 95%, 96%, 97%, 98%, 99%, or 100% sequence identify to a peptide selected from (1) QETNPTENLYFQQKNMQCQRRF-YEALHDPNLNEEQRNARIRSIRDDDC (SEQ ID NO: 261); (2) QTADNQKNMQCQRRFYEALHDPNLNEEQR-NARIRSIRDDCSQSANLLAEAQQLNDAQA PQA (SEQ ID NO: 262); (3) QETKNMQCQRRFYEALHDPNLNE-EQRNARIRSIRDDDC (SEQ ID NO:263); (4) QETFNKQCQRRFYEALHDPNLNEEQRNARIR-SIRDDDC (SEQ ID NO: 264); (5) QETFNMQCQRRF-YEALHDPNLNKEQRNARIRSIRDDDC (SEQ ID NO: 265); (6) QETFNMQCQRRFYEALHDPNLNEEQR-NARIRSIKDDC (SEQ ID NO: 266); (7) QETMQCQRRF-YEALHDPNLNEEQRNARIRSIKDDC (SEQ ID NO: 267); (8) QETQCQRRFYEALHDPNLNEEQRNARIR-SIKDDC (SEQ ID NO: 268); (9) QETCQRRF-YEALHDPNLNEEQRNARIRSIKDDC (SEQ ID NO: 269); (10) QETRGNCAYHKGQLVWCTYH (SEQ ID NO: 270); and (11) QETRGNCAYHKGQIIWCTYH (SEQ ID NO: 271), or a corresponding peptide which has been truncated at the N-terminus by one, two, three, four, or five residues.

An exemplary affinity peptide with cleavable linker and conjugation handle payload capable of attaching the payload to residue K248 of an antibody as provided herein is shown below (as reported in Matsuda et al., "Chemical Site-Specific Conjugation Platform to Improve the Pharmacokinetics and Therapeutic Index of Antibody-Drug Conjugates," *Mol. Pharmaceutics* 2021, 18, 11, 4058-4066.

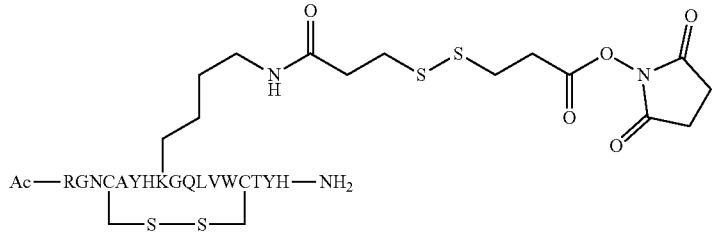

Alternative affinity peptides targeting alternative residues of the Fc region are described in the references cited above for AJICAP™ technology, and such affinity peptides can be used to attach the desired functionality to an alternative residue of the Fc region (e.g., K246, K288, etc.). For example, the disulfide group of the above affinity peptide could instead be replaced with a thioester to provide a sulfhydryl protecting group as a cleavable portion of the linking group (e.g., the relevant portion of the affinity peptide would have a structure of

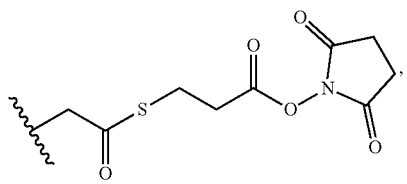 [SMILES: *CC(=O)SCCC(=O)ON1C(=O)CCC1=O]

or another of the cleavable linkers discussed below). Such alternative affinity peptides include those described in, for example "AJICAP Second Generation: Improved Chemical Site-Specific Conjugation Technology for Antibody-Drug Conjugation Technology for Antibody-Drug Conjugate Production" (Working Paper, Fujii et al., DOI: 10.26434/chemrxiv-2023-9p5p7, chemrxiv.org/engage/chemrxiv/article-details/63d5f7131125965a9e7df8a5 (Accessed 20 Feb. 2023, Version 1 published 30 Jan. 2023)). Exemplary affinity peptides provided therein include those shown below, wherein the left structure targets K248 of the Fc region and the right structure targets K288 of the Fc region (EU numbering).

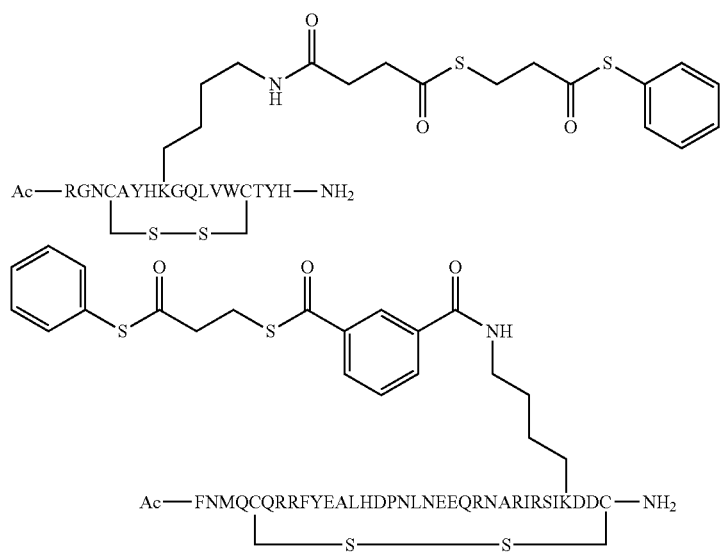

The affinity peptide of the disclosure can comprise a cleavable linker. In some embodiments, the cleavable linker of the affinity peptide connects the affinity peptide to the group which is to be attached to the Fc region and is configured such that the peptide can be cleaved after the group comprising the linker or conjugation handle has been attached. In some embodiments, the cleavable linker is a divalent group. In some embodiments, the cleavable linker can comprise a thioester group, an ester group, a sulfane group; a methanimine group; an oxyvinyl group; a thiopropanoate group; an ethane-1,2-diol group; an (imidazole-1-yl)methan-1-one group; a seleno ether group; a silylether group; a di-oxysilane group; an ether group; a di-oxymethane group; a tetraoxospiro[5.5]undecane group; an acetamidoethyl phosphoramidite group; a bis(methylthio)-pyrazolopyrazole-dione group; a 2-oxo-2-phenylethyl formate group; a 4-oxybenzylcarbamate group; a 2-(4-hydroxy-oxyphenyl)diazinyl)benzoic acid group; a 4-amino-2-(2-amino-2-oxoethyl)-4-oxobut-2-enoic acid group; a 2-(2-methylenehydrazineyl)pyridine group; an N'-methyleneformohydrazide group; or an isopropylcarbamate group, any of which is unsubstituted or substituted. Composition and points of attachment of the cleavable linker to the affinity peptide, as well as related methods of use, are described in, at least, PCT Publication No. WO2018199337A1, PCT Publication No. WO2019240288A1, PCT Publication No. WO2019240287A1, and PCT Publication No. WO2020090979A1.

In some embodiments, the cleavable linker is:

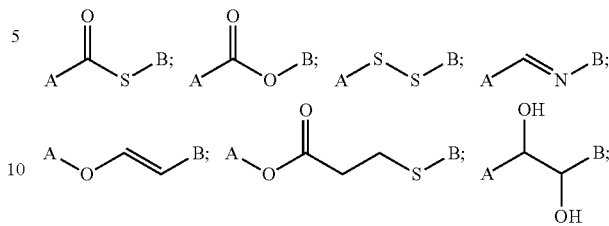

-continued

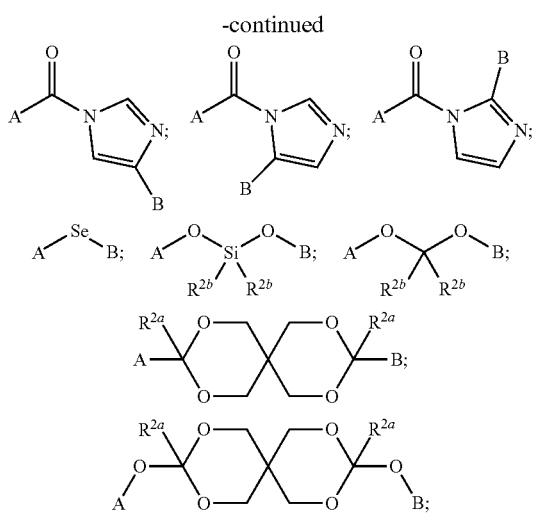

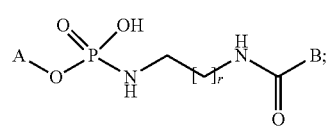

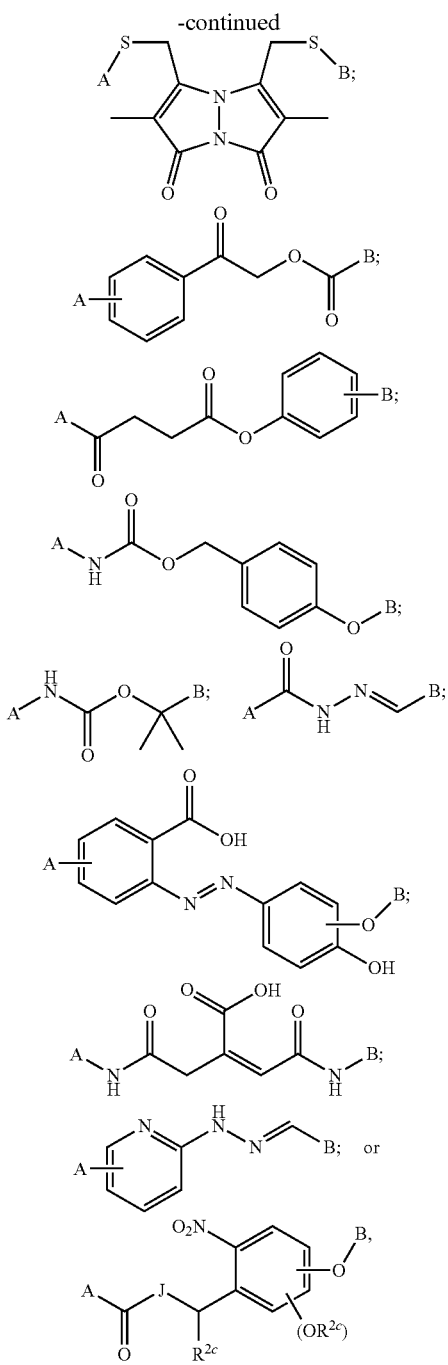

wherein:
one of A or B is a point of attachment the linker and the other of A or B is a point of attachment to the affinity peptide;
each $R^{2a}$ is independently H or optionally substituted alkyl;
each $R^{2b}$ is independently H or optionally substituted alkyl;
$R^{2c}$ is a H or optionally substituted alkyl;
J is a methyl, a N, a S, a Si, or an O atom; and
r is 1, 2, 3, 4, 5, 6, 7, 8, 9, or 10.

The affinity peptide comprises a reactive group which is configured to enable the covalent attachment of the linker/conjugation handle to the Fc region. In some embodiments, the reactive group is selective for a functional group of a specific amino acid residue, such as a lysine residue, tyrosine residue, serine residue, cysteine residue, or an unnatural amino acid residue of the Fc region incorporated to facilitate the attachment of the linker. The reactive group may be any suitable functional group, such as an activated ester for reaction with a lysine (e.g., N-hydroxysuccinimide ester or a derivate thereof, a pentafluorophenyl ester, etc.) or a sulfhydryl reactive group for reaction with a cysteine (e.g., a Michael acceptor, such as an alpha-beta unsaturated carbonyl or a maleimide). In some embodiments, the reactive group is:

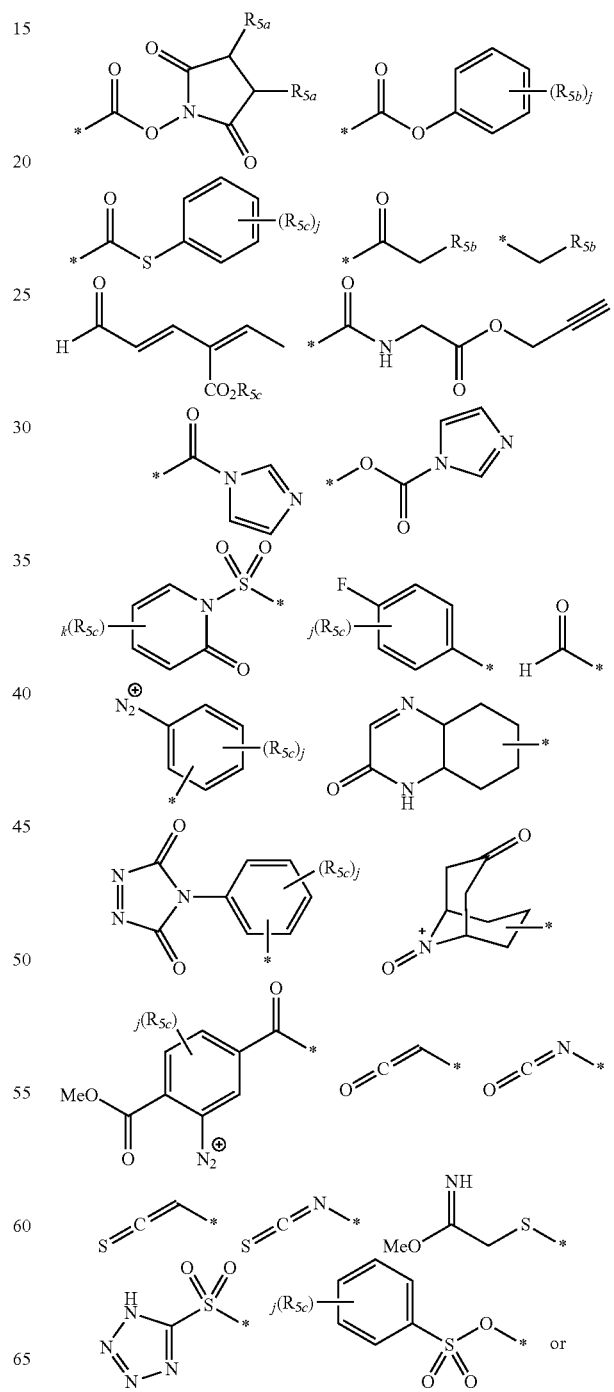

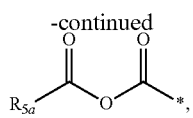

wherein:
each $R_{5a}$, $R_{5b}$, and $R_{5c}$ is independently H, halogen, or optionally substituted alkyl;
each j is 1, 2, 3, 4, or 5; and
each k is 1, 2, 3, 4, or 5.

In some embodiments, the affinity peptide is used to deliver a reactive moiety to the desired amino acid residue such that the reactive moiety is exposed upon cleavage of the cleavable linker. By way of non-limiting example, the reactive group forms a covalent bond with a desired residue of the Fc region of the antibody or antigen binding fragment due to an interaction between the affinity peptide and the Fc region. Following this covalent bond formation, the cleavable linker is cleaved under appropriate conditions to reveal a reactive moiety (e.g., if the cleavable linker comprises a thioester, a free sulfhydryl group is attached to the Fc region following cleavage of the cleavable linker). This new reactive moiety can then be used to subsequently add an additional moiety, such as a conjugation handle, by way of reagent comprising the conjugation handle tethered to a sulfhydryl reactive group (e.g., alpha-halogenated carbonyl group, alpha-beta unsaturated carbonyl group, maleimide group, etc.).

In some embodiments, an affinity peptide is used to deliver a free sulfhydryl group to a lysine of the Fc region. In some embodiments, the free sulfhydryl group is then reacted with a bifunctional linking reagent to attach a new conjugation handle to the Fc region. In some embodiments, the new conjugation handle is then used to form the linker to the attached cytokine. In some embodiments, the new conjugation handle is an alkyne functional group. In some embodiments, the new conjugation handle is a DBCO functional group.

Exemplary bifunctional linking reagents useful for this purpose are of a formula A-B-C, wherein A is the sulfhydryl reactive conjugation handle (e.g., maleimide, α,β-unsaturated carbonyl, a-halogenated carbonyl), B is a linking group, and C is the new conjugation handle (e.g., an alkyne such as DBCO). Specific non-limiting examples of bifunctional linking reagents include

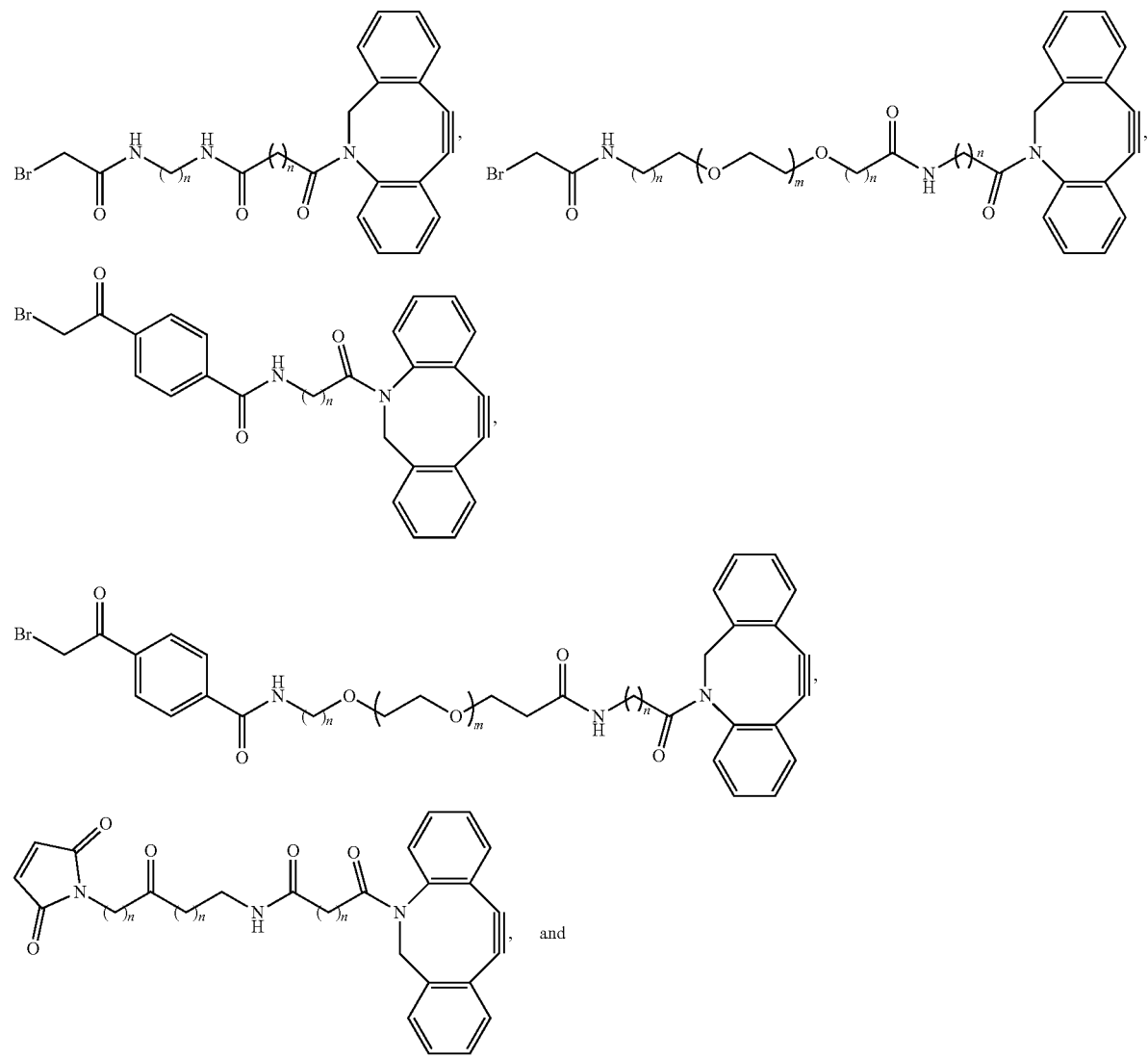

-continued

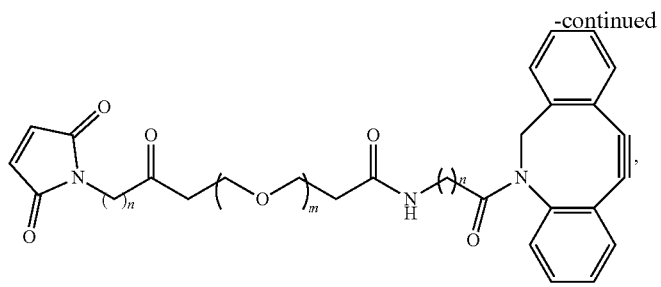

wherein each n is independently an integer from 1-6 and each m is independently an integer from 1-30, and related molecules (e.g., isomers).

Alternatively, the affinity peptide can be configured such that a conjugation handle is added to the Fc region (such as by a linker group) immediately after covalent bond formation between the reactive group and a residue of the Fc region. In such cases, the affinity peptide is cleaved and the conjugation handle is immediately ready for subsequent conjugation to the IL-18 polypeptide.

Alternative Methods of Modifying Fc Region

While the affinity peptide mediated modification of an Fc region of an antibody provide supra possesses many advantages over other methods which can be used to site-specifically modify the Fc region (e.g., ease of use, ability to rapidly generate many different antibody conjugates, ability to use many "off-the-shelf" commercial antibodies without the need to do time consuming protein engineering, etc.), other methods of performing the modification are also contemplated as being within the scope of the present disclosure.

In some embodiments, the present disclosure relates generally to transglutaminase-mediated site-specific antibody-drug conjugates (ADCs) comprising: 1) glutamine-containing tags, endogenous glutamines (e.g., native glutamines without engineering, such as glutamines in variable domains, CDRs, etc.), and/or endogenous glutamines made reactive by antibody engineering or an engineered transglutaminase; and 2) amine donor agents comprising amine donor units, linkers, and agent moieties. Non-limiting examples of such transglutaminase mediated site-specific modifications can be found at least in publications PCT Publication No. WO2020188061, US Patent Publication No. US2019194641, US Patent Publication No. US2021128743, U.S. Pat. No. 9,764,038, and U.S. patent Ser. No. 10/434,180, which are incorporated by reference as if set forth herein in their entirety.

In another aspect, the disclosure provides an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX, wherein X is any amino acid (e.g., X can be the same or different amino acid), and wherein the engineered Fc-containing polypeptide conjugate comprises an amino acid substitution from glutamine to asparagine at position 295 (Q295N; EU numbering scheme).

In some embodiments, the acyl donor glutamine-containing tag is not spatially adjacent to a reactive Lys (e.g., the ability to form a covalent bond as an amine donor in the presence of an acyl donor and a transglutaminase) in the polypeptide or the Fc-containing polypeptide. In some embodiments, the polypeptide or the Fc-containing polypeptide comprises an amino acid modification at the last amino acid position in the carboxyl terminus relative to a wild-type polypeptide at the same position. The amino acid modification can be an amino acid deletion, insertion, substitution, mutation, or any combination thereof.

In some embodiments, the immunocytokine composition comprises a full length antibody heavy chain and an antibody light chain, wherein the acyl donor glutamine-containing tag is located at the carboxyl terminus of a heavy chain, a light chain, or both the heavy chain and the light chain.

In some embodiments, the immunocytokine composition comprises an antibody, wherein the antibody is a monoclonal antibody, a polyclonal antibody, a human antibody, a humanized antibody, a chimeric antibody, a bispecific antibody, a minibody, a diabody, or an antibody fragment. In some embodiments, the antibody is an IgG.

In another aspect, provided herein is a method for preparing an engineered Fc-containing polypeptide conjugate comprising the formula: (Fc-containing polypeptide-T-A), wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the Fc-containing polypeptide, wherein the acyl donor glutamine-containing tag comprises an amino acid sequence XXQX, wherein X is any amino acid (e.g., X can be the same or a different amino acid), and wherein the engineered Fc-containing polypeptide conjugate comprises an amino acid substitution from glutamine to asparagine at position 295 (Q295N; EU numbering scheme), comprising the steps of: a) providing an engineered (Fc-containing polypeptide)-T molecule comprising the Fc-containing polypeptide and the acyl donor glutamine-containing tag; b) contacting the amine donor agent with the engineered (Fc-containing polypeptide)-T molecule in the presence of a transglutaminase; and c) allowing the engineered (Fc-containing polypeptide)-T to covalently link to the amine donor agent to form the engineered Fc-containing polypeptide conjugate.

In another aspect, provided herein is a method for preparing an engineered polypeptide conjugate comprising the formula: polypeptide-T-A, wherein T is an acyl donor glutamine-containing tag engineered at a specific site, wherein A is an amine donor agent, wherein the amine donor agent is site-specifically conjugated to the acyl donor glutamine-containing tag at a carboxyl terminus, an amino terminus, or at an another site in the polypeptide, and wherein the acyl donor glutamine-containing tag comprises an amino acid sequence LLQGPX, wherein X is A or P (SEQ ID NO: 272), or GGLLQGPP (SEQ ID NO: 273), comprising the steps of: a) providing an engineered polypeptide-T molecule comprising the polypeptide and the acyl donor glutamine-containing tag; b) contacting the amine donor agent with the engineered polypeptide-T molecule in the presence of a transglutaminase; and c) allowing the engineered polypeptide-T to covalently link to the amine donor agent to form the engineered Fc-containing polypeptide conjugate.

In some embodiments, the engineered polypeptide conjugate (e.g., the engineered Fc-containing polypeptide conjugate, the engineered Fab-containing polypeptide conjugate, or the engineered antibody conjugate) as described herein has conjugation efficiency of at least about 51%. In another aspect, the invention provides a pharmaceutical composition comprising the engineered polypeptide conjugate as described herein (e.g., the engineered Fc-containing polypeptide conjugate, the engineered Fab-containing polypeptide conjugate, or the engineered antibody conjugate) and a pharmaceutically acceptable excipient.

In some embodiments, provided herein is a method for conjugating a moiety of interest (Z) to an antibody, comprising the steps of: (a) providing an antibody having (e.g., within the primary sequence of a constant region) at least one acceptor amino acid residue (e.g., a naturally occurring amino acid) that is reactive with a linking reagent (linker) in the presence of a coupling enzyme, e.g., a transamidase; and (b) reacting said antibody with a linking reagent (e.g., a linker comprising a primary amine) comprising a reactive group (R), optionally a protected reactive group or optionally an unprotected reactive group, in the presence of an enzyme capable of causing the formation of a covalent bond between the acceptor amino acid residue and the linking reagent (other than at the R moiety), under conditions sufficient to obtain an antibody comprising an acceptor amino acid residue linked (covalently) to a reactive group (R) via the linking reagent. Optionally, said acceptor residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further-within the CH2 domain Optionally, the antibody is free of heavy chain N297-linked glycosylation. Optionally, the acceptor glutamine is at position 295 and the residue at the +2 position is the residue at position 297 (EU index numbering) of an antibody heavy chain.

In one aspect, provided herein is a method for conjugating a moiety of interest (Z) to an antibody, comprising the steps of: (a) providing an antibody having at least one acceptor glutamine residue; and (b) reacting said antibody with a linker comprising a primary amine (a lysine-based linker) comprising a reactive group (R), preferably a protected reactive group, in the presence of a transglutaminase (TGase), under conditions sufficient to obtain an antibody comprising an acceptor glutamine linked (covalently) to a reactive group (R) via said linker. Optionally, said acceptor glutamine residue of the antibody or antibody fragment is flanked at the +2 position by a non-aspartic acid residue. Optionally, the residue at the +2 position is a non-aspartic acid residue. In one embodiment, the residue at the +2 position is a non-aspartic acid, non-glutamine residue. In one embodiment, the residue at the +2 position is a non-aspartic acid, non-asparagine residue. In one embodiment, the residue at the +2 position is a non-negatively charged amino acid (an amino acid other than an aspartic acid or a glutamic acid). Optionally, the acceptor glutamine is in an Fc domain of an antibody heavy chain, optionally further-within the CH2 domain Optionally, the antibody is free of heavy chain N297-linked glycosylation. Optionally, the acceptor glutamine is at position 295 and the residue at the +2 position is the residue at position 297 (EU index numbering) of an antibody heavy chain. The antibody comprising an acceptor residue or acceptor glutamine residue linked to a reactive group (R) via a linker comprising a primary amine (a lysine-based linker) can thereafter be reacted with a reaction partner comprising a moiety of interest (Z) to generate an antibody comprising an acceptor residue or acceptor glutamine residue linked to a moiety of interest (Z) via the linker. Thus, in one embodiment, the method further comprises a step (c): reacting (i) an antibody of step b) comprising an acceptor glutamine linked to a reactive group (R) via a linker comprising a primary amine (a lysine-based linker), optionally immobilized on a solid support, with (ii) a compound comprising a moiety of interest (Z) and a reactive group (R') capable of reacting with reactive group R, under conditions sufficient to obtain an antibody comprising an acceptor glutamine linked to a moiety of interest (Z) via a linker comprising a primary amine (a lysine-based linker). Preferably, said compound comprising a moiety of interest (Z) and a reactive group (R') capable of reacting with reactive group R is provided at a less than 80 times, 40 times, 20 times, 10 times, 5 times or 4 molar equivalents to the antibody. In one embodiment, the antibody comprises two acceptor glutamines and the compound comprising a moiety of interest (Z) and a reactive group (R') is provided at 10 or less molar equivalents to the antibody. In one embodiment, the antibody comprises two acceptor glutamines and the compound comprising a moiety of interest (Z) and a reactive group (R') is provided at 5 or less molar equivalents to the antibody. In one embodiment, the antibody comprises four acceptor glutamines and the compound comprising a moiety of interest (Z) and a reactive group (R') is provided at 20 or less molar equivalents to the antibody. In one embodiment, the antibody comprises four acceptor glutamines and the compound comprising a moiety of interest (Z) and a reactive group (R') is provided at 10 or less molar equivalents to the antibody. In one embodiment, steps (b) and/or (c) are carried out in aqueous conditions. Optionally, step (c) comprises: immobilizing a sample of an antibody comprising a functionalized acceptor glutamine residue of Formula II on a solid support to provide a sample comprising immobilized antibodies, reacting the sample comprising immobilized antibodies, optionally recovering any unreacted compound and re-introducing such recovered compound to the solid support for reaction with immobilized antibodies, and eluting the antibody conjugates to provide an antibody composition comprising a Z moiety.

In an alternative embodiment, an amino acid residue comprising a conjugation handle can be incorporated into the Fc region of the antibody (e.g., during expression of the antibody) at a desired location (e.g., any of the locations provided herein). In some embodiments, the amino acid residue comprising the conjugation handle is an unnatural amino acid.

Conjugation Handle Chemistry

In some embodiments, the appropriately modified Fc region of the antibody or antigen binding fragment will comprise a conjugation handle which is used to conjugate the antibody or antigen binding fragment to an IL-18 polypeptide to produce an immunocytokine composition provided herein.

Any suitable reactive group capable of reacting with a complementary reactive group attached to the IL-18 polypeptide can be used as the conjugation handle. In some embodiments, the conjugation handle comprises a reagent for a Cu(I)-catalyzed or "copper-free" alkyne-azide triazole-forming reaction (e.g., strain promoted cycloadditions), the Staudinger ligation, inverse-electron-demand Diels-Alder (IEDDA) reaction, "photo-click" chemistry, tetrazine cycloadditions with trans-cyclooctenes, potassium acyl trifluoroborate (KAT) ligation or a metal-mediated process such as olefin metathesis and Suzuki-Miyaura or Sonogashira cross-coupling.

In some embodiments, the conjugation handle comprises a reagent for a "copper-free" alkyne azide triazole-forming reaction. Non-limiting examples of alkynes for said alkyne, azide triazole forming reaction include cyclooctyne reagents (e.g., (1R,8S,9s)-Bicyclo[6.1.0]non-4-yn-9-ylmethanol containing reagents, dibenzocyclooctyne-amine reagents, difluorocyclooctynes, or derivatives thereof). In some embodiments, the alkyne functional group is attached to the Fc region. In some embodiments, the azide functional group is attached to the Fc region.

In some embodiments, the conjugation handle comprises a reactive group selected from azide, alkyne, tetrazine, halide, sulfhydryl, disulfide, maleimide, activated ester, alkene, aldehyde, ketone, imine, hydrazine, potassium acyl trifluoroborate, hydroxylamine (e.g., 0-substituted hydroxylamine) and hydrazide. In some embodiments, the IL-18 polypeptide comprises a reactive group complementary to the conjugation handle of the Fc region. In some embodiments, the conjugation handle and the complementary conjugation handle comprise "CLICK" chemistry reagents. Exemplary groups of click chemistry residue are shown in Hein et al., "Click Chemistry, A Powerful Tool for Pharmaceutical Sciences," Pharmaceutical Research, volume 25, pages 2216-2230 (2008); Thirumurugan et al., "Click Chemistry for Drug Development and Diverse Chemical-Biology Applications," Chem. Rev. 2013, 113, 7, 4905-4979; US20160107999A1; U.S. Ser. No. 10/266,502B2; and US20190204330A1, each of which is incorporated by reference in its entirety.

Linker Structure

In some embodiments, the linker used to attach the antibody or antigen binding fragment and the IL-18 polypeptide comprises points of attachment at both moieties. The points of attachment can be any of the residues for facilitating the attachment as provided herein. The linker structure can be any suitable structure for creating the spatial attachment between the two moieties. In some embodiments, the linker provides covalent attachment of both moieties. In some embodiments, the linker is a chemical linker (e.g., not an expressed polypeptide as in a fusion protein). In some embodiments, the linker is a peptide linker. In some embodiments, the linker is a non-peptide linker (e.g., does not consist of amino acid residues).

Chemical Linkers

In some embodiments, the linker is a chemical linker. In some embodiments, the chemical linker comprises at least one portion which is not comprised of amino acid residues. In some embodiments, the linker comprises a polymer. In some embodiments, the linker comprises a water soluble polymer. In some embodiments, the linker comprises poly (alkylene oxide), polysaccharide, poly(vinyl pyrrolidone), poly(vinyl alcohol), polyoxazoline, poly(acryloylmorpholine), or a combination thereof. In some embodiments, the linker comprises poly(alkylene oxide). In some embodiments, the poly(alkylene oxide) is polyethylene glycol or polypropylene glycol, or a combination thereof. In some embodiments, the poly(alkylene oxide) is polyethylene glycol.

In some embodiments, the linker is a bifunctional linker. In some embodiments, the bifunctional linker comprises an amide group, an ester group, an ether group, a thioether group, or a carbonyl group. In some embodiments, the linker comprises a non-polymer linker. In some embodiments, the linker comprises a non-polymer, bifunctional linker. In some embodiments, the non-polymer, bifunctional linker comprises succinimidyl 4-(N-maleimidomethyl)cyclohexane-1-carboxylate; Maleimidocaproyl; Valine-citrulline; Allyl(4-methoxyphenyl)dimethylsilane; 6-(Allyloxycarbonylamino)-1-hexanol; 4-Aminobutyraldehyde diethyl acetal; or (E)-N-(2-Aminoethyl)-4-{2-[4-(3-azidopropoxy)phenyl]diazenyl}benzamide hydrochloride.

The linker can be branched or linear. In some embodiments, the linker is linear. In some embodiments, the linker is branched. In some embodiments, the linker comprises a linear portion (e.g., between the first point of attachment and the second point of attachment) of a chain of at least 10, 20, 50, 100, 500, 1000, 2000, 3000, or 5000 atoms. In some embodiments, the linker comprises a linear portion of a chain of at least 10, 20, 30, 40, or 50 atoms. In some embodiments, the linker comprises a linear portion of at least 10 atoms. In some embodiments, the linker is branched and comprises a linear portion of a chain of at least 10, 20, 50, 100, 500, 1000, 2000, 3000, or 5000 atoms. In some embodiments, the linker comprises a linear portion of at from 1 to 1000 atoms, 1 to 900 atoms, 1 to 800 atoms, 1 to 500 atoms, 1 to 400 atoms, 1 to 300 atoms, 1 to 200 atoms, 1 to 100 atoms, 1 to 50 atoms, 10 to 1000 atoms, 10 to 900 atoms, 10 to 800 atoms, 10 to 500 atoms, 10 to 400 atoms, 10 to 300 atoms, 10 to 200 atoms, 10 to 100 atoms, 10 to 50 atoms, 25 to 1000 atoms, 25 to 900 atoms, 25 to 800 atoms, 25 to 500 atoms, 25 to 400 atoms, 25 to 300 atoms, 25 to 200 atoms, 25 to 100 atoms, 25 to 50 atoms, 50 to 1000 atoms, 50 to 900 atoms, 50 to 800 atoms, 50 to 500 atoms, 50 to 400 atoms, 50 to 300 atoms, 50 to 200 atoms, or 50 to 100 atoms. In some embodiments, the linker has a linear length of from about 10 angstroms to about 200 angstroms. In some embodiments, the linker has a linear length of from about 10 to 500, 10 to 200, 10 to 150, 10 to 125, 10 to 100, 10 to 75, 10 to 50, 25 to 200, 25 to 150, 25 to 125, 25 to 100, 25 to 75, 25 to 50, 50 to 200, 50 to 150, 50 to 100, or 50 to 75 angstroms.

In some embodiments, the linker has a molecular weight of about 200 Daltons to about 2000 Daltons. In some embodiments, the linker has a molecular weight of about 200 Daltons to about 5000 Daltons. In some embodiments, the linker has a molecular weight of 200 Daltons to 100,000 Daltons. In some embodiments, the linker has a molecular weight of at least about 500 Daltons, at least about 1,000 Daltons, at least about 5,000 Daltons, at least about 10,000 Daltons, at least about 15,000 Daltons, at least about 20,000 Daltons, at least about 25,000 Daltons, or at least about 30,000 Daltons. In some embodiments, the linker as a molecular weight of at most about 100,000 Daltons, at most about 50,000 Daltons, at most about 40,000 Daltons, at most about 30,000 Daltons, at most about 25,000 Daltons, at most about 20,000 Daltons at most about 15,000 Daltons, at most about 10,000 Daltons, or at most about 5,000 Daltons.

In some embodiments, the linker comprises a reaction product of one or more pairs of conjugation handles and a complementary conjugation handle thereof. In some embodiments, the reaction product comprises a triazole, a hydrazone, pyridazine, a sulfide, a disulfide, an amide, an ester, an ether, an oxime, an alkene, or any combination thereof. In some embodiments, the reaction product comprises a triazole. The reaction product can be separated from the first point of attachment and the second point of attachment by any portion of the linker. In some embodiments, the reaction product is substantially in the center of the linker. In some embodiments, the reaction product is substantially closer to one point of attachment than the other is.

In some embodiments, the linker comprises a structure of Formula (X)

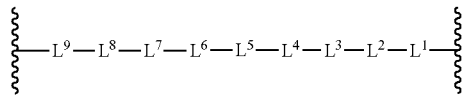

wherein each of $L^1$, $L^2$, $L^3$, $L^4$, $L^5$, $L^6$, $L^7$, $L^8$, and $L^9$ is independently —O—, —$NR^L$—, —($C_1$-$C_6$ alkylene) $NR^L$—, —$NR^L$($C_1$-$C_6$ alkylene)-, —$N(R^L)_2{}^+$—, —($C_1$-$C_6$ alkylene)$N(R^L)_2{}^+$—, —$N(R^L)_2{}^+$—($C_1$-$C_6$ alkylene)-, —OP(=O)($OR^L$)O—, —S—, —($C_1$-$C_6$ alkylene)S—, —S($C_1$-$C_6$ alkylene)-, —S(=O)—, —S(=O)$_2$—, —C(=O)—, —($C_1$-$C_6$ alkylene)C(=O)—, —C(=O) ($C_1$-$C_6$ alkylene)-, —C(=O)O—, —OC(=O)—, —OC(=O)O—, —C(=O)$NR^L$—, —C(=O)$NR^L$($C_1$-$C_6$ alkylene)-, —($C_1$-$C_6$ alkylene)C(=O)$NR^L$—, —$NR^L$C(=O)—, —($C_1$-$C_6$ alkylene)$NR^L$C(=O)—, —$NR^L$C(=O)($C_1$-$C_6$ alkylene)-, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$, —$NR^L$S(=O)$_2$—, —S(=O)$_2$$NR^L$—, —C(=O)$NR^L$S(=O)$_2$—, —S(=O)$_2$$NR^L$C(=O)—, substituted or unsubstituted $C_1$-$C_6$ alkylene, substituted or unsubstituted $C_1$-$C_6$ heteroalkylene, substituted or unsubstituted $C_2$-$C_6$ alkenylene, substituted or unsubstituted $C_2$-$C_6$ alkynylene, substituted or unsubstituted $C_6$-$C_{20}$ arylene, substituted or unsubstituted $C_2$-$C_{20}$ heteroarylene, —(CH2-CH2-0)$_{qa}$—, —(O—CH2-CH2)$_{qb}$—, —(CH$_2$—CH(CH$_3$)—O)$_{qc}$—, —(O—CH(CH$_3$)—CH$_2$)$_{qd}$—, a reaction product of a conjugation handle and a complementary conjugation handle, or absent;

each $R^L$ is independently hydrogen, substituted or unsubstituted $C_1$-$C_4$ alkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; and each of qa, qb, qc and qd is independently an integer from 1-100, wherein each

is a point of attachment to the antibody or antigen binding fragment or the IL-18 polypeptide.

In some embodiments, the linker consists of a plurality of structures of Formula (X) to form the linkage between the antibody or antigen binding fragment and the IL-18 polypeptide (e.g., 1, 2, 3, 4, 5, 6, 7, 8, 9, 10, or more structures of Formula (X) appended from end to end, where

only the terminal denote points of attachment to the antibody or antigen binding fragment or the IL-18 polypeptide).

In some embodiments, the polymer comprises a linker comprising a structure of Formula (X')

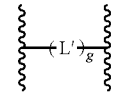

wherein each L' is independently —O—, —$NR^L$—, —($C_1$-$C_6$ alkylene)$NR^L$—, —$NR^L$($C_1$-$C_6$ alkylene)-, —$N(R^L)_2{}^+$—, —($C_1$-$C_6$ alkylene)$N(R^L)_2{}^+$—, —$N(R^L)_2{}^+$—($C_1$-$C_6$ alkylene)-, —OP(=O)($OR^L$)O—, —S—, —($C_1$-$C_6$ alkylene)S—, —S($C_1$-$C_6$ alkylene)-, —S(=O)—, —S(=O)$_2$—, —C(=O)—, —($C_1$-$C_6$ alkylene)C(=O)—, —C(=O) ($C_1$-$C_6$ alkylene)-, —C(=O)O—, —OC(=O)—, —OC(=O)O—, —C(=O)$NR^L$—, —C(=O)$NR^L$($C_1$-$C_6$ alkylene)-, —($C_1$-$C_6$ alkylene)C(=O)$NR^L$—, —$NR^L$C(=O)—, —($C_1$-$C_6$ alkylene)$NR^L$C(=O)—, —$NR^L$C(=O)($C_1$-$C_6$ alkylene)-, —OC(=O)$NR^L$—, —$NR^L$C(=O)O—, —$NR^L$C(=O)$NR^L$—, —$NR^L$C(=S)$NR^L$—, —$CR^L$=N—, —N=$CR^L$, —$NR^L$S(=O)$_2$—, —S(=O)$_2$$NR^L$—, —C(=O)$NR^L$S(=O)$_2$—, —S(=O)$_2$$NR^L$C(=O)—, substituted or unsubstituted $C_1$-$C_6$ alkylene, substituted or unsubstituted $C_1$-$C_6$ heteroalkylene, substituted or unsubstituted $C_2$-$C_6$ alkenylene, substituted or unsubstituted $C_2$-$C_6$ alkynylene, substituted or unsubstituted $C_6$-$C_{20}$ arylene, substituted or unsubstituted $C_2$-$C_{20}$ heteroarylene, —(CH$_2$—CH$_2$—O)$_{qa}$—, —(O—CH$_2$—CH$_2$)$_{qb}$—, —(CH$_2$—CH(CH$_3$)—O)$_{qc}$—, —(O—CH(CH$_3$)—CH$_2$)$_{qd}$—, a reaction product of a conjugation handle and a complementary conjugation handle, or absent; ($C_1$-$C_6$ alkylene);

each $R^L$ is independently hydrogen, substituted or unsubstituted $C_1$-$C_4$ alkyl, substituted or unsubstituted $C_1$-$C_4$ heteroalkyl, substituted or unsubstituted $C_2$-$C_6$ alkenyl, substituted or unsubstituted $C_2$-$C_5$ alkynyl, substituted or unsubstituted $C_3$-$C_8$ cycloalkyl, substituted or unsubstituted $C_2$-$C_7$ heterocycloalkyl, substituted or unsubstituted aryl, or substituted or unsubstituted heteroaryl; and each of qa, qb, qc and qd is independently an integer from 1-100, g is an integer from 1-100, wherein each

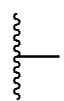

is a point of attachment to the modified IL-18 polypeptide or the antibody or antigen binding fragment.

In some embodiments, the linker of Formula (X) or Formula (X') comprises the structure:

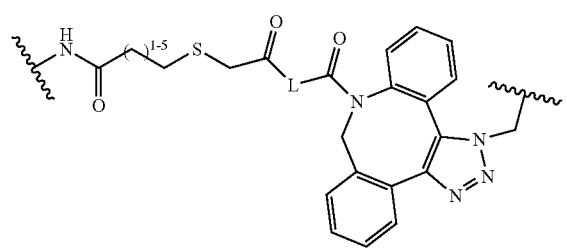

wherein

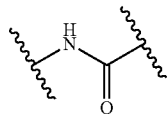 [SMILES: *NC(*)=O]

is the first point of attachment to a lysine residue of the antibody or antigen binding fragment;
L is a linking group; and

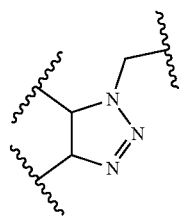 [SMILES: *CN1N=NC(*)C1*]

is a point of attachment to a linking group which connects to the first point of attachment,
or a regioisomer thereof.

In some embodiments, L has a structure

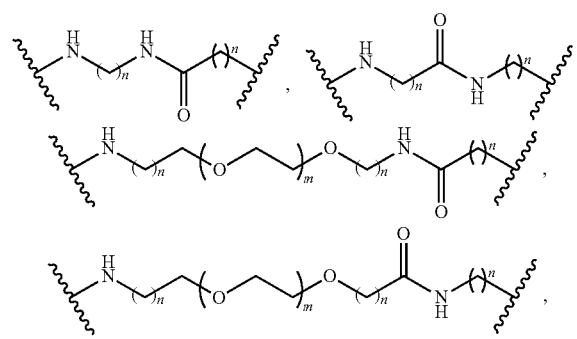

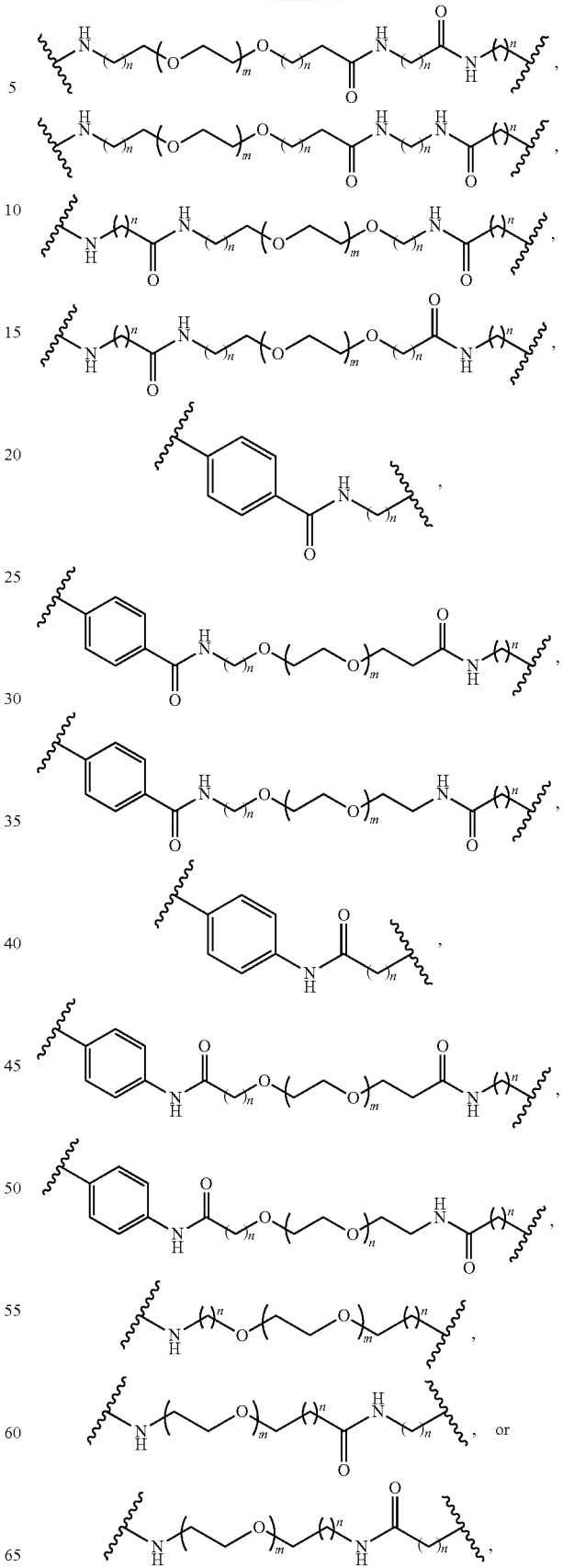

In some embodiments, the linker of Formula (X) or of Formula (X$^a$) or of Formula (X') comprises the structure:

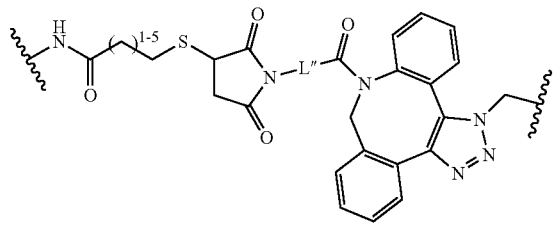

wherein

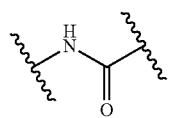 [SMILES: *NC(*)=O]

is the first point of attachment to a lysine residue of the polypeptide which selectively binds to PD-1;

L is a linking group; and

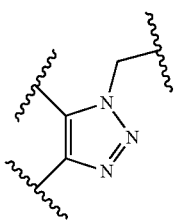 [SMILES: *Cn1nnc(*)c1*]

is a point of attachment to a linking group which connects to the first point of attachment, or a regioisomer thereof.

In some embodiments, L" has a structure

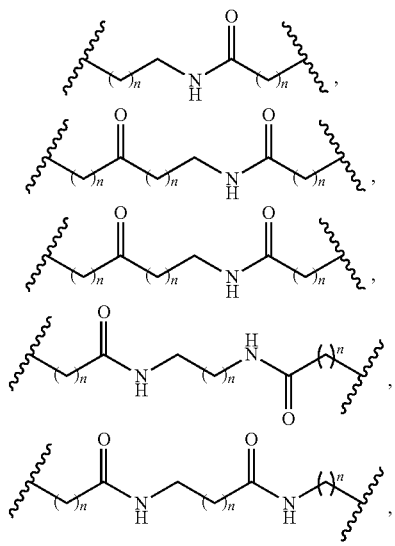

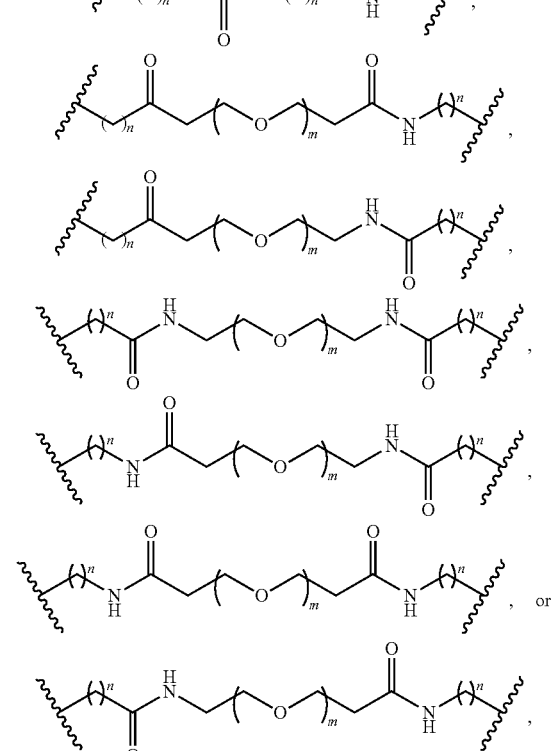

wherein each n is independently an integer from 1-6 and each m is independently an integer from 1-30. In some embodiments, each m is independently 2 or 3. In some embodiments, each m is an integer from 1-24, from 1-18, from 1-12, or from 1-6.

In some embodiments, L or L" comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more subunits each independently selected from

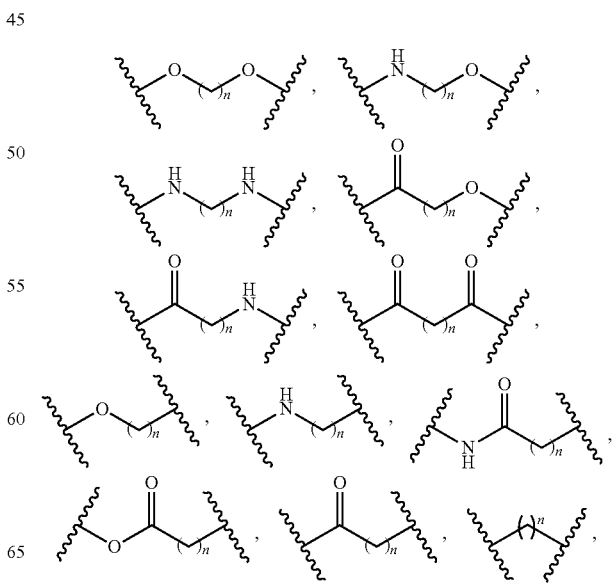

-continued

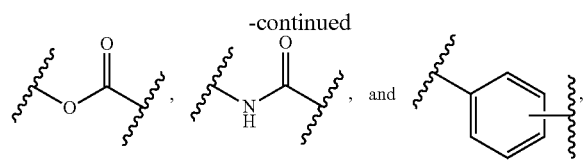

wherein each n is independently an integer from 1-30. In some embodiments, each n is independently an integer from 1-6. In some embodiments, L or L" comprise 1, 2, 3, 4, 5, 6, 7, 8, 9, or 10 of the subunits.

In some embodiments, L or L" is a structure of Formula (X")

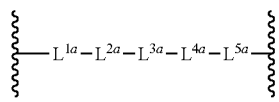

wherein each of $L^{1a}$, $L^{2}a$, $L^{3}a$, $L^{4}a$, $L^{5a}$, is independently —O—, —NR$^{La}$—, —(C$_1$-C$_6$ alkylene)NR$^{La}$—, —NR$^{La}$(C$_1$-C$_6$ alkylene)-, —N(R$^L$)$_2$$^+$—, —(C$_1$-C$_6$ alkylene)N(R$^{La}$)$_2$$^+$—(C$_1$-C$_6$ alkylene)-, —N(R$^L$)$_2$$^+$—, —OP(=O)(OR$^{La}$)O—, —S—, —(C$_1$-C$_6$ alkylene)S—, —S(C$_1$-C$_6$ alkylene)-, —S(=O)—, —S(=O)$_2$—, —C(=O)—, —(C$_1$-C$_6$ alkylene)C(=O)—, —C(=O)(C$_1$-C$_6$ alkylene)-, —C(=O)O—, —OC(=O)—, —OC(=O)O—, —C(=O)NR$^{La}$—, —C(=O)NR$^{La}$(C$_1$-C$_6$ alkylene)-, —(C$_1$-C$_6$ alkylene)C(=O)NR$^{La}$—, —NR$^{La}$C(=O), —(C$_1$-C$_6$ alkylene)NR$^{La}$C(=O)—, —NR$^{La}$C(=O)(C$_1$-C$_6$ alkylene)-, —OC(=O)NR$^{La}$—, —NR$^{La}$C(=O)O—, —NR$^{La}$C(=O)NR$^{La}$—, —NR$^{La}$C(=S)NR$^{La}$, —CR$^{La}$=N—, —N=CR$^{La}$, —NR$^{La}$S(=O)$_2$—, —S(=O)$_2$NR$^{La}$—, —C(=O)NR$^{La}$S(=O)$_2$—, —S(=O)$_2$NR$^{La}$C(=O)—, substituted or unsubstituted C$_1$-C$_6$ alkylene, substituted or unsubstituted C$_1$-C$_6$ heteroalkylene, substituted or unsubstituted C$_2$-C$_6$ alkenylene, substituted or unsubstituted C$_2$-C$_6$ alkynylene, substituted or unsubstituted C$_6$-C$_{20}$ arylene, substituted or unsubstituted C$_2$-C$_{20}$ heteroarylene, —(CH$_2$—CH$_2$—O)$_{qe}$—, —(O—CH$_2$—CH$_2$)$_{qf}$—, —(CH$_2$—CH(CH$_3$)—O)$_{qg}$—, —(O—CH(CH$_3$)—CH$_2$)$_{qh}$—, a reaction product of a conjugation handle and a complementary conjugation handle, or absent; (C$_1$-C$_6$ alkylene)

each R$^{La}$ is independently hydrogen, substituted or unsubstituted C$_1$-C$_4$ alkyl, substituted or unsubstituted C$_1$-C$_4$ heteroalkyl, substituted or unsubstituted C$_2$-C$_6$ alkenyl, substituted or unsubstituted C$_2$-C$_5$ alkynyl, substituted or unsubstituted C$_3$-C$_8$ cycloalkyl, substituted or unsubstituted C$_2$-C$_7$ heterocycloalkyl, substituted or unsubstituted aryl, or substituted or unsubstituted heteroaryl; and each of qe, qf, qg and qh is independently an integer from 1-100.

In some embodiments, L or L" comprises a linear chain of 2 to 10, 2 to 15, 2 to 20, 2 to 25, or 2 to 30 atoms. In some embodiments, the linear chain comprises one or more alkyl groups (e.g., lower alkyl (C$_1$-C$_4$)), one or more aromatic groups (e.g., phenyl), one or more amide groups, one or more ether groups, one or more ester groups, or any combination thereof.

In some embodiments, the linking group which connects to the first point of attachment (e.g., the point of attachment to the IL-18 polypeptide) comprises poly(ethylene glycol).

In some embodiments, the linking group comprises about 2 to about 30 poly(ethylene glycol)units. In some embodiments, the linking group which connects to the first point of attachment (e.g., the point of attachment to the IL-18 polypeptide) is a functionality attached to a cytokine provided herein which comprises an azide (e.g., the triazole is the reaction product of the azide).

In some embodiments, each reaction product of a conjugation handle and a complementary conjugation handle independently comprises a triazole, a hydrazone, pyridazine, a sulfide, a disulfide, an amide, an ester, an ether, an oxime, or an alkene. In some embodiments, each reaction product of a conjugation handle and a complementary conjugation handle comprises a triazole. In some embodiments, each reaction product of a conjugation handle and a complementary conjugation handle comprise a structure of

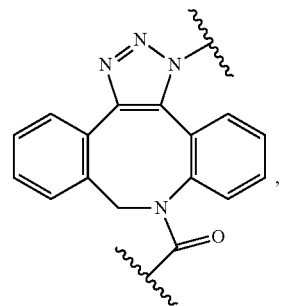

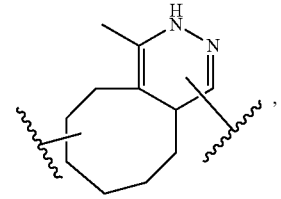

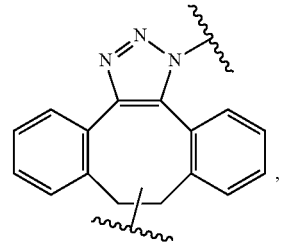

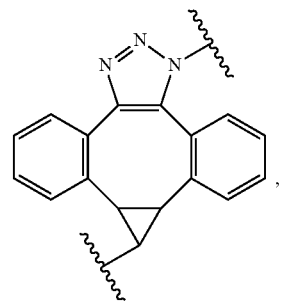

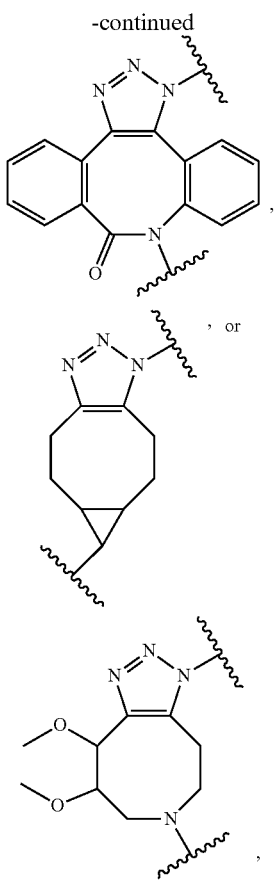

or a regioisomer or derivative thereof.

Peptide Linkers

In some embodiments, the antibody or antigen binding fragment is linked to the IL-18 polypeptide through a peptide linker. In some embodiments, the antibody or antigen binding fragment is linked to the IL-18 polypeptide as a fusion protein. In such instances, the linker comprises one or more peptide bonds between the antibody or antigen binding fragment and the IL-18 polypeptide. In some embodiments, the linker between the fusion protein of the antibody or antigen binding fragment and the IL-18 polypeptide is a bond. In some embodiments, the linker between the fusion protein of the antibody or antigen binding fragment and the IL-18 polypeptide is a linking peptide. Non-limiting examples of linking peptides include, but are not limited to (GS)$_n$ (SEQ ID NO: 224), (GGS)$_n$ (SEQ ID NO: 225), (GGGS)$_n$ (SEQ ID NO: 226), (GGSG)$_n$ (SEQ ID NO: 227), or (GGSGG)$_n$ (SEQ ID NO: 228), (GGGGS)$_n$ (SEQ ID NO: 229), wherein n is 1, 2, 3, 4, 5, 6, 7, 8, 9, or 10. For example, a linking peptide can be (GGGGS)$_3$ (SEQ ID NO: 230) or (GGGGS)$_4$ (SEQ ID NO: 231). In some embodiments, the IL-18 polypeptide is fused to the C-terminal end of the antibody or antigen binding fragment (optionally through a linking peptide). In some embodiments, the IL-18 polypeptide is fused to the N-terminal end of the antibody or antigen binding fragment (optionally through a linking peptide).

Cleavable Linkers

In some embodiments, the linker (e.g., a chemical or peptide linker as provided herein) is a cleavable linker. In some embodiments, the cleavable linker is cleaved at, near, or in a tumor microenvironment. In some embodiments, the tumor is mechanically or physically cleaved at, near, or in the tumor microenvironment. In some embodiments, the tumor is chemically cleaved at, near, or in a tumor microenvironment. In some embodiments, the cleavable linker is a reduction sensitive linker. In some embodiments, the cleavable linker is an oxidation sensitive linker. In some embodiments, the cleavable linker is cleaved as a result of pH at, near, or in the tumor microenvironment. In some embodiments, the cleavable linker is cleaved by a tumor metabolite at, near, or in the tumor microenvironment. In some embodiments, the cleavable linker is cleaved by a protease at, near, or in the tumor microenvironment.

IL-18 Polypeptides

The present disclosure describes antibodies or antigen binding fragments linked to interleukin-18 (IL-18) polypeptides as immunocytokine compositions and their use as therapeutic agents. IL-18 is a pro-inflammatory cytokine that elicits biological activities that initiate or promote host defense and inflammation following infection or injury. IL-18 has been implicated in autoimmune diseases, myocardial function, emphysema, metabolic syndromes, psoriasis, inflammatory bowel disease, hemophagocytic syndromes, macrophage activation syndrome, sepsis, and acute kidney injury. In some models of disease, IL-18 plays a protective role.

IL-18 also plays a major role in the production of IFNγ from T-cells and natural killer cells. IFNγ is a T helper type 1 cytokine mainly produced by T cells, NK cells, and macrophages and is critical for innate and adaptive immunity against viral, some bacterial, and protozoal infections. IFNγ is also an important activator of macrophages and inducer of Class II major histocompatibility complex (MHC) molecule expression.

IL-18 forms a signaling complex by binding to the IL-18 alpha chain (IL-18Rα), which is the ligand binding chain for mature IL-18. However, the binding affinity of IL-18 to IL-18Rα is low. In cells that express the co-receptor, IL-18 receptor beta chain (IL-18Rβ), a high affinity heterodimer complex is formed, which then activates cell signaling.

Figure 4:
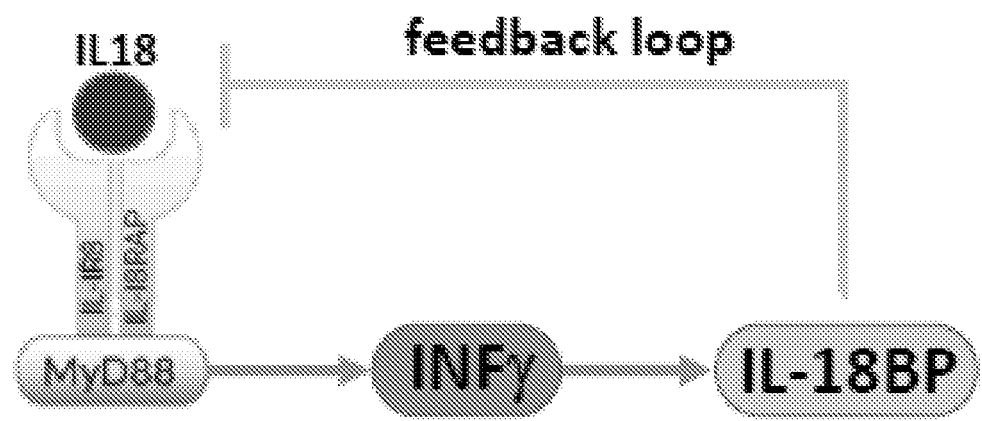
FIG. 4 illustrates the mechanism of action of IL-18 on IFNγ and IL-18BP production, and IL-18 inhibitory activity by IL-18BP.
Figure 5:
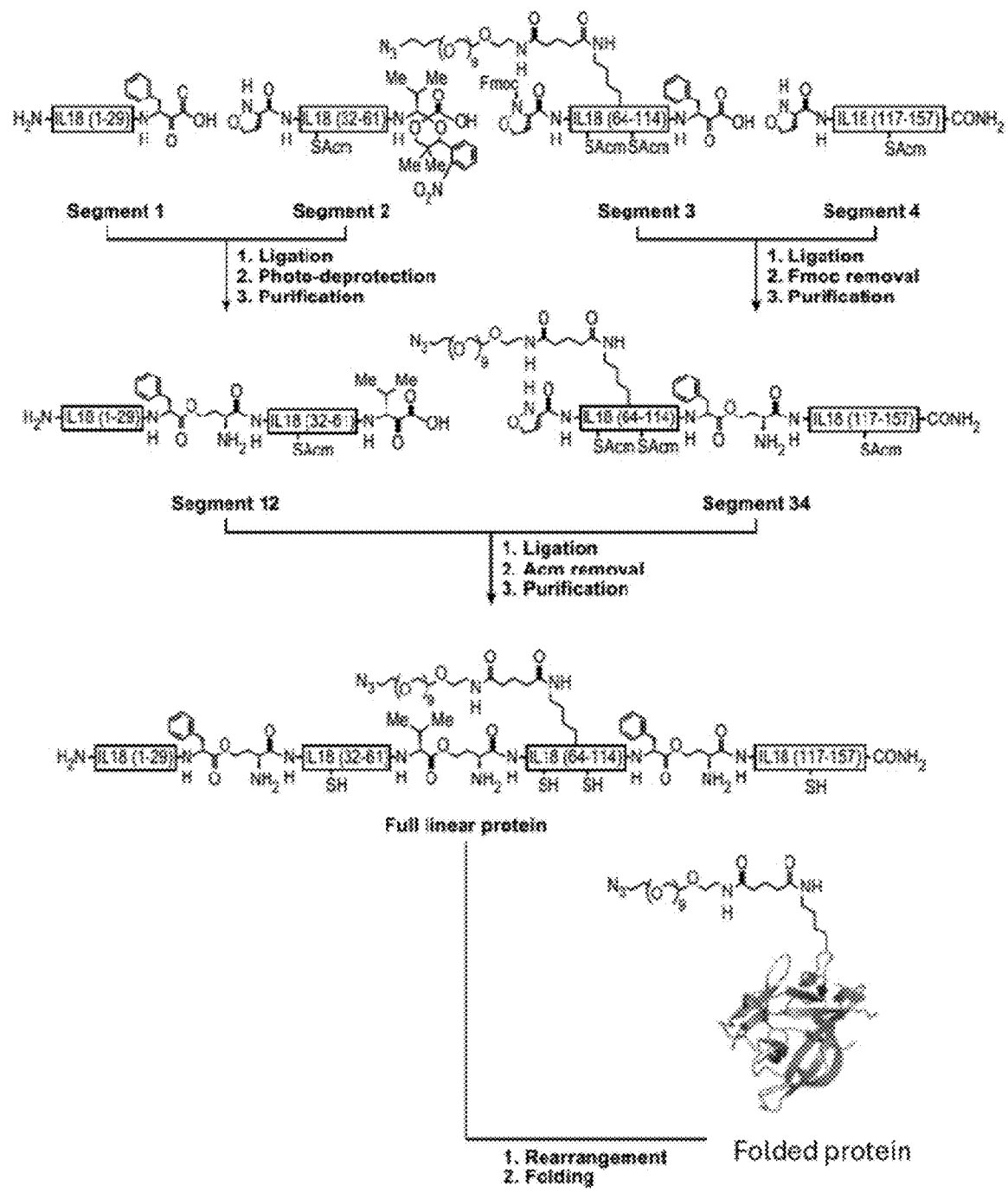
FIG. 5 shows a schematic of a synthetic route which can be used to synthesize an IL-18 polypeptide for conjugation to an antibody.

The activity of IL-18 is balanced by the presence of a high affinity, naturally occurring IL-18 binding protein (IL-18BP). IL-18BP binds IL-18 and neutralizes the biological activity of IL-18. Cell surface IL-18Rα competes with IL-18BP for IL-18 binding. Increased disease severity can be associated with an imbalance of IL-18 to IL-18BP such that levels of free IL-18 are elevated in the circulation. FIG. 4 illustrates the mechanism of action of IL-18, IFNγ production, IL-18BP production, and inhibition of IL-18 activity by IL-18BP. IL-18 induces IFNγ production, which in turn induces IL-18BP production. IL-18BP then competes with IL-18Rα to inhibit IL-18 activity.

In some embodiments, the IL-18 polypeptides of the immunocytokines provided herein display reduced binding to IL-18BP and retain binding to the IL-18 receptor. The IL-18 polypeptides with this property provided herein are able to retain IL-18 receptor signaling activity (including inducing production of IFNγ) even in the presence of IL-18BP. This allows the immunocytokines provided herein to retain IL-18 signaling activity well beyond a short period of time after administration, or upon repeat administrations. In some embodiments, the modified IL-18 polypeptides with this property comprise a modification (e.g., substitution, polymer attachment, or deletion) at one or more amino acid residues which convey this property to the IL-18 polypeptide. Examples of IL-18 polypeptides with this property are provided herein, as well as those otherwise known, such as those described in Patent Cooperation Treaty Publication No. WO2019051015A1, which is hereby incorporated by reference as if set forth herein in its entirety. In addition to IL-18 polypeptides provided herein, these otherwise known IL-18 polypeptides or their analogs may similarly be modified with points of attachment to the linker as provided herein.

Points of Attachment of Chemical Linkers to IL-18 Polypeptides

The immunocytokines provided herein comprise linkers which have a point of attachment to the IL-18 polypeptide. In some embodiments, the linker is a chemical linker. As discussed supra, the linker has another point of attachment to the antibody or antigen binding fragment at any residue as provided herein. The point of attachment to the IL-18 polypeptide is to a residue as provided herein.

In some embodiments, the linker is attached to an amino acid residue of the IL-18 polypeptide. In some embodiments, the linker is attached to any amino acid residue of the IL-18 polypeptide (e.g., at a position corresponding to any one of positions 1-157 of SEQ ID NO: 1). In some embodiments, the linker is attached at a non-terminal residue of the IL-18 polypeptide (e.g., a residue at position corresponding to any one of positions 2-156 of SEQ ID NO: 1). In some embodiments, the linker is attached at a non-terminal residue of the IL-18 polypeptide, wherein the IL-18 polypeptide has been extended or truncated by one or more amino acids relative to SEQ ID NO: 1.

In some embodiments, the linker is attached to the IL-18 polypeptide at a residue in a region comprising residues 2-156, wherein residue position numbering is based on SEQ ID NO: 1 as a reference sequence. In some embodiments, the linker is attached to the IL-18 polypeptide at a residue in a region comprising residues 30-150. In some embodiments, the linker is attached to the IL-18 polypeptide at a residue in a region comprising residues 33-43, residues 60-100, residues 65-75, residues 80-90, residues 85-100, residues 90-110, residues 115-130, residues 120-130, or residues 140-150. In some embodiments, the linker is attached to the IL-18 polypeptide at a residue selected from residue 38, 68, 69, 70, 76, 78, 85, 86, 95, 98, 121, 127, and 144. In some embodiments, the linker is attached to the IL-18 polypeptide at a residue selected from 68, 69, 70, 85, 86, and 98. In some embodiments, the linker is attached to the IL-18 polypeptide at residue 68, 69, or 70. In some embodiments, the linker is attached to the IL-18 polypeptide at residue 85, 86, 95, or 98. In some embodiments, the linker is attached to the IL-18 polypeptide at residue 68. In some embodiments, the linker is attached to the IL-18 polypeptide at residue 69. In some embodiments, the linker is attached to the IL-18 polypeptide at residue 70. In some embodiments, the linker is attached to the IL-18 polypeptide at residue 85. In some embodiments, the linker is attached to the IL-18 polypeptide at residue 86. In some embodiments, the linker is attached to the IL-18 polypeptide at residue 95. In some embodiments, the linker is attached to the IL-18 polypeptide at residue 98.

In some embodiments, the linker is attached to the IL-18 polypeptide at a residue which is known in the art to be compatible with attachment of a polymer to the IL-18 polypeptide without having a profound impact on the bioactivity of the IL-18 polypeptide. Examples of these residues include residues 38, 76, 78, 121, 127, and 144, as described in PCT Pub. No. WO2004091517A2, which is hereby incorporated by reference as if set forth in its entirety.

In some embodiments, the residue to which the linker is attached is a natural amino acid residue. In some embodiments, the residue to which the linker is covalently attached is selected from cysteine, aspartate, asparagine, glutamate, glutamine, serine, threonine, lysine, and tyrosine. In some embodiments, the residue to which the linker is covalently attached is selected from asparagine, aspartic acid, cysteine, glutamic acid, glutamine, lysine, and tyrosine. In some embodiments, the linker is covalently attached to a cysteine. In some embodiments, the linker is covalently attached to a lysine. In some embodiments, the linker is covalently attached to a glutamine. In some embodiments, the linker is covalently attached to an asparagine. In some embodiments, the residue to which the linker is attached is a tyrosine. In some embodiments, the residue to which the linker is attached is the natural amino acid in that position in SEQ ID NO: 1.

In some embodiments, the linker is attached to a different natural amino acid which is substituted at the relevant position. The substitution can be for a naturally occurring amino acid which is more amenable to attachment of additional functional groups (e.g., aspartic acid, cysteine, glutamic acid, lysine, serine, threonine, or tyrosine), a derivative of modified version of any naturally occurring amino acid, or any unnatural amino acid (e.g., an amino acid containing a desired conjugation handle, such as a CLICK chemistry reagent such as an azide, alkyne, etc.). In some embodiments, the linker is covalently attached to site-specifically to a natural amino acid.

In some embodiments, the linker is attached at an unnatural amino acid residue. In some embodiments, the unnatural amino acid residue comprises a conjugation handle. In some embodiments, the conjugation handle facilitates the addition of the linker to the modified IL-18 polypeptide. The conjugation handle can be any of the conjugation handles provided herein. In some embodiments, the linker is covalently attached site-specifically to the unnatural amino acid. Non-limiting examples of amino acid residues comprising conjugation handles can be found, for example, in PCT Pub. Nos. WO2015054658A1, WO2014036492A1, WO2021133839A1 WO2006069246A2, and WO2007079130A2, each of which is incorporated by reference as if set forth in its entirety.

In some embodiments, the linker is covalently attached at residue 68. In some embodiments, the linker is covalently attached at residue C68, C68E, C68D, C68Q, C68K, C68N, or C68Y. In some embodiments, the linker is covalently attached at residue C68. In some embodiments, the linker is covalently attached to an unnatural amino acid at residue 68.

In some embodiments, the linker is covalently attached at residue 69. In some embodiments, the linker is covalently attached at residue E69, E69C, E69D, E69Q, E69K, E69N, or E69Y. In some embodiments, the linker is covalently attached at residue E69. In some embodiments, the linker is covalently attached residue E69C. In some embodiments, the linker is covalently attached to an unnatural amino acid at residue 69.

In some embodiments, the linker is covalently attached at residue 70. In some embodiments, the linker is covalently attached at residue K70, K70C, K70D, K70Q, K70E, K70N, or K70Y. In some embodiments, the linker is covalently attached at residue K70. In some embodiments, the linker is covalently attached residue K70C. In some embodiments, the linker is covalently attached to an unnatural amino acid at residue 70.

In some embodiments, the linker is covalently attached at residue 85. In some embodiments, the linker is covalently attached at residue E85, E85C, E85D, E85Q, E85K, E85N, or E85Y. In some embodiments, the linker is covalently attached at residue E85. In some embodiments, the linker is covalently attached residue E85C. In some embodiments, the linker is covalently attached to an unnatural amino acid at residue 85.

In some embodiments, the linker is covalently attached at residue 86. In some embodiments, the linker is covalently attached at residue M86C, M86D, M86Q, M86K, M86N, M86E, or M86Y. In some embodiments, the linker is covalently attached M86C. In some embodiments, the linker is covalently attached to an unnatural amino acid at residue 86.

In some embodiments, the polymer is covalently attached at residue 95. In some embodiments, the polymer is covalently attached at residue T95, T95C, T95D, T95Q, T95K, T95N, T95E, or T95Y. In some embodiments, the polymer is covalently attached at residue T95C, T95D, T95Q, T95K, T95N, T95E, or T95Y. In some embodiments, the polymer is covalently attached at residue T95C. In some embodiments, the polymer is covalently attached to an unnatural amino acid at residue 95.

In some embodiments, the linker is covalently attached at residue 98. In some embodiments, the linker is covalently attached at residue D98, D98C, D98Q, D98K, D98N, D98E, or D98Y. In some embodiments, the linker is covalently attached at residue D98C. In some embodiments, the linker is covalently attached to an unnatural amino acid at residue 98.

In some embodiments, the linker is covalently attached through a modified natural amino acid. In some embodiments, the modified natural amino acid comprises a conjugation handle. In some embodiments, the linker is covalently attached through a modified amino acid a. In some embodiments, the modified amino acid a is an amino-acid-PEG-azide group. In some embodiments, the modified amino acid a is a glutamate, aspartate, lysine, cysteine, or tyrosine modified to incorporate an azide group linked to the amino acid through a PEG spacer. In some embodiments, the modified amino acid a has a structure selected from:

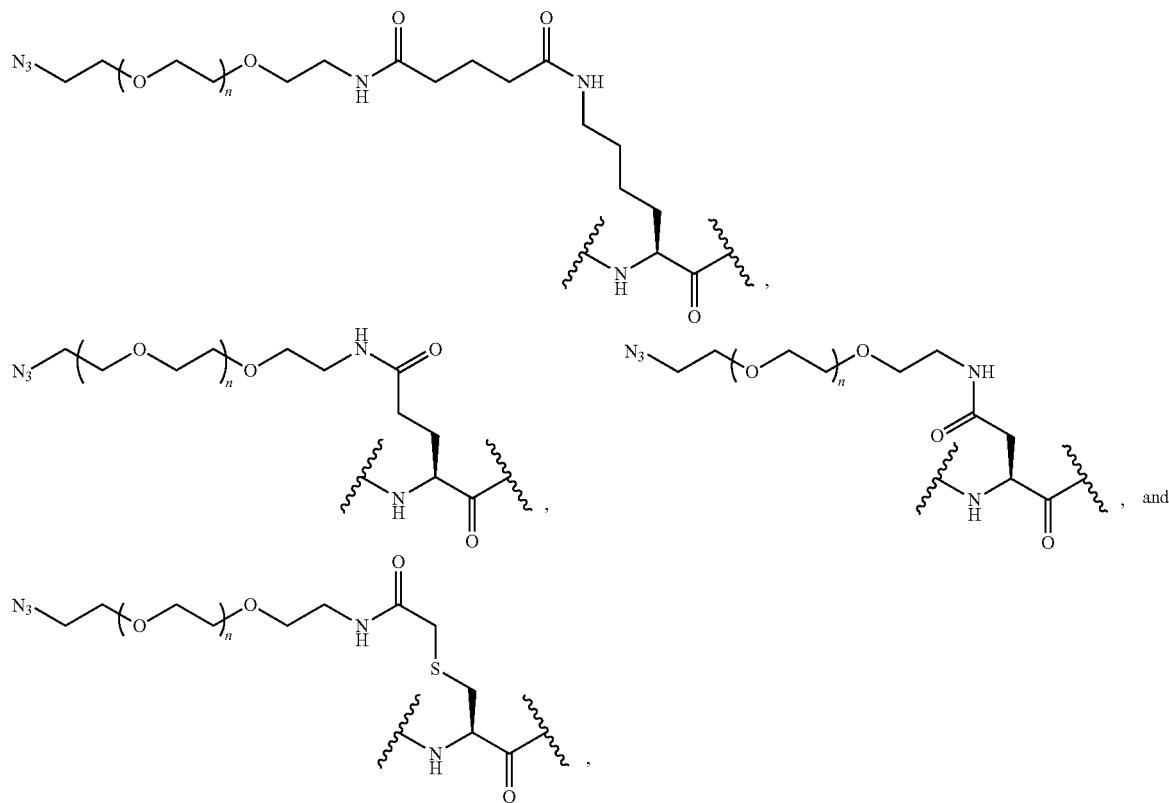

wherein each n is independently an integer from 1-30. In some embodiments, n is an integer from 1-20, 1-10, 2-30, 2-20, 2-10, 5-30, 5-20, or 5-10. In some embodiments, n is 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some embodiments, n is 10. In some embodiments, n is 8. In some embodiments, n is 6. In some embodiments, n is 12. The modified amino acid a can be incorporated at any point of attachment of the IL-18 polypeptide as provided herein. In some embodiments, the modified amino acid a is located at a position on the modified IL-18 polypeptide selected from residue 68, residue 69, residue 70, residue 85, residue 86, residue 95, or residue 98.

Where IL-18 polypeptides contain unnatural amino acids or modified natural amino acids (e.g., those provided herein for purposes of conjugation), these amino acids may be incorporated into the IL-18 polypeptides using many techniques known in the art for introduction such modifications. For example, recombinant proteins with unnatural amino acids can be made using methods as described in Patent Cooperation Treaty Publication Nos. WO2016115168, WO2002085923, WO2005019415, and WO2005003294.

Alternatively or in combination, unnatural or modified natural amino acids can be incorporated into chemically synthesized proteins during synthesis.

Modifications to IL-18 Polypeptides

In some embodiments, the IL-18 polypeptide of the immunocytokine comprises one or more modifications to that of SEQ ID NO: 1. The modifications provided herein are in addition to any modification at the point of attachment as discussed supra. In some embodiments, the residue position numbering of the modified IL-18 polypeptide is based on SEQ ID NO: 1 as a reference sequence.

Modifications to the IL-18 polypeptide described herein encompass mutations, addition of various functionalities, deletion of amino acids, addition of amino acids, or any other alteration of the wild-type version of the protein or protein fragment. Functionalities which may be added to polypeptides include polymers, linkers, alkyl groups, detectable molecules such as chromophores or fluorophores, reactive functional groups, or any combination thereof. In some embodiments, functionalities are added to individual amino acids of the polypeptides. In some embodiments, functionalities are added site-specifically to the polypeptides.

In some embodiments, the IL-18 polypeptide of the immunocytokine comprise one or more modifications in addition to a modification needed to attach the linker to the relevant residue of the IL-18 polypeptide (e.g., an amino acid substitution at a residue to which the linker is not attached). In some embodiments, the modification is in the range of amino acid residues 1-127, based on the sequence of human IL-18$^{37\text{-}193}$ (SEQ ID NO: 1). SEQ ID NO: 1 reflects the bioactive form of IL-18. Endogenously, IL-18 is initially expressed with an additional 36 amino acid segment at the N-terminus which is cleaved by caspases to mediate biologic activity.

In some embodiments, the IL-18 polypeptide of the immunocytokine described herein contain 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more modified amino acid residues.

In some embodiments, the IL-18 polypeptide of the immunocytokine comprises an amino acid sequence having at least 80%, 85%, 90%, 91%, 92%, 93%, 94%, 95%, 96%, 97%, 98%, or 99% sequence identity to the sequence set forth in SEQ ID NO: 1.

In some embodiments, the IL-18 polypeptide of the immunocytokine provided herein comprises an amino acid sequence of any one of SEQ ID NOs: 2-203 provided herein. In some embodiments, the IL-18 polypeptide comprises an amino acid sequence at least 85% identical to the sequence of any one of SEQ ID NOs: 2-203. In some embodiments, the IL-18 polypeptide comprises an amino acid sequence of SEQ ID NO: 30. In some embodiments, the IL-18 polypeptide comprises an amino acid sequence at least 85% identical to the sequence of SEQ ID NO: 30. In some embodiments, the IL-18 polypeptide comprises an amino acid sequence of SEQ ID NO: 59. In some embodiments, the IL-18 polypeptide comprises an amino acid sequence at least 85% identical to the sequence of SEQ ID NO: 59.

In some embodiments, the IL-18 polypeptide of the immunocytokine described herein comprises at least 1, at least 2, at least 3, at least 4, at least 5, at least 6, at least 7, or at least 9 amino acid substitutions, wherein the amino acid substitutions are relative to SEQ ID NO: 1. In some embodiments, the IL-18 polypeptide comprises 1 to 9 amino acid substitutions. In some embodiments, the IL-18 polypeptide comprises 1 or 2 amino acid substitutions, 1 to 3 amino acid substitutions, 1 to 4 amino acid substitutions, 1 to 5 amino acid substitutions, 1 to 6 amino acid substitutions, 1 to 7 amino acid substitutions, 1 to 8 amino acid substitutions, 2 to 3 amino acid substitutions, 2 to 4 amino acid substitutions, 2 to 5 amino acid substitutions, 2 to 6 amino acid substitutions, 2 to 7 amino acid substitutions, 2 to 8 amino acid substitutions, 2 to 9 amino acid substitutions 3 or 4 amino acid substitutions, 3 to 5 amino acid substitutions, 3 to 6 amino acid substitutions, 3 to 7 amino acid substitutions, 3 to 9 amino acid substitutions, 4 or 5 amino acid substitutions, 4 to 6 amino acid substitutions, 4 to 7 amino acid substitutions, 4 to 9 amino acid substitutions, 5 or 6 amino acid substitutions, 5 to 7 amino acid substitutions, 5 to 9 amino acid substitutions, 6 or 7 amino acid substitutions, 6 to 9 amino acid substitutions, or 7 to 9 amino acid substitutions. In some embodiments, the IL-18 polypeptide comprises 3 amino acid substitutions, 4 amino acid substitutions, 5 amino acid substitutions, 6 amino acid substitutions, 7 amino acid substitutions, or 9 amino acid substitutions. In some embodiments, the IL-18 polypeptide comprises at most 4 amino acid substitutions, 5 amino acid substitutions, 6 amino acid substitutions, 7 amino acid substitutions, or 9 amino acid substitutions.

In some embodiments, the IL-18 polypeptide comprising of the immunocytokine described herein comprises at least 1, at least 2, at least 3, at least 4, at least 5, at least 6, at least 7, or at least 9 natural amino acid substitutions, wherein the natural amino acid substitutions are relative to SEQ ID NO: 1. In some embodiments, the IL-18 polypeptide comprises 1 to 9 natural amino acid substitutions. In some embodiments, the IL-18 polypeptide comprises 1 or 2 natural amino acid substitutions, 1 to 3 natural amino acid substitutions, 1 to 4 natural amino acid substitutions, 1 to 5 natural amino acid substitutions, 1 to 6 natural amino acid substitutions, 1 to 7 natural amino acid substitutions, 1 to 8 natural amino acid substitutions, 2 to 3 natural amino acid substitutions, 2 to 4 natural amino acid substitutions, 2 to 5 natural amino acid substitutions, 2 to 6 natural amino acid substitutions, 2 to 7 natural amino acid substitutions, 2 to 8 natural amino acid substitutions, 2 to 9 natural amino acid substitutions, 3 or 4 natural amino acid substitutions, 3 to 5 natural amino acid substitutions, 3 to 6 natural amino acid substitutions, 3 to 7 natural amino acid substitutions, 3 to 9 natural amino acid substitutions, 4 or 5 natural amino acid substitutions, 4 to 6 natural amino acid substitutions, 4 to 7 amino acid substitutions, 4 to 9 natural amino acid substitutions, 5 or 6 natural amino acid substitutions, 5 to 7 natural amino acid substitutions, 5 to 9 natural amino acid substitutions, 6 or 7 natural amino acid substitutions, 6 to 9 natural amino acid substitutions, or 7 to 9 natural amino acid substitutions. In some embodiments, the IL-18 polypeptide comprises 3 natural amino acid substitutions, 4 natural amino acid substitutions, 5 amino acid substitutions, 6 natural amino acid substitutions, 7 natural amino acid substitutions, or 9 natural amino acid substitutions. In some embodiments, the IL-18 polypeptide comprises at most 4 natural amino acid substitutions, 5 natural amino acid substitutions, 6 natural amino acid substitutions, 7 natural amino acid substitutions, or 9 natural amino acid substitutions. In some embodiments, the IL-18 polypeptide further comprises up to 10 non-canonical amino acid substitutions. In some embodiments, the IL-18 polypeptide comprises 1, 2, 3, 4, 5, 6, 7, 8, 9 or 10 unnatural amino acid substitutions. In some embodiments, the IL-18 polypeptide further comprises unnatural amino acid substitutions at residues M33, M51, N60, M86, M113, and/or M150. In some embodiments, the unnatural amino acid residues substituted for the methionines are each independently norleucine or O-methyl-homoserine. In some embodiments, the IL-18 polypeptide further unnatural amino acid substitutions at residues 31, 75, and 116. In some embodiments, the IL-18 polypeptide further comprises homoserine (Hse) 31, Hse 75, and Hse 116. In some embodiments, the IL-18 polypeptide further unnatural amino acid substitutions at residues 31, 63, and 116. In some embodiments, the IL-18 polypeptide further comprises homoserine (Hse) 31, Hse 63, and Hse 116. In some embodiments, the modified IL-18 polypeptide further unnatural amino acid substitutions at residues 31, 63, 75, and 116. In some embodiments, the modified IL-18 polypeptide further comprises homoserine (Hse) 31, Hse 63, Hse 75, and Hse 116. In some embodiments, the modified IL-18 polypeptide further unnatural amino acid substitutions at residues 31, 67, 75, and 116. In some embodiments, the modified IL-18 polypeptide further comprises homoserine (Hse) 31, Hse 67, Hse 75, and Hse 116. In some embodiments, the modified IL-18 polypeptide further unnatural amino acid substitutions at residues 31, 57, 75, and 116. In some embodiments, the modified IL-18 polypeptide further comprises homoserine (Hse) 31, Hse 57, Hse 75, and Hse 116. In some embodiments, the modified IL-18 polypeptide further unnatural amino acid substitutions at residues 31, 50, 75, and 116. In some embodiments, the modified IL-18 polypeptide further comprises homoserine (Hse) 31, Hse 50, Hse 75, and Hse 116. In some embodiments, the modified IL-18 polypeptide further unnatural amino acid substitutions at residues 31, 50, 75, and 121. In some embodiments, the modified IL-18 polypeptide further comprises homoserine (Hse) 31, Hse 50, Hse 75, and Hse 121.

In some embodiments, the IL-18 polypeptide of the immunocytokine described herein comprises at least 1, at least 2, at least 3, at least 4, at least 5, at least 6, at least 7, or at least 9 amino acid substitutions, wherein the amino acid substitutions are relative to any one of SEQ ID NOs: 68, 92, 116, 140, or 170. In some embodiments, a modified IL-18 polypeptide described herein comprises at least 1, at least 2, at least 3, at least 4, at least 5, at least 6, at least 7, or at least 9 additional amino acid substitutions, wherein the amino acid substitutions are relative to any one of SEQ ID NOs: 68, 92, 116, 140, or 170. In some embodiments, the IL-18 polypeptide comprises 1 to 9 amino acid substitutions. In some embodiments, the IL-18 polypeptide comprises 1 or 2 amino acid substitutions, 1 to 3 amino acid substitutions, 1 to 4 amino acid substitutions, 1 to 5 amino acid substitutions, 1 to 6 amino acid substitutions, 1 to 7 amino acid substitutions, 1 to 8 amino acid substitutions, 2 to 3 amino acid substitutions, 2 to 4 amino acid substitutions, 2 to 5 amino acid substitutions, 2 to 6 amino acid substitutions, 2 to 7 amino acid substitutions, 2 to 8 amino acid substitutions, 2 to 9 amino acid substitutions 3 or 4 amino acid substitutions, 3 to 5 amino acid substitutions, 3 to 6 amino acid substitutions, 3 to 7 amino acid substitutions, 3 to 9 amino acid substitutions, 4 or 5 amino acid substitutions, 4 to 6 amino acid substitutions, 4 to 7 amino acid substitutions, 4 to 9 amino acid substitutions, 5 or 6 amino acid substitutions, 5 to 7 amino acid substitutions, 5 to 9 amino acid substitutions, 6 or 7 amino acid substitutions, 6 to 9 amino acid substitutions, or 7 to 9 amino acid substitutions. In some embodiments, the IL-18 polypeptide comprises 3 amino acid substitutions, 4 amino acid substitutions, 5 amino acid substitutions, 6 amino acid substitutions, 7 amino acid substitutions, or 9 amino acid substitutions. In some embodiments, the IL-18 polypeptide comprises at most 4 amino acid substitutions, 5 amino acid substitutions, 6 amino acid substitutions, 7 amino acid substitutions, or 9 amino acid substitutions.

In some embodiments, one modification is at amino acid residue 6. In some embodiments, one modification is in the range of amino acid residues 53-63. In some embodiments, one modification is at amino acid residue 53. In some embodiments, one modification is at amino acid residue 63.

In some embodiments, the IL-18 polypeptide comprises at least one modification to the amino acid sequence of SEQ ID NO: 1 selected from: Y01X, F02X, E06X, S0X, V11X, D17X, C38X, M51X, K53X, D54X, S55X, T63X, C68X, C76X, AND C127X, wherein each X is independently a natural or non-natural amino acid. In some embodiments, the IL-18 polypeptide further comprises an amino acid substitution at the point of attachment of the linker, such as residue 69, residue 70, residue 85, residue 86, residue 95, or residue 98. In some embodiments, the IL-18 polypeptide comprises at least one modification to the amino acid sequence of SEQ ID NO: 1 selected from: Y01G, F02A, E06K, S10T, V11I, D17N, C38S, C38A, C38Q, M51G, K53A, D54A, S55A, T63A, C68S, C68A, C76S, C76A, C127A, and C127S. In some embodiments, the IL-18 polypeptide further comprises an amino acid substitution at the point of attachment of the linker, such as E69C, K70C, E85C, M86C, T95C, or D98C.

In one aspect, described herein is a modified interleukin-18 (IL-18) polypeptide comprising E06K and K53A, wherein residue position numbering of the IL-18 polypeptide is based on SEQ ID NO: 1 as a reference sequence. In some embodiments, the IL-18 polypeptide further comprises V11I. In some embodiments, the IL-18 polypeptide further comprises T63A. In some embodiments, the IL-18 polypeptide further comprises at least one of Y01X, S55X, F02X, D54X, C38X, C68X, E69X, K70X, C76X, or C127X, wherein each X is independently an amino acid or an amino acid derivative. In some embodiments, the IL-18 polypeptide further comprises at least one of Y01G, S55A, F02A, D54A, C38S, C38A, C38Q, C68S, C68A, E69C, K70C, C76S, C76A, C127S, or C127A. In some embodiments, the IL-18 polypeptide further comprises an amino acid substitution at the point of attachment of the linker, such as residue 69, residue 70, residue 85, residue 86, residue 95, or residue 98.

In some embodiments, the IL-18 peptide comprises at least one modification to the amino acid sequence of SEQ ID NO: 1, wherein the modification is E06X, V11X, K53X, S55X, or T63X, wherein X is a natural or non-natural amino acid. In some embodiments, the IL-18 peptide comprises at least two modifications to the amino acid sequence of SEQ ID NO: 1, wherein the modifications comprise E06X and K53X; E06X and S55X; K53X and S55X; E06X and T63X; or K53X and T63X, wherein X is a natural or non-natural amino acid. In some embodiments, the IL-18 peptide comprises at least three modifications to the amino acid sequence of SEQ ID NO: 1, wherein the modifications comprise E06X, K53X, and S55X; or E06X, K53X, and T63X, wherein X is a natural or non-natural amino acid. In some embodiments, the IL-18 peptide comprises at least four modifications to the amino acid sequence of SEQ ID NO: 1, wherein the modifications comprise E06X, K53X, S55X, and T63X; E06X, K53X, S55X, and Y01X; E06X, K53X, S55X, and F02X; E06X, K53X, S55X, and D54X; E06X, K53X, S55X, and M51X; or C38X, C68X, C76X, and C127X, wherein X is a natural or non-natural amino acid. In each embodiment wherein a plurality of amino acids residues are replaced with a natural or non-natural amino acid X, each X is independently the same or a different amino acid.

In some embodiments, the IL-18 peptide comprises at least one modification to the amino acid sequence of SEQ ID NO: 1, wherein the modification is E06K, V11, K53A, S55A, or T63A. In some embodiments, the IL-18 peptide comprises at least two modifications to the amino acid sequence of SEQ ID NO: 1, wherein the modifications comprise E06K and K53A; E06K and S55A; K53A and S55A; E06K and T63A; or K53A and T63A. In some embodiments, the IL-18 peptide comprises at least three modifications to the amino acid sequence of SEQ ID NO: 1, wherein the modifications comprise E06K, K53A, and S55A; E06K, V11I, and K53A; E06K, C38A, and K53A; or E06K, K53A, and T63A. In some embodiments, the IL-18 peptide comprises at least four modifications to the amino acid sequence of SEQ ID NO: 1, wherein the modifications comprise E06K, K53A, S55A, and T63A; E06K, K53A, S55A, and Y01G; E06K, K53A, S55A, and F02A; E06K, K53A, S55A, and D54A; E06K, K53A, S55A, and M51G; or C38S, C68S, C76S, and C127S. In some embodiments, the IL-18 peptide comprises at least six modifications to the amino acid sequence of SEQ ID NO: 1, wherein the modifications comprise E06K, K53A, C38S, C68S, C76S, and C127S; or K53A, T63A, C38S, C68S, C76S, and C127S. In some embodiments, the modified IL-18 polypeptide comprises at least seven modifications to the sequence of SEQ ID NO: 1, wherein the seven modifications comprise E6K, V11, C38A, K53A, T63A, C76A, C127A. In some embodiments, the IL-18 peptide comprises at least eight modifications to the amino acid sequence of SEQ ID NO: 1, wherein the modifications comprise Y01G, F02A, E06K, M51G, K53A, D54A, S55A, and T63A. In some embodiments, the IL-18 peptide comprises at least eight modifications to the amino acid sequence of SEQ ID NO: 1, wherein the modifications comprise Y01G, F02A, E06K, M51G, K53A, D54A, S55A, and T63A.

In one aspect, provided herein, is a modified IL-18 polypeptide as provided herein, further comprising E06K and K53A, wherein residue position numbering of the IL-18 polypeptide is based on SEQ ID NO: 1 as a reference sequence. In some embodiments, the IL-18 polypeptide comprises an amino acid sequence at least 80%, at least 85%, at least 90%, at least 95%, or at least 98% identical to the amino acid sequence of SEQ ID NO: 30. In some embodiments, the IL-18 polypeptide comprises an amino acid sequence at least 80%, at least 85%, at least 90%, at least 95%, or at least 98% identical to the amino acid sequence of SEQ ID NO: 59. In some embodiments, the IL-18 polypeptide further comprises an amino acid substitution at one or more cysteine residues. In some embodiments, the IL-18 polypeptide comprises one or more cysteines substituted with either serine or alanine. In some embodiments, the IL-18 polypeptide comprise amino acid substitutions at each cysteine residue of SEQ ID NO: 1. In some embodiments, each cysteine residue is substituted with serine or alanine. In some embodiments, the IL-18 polypeptide comprises amino acid substitutions at 1, 2, 3, 4, 5, or 6 methionine residues. In some embodiments, each substitution at a methionine residue is for an O-methyl-L-homoserine residue or a norleucine residue. In some embodiments, each methionine residue is substituted with an O-methyl-L-homoserine residue. In some embodiments, the IL-18 polypeptide comprises homoserine residues at positions 31, 116, and one of 63 and 75. In some embodiments, the modified TL-18 polypeptide comprises homoserine residues at positions 31, 116, 75, and one of 50, 57, 63, and 67. In some embodiments, the modified IL-18 polypeptide comprises homoserine residues at positions 31, 121, 75, and one of 50, 57, 63, and 67.

In some embodiments, the IL-18 polypeptide comprises a polypeptide sequence having at least about 80%, at least about 85%, at least about 90%, at least about 95%, at least about 98%, at least about 99%, or about 100% sequence identity to SEQ ID NO: 2-12. In some embodiments, the IL-18 polypeptide comprises a polypeptide sequence having at least about 80%, at least about 85%, at least about 90%, at least about 95%, at least about 98%, at least about 99%, or about 100% sequence identity to SEQ ID NO: 13-23. In some embodiments, the modified IL-18 polypeptide comprises a polypeptide sequence having at least about 80%, at least about 85%, at least about 90%, at least about 95%, at least about 98%, or at least about 99% sequence identity to SEQ ID NO: 24-33 In some embodiments, the polypeptide sequence is at least about 80% identical to SEQ ID NO: 30 or SEQ ID NO: 59. In some embodiments, the polypeptide sequence is at least about 80% identical to SEQ ID NO: 30. In some embodiments, the polypeptide sequence is at least about 90% identical to SEQ ID NO: 30. In some embodiments, the polypeptide sequence is at least about 95% identical to SEQ ID NO: 30. In some embodiments, the polypeptide sequence is identical to SEQ ID NO: 30. In some embodiments, the polypeptide sequence is at least about 80% identical to SEQ ID NO: 59. In some embodiments, the polypeptide sequence is at least about 90% identical to SEQ ID NO: 59. In some embodiments, the polypeptide sequence is at least about 95% identical to SEQ ID NO: 59. In some embodiments, the IL-18 polypeptide is recombinant. In some embodiments, the IL-18 polypeptide is one provided in Table 2. In some embodiments, the IL-18 polypeptide is one described in Table 3.

Biological Activity

In some embodiments, the immunocytokine composition exhibits one or more activities associated with the antibody or antigen binding fragment and/or an IL-18 polypeptide.

In some embodiments, the immunocytokine composition exhibits an ability to bind to the IL-18 receptor. In some embodiments, the immunocytokine composition exhibits an ability to bind to the IL-18 receptor which is comparable to WT IL-18. In some embodiments, immunocytokine composition exhibits an ability to bind to the IL-18 receptor (IL-18Rαβ) which is reduced by at most 2-fold, at most 5-fold, at most 10-fold, at most 20-fold, at most 50-fold, at most 100-fold, at most 200-fold, at most 300-fold, at most 400-fold, or at most 1000-fold compared to WT IL-18. In some embodiments, the immunocytokine composition exhibits an enhanced ability to bind the IL-18Rαβ. In some embodiments, the immunocytokine composition exhibits an ability to bind to the IL-18Rαβ which is increased by at least 2-fold, at least 3-fold, at least 5-fold, or at least 10-fold compared to WT IL-18.

In some embodiments, immunocytokine composition exhibits an ability to stimulate production of IFNγ upon contact with a cell (e.g., an immune cell, such as an NK cell). In some embodiments, the ability of the immunocytokine composition to stimulate IFNγ production is somewhat reduced compared to WT IL-18. In some embodiments, a half-maximal effective concentration ($EC_{50}$) of the ability of the immunocytokine composition to stimulate production of IFNγ is at most 100-fold higher than, at most 50-fold higher than, at most 20-fold higher than, at most 10-fold higher than, at most 5-fold higher than, or at most 2-fold higher than that of a WT IL-18. In some embodiments, the ability of the immunocytokine composition to stimulate IFNγ production is enhanced compared to WT IL-18. In some embodiments, a half-maximal effective concentration ($EC_{50}$) of the ability of the immunocytokine composition to stimulate production of IFNγ is at least 5-fold lower than, at least 10-fold lower than, at least 20-fold lower than, at least 50-fold lower than, at least 75-fold lower than, or at least 100-fold higher than that of a WT IL-18.

In some embodiments, the immunocytokine composition exhibits an ability to stimulate production of IFNγ upon contact with a cell (e.g., an immune cell, such as an NK cell) which is only somewhat reduced as compared to the IL-18 polypeptide not comprised in the immunocytokine composition (e.g., unconjugated IL-18 polypeptide). In some embodiments, the $EC_{50}$ of IFNγ stimulation is at most 5-fold greater than, at most 10-fold greater than, at most 50-fold greater than, or at most 100-fold greater than that of the IL-18 polypeptide not comprised in the immunocytokine composition. In some embodiments, the immunocytokine composition exhibits an ability to induce IFNγ production in a cell as measured by half-maximal effective concentration ($EC_{50}$) which is within about 100-fold of the corresponding IL-18 polypeptide not comprised in the immunocytokine composition. In some embodiments, the immunocytokine composition exhibits a lower $EC_{50}$ than WT IL-18. In some embodiments, the immunocytokine composition exhibits a lower $EC_{50}$ than WT IL-18 by at least 2-fold, 5-fold, 10-fold, 20-fold, 30-fold, 50-fold, or 100-fold.

In some embodiments, the immunocytokine composition exhibits a reduced ability to bind IL-18 binding protein (IL-18BP). In some embodiments, the ability of immunocytokine composition to bind IL-18BP is reduced by at least 2-fold, at least 5-fold, at least 10-fold, at least 20-fold, at least 30-fold, at least 50-fold, or at least 100-fold compared to WT IL-18. In some embodiments, the immunocytokine composition does not display any substantial ability to bind IL-18 BP.

In some embodiments, the immunocytokine composition exhibits a reduced ability to have its IFNγ production stimulatory activity inhibited by IL-18BP. In some embodiments, the ability of the immunocytokine composition to be inhibited by IL-18BP is measured as a half maximal inhibitory concentration ($IC_{50}$). In some embodiments, the immunocytokine composition exhibits an $IC_{50}$ by IL-18BP that is at least 2-fold higher than, at least 5-fold higher than, at least 10-fold higher than, at least 15-fold higher than, at least 20-fold higher than, at least 25-fold higher than, at least 30-fold higher than, at least 40-fold higher than, or at least 50-fold higher than an $IC_{50}$ of WT IL-18's inhibition by IL-18BP. In some embodiments, the immunocytokine composition exhibits an $IC_{50}$ by IL-18BP that is at least 100-fold higher than an $IC_{50}$ of WT IL-18's inhibition by IL-18BP. In some embodiments, the immunocytokine composition exhibits an $IC_{50}$ by IL-18BP that is at least 200-fold higher than an $IC_{50}$ of WT IL-18's inhibition by IL-18BP. In some embodiments, the immunocytokine composition exhibits an $IC_{50}$ by IL-18BP that is at least 500-fold higher than an $IC_{50}$ of WT IL-18's inhibition by IL-18BP. In some embodiments, the immunocytokine composition exhibits an $IC_{50}$ by IL-18BP that is at least 1000-fold higher than an $IC_{50}$ of WT IL-18's inhibition by IL-18BP.

In some embodiments, the immunocytokine composition retains binding associated with the antibody or antigen binding fragment. In some embodiments, the immunocytokine composition retains binding to the antigen of the antibody or antigen binding fragment. In some embodiments, the immunocytokine composition exhibits binding affinity ($K_D$) to the antigen of the antibody which is within 5-fold of the binding affinity of the antibody not attached to the IL-18 polypeptide. In some embodiments, the immunocytokine composition exhibits binding affinity ($K_D$) to the antigen of the antibody which is within 2.5-fold of the binding affinity of the antibody not attached to the IL-18 polypeptide. In some embodiments, the binding is determined by ELISA. In some embodiments, the binding is determined by BLI.

In some embodiments, the immunocytokine composition retains binding to one or more Fc receptors associated with the antibody or antigen binding fragment. In some embodiments, the Fc receptor is selected from FcRn, CD64, CD32a, CD16, and CD32b, or any combination thereof. In some embodiments, the immunocytokine composition exhibits a binding affinity ($K_D$) to at least one Fc receptor which is within 10-fold of the binding affinity of the antibody not attached to the IL-18 polypeptide. In some embodiments, the immunocytokine composition exhibits a binding affinity ($K_D$) to at least one Fc receptor which is less than 10-fold higher, less than 5-fold higher, less than 4-fold higher, less than 3-fold higher, less than 2-fold higher, or less than the binding affinity of the antibody not attached to the IL-18 polypeptide. In some embodiments, the immunocytokine composition exhibits a binding affinity ($K_D$) to each of FcRn, CD64, CD32a, CD16, and CD32B which is less than 10-fold higher, less than 5-fold higher, less than 4-fold higher, less than 3-fold higher, less than 2-fold higher, or less than the binding affinity of the antibody not attached to the IL-18 polypeptide. In some embodiments, the immunocytokine composition exhibits a binding affinity ($K_D$) to each of FcRn, CD64, CD32a, CD16, and CD32B which is within 10-fold of the binding affinity of the antibody not attached to the IL-18 polypeptide. In some embodiments, the immunocytokine composition exhibits a binding affinity ($K_D$) to each of FcRn, CD64, CD32a, CD16, and CD32B which is within 20-fold of the binding affinity of the antibody not attached to the IL-18 polypeptide. In some embodiments, the immunocytokine composition exhibits a binding affinity ($K_D$) to each of FcRn, CD64, CD32a, CD16, and CD32B which is within 50-fold of the binding affinity of the antibody not attached to the IL-18 polypeptide. In some embodiments, the immunocytokine composition exhibits a binding affinity ($K_D$) to each of FcRn, CD64, CD32a, CD16, and CD32B which is within 100-fold of the binding affinity of the antibody not attached to the IL-18 polypeptide.

In some embodiments, the immunocytokine composition exhibits synergistic efficacy owing to the presence of both molecules in one molecule. In some embodiments, the immunocytokine composition exhibits enhanced activity compared to either molecule alone. In some embodiments, the immunocytokine composition exhibits enhanced anti-tumor growth inhibition compared to the antibody alone. In some embodiments, the immunocytokine composition exhibits enhanced anti-tumor growth inhibition compared to the antibody and the IL-18 polypeptide administered in combination. In some embodiments, the IL-18 polypeptide is administered as a half-life extended version (e.g., PEGylated, attached to an Fc region (e.g., an Fc fusion), or attached to a negative control antibody). In some embodiments, the immunocytokine composition exhibits similar or enhanced antitumor activity at the same concentration as the antibody administered alone. In some embodiments, the immunocytokine composition exhibits similar or enhanced antitumor activity when administered at a dose which is less that 0.5-fold, 0.25-fold, or 0.1-fold the dose of the antibody alone.

Orthogonal Payloads

In one non-limiting instant, the antibody/IL-18 immunocytokines of the disclosure can comprise dual orthogonal payloads. The antibody/IL-18 immunocytokines can comprise an antibody, one IL-18 polypeptide, and one payload linked to the antibody by a chemical orthogonal linking group. The orthogonal payload can be an amino acid, amino acid derivative, peptide, protein, cytokine, alkyl group, aryl or heteroaryl group, therapeutic small molecule drug, polyethylene glycol (PEG) moiety, lipid, sugar, biotin, biotin derivative, deoxyribonucleic acid (DNA), ribonucleic acid (RNA), or peptide nucleic acid (PNA), any of which is substituted, unsubstituted, modified, or unmodified. In some embodiments, the orthogonal payload is a therapeutic small molecule. In some embodiments, the orthogonal payload is a PEG moiety. In some embodiments, the orthogonal payload is an additional cytokine such as, for example, IL-7 or IL-2. In one exemplary instance, human IL-7 has an amino acid sequence of DCDIEGKDGKQYESVLMVSIDQLLDSMKEIGSNCLNNEFNFFKRHICDANKEGMFLFRAARKLRQFLKMNSTGDFDLHLLKVSEGTTILLNCTGQVKGRKPAALGEAQPTKSLEENKSLKEQKKLNDLCFLKRLLQEIKTCWNKILMGTKEH (SEQ ID NO: 210), or is a modified human IL-7 (e.g., an IL-7 having at least about 80%, 85%, 90%, 91%, 92%, 93%, 94%, 95%, 96%, 97%, 98%, or 99% sequence identity to human IL-7). In one exemplary instance, human IL-2 has an amino acid sequence of APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLNR WITFCQSIISTLT (SEQ ID NO: 211), or is a modified human IL-2 (e.g., an IL-2 having at least about 80%, 85%, 90%, 91%, 92%, 93%, 94%, 95%, 96%, 97%, 98%, or 99/6 sequence identity to human IL-2).

Compositions

In one aspect, provided herein is a pharmaceutical composition comprising an antibody linked to a modified IL-18 polypeptide described herein; and a pharmaceutically acceptable carrier or excipient. In some embodiments, the pharmaceutical composition further comprises one or more excipients, wherein the one or more excipients include, but are not limited to, a carbohydrate, an inorganic salt, an antioxidant, a surfactant, a buffer, or any combination thereof. In some embodiments the pharmaceutical composition further comprises one, two, three, four, five, six, seven, eight, nine, ten, or more excipients, wherein the one or more excipients include, but are not limited to, a carbohydrate, an inorganic salt, an antioxidant, a surfactant, a buffer, or any combination thereof.

In some embodiments, the pharmaceutical composition further comprises a carbohydrate. In certain embodiments, the carbohydrate is selected from the group consisting of fructose, maltose, galactose, glucose, D-mannose, sorbose, lactose, sucrose, trehalose, cellobiose raffinose, melezitose, maltodextrins, dextrans, starches, mannitol, xylitol, maltitol, lactitol, xylitol, sorbitol (glucitol), pyranosyl sorbitol, myo-inositol, cyclodextrins, and combinations thereof.

Alternately, or in addition, the pharmaceutical composition further comprises an inorganic salt. In certain embodiments, the inorganic salt is selected from the group consisting of sodium chloride, potassium chloride, magnesium chloride, calcium chloride, sodium phosphate, potassium phosphate, sodium sulfate, or combinations thereof.

Alternately, or in addition, the pharmaceutical composition further comprises an antioxidant. In certain embodiments, the antioxidant is selected from the group consisting of ascorbyl palmitate, butylated hydroxyanisole, butylated hydroxytoluene, potassium metabisulfite, propyl gallate, sodium metabisulfite, sodium thiosulfate, vitamin E, 3,4-dihydroxybenzoic acid, and combinations thereof.

Alternately, or in addition, the pharmaceutical composition further comprises a surfactant. In certain embodiments, the surfactant is selected from the group consisting of polysorbates, sorbitan esters, lipids, phospholipids, phosphatidylethanolamines, fatty acids, fatty acid esters, steroids, EDTA, zinc, and combinations thereof.

Alternately, or in addition, the pharmaceutical composition further comprises a buffer. In certain embodiments, the buffer is selected from the group consisting of citric acid, sodium phosphate, potassium phosphate, acetic acid, ethanolamine, histidine, amino acids, tartaric acid, succinic acid, fumaric acid, lactic acid, tris, HEPES, or combinations thereof.

In some embodiments, the pharmaceutical composition is formulated for parenteral or enteral administration. In some embodiments, the pharmaceutical composition is formulated for intravenous (IV) or subcutaneous (SQ) administration. In some embodiments, the pharmaceutical composition is in a lyophilized form.

In one aspect, described herein is a liquid or lyophilized composition that comprises a described antibody or antigen binding fragment linked to a modified IL-18 polypeptide. In some embodiments, the antibody or antigen binding fragment linked to the IL-18 polypeptide modified IL-18 polypeptide is a lyophilized powder. In some embodiments, the lyophilized powder is resuspended in a buffer solution. In some embodiments, the buffer solution comprises a buffer, a sugar, a salt, a surfactant, or any combination thereof. In some embodiments, the buffer solution comprises a phosphate salt. In some embodiments, the phosphate salt is sodium $Na_2HPO_4$. In some embodiments, the salt is sodium chloride. In some embodiments, the buffer solution comprises phosphate buffered saline. In some embodiments, the buffer solution comprises mannitol. In some embodiments, the lyophilized powder is suspended in a solution comprising about 10 mM $Na_2HPO_4$ buffer, about 0.022% SDS, and about 50 mg/mL mannitol, and having a pH of about 7.5.

Dosage Forms

The immunocytokine compositions described herein can be in a variety of dosage forms. In some embodiments, the immunocytokine composition is dosed as a lyophilized powder. In some embodiments, the immunocytokine composition is dosed as a suspension. In some embodiments, the immunocytokine composition is dosed as a solution. In some embodiments, the immunocytokine composition is dosed as an injectable solution. In some embodiments, the immunocytokine composition is dosed as an IV solution.

Methods of Treatment

In one aspect, described herein, is a method of treating cancer in a subject in need thereof, comprising: administering to the subject an effective amount of an immunocytokine composition or a pharmaceutical composition as described herein. In some embodiments, the cancer is a solid cancer. A cancer or tumor can be, for example, a primary cancer or tumor or a metastatic cancer or tumor. In some embodiments, the cancer is a solid cancer. In some embodiments, the solid cancer is adrenal cancer, anal cancer, bile duct cancer, bladder cancer, bone cancer, brain cancer, breast cancer, carcinoid cancer, cervical cancer, colorectal cancer, esophageal cancer, eye cancer, gallbladder cancer, gastrointestinal stromal tumor, germ cell cancer, head and neck cancer, kidney cancer, liver cancer, lung cancer, nasal cavity and paranasal sinus cancer, nasopharyngeal cancer, neuroblastoma, neuroendocrine cancer, oral cancer, oropharyngeal cancer, ovarian cancer, pancreatic cancer, pediatric cancer, penile cancer, pituitary cancer, prostate cancer, skin cancer, soft tissue cancer, spinal cord cancer, stomach cancer, testicular cancer, thymus cancer, thyroid cancer, ureteral cancer, uterine cancer, vaginal cancer, or vulvar cancer.

In some embodiments, the cancer is a blood cancer. In some embodiments, the blood cancer is leukemia, non-Hodgkin lymphoma, Hodgkin lymphoma, an AIDS-related lymphoma, multiple myeloma, plasmacytoma, post-transplantation lymphoproliferative disorder, or Waldenstrom macroglobulinemia Combination therapies with one or more additional active agents are contemplated herein.

An effective response is achieved when the subject experiences partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year, about at least 2 years, about at least 3 years, about at least 4 years, about at least 5 years, etc. Overall or progression-free survival can be also measured in months to years. Alternatively, an effective response may be that a subject's symptoms or cancer burden remain static and do not worsen. Further treatment of indications are described in more detail below. In some instances, a cancer or tumor is reduced by at least 2%, 5%, 10%, 15%, 20%, 25%, 30%, 35%, 40%, 45%, 50%, 55%, 60%, 65%, 70%, 75%, 80%, 85%, 90%, 95%, or 100%.

In some embodiments, the immunocytokine composition is administered in a single dose of the effective amount of immunocytokine composition, including further embodiments in which (i) the immunocytokine composition is administered once a day; or (ii) the immunocytokine composition is administered once a day; or (ii) the immunocytokine composition is administered to the subject multiple times over the span of one day. In some embodiments, the conjugate is administered daily, every other day, twice a week, 3 times a week, once a week, every 2 weeks, every 3 weeks, every 4 weeks, every 5 weeks, every 6 weeks, every 12 weeks, every 3 days, every 4 days, every 5 days, every 6 days, 2 times a week, 3 times a week, 4 times a week, 5 times a week, 6 times a week, once a month, twice a month, 3 times a month, 4 times a month, once every 2 months, once every 3 months, once every 4 months, once every 5 months, or once every 6 months. Administration includes, but is not limited to, injection by any suitable route (e.g., parenteral, enteral, intravenous, subcutaneous, etc.).

Methods of Manufacturing

In one aspect, described herein, is a method of making an immunocytokine composition, comprising providing an antibody or antigen binding fragment thereof (e.g., an antibody or antigen binding fragment provided herein), wherein the antibody comprises a reactive group (e.g., a conjugation handle), contacting the reactive group with a complementary reactive group attached to an IL-18 polypeptide, and forming the immunocytokine composition. The resulting composition is any of the compositions provided herein.

In some embodiments, providing the antibody comprising the reactive group comprises attaching the reactive group to the antibody. In some embodiments, the reactive group is added site-specifically. In some embodiments, attaching the reactive group to the antibody comprises contacting the antibody with an affinity group comprising a reactive functionality which forms a bond with a specific residue of the antibody. In some embodiments, attaching the reactive group to the antibody comprises contacting the antibody with an enzyme. In some embodiments, the enzyme is configured to site-specifically attach the reactive group to a specific residue of the antibody. In some embodiments, the enzyme is glycosylation enzyme or a transglutaminase enzyme.

In some embodiments, the method further comprises attaching the complementary reactive group to the cytokine.

Definitions

All terms are intended to be understood as they would be understood by a person skilled in the art. Unless defined otherwise, all technical and scientific terms used herein have the same meaning as commonly understood by one of ordinary skill in the art to which the disclosure pertains.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only and is not intended to be limiting.

The terminology used herein is for the purpose of describing particular cases only and is not intended to be limiting. In this application, the use of the singular includes the plural unless specifically stated otherwise. As used herein, the singular forms "a", "an" and "the" are intended to include the plural forms as well, unless the context clearly indicates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 15%, up to 10%, up to 5%, or up to 1% of a given value. Alternatively, particularly with respect to biological systems or processes, the term can mean within an order of magnitude, within 5-fold, or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

Referred to herein are groups which are "attached" or "covalently attached" to residues of IL-18 polypeptides or other polypeptides. As used herein, "attached" or "covalently attached" means that the group is tethered to the indicated reside, and such tethering can include a linking group (i.e., a linker). Thus, for a group "attached" or "covalently attached" to a residue, it is expressly contemplated that such linking groups are also encompassed.

As used herein, an "alpha-keto amino acid" or the phrase "alpha-keto" before the name of an amino acid refers to an amino acid or amino acid derivative having a ketone functional group positioned between the carbon bearing the amino group and the carboxylic acid of an amino acid. Alpha-keto amino acids of the instant disclosure have a structure as set forth in the following formula:

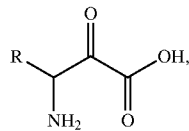

wherein R is the side chain of any natural or unnatural amino acid. The R functionality can be in either the L or D orientation in accordance with standard amino acid nomenclature. In preferred embodiments, alpha-keto amino acids are in the L orientation. When the phrase "alpha-keto" is used before the name of a traditional natural amino acid (e.g., alpha-keto leucine, alpha-keto phenylalanine, etc.) or a common unnatural amino acid (e.g., alpha-keto norleucine, alpha-keto O-methyl-homoserine, etc.), it is intended that the alpha-keto amino acid referred to matches the above formula with the side chain of the referred to amino acid. When an alpha-keto amino acid residue is set forth in a peptide or polypeptide sequence herein, it is intended that a protected version of the relevant alpha-keto amino acid is also encompassed (e.g., for a sequence terminating in a C-terminal alpha-keto amino acid, the terminal carboxylic acid group may be appropriately capped with a protecting group such as a tert-butyl group, or the ketone group with an acetal protecting group). Other protecting groups encompassed are well known in the art.

Binding affinity refers to the strength of a binding interaction between a single molecule and its ligand/binding partner. A higher binding affinity refers to a higher strength bond than a lower binding affinity. In some instances, binding affinity is measured by the dissociation constant ($K_D$) between the two relevant molecules. When comparing $K_D$ values, a binding interaction with a lower value will have a higher binding affinity than a binding interaction with a higher value. For a protein-ligand interaction, $K_D$ is calculated according to the following formula:

$$K_D = \frac{[L][P]}{[LP]}$$

where [L] is the concentration of the ligand, [P] is the concentration of the protein, and [LP] is the concentration of the ligand/protein complex.

Referred to herein are certain amino acid sequences (e.g., polypeptide sequences) which have a certain percent sequence identity to a reference sequence or refer to a residue at a position corresponding to a position of a reference sequence. Sequence identity is measured by protein-protein BLAST algorithm using parameters of Matrix BLOSUM62, Gap Costs Existence:11, Extension:1, and Compositional Adjustments Conditional Compositional Score Matrix Adjustment. This alignment algorithm is also used to assess if a residue is at a "corresponding" position through an analysis of the alignment of the two sequences being compared.

Unless otherwise specified, is contemplated that "protected" versions of amino acids (e.g., those containing a chemical protecting group affixed to a functionality of the amino acid, particularly a side chain of the amino acid but also at another point of the amino acid) qualify as the same amino acid as the "unprotected" version for sequence identity purposes, particularly for chemically synthesized polypeptides. It is also contemplated that such protected versions are also encompassed by the SEQ ID NOs provided herein. Non-limiting examples of protecting groups which may be encompassed include fluorenylmethyloxycarbonyl (Fmoc), triphenylmethyl (trityl or trt), tert-Butyloxycarbonyl (Boc), 2,2,4,6,7-pentamethyldihydrobenzofuran-5-sulfonyl (Pbf), acetamidomethyl (Acm), tert-butyl (tBu or OtBu), 2,2-dimethyl-1-(4-methoxyphenyl)propane-1,3-diol ketal or acetal, and 2,2-dimethyl-1-(2-nitrophenyl)propane-1,3-diol ketal or acetal. Other protecting groups well known in the art are also encompassed. Similarly, modified versions of natural amino acids are also intended to qualify as natural version of the amino acid for sequence identity purposes. For example, an amino acid comprising a side chain heteroatom which can be covalently modified (e.g., to add a conjugation handle, optionally through a linker), such as a lysine, glutamine, glutamic acid, asparagine, aspartic acid, cysteine, or tyrosine, which has been covalently modified would be counted as the base amino acid (see, e.g., Structure 2 below, which would be counted as a lysine for sequence identity and SEQ ID purposes). Similarly, an amino acid comprising another group added to the C or N-terminus would be counted as the base amino acid.

The term "pharmaceutically acceptable" refers to approved or approvable by a regulatory agency of the federal or a state government or listed in the U.S. Pharmacopeia (U.S.P.) or other generally recognized pharmacopeia for use in animals, including humans.

A "pharmaceutically acceptable excipient, carrier, or diluent" refers to an excipient, carrier, or diluent that can be administered to a subject, together with an agent, and which does not destroy the pharmacological activity thereof and is nontoxic when administered in doses sufficient to deliver a therapeutic amount of the agent.

A "pharmaceutically acceptable salt" suitable for the disclosure may be an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethyl sulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)n-COOH where n is 0-4, and the like. Similarly, pharmaceutically acceptable cations include, but are not limited to sodium, potassium, calcium, aluminum, lithium and ammonium. Those of ordinary skill in the art will recognize from this disclosure and the knowledge in the art that further pharmaceutically acceptable salts include those listed by Remington's Pharmaceutical Sciences, 17th ed., Mack Publishing Company, Easton, PA, p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Certain formulas and other illustrations provided herein depict triazole reaction products resulting from azide-alkyne cycloaddition reactions. While such formulas generally depict only a single regioisomer of the resulting triazole formed in the reaction, it is intended that the formulas encompass both resulting regioisomers. Thus, while the formulas depict only a single regioisomer (e.g. 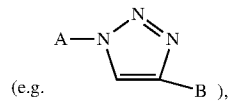 B ), it is intended that the other regioisomer (e.g. 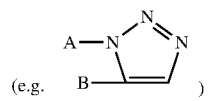 )

is also encompassed.

The term "subject" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

The term "optional" or "optionally" denotes that a subsequently described event or circumstance can but need not occur, and that the description includes instances where the event or circumstance occurs and instances in which it does not.

The term "moiety" refers to a specific segment or functional group of a molecule. Chemical moieties are often recognized chemical entities embedded in or appended to a molecule.

As used herein, the term "number average molecular weight" (Mn) means the statistical average molecular weight of all the individual units in a sample, and is defined by Formula (1):

$$Mn = \frac{\sum N_i M_i}{\sum N_i} \qquad \text{Formula (1)}$$

where M$_i$ is the molecular weight of a unit and Ni is the number of units of that molecular weight.

As used herein, the term "weight average molecular weight" (Mw) means the number defined by Formula (2):

$$Mw = \frac{\sum N_i M_i^2}{\sum N_i M_i} \qquad \text{Formula (2)}$$

where M$_i$ is the molecular weight of a unit and Ni is the number of units of that molecular weight.

As used herein, "peak molecular weight" (Mp) means the molecular weight of the highest peak in a given analytical method (e.g., mass spectrometry, size exclusion chromatography, dynamic light scattering, analytical centrifugation, etc.).

As used herein, "conjugation handle" refers to a reactive group capable of forming a bond upon contacting a complementary reactive group. In some instances, a conjugation handle preferably does not have a substantial reactivity with other molecules which do not comprise the intended complementary reactive group. Non-limiting examples of conjugation handles, their respective complementary conjugation handles, and corresponding reaction products can be found in the table below. While table headings place certain reactive groups under the title "conjugation handle" or "complementary conjugation handle," it is intended that any reference to a conjugation handle can instead encompass the complementary conjugation handles listed in the table (e.g., a trans-cyclooctene can be a conjugation handle, in which case tetrazine would be the complementary conjugation handle). In some instances, amine conjugation handles and conjugation handles complementary to amines are less preferable for use in biological systems owing to the ubiquitous presence of amines in biological systems and the increased likelihood for off-target conjugation.

Table of Conjugation Handles

| Conjugation Handle | Complementary Conjugation Handle | Reaction Product |
|---|---|---|
| Sulfhydryl | alpha-halo-carbonyl (e.g., bromo-acetamide), alpha-beta unsaturated carbonyl (e.g., maleimide, acrylamide) | thioether |
| Azide | alkyne (e.g., terminal alkyne, substituted cyclooctyne (e.g., dibenzocyclooctne (DBCO), difluorocyclooctyne, bicyclo[6.1.0]nonyne, etc.) ) | triazole |
| Phosphine | Azide/ester pair | amide |
| Tetrazine | trans-cyoclooctene | dihydro-pyridazine |
| Amine | Activated ester (e.g., N-hydroxy-succinimide ester, pentaflurophenyl ester) | amide |
| isocyanate | amine | urea |
| epoxide | amine | alkyl-amine |
| hydroxyl amine | aldehyde, ketone | oxime |
| hydrazide | aldehyde, ketone | hydrazone |
| potassium acyl trifluoroborate | O-substituted hydroxylamine (e.g., O-carbamoylhydroxylamine) | amide |

Throughout the instant application, prefixes are used before the term "conjugation handle" to denote the functionality to which the conjugation handle is linked. For example, a "protein conjugation handle" is a conjugation handle attached to a protein (either directly or through a linker), an "antibody conjugation handle" is a conjugation handle attached to an antibody (either directly or through a linker), and a "linker conjugation handle" is a conjugation handle attached to a linker group (e.g., a bifunctional linker used to link a synthetic protein and an antibody).

The term "alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methyl ethyl (i-propyl), n-butyl, i-butyl, 5-butyl, n-pentyl, 1,1-dimethyl ethyl (i-butyl), 3-methylhexyl, 2-methylhexyl, 1-ethyl-propyl, and the like. In some embodiments, the alkyl is methyl or ethyl. In some embodiments, the alkyl is —CH(CH$_3$)$_2$ or —C(CH$_3$)$_3$. Unless stated otherwise specifically in the specification, an alkyl group may be optionally substituted. "Alkylene" or "alkylene chain" refers to a straight or branched divalent hydrocarbon chain linking the rest of the molecule to a radical group. In some embodiments, the alkylene is —CFF—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—. Unless stated otherwise specifically in the specification, an alkylene group may be optionally substituted.

The term "alkenylene" or "alkenylene chain" refers to a straight or branched divalent hydrocarbon chain in which at least one carbon-carbon double bond is present linking the rest of the molecule to a radical group. In some embodiments, the alkenylene is —CH=CH—, —CH$_2$CH=CH—, or —CH=CHCH$_2$—. In some embodiments, the alkenylene is —CH=CH—. In some embodiments, the alkenylene is —CH$_2$CH=CH—. In some embodiments, the alkenylene is —CH=CHCH$_2$—.

The term "alkynyl" refers to a type of alkyl group in which at least one carbon-carbon triple bond is present. In one embodiment, an alkenyl group has the formula —C≡C-R$^x$, wherein R$^x$ refers to the remaining portions of the alkynyl group. In some embodiments, R$^x$ is H or an alkyl. In some embodiments, an alkynyl is selected from ethynyl, propynyl, butynyl, pentynyl, hexynyl, and the like. Non-limiting examples of an alkynyl group include —C≡CH, —C≡CCH$_3$, —C≡CCH$_2$CH, and —CH$_2$C≡CH.

The term "aryl" refers to a radical comprising at least one aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted. In some embodiments, an aryl group comprises a partially reduced cycloalkyl group defined herein (e.g., 1,2-dihydronaphthalene). In some embodiments, an aryl group comprises a fully reduced cycloalkyl group defined herein (e.g., 1,2,3,4-tetrahydronaphthalene). When aryl comprises a cycloalkyl group, the aryl is bonded to the rest of the molecule through an aromatic ring carbon atom. An aryl radical can be a monocyclic or polycyclic (e.g., bicyclic, tricyclic, or tetracyclic) ring system, which may include fused, spiro or bridged ring systems.

The term "cycloalkyl" refers to a monocyclic or polycyclic non-aromatic radical, wherein each of the atoms forming the ring (i.e. skeletal atoms) is a carbon atom. In some embodiments, cycloalkyls are saturated or partially unsaturated. In some embodiments, cycloalkyls are spirocyclic or bridged compounds. In some embodiments, cycloalkyls are fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopentyl. In some embodiments, the monocyclic cycloalkyl is cyclopentenyl or cyclohexenyl. In some embodiments, the monocyclic cycloalkyl is cyclopentenyl. Polycyclic radicals include, for example, adamantyl, 1,2-dihydronaphthalenyl, 1,4-dihydronaphthalenyl, tetrainyl, decalinyl, 3,4-dihydronaphthalenyl-1(2H)-one, spiro[2.2]pentyl, norbornyl and bicycle[1.1.1]pentyl. Unless otherwise stated specifically in the specification, a cycloalkyl group may be optionally substituted.

The term "heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkylene groups include, but are not limited to —CH$_2$—O—CH$_2$—, —CH$_2$—N(alkyl)-CH$_2$—, —CH$_2$—N(aryl)-CH$_2$—, —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

The term "heteocycloalkyl" refers to a cycloalkyl group that includes at least one heteroatom selected from nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of heterocycloalkyl radicals include, but are not limited to, dioxolanyl, thienyl[1,3]dithianyl, tetrahydroquinolyl, tetrahydroisoquinolyl, decahydroquinolyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 12 carbons in the ring. In some embodiments, heterocycloalkyls have from 2 to 10 carbons in the ring. In some embodiments, heterocycloalkyls have from 2 to 10 carbons in the ring and 1 or 2 N atoms. In some embodiments, heterocycloalkyls have from 2 to 10 carbons in the ring and 3 or 4 N atoms. In some embodiments, heterocycloalkyls have from 2 to 12 carbons, 0-2 N atoms, 0-2 O atoms, 0-2 P atoms, and 0-1 S atoms in the ring. In some embodiments, heterocycloalkyls have from 2 to 12 carbons, 1-3 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "heteroaryl" refers to an aryl group that includes one or more ring heteroatoms selected from nitrogen, oxygen, and sulfur. In some embodiments, heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-6 N atoms in the ring. In some embodiments, a heteroaryl contains 1-4 N atoms in the ring. In some embodiments, a heteroaryl contains 4-6 N atoms in the ring. In some embodiments, a heteroaryl contains 0-4 N atoms, 0-1 O atoms, 0-1 P atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl. In some embodiments, a heteroaryl group comprises a partially reduced cycloalkyl or heterocycloalkyl group defined herein (e.g., 7,8-dihydroquinoline). In some embodiments, a heteroaryl group comprises a fully reduced cycloalkyl or heterocycloalkyl group defined herein (e.g., 5,6,7, 8-tetrahydroquinoline). When heteroaryl comprises a cycloalkyl or heterocycloalkyl group, the heteroaryl is bonded to the rest of the molecule through a heteroaromatic ring carbon or hetero atom. A heteroaryl radical can be a monocyclic or polycyclic (e.g., bicyclic, tricyclic, or tetracyclic) ring system, which may include fused, spiro or bridged ring systems.

The term "optionally substituted" or "substituted" means that the referenced group is optionally substituted with one or more additional group(s) individually and independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from D, halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —SC$_1$-C$_4$alkyl, —S(=O)C$_1$-C$_4$alkyl, and —S(=O)$_2$C$_1$-C$_4$alkyl. In some embodiments, optional substituents are independently selected from D, halogen, —CN, —NH$_2$, —OH, —NH(CH$_3$), —N(CH$_3$)$_2$, —NH(cyclopropyl), —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

As used herein, "AJICAP™ technology," ".AJICAP™ methods," and similar terms refer to systems and methods (currently produced by Ajinomoto Bio-Pharma Services ("Ajinomoto")) for the site specific functionalization of antibodies and related molecules using affinity peptides to deliver the desired functionalization to the desired site. General protocols for the AJICAP™ methodology are found at least in PCT Publication No. WO2018199337A1, PCT Publication No. WO2019240288A1, PCT Publication No. WO2019240287A1, PCT Publication No. WO2020090979A1, Matsuda et al., *Mol. Pharmaceutics* 2021, 18, 4058-4066, and Yamada et al., AJICAP: Affinity Peptide Mediated Regiodivergent Functionalization of Native Antibodies. *Angew. Chem., Int. Ed.* 2019, 58, 5592-5597, and in particular Examples 2-4 of US Patent Publication No. US20200190165A1. In some embodiments, such methodologies site specifically incorporate the desired functionalization at lysine residues at a position selected from position 246, position 248, position 288, position 290, and position 317 of an antibody Fc region (e.g., an IgG1 Fc region) (EU numbering). In some embodiments, the desired functionalization is incorporated at residue position 248 of an antibody Fc region (EU numbering). In some embodiments, position 248 corresponds to the 18th residue in a human IgG CH$_2$ region (EU numbering).

Sequences (SEQ ID NOS) of IL-18 Polypeptides

TABLE 2

| SEQ ID NO: | Modification | Sequence |
|---|---|---|
| 1 | Native sequence | YFGKLESKLS VIRNLNDQVL FIDQGNRPLF EDMTDSDCRD NAPRTIFIIS MYKDSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 2 | E6K, C38A, K53A, C68A, E85C | YFGKLKSKLS VIRNLNDQVL FIDQGNRPLF EDMTDSDARD NAPRTIFIIS MYADSQPRGM AVTISVKAEK ISTLSCENKI ISFKCMNPPD NIKDTKSDII FFQRSVPGHD NKMQFESSSY EGYFLACEKE RDLFKLILKK EDELGDRSIM FTVQNED |
| 3 | E6K, V11I, C38A, K53A, T63A, C68A, C76A, E85C, C127A | YFGKLKSKLS IIRNLNDQVL FIDQGNRPLF EDMTDSDARD NAPRTIFIIS MYADSQPRGM AVAISVKAEK ISTLSAENKI ISFKCMNPPD NIKDTKSDII FFQRSVPGHD NKMQFESSSY EGYFLAAEKE RDLFKLILKK EDELGDRSIM FTVQNED |
| 4 | E6K, C38A, K53A, C68A, M86C | YFGKLKSKLS VIRNLNDQVL FIDQGNRPLF EDMTDSDARD NAPRTIFIIS MYADSQPRGM AVTISVKAEK ISTLSCENKI ISFKECNPPD NIKDTKSDII FFQRSVPGHD NKMQFESSSY EGYFLACEKE RDLFKLILKK EDELGDRSIM FTVQNED |
| 5 | E6K, V11I, C38A, K53A, T63A, C68A, C76A, M86C, C127A | YFGKLKSKLS IIRNLNDQVL FIDQGNRPLF EDMTDSDARD NAPRTIFIIS MYADSQPRGM AVAISVKAEK ISTLSAENKI ISFKECNPPD NIKDTKSDII FFQRSVPGHD NKMQFESSSY EGYFLAAEKE RDLFKLILKK EDELGDRSIM FTVQNED |
| 6 | E6K, V11I, C38A, K53A, T63A, C68A, C76A, D98C, C127A | YFGKLKSKLS IIRNLNDQVL FIDQGNRPLF EDMTDSDARD NAPRTIFIIS MYADSQPRGM AVAISVKAEK ISTLSAENKI ISFKEMNPPD NIKDTKSCII FFQRSVPGHD NKMQFESSSY EGYFLAAEKE RDLFKLILKK EDELGDRSIM FTVQNED |
| 7 | E6K, C38A, K53A, C68A, C76A, M86C, C127A | YFGKLKSKLS VIRNLNDQVL FIDQGNRPLF EDMTDSDARD NAPRTIFIIS MYADSQPRGM AVTISVKAEK ISTLSAENKI ISFKECNPPD NIKDTKSDII FFQRSVPGHD NKMQFESSSY EGYFLAAEKE RDLFKLILKK EDELGDRSIM FTVQNED |
| 8 | E6K, V11I, C38A, K53A, T63A, C68A, C76A, T95C, C127A | YFGKLKSKLS IIRNLNDQVL FIDQGNRPLF EDMTDSDARD NAPRTIFIIS MYADSQPRGM AVAISVKAEK ISTLSAENKI ISFKEMNPPD NIKDCKSDII FFQRSVPGHD NKMQFESSSY EGYFLAAEKE RDLFKLILKK EDELGDRSIM FTVQNED |
| 9 | E6K, C38A, K53A, C68A, D98C | YFGKLKSKLS VIRNLNDQVL FIDQGNRPLF EDMTDSDARD NAPRTIFIIS MYADSQPRGM AVTISVKAEK ISTLSCENKI ISFKEMNPPD NIKDTKSCII FFQRSVPGHD NKMQFESSSY EGYFLACEKE RDLFKLILKK EDELGDRSIM |
| 10 | E6K, C38A, K53A, C68A, C76A, D98C, C127A | YFGKLKSKLS VIRNLNDQVL FIDQGNRPLF EDMTDSDARD NAPRTIFIIS MYADSQPRGM AVTISVKAEK ISTLSCENKI ISFKEMNPPD NIKDTKSCII FFQRSVPGHD NKMQFESSSY EGYFLAAEKE RDLFKLILKK EDELGDRSIM FTVQNED |
| 11 | E6K, V11I, C38A, K53A, C76A, C127A | YFGKLKSKLS IIRNLNDQVL FIDQGNRPLF EDMTDSDARD NAPRTIFIIS MYADSQPRGM AVTISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 12 | E6K, C38A, K53A, T63A, C76A, C127A | YFGKLKSKLS VIRNLNDQVL FIDQGNRPLF EDMTDSDARD NAPRTIFIIS MYADSQPRGM AVAISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 13 | E6K, K53A, T63N | YFGKLKSKLS VIRNLNDQVL FIDQGNRPLF EDMTDSDCRD NAPRTIFIIS MYADSQPRGM AVNISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 14 | E6K, K53A, S50A, T63N | YFGKLKSKLS VIRNLNDQVL FIDQGNRPLF EDMTDSDCRD NAPRTIFIIA MYADSQPRGM AVNISVKCEK ISTLSCENKI ISFKEMNPPD NIKDTKSDII FFQRSVPGHD NKMQFESSSY EGYFLACEKE RDLFKLILKK EDELGDRSIM FTVQNED |

TABLE 2-continued

| SEQ ID NO: | Modification | Sequence |
|---|---|---|
| 15 | E6K, K53A, S50H, T63N | YFGKLKSKLS VIRNLNDQVL FIDQGNRPLF EDMTDSDCRD NAPRTIFIIH MYADSQPRGM AVNISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 16 | E6K, K53A, T63N, S65A | YFGKLKSKLS VIRNLNDQVL FIDQGNRPLF EDMTDSDCRD NAPRTIFIIS MYADSQPRGM AVNIAVKCEK ISTLSCENKI ISFKEMNPPD NIKDTKSDII FFQRSVPGHD NKMQFESSSY EGYFLACEKE RDLFKLILKK EDELGDRSIM FTVQNED |
| 17 | E6K, K53A, S50H | YFGKLKSKLS VIRNLNDQVL FIDQGNRPLF EDMTDSDCRD NAPRTIFIIH MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 18 | E6K, C38A, K53A, C68A | YFGKLKSKLS VIRNLNDQVL FIDQGNRPLF EDMTDSDARD NAPRTIFIIS MYADSQPRGM AVTISVKAEK ISTLSCENKI ISFKEMNPPD NIKDTKSDII FFQRSVPGHD NKMQFESSSY EGYFLACEKE RDLFKLILKK EDELGDRSIM FTVQNED |
| 19 | E6K, K53A, K79A | YFGKLKSKLS VIRNLNDQVL FIDQGNRPLF EDMTDSDCRD NAPRTIFIIS MYADSQPRGM AVTISVKCEK ISFKEMNPPD NIKDTKSDII FFQRSVPGHD ISTLSCENAI NKMQFESSSY EGYFLACEKE RDLFKLILKK EDELGDRSIM FTVQNED |
| 20 | E6K, K53A, R104A | YFGKLKSKLS VIRNLNDQVL FIDQGNRPLF EDMTDSDCRD NAPRTIFIIS MYADSQPRGM AVTISVKCEK ISTLSCENAI ISFKEMNPPD NIKDTKSDII FFQRSVPGHD NKMQFESSSY EGYFLACEKE RDLFKLILKK EDELGDRSIM FTVQNED |
| 21 | E6K, K53A, G108A | YFGKLKSKLS VIRNLNDQVL FIDQGNRPLF EDMTDSDCRD NAPRTIFIIS MYADSQPRGM AVTISVKCEK ISTLSCENKI ISFKEMNPPD NIKDTKSDII FFQRSVPAHD NKMQFESSSY EGYFLACEKE RDLFKLILKK EDELGDRSIM FTVQNED |
| 22 | E6K, K53A, H109A | YFGKLKSKLS VIRNLNDQVL FIDQGNRPLF EDMTDSDCRD NAPRTIFIIS MYADSQPRGM AVTISVKCEK ISTLSCENKI ISFKEMNPPD NIKDTKSDII FFQRSVPGAD NKMQFESSSY EGYFLACEKE RDLFKLILKK EDELGDRSIM FTVQNED |
| 23 | E6K, K53A, K112A | YFGKLKSKLS VIRNLNDQVL FIDQGNRPLF EDMTDSDCRD NAPRTIFIIS MYADSQPRGM AVTISVKCEK ISTLSCENKI ISFKEMNPPD NIKDTKSDII FFQRSVPGHD NAMQFESSSY EGYFLACEKE RDLFKLILKK EDELGDRSIM FTVQNED |
| 24 | E6K, C38A, K53A, T63A, C76A | YFGKLKSKLS VIRNLNDQVL FIDQGNRPLF EDMTDSDARD NAPRTIFIIS MYADSQPRGM AVAISVKCEK ISTLSAENKI ISFKEMNPPD NIKDTKSDII FFQRSVPGHD NKMQFESSSY EGYFLACEKE RDLFKLILKK EDELGDRSIM FTVQNED |
| 25 | E6K, C38Q, K53A, T63A, C76A | YFGKLKSKLS VIRNLNDQVL FIDQGNRPLF EDMTDSDQRD NAPRTIFIIS MYADSQPRGM AVAISVKCEK ISTLSAENKI ISFKEMNPPD NIKDTKSDII FFQRSVPGHD NKMQFESSSY EGYFLACEKE RDLFKLILKK EDELGDRSIM FTVQNED |
| 26 | E6K, C38A, K53A, T63A, C127A | YFGKLKSKLS VIRNLNDQVL FIDQGNRPLF EDMTDSDARD NAPRTIFIIS MYADSQPRGM AVAISVKCEK ISTLSCENKI ISFKEMNPPD NIKDTKSDII FFQRSVPGHD NKMQFESSSY EGYFLAAEKE RDLFKLILKK EDELGDRSIM FTVQNED |
| 27 | E6K, C38Q, K53A, T63A, C127A | YFGKLKSKLS VIRNLNDQVL FIDQGNRPLF EDMTDSDQRD NAPRTIFIIS MYADSQPRGM AVAISVKCEK ISTLSCENKI ISFKEMNPPD NIKDTKSDII FFQRSVPGHD NKMQFESSSY EGYFLAAEKE RDLFKLILKK EDELGDRSIM FTVQNED |
| 28 | E6K, C38A, K53A, T63A, C76A, C127A | YFGKLKSKLS VIRNLNDQVL FIDQGNRPLF EDMTDSDARD NAPRTIFIIS MYADSQPRGM AVAISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 29 | E6K, V11I, C38A, K53A, T63A | YFGKLKSKLS ISFKEMNPPD FIDQGNRPLF EDMTDSDARD NAPRTIFIIS MYADSQPRGM AVAISVKCEK ISTLSCENKI IIRNLNDQVL NIKDTKSDII FFQRSVPGHD NKMQFESSSY EGYFLACEKE RDLFKLILKK EDELGDRSIM FTVQNED |

TABLE 2-continued

| SEQ ID NO: | Modification | Sequence |
|---|---|---|
| 30 | E6K, V11I, C38A, K53A, T63A, C76A, C127A | YFGKLKSKLS IIRNLNDQVL FIDQGNRPLF EDMTDSDARD NAPRTIFIIS MYADSQPRGM AVAISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 31 | C38A, C76A, C127A | YFGKLESKLS VIRNLNDQVL FIDQGNRPLF EDMTDSDARD NAPRTIFIIS MYKDSQPRGM AVTISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 32 | C38A | YFGKLESKLS VIRNLNDQVL FIDQGNRPLF EDMTDSDARD NAPRTIFIIS MYKDSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 33 | E6K, C38A, K53A, T63A | YFGKLKSKLS VIRNLNDQVL FIDQGNRPLF EDMTDSDARD NAPRTIFIIS MYADSQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 34 | E06K, K53A, S55A | YFGKLKSKLS VIRNLNDQVL FIDQGNRPLF EDMTDSDCRD NAPRTIFIIS MYADAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 35 | Y01G, F02A, E06K, M51G, K53A, D54A, S55A, T63A | GAGKLKSKLS VIRNLNDQVL FIDQGNRPLF EDMTDSDCRD NAPRTIFIIS GYAAAQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 36 | K53A | YFGKLESKLS VIRNLNDQVL FIDQGNRPLF EDMTDSDCRD NAPRTIFIIS MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 37 | S55A | YFGKLESKLS VIRNLNDQVL FIDQGNRPLF EDMTDSDCRD NAPRTIFIIS MYKDAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 38 | E06K | YFGKLKSKLS VIRNLNDQVL FIDQGNRPLF EDMTDSDCRD NAPRTIFIIS MYKDSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 39 | E06K, K53A | YFGKLKSKLS VIRNLNDQVL FIDQGNRPLF EDMTDSDCRD NAPRTIFIIS MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 40 | E06K, S55A | YFGKLKSKLS VIRNLNDQVL FIDQGNRPLF EDMTDSDCRD NAPRTIFIIS MYKDAQPRGM AVTISVKCEK ISFKEMNPPD ISTLSCENKI NIKDTKSDII FFQRSVPGHD NKMQFESSSY EGYFLACEKE RDLFKLILKK EDELGDRSIM FTVQNED |
| 41 | K53A, S55A | YFGKLESKLS VIRNLNDQVL FIDQGNRPLF EDMTDSDCRD NAPRTIFIIS MYADAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 42 | E06K, K53A, S55A, T63A | YFGKLKSKLS VIRNLNDQVL FIDQGNRPLF EDMTDSDCRD NAPRTIFIIS MYADAQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 43 | E06K, K53A, S55A, Y01G | GFGKLKSKLS VIRNLNDQVL FIDQGNRPLF EDMTDSDCRD NAPRTIFIIS MYADAQPRGM ISTLSCENKI AVTISVKCEK ISFKEMNPPD NIKDTKSDII FFQRSVPGHD NKMQFESSSY EGYFLACEKE RDLFKLILKK EDELGDRSIM FTVQNED |
| 44 | E06K, K53A, S55A, F02A | YAGKLKSKLS VIRNLNDQVL FIDQGNRPLF EDMTDSDCRD NAPRTIFIIS MYADAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |

TABLE 2-continued

| SEQ ID NO: | Modification | Sequence |
|---|---|---|
| 45 | E06K, K53A, S55A, D54A | YFGKLKSKLS VIRNLNDQVL FIDQGNRPLF EDMTDSDCRD NAPRTIFIIS MYAAAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 46 | E06K, K53A, S55A, M51G | YFGKLKSKLS VIRNLNDQVL FIDQGNRPLF EDMTDSDCRD NAPRTIFIIS GYADAQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 47 | C38S, C68S, C76S, C127S | YFGKLESKLS VIRNLNDQVL FIDQGNRPLF EDMTDSDSRD NAPRTIFIIS MYKDSQPRGM AVTISVKSEK ISTLSSENKI ISFKEMNPPD NIKDTKSDII FFQRSVPGHD NKMQFESSSY EGYFLASEKE RDLFKLILKK EDELGDRSIM FTVQNED |
| 48 | C38S, C68S, C76S, C127S, K70C | YFGKLESKLS VIRNLNDQVL FIDQGNRPLF EDMTDSDSRD NAPRTIFIIS MYKDSQPRGM ISTLSSENKI AVTISVKSEC ISFKEMNPPD NIKDTKSDII FFQRSVPGHD NKMQFESSSY EGYFLASEKE RDLFKLILKK EDELGDRSIM FTVQNED |
| 49 | E06K, K53A, S55A, C38S, C68S, C76S, C127S, K70C | YFGKLKSKLS VIRNLNDQVL FIDQGNRPLF EDMTDSDSRD NAPRTIFIIS MYADAQPRGM AVTISVKSEC ISTLSSENKI ISFKEMNPPD NIKDTKSDII FFQRSVPGHD NKMQFESSSY EGYFLASEKE RDLFKLILKK EDELGDRSIM FTVQNED |
| 50 | E06K, K53A, T63A | YFGKLKSKLS VIRNLNDQVL FIDQGNRPLF EDMTDSDCRD NAPRTIFIIS MYADSQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 51 | T63A | YFGKLESKLS VIRNLNDQVL FIDQGNRPLF EDMTDSDCRD NAPRTIFIIS MYKDSQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 52 | E06K, T63A | YFGKLKSKLS VIRNLNDQVL FIDQGNRPLF EDMTDSDCRD NAPRTIFIIS MYKDSQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 53 | K53A, T63A | YFGKLESKLS VIRNLNDQVL FIDQGNRPLF EDMTDSDCRD NAPRTIFIIS MYADSQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 54 | E06K, K53A, C38S, C68S, C76S, C127S, K70C | YFGKLKSKLS VIRNLNDQVL FIDQGNRPLF EDMTDSDSRD NAPRTIFIIS MYADSQPRGM AVTISVKSEC ISTLSSENKI ISFKEMNPPD NIKDTKSDII FFQRSVPGHD NKMQFESSSY EGYFLASEKE RDLFKLILKK EDELGDRSIM FTVQNED |
| 55 | K53A, T63A, C38S, C68S, C76S, C127S, K70C | YFGKLESKLS VIRNLNDQVL FIDQGNRPLF EDMTDSDSRD NAPRTIFIIS MYADSQPRGM AVAISVKSEC ISTLSSENKI ISFKEMNPPD NIKDTKSDII FFQRSVPGHD NKMQFESSSY EGYFLASEKE RDLFKLILKK EDELGDRSIM FTVQNED |
| 56 | E6K, K53A, C38S, C76S, C127S | YFGKLKSKLS VIRNLNDQVL FIDQGNRPLF EDMTDSDSRD NAPRTIFIIS MYADSQPRGM AVTISVKCEK ISTLSSENKI ISFKEMNPPD NIKDTKSDII FFQRSVPGHD NKMQFESSSY EGYFLASEKE RDLFKLILKK EDELGDRSIM FTVQNED |
| 57 | E6K, C38S, K53A | YFGKLKSKLS VIRNLNDQVL FIDQGNRPLF EDMTDSDSRD NAPRTIFIIS MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 58 | E6K, K53A, C38S, C68S, C76S, C127S, K70C | YFGKLKSKLS VIRNLNDQVL FIDQGNRPLF EDMTDSDSRD NAPRTIFIIS MYADSQPRGM AVTISVKSEC ISTLSSENKI ISFKEMNPPD NIKDTKSDII FFQRSVPGHD NKMQFESSSY EGYFLASEKE RDLFKLILKK EDELGDRSIM FTVQNED |
| 59 | E6K, C38A, K53A | YFGKLKSKLS VIRNLNDQVL FIDQGNRPLF EDMTDSDARD NAPRTIFIIS MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |

TABLE 2-continued

| SEQ ID NO: | Modification | Sequence |
|---|---|---|
| 60 | E6K, C38Q, K53A | YFGKLKSKLS VIRNLNDQVL FIDQGNRPLF EDMTDSDQRD NAPRTIFIIS MYADSQPRGM AVTISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 61 | E6K, C38A, K53A, C76A | YFGKLKSKLS VIRNLNDQVL FIDQGNRPLF EDMTDSDARD NAPRTIFIIS MYADSQPRGM AVTISVKCEK ISTLSAENKI ISFKEMNPPD NIKDTKSDII FFQRSVPGHD NKMQFESSSY EGYFLACEKE RDLFKLILKK EDELGDRSIM FTVQNED |
| 62 | E6K, C38A, K53A, C127A | YFGKLKSKLS VIRNLNDQVL FIDQGNRPLF EDMTDSDARD NAPRTIFIIS MYADSQPRGM AVTISVKCEK ISTLSCENKI ISFKEMNPPD NIKDTKSDII FFQRSVPGHD NKMQFESSSY EGYFLAAEKE RDLFKLILKK EDELGDRSIM FTVQNED |
| 63 | E6K, C38A, K53A, C76A, C127A | YFGKLKSKLS VIRNLNDQVL FIDQGNRPLF EDMTDSDARD NAPRTIFIIS MYADSQPRGM AVTISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 64 | E6K, K53A, C38A, S55A, T63A | YFGKLKSKLS VIRNLNDQVL FIDQGNRPLF EDMTDSDARD NAPRTIFIIS MYADAQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 65 | E6K, C38Q, K53A, S55A, T63A | YFGKLKSKLS VIRNLNDQVL FIDQGNRPLF EDMTDSDQRD NAPRTIFIIS MYADAQPRGM AVAISVKCEK ISTLSCENKI ISFKEMNPPD NIKDTKSDII FFQRSVPGHD NKMQFESSSY EGYFLACEKE RDLFKLILKK EDELGDRSIM FTVQNED |
| 66 | E6K, K53A, K84A | YFGKLKSKLS VIRNLNDQVL FIDQGNRPLF EDMTDSDCRD NAPRTIFIIS MYADSQPRGM AVTISVKCEK ISTLSCENKI ISFAEMNPPD NIKDTKSDII FFQRSVPGHD NKMQFESSSY EGYFLACEKE RDLFKLILKK EDELGDRSIM FTVQNED |
| 67 | E6K, K53A, D98A | YFGKLKSKLS VIRNLNDQVL FIDQGNRPLF EDMTDSDCRD NAPRTIFIIS MYADSQPRGM AVTISVKCEK ISTLSCENKI ISFKEMNPPD NIKDTKSAII FFQRSVPGHD NKMQFESSSY EGYFLACEKE RDLFKLILKK EDELGDRSIM FTVQNED |
| 68 (a.k.a. C146) | V11I, C38A, M51G, K53A, C76A, C127A | YFGKLESKLS IIRNLNDQVL FIDQGNRPLF EDMTDSDARD NAPRTIFIIS GYADSQPRGM AVTISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 69 (a.k.a. C183) | E6K, V11I, C38A, M51G, K53A, T63A, C76A, C127A | YFGKLKSKLS IIRNLNDQVL FIDQGNRPLF EDMTDSDARD NAPRTIFIIS GYADSQPRGM AVAISVKCEK ISTLSAENKI ISFKEMNPPD NIKDTKSDII FFQRSVPGHD NKMQFESSSY EGYFLAAEKE RDLFKLILKK EDELGDRSIM FTVQNED |
| 70 (a.k.a. C192) | N-terminal G, E6K, V11I, C38A, M51G, K53A, T63A, C76A, C127A | GYFGKLKSKL SIIRNLNDQV LFIDQGNRPL FEDMTDSDAR DNAPRTIFII SGYADSQPRG MAVAISVKCE KISTLSAENK IISFKEMNPP DNIKDTKSDI IFFQRSVPGH DNKMQFESSS YEGYFLAAEK ERDLFKLILK KEDELGDRSI MFTVQNED |
| 71 (a.k.a. C141) | N-terminal G, E6K, V11I, C38A, K53A, T63A, C76A, C127A | GYFGKLKSKL SIIRNLNDQV LFIDQGNRPL FEDMTDSDAR DNAPRTIFII SMYADSQPRG MAVAISVKCE KISTLSAENK IISFKEMNPP DNIKDTKSDI IFFQRSVPGH DNKMQFESSS YEGYFLAAEK ERDLFKLILK KEDELGDRSI MFTVQNED |
| 72 (a.k.a. C140) | N-terminal 4xG, E6K, V11I, C38A, K53A, T63A, C76A, C127A | GGGGYFGKLK SKLSIIRNLN DQVLFIDQGN RPLFEDMTDS DARDNAPRTI FIISMYADSQ PRGMAVAISVKCEKISTLSA ENKIISFKEM NPPDNIKDTK SDIIFFQRSV PGHDNKMQFE SSSYEGYFLA AEKERDLFKL ILKKEDELGD RSIMFTVQNE D |

Additional Exemplary Il-18 Constructs

Also provided herein are IL-18 polypeptides which comprise the modifications to SEQ ID NO: 1 listed in the table below, each of which is assigned a Composition ID, which can be incorporated into an immunocytokine composition as provided herein. In some embodiments, the IL-18 polypeptide of an immunocytokine composition comprises the set of amino acid substitutions shown for any one of the constructs depicted below. In the constructs depicted below, each of the substitutions is listed using SEQ TD NO: 1 as a reference sequence. In some embodiments, the IL-18 polypeptide an immunocytokine composition comprises only the substitutions shown for a construct below relative to SEQ TD NO: 1 (i.e., the IL-18 polypeptide has only the indicated set of substitutions and the remaining residues are those set forth in SEQ ID NO: 1).

TABLE 3

Additional IL-18 Polypeptide

| Composition ID/ Substitutions to SEQ ID NO: 1 | | Composition ID/ Substitutions to SEQ ID NO: 1 | | Composition ID/ Substitutions to SEQ ID NO: 1 | |
|---|---|---|---|---|---|
| C143 | V11I, C38A, K53A, C76A, C127A | C156 | V11I, C38A, N41A, K53A, C76A, C127A | C168 | V11I, C38A, C76A, S105K, C127A |
| C144 | V11I, C38A, K53A, T63A, C76A, C127A | C157 | V11I, C38A, K53A, C76A, C127A, D132A | C174 | K8L, E6K, V11I, C38A, K53A, T63A, C76A, C127A |
| C145 | V11I, C38A, K53A, S55A, C76A, C127A | C158 | V11I, C38A, K53A, C76A, G108A, C127A | C175 | E6K, V11I, C38A, I49E, K53A, T63A, C76A, C127A |
| C147 | V11I, C38A, K53A, D54A, C76A, C127A | C159 | V11I, C38A, K53A, C76A, H109A, C127A | C176 | E6K, V11I, C38A, I49M, K53A, T63A, C76A, C127A |
| C148 | F2A, V11I, C38A, K53A, C76A, C127A | C160 | V11I, C38A, K53A, C76A, D110A, C127A | C177 | E6K, V11I, C38A, I49R, K53A, T63A, C76A, C127A |
| C149 | V11I, E31A, C38A, K53A, C76A, C127A | C161 | K8R, V11I, C38A, C76A, Q103E, C127A | C178 | E6K, V11I, C38A, K53A, T63A, C76A, Q103R, C127A |
| C150 | V11I, T34A, C38A, K53A, C76A, C127A | C162 | K8E, V11I, C38A, C76A, Q103R, C127A | C179 | E6K, K8E, V11I, C38A, K53A, T63A, C76A, Q103R, C127A |
| C151 | V11I, D35A, C38A, K53A, C76A, C127A | C163 | V11I, C38A, C76A, Q103K, C127A | C180 | E6K, V11I, C38A, K53A, T63A, C76A, C127A, V153R |
| C152 | V11I, S36A, C38A, K53A, C76A, C127A | C164 | V11I, C38A, S55H, C76A, C127A | C181 | E6K, V11I, C38A, K53A, T63A, C76A, C127A, V153E |
| C153 | V11I, D37A, C38A, K53A, C76A, C127A | C165 | V11I, C38A, S55R, C76A, C127A | C182 | E6K, V11I, C38A, K53A, T63A, C76A, C127A, V153Y |
| C154 | V11I, E31A, D37A, C38A, K53A, C76A, C127A | C166 | V11I, C38A, S55T, C76A, C127A | C184 | E6R, V11I, C38A, K53A, T63A, C76A, C127A |
| C155 | V11I, C38A, D40A, K53A, C76A, C127A | C167 | V11I, C38A, C76A, S105I, C127A | C142 | Y1M, E6K, V11I, C38A, K53A, T63A, C76A, C127A |

Although the present disclosure and its advantages have been described in detail, it should be understood that various changes, substitutions and alterations can be made herein without departing from the spirit and scope of the disclosure as defined in the appended claims.

The present disclosure is further illustrated in the following Examples which are given for illustration purposes only and are not intended to limit the disclosure in any way.

EXAMPLES

Example 1A—Recombinant IL18 Expression and Purification

Recombinant TL-18 variants suitable for linking to an antibody or antigen binding fragment as provided herein can be prepared according to the protocols provided below. In some instances, the recombinant IL-18 will contain a cysteine residue at the desired point of attachment of the linker, or may include an unnatural amino acid (e.g., azidolysine) suitable for attachment of the linker at the desired point of attachment.

Soluble His-SUMO-IL18 Variants

E. coli BL21 (DE3) harboring a plasmid encoding a N-His-SUMO tagged IL-18 variant fusion is inoculated into 3 L LB culture medium and induced with 0.4 mM IPTG at 30° C. for 6 h. Cells are pelleted and cell lysis is done by sonication in lysis buffer: PBS, pH 7.4. Soluble protein is purified via Ni-NTA beads 6FF (wash 1 with: PBS, 20 mM imidazole, pH7.4; wash 2 with PBS, 50 mM Imidazole, pH7.4; elution with PBS, 500 mM imidazole, pH7.4).

Fractions containing the protein are pooled, dialyzed into PBS pH 7.4 and followed by SUMO digestion. Then the protein is two-step purified with Ni-NTA beads (continue with flow through sample) and gel filtration. Fractions containing the protein are pooled and QC is performed using analytical techniques, such as SDS-PAGE and analytical SEC.

Insoluble his-SUMO-IL18 Variants

*E. coli* BL21 (DE3) harboring a plasmid encoding a N-His-SUMO tagged IL-18 variant fusion are inoculated into 10 L LB culture medium and induced with 0.4 mM IPTG at 30° C. for 6 h. Cells are pelleted and cell lysis is done by sonication in lysis buffer: PBS, 8 M urea, pH 7.4. Protein is purified via Ni-NTA beads 6FF (wash 1 with: PBS, 8 M urea, 20 mM imidazole, pH7.4; wash 2 with PBS, 8 M urea, 50 mM Imidazole, pH7.4; elution with PBS, 8 M urea, 500 mM imidazole, pH7.4).

Fractions containing the protein are pooled, dialyzed into PBS pH 7.4 and followed by SUMO digestion. Then the protein is purified with Ni-NTA beads (equilibrate column with PBS, 8 M urea, pH 7.4, wash with PBS, 8 M urea, pH 7.4, elution with PBS, 8 M urea, pH 7.4). Fractions containing the protein are pooled, dialyzed into PBS pH 7.4 and QC is performed using analytical techniques, such as SDS-PAGE and analytical SEC.

Insoluble Tagless IL18 Variants

E. coli BL21 (DE3) harboring a plasmid encoding mIL-18 is inoculated into 2 L LB culture medium and induced with 0.4 mM IPTG at 30° C. for 6 h. Cells are pelleted and cell lysis was done by sonication in lysis buffer: 110 mM Tris, 1.1 M guanidine HCl, 5 mM DTT, pH 8.9. Protein as purified via Q Sepharose FF (balance buffer 20 mM MES, pH 7.0, elution with an increasing gradient from 0 to 1 M NaCl).

Example 1B—Additional Methods for Recombinant IL18 Expression and Purification

The following protocols were also used to prepare certain IL-18 polypeptides provided herein which were subsequently used either in assays for conversion into immunocytokine compositions as provided herein.

Expression of IL-18 Polypeptides

IL-18 polypeptides were produced as an N-terminal fusion to N-His-SUMO-IL18. The gene was synthesized and cloned by a commercial vendor. Plasmids were transformed into E. coli BL21 (DE3). Expression was performed in shake flasks with TB medium. The cells were grown at 37° C. until an OD600 of approximately 1.2 was reached, after which they were induced by 0.1 mM IPTG and cultured for another 20 hours at 18° C. Cells were harvested by centrifugation.

Purification of IL18 Polypeptides

Cell lysis—Cells were resuspended in lysis buffer (20 mM Tris/HCl, pH 8.0, 0.15 M NaCl, 10 mM Imidazole, 1 tablet of EDTA-free complete protease inhibitor (Roche, COEDTAF-RO) per liter production) at 100 mL buffer/L culture and disrupted twice with a homogenizer at 1000 bar. The lysate was cleared of debris by centrifugation at 40'000 g for 2×45 minutes, changing flask in between, and subsequent filtration through a 0.22 µm filter.

Affinity Purification and Endotoxin Removal—The lysate was loaded on Ni NTA resin (Cytiva, 17524802) pre-equilibrated with 20 mM Tris/HCl, pH 8.0, 0.15 M NaCl, 10 mM Imidazole, at 5 mL/min and washed with the same buffer for 5 CV. To remove endotoxins, the column was washed with 20 mM Tris/HCl, pH 8.0, 0.15 M NaCl, 10 mM Imidazole, 0.1% Tryton X-114 at 10 mL/min for 30 CV. The column was washed with 20 mM Tris/HCl, pH 8.0, 0.15 M NaCl, 10 mM Imidazole, for 5 CV at 5 mL/min and the protein of interest eluted by linear increase of imidazole concentration. The column was then regenerated by 0.5M NaOH.

SUMO digestion and dialysis—To cleave the SUMO tag, SUMO protease was added to the elution pool at a w/w ratio of 1:250 (protein:SUMO enzyme) and incubated for 18 hours at 4° C. At the same time, the protein was dialysed (20 mM Tris, pH 8.0, 150 mM NaCl), to reduce the imidazole concentration.

Purification by reverse IMAC—In order to remove the cleaved tag and the SUMO protease, the digested protein was flown through a Ni NTA resin column pre-equilibrated with 20 mM Tris/HCl, pH 8.0, 0.15 M NaCl, 10 mM Imidazole, at 5 mL/min. The flow-through was collected.

Buffer Exchange—The flow-through was concentrated to 2.6 mg/mL and buffer exchanged into either 20 mM HEPES, 150 mM NaCl, 0.5 mM TCEP, 10% glycerol, pH7.5 or PBS, 10% glycerol, pH7.4. Proteins were stored at −70° C. until further quality controls.

Example 2—Conjugation of IL-18 Polypeptide with Bifunctional Linking Group

Figure 6:
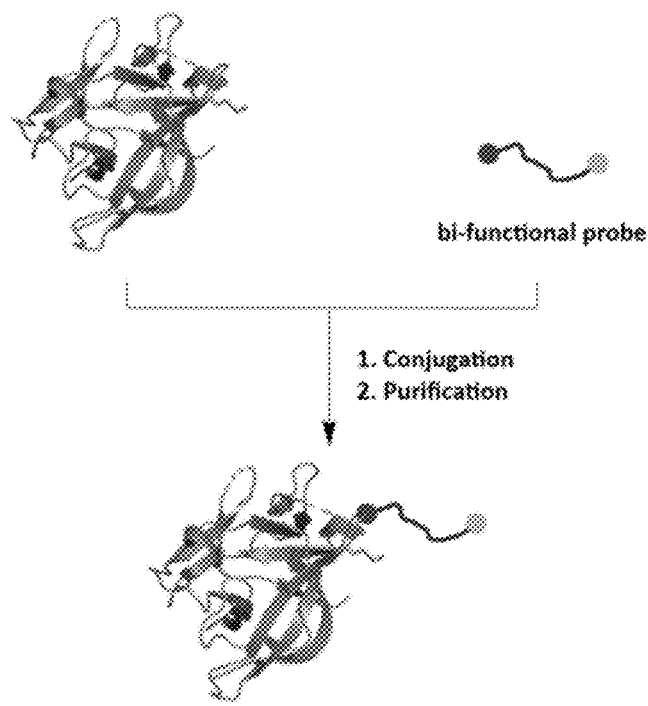
FIG. 6 shows a schematic representation of coupling of a bifunctional probe (also referred to as bifunctional linking reagent herein) to an IL-18 polypeptide provided herein.

An IL-18 polypeptide as provided herein can conjugated to a bifunctional linking group prior to forming the full linker of the immunocytokine composition. In some cases, the bifunctional linking group first attaches to a desired residue of the IL-18 polypeptide at the point of attachment of the linker. Once attached to the IL-18 polypeptide, the second functionality of the bifunctional linking group is used to attach to a second portion. An exemplary schematic of such a process is shown in FIG. 6. The process shown in FIG. 6 is not needed for all IL-18 polypeptides, as some IL-18 polypeptides provided herein (e.g., an IL-18 with the desired conjugation handle for final linkage with the antibody already attached). An exemplary protocol on an IL-18 polypeptide with a cysteine residue point of attachment provided herein is described below.

Conjugation—The IL-18 polypeptide is stored at a concentration of 2.4 mg/mL at −80° C. in potassium phosphate buffer (pH 7.0) containing 50 mM KCl and 1 mM DTT. The sample is thawed on ice yielding a clear solution. The protein solution is diluted in PBS, pH 7.4. A clear solution is obtained at a concentration of ~0.4 mg/mL.

The protein solution is dialyzed against PBS, pH 7.4 (twice against 600 mL for 2 h and once against 800 mL for 18 h). After dialysis, a clear solution is obtained with no sign of precipitation. Protein concentration is obtained using UV absorbance at 280 nm and by BCA protein assay.

A stock solution of bi-functional linking group (e.g., bromoacetamido-PEG5-azide, CAS: 1415800-37-1) in water is prepared at a concentration of 20 mM. 500 µL of the protein solution are mixed with 25 µL of linking group solution. pH was adjusted to 7.5 and it was let to react for 3 h at 20° C.

The progress of the synthesis is monitored by reverse-phase HPLC using a gradient of 5 to 30% (2.5 min) and 30 to 75% (7.5 min) CH$_3$CN with 0.1% TFA (v v) on a Aeris WIDEPORE C18 200 Å column (3.6 m, 150×4.6 mm) at a flow rate of 1 mL/min at 40° C. and by MALDI-TOF MS.

Purification—In some cases, ion-exchange chromatography is used to purify the conjugated protein. To remove the excess of probe, the reaction mixture (volume is around 500 µL) is flowed through a Hi-Trap-G-FF-1 mL column using 25 mM Tris (pH 7.4) as the buffer. The column is eluted with a linear gradient of 0-0.35 M NaCl in the same buffer. The fractions containing the target protein are gathered, buffer exchanged (25 mM Tris, pH 7.4, 75 mM NaCl, 5% glycerol) and concentrated at 0.4 mg/mL. The concentration of purified protein is determined by UV absorbance at 280 nm and by BCA protein assay. The protein solution is kept at −80° C.

Characterization—The purity and identity of the recombinant protein from commercial source and the conjugated protein is confirmed by aSEC, HPLC and MALDI-TOF MS.

Example 3—Conjugation of IL-18 Polypeptide to Antibody

Preparation of a Conjugatable Antibody

Figure 3:
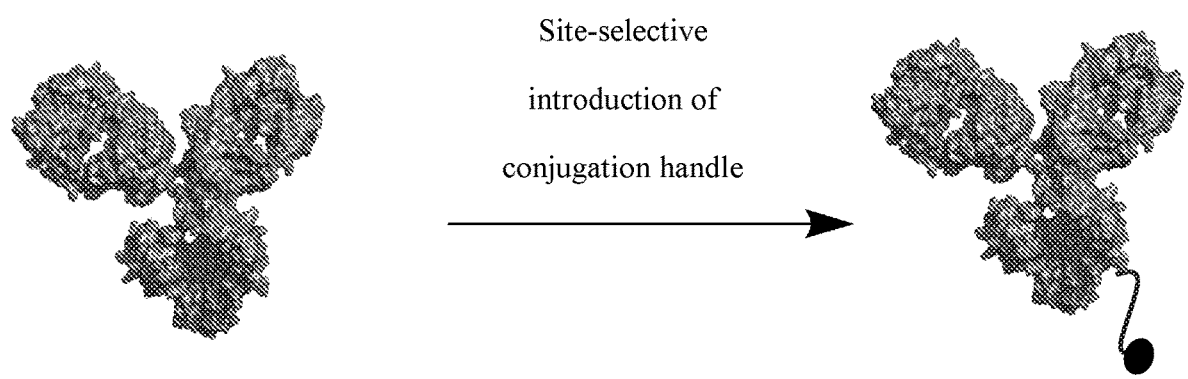
FIG. 3 shows an illustration of a site selective introduction of a conjugation handle to an antibody as provided herein.

A modified antibody (e.g., an anti-PD-1 antibody such as nivolumab or LZM-009) comprising a DBCO conjugation handle is prepared using a protocol modified from Examples 2-4 of US Patent Publication No. US2020019165A1. An exemplary illustration of this process resulting in the attachment of one DBCO conjugation handle is shown in FIG. 3. Briefly, the CD20 antibody with a free sulfhydryl group attached to a lysine residue side chain in the Fc region is prepared by reacting the antibody with an affinity peptide configured to deliver a protected version of the sulfhydryl group (e.g., a thioester) to the lysine residue. The protecting group is then removed to reveal the free sulfhydryl. The free sulfhydryl is then reacted with a bifunctional reagent comprising a bromoacetamide group connected to the DBCO conjugation handle through a linking group (e.g., bromoacetamido-dPEG®$_4$-amido-DBCO). The method can be used to produce an antibody with one DBCO group present (DAR1) and/or two DBCO groups attached to the antibody (DAR2, one DBCO group linked to each Fc of the antibody).

Conjugation of Antibody to IL-18 Polypeptide

Figure 7:
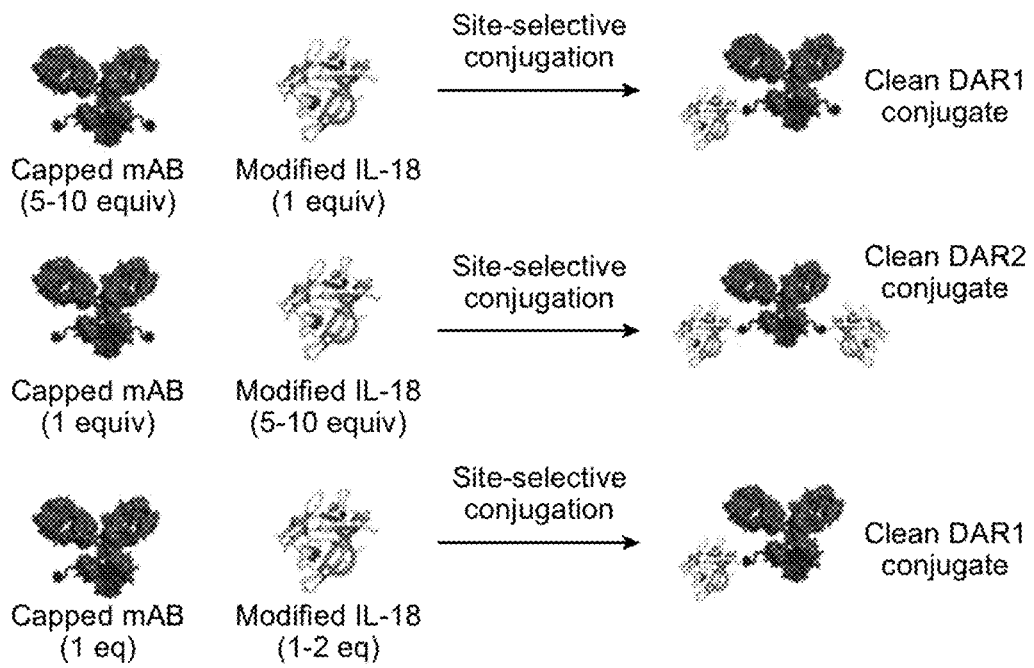
FIG. 7 shows exemplary reaction scheme which can be used to prepare antibody/IL-18 immunocytokine compositions provided herein with drug antibody ratio of 1 (top) or 2 (bottom).

The DBCO modified antibody is then conjugated to a IL-18 polypeptide comprising an azide moiety at a desired point of attachment (e.g., an IL-18 polypeptide which contains an amino acid with an azide side chain or an IL-18 linked to an azide using a bifunctional linking group as in Example 4). DBCO modified antibody with one (DAR1) or two (DAR2) reactive handles are reacted with 2-10 equivalents of azide containing IL-18 (pH 5.2 buffer, 5% trehalose, rt, 24 h). In an alternative embodiment, antibody comprising two DBCO conjugation handles is reacted either as an excess reagent (e.g., 5-10 equivalents) with 1 equivalent of IL-18 comprising an azide functionality to produce a DAR1 antibody or the antibody comprising two DBCO conjugation handles is reacted with 1 equivalent of antibody with excess reagent of IL-18 comprising an azide (e.g., 5-10 equivalents) to produce a DAR2 antibody. An illustration of this protocol is shown in FIG. 7.

Purification and Characterization of Antibody-IL-18 Immunocytokine

The resulting immunocytokine is purified by cation-exchange chromatography and/or size exclusion chromatography to obtain purified immunocytokine. Antibody-IL-18 polypeptide immunocytokine is purified from unreacted IL-18 and aggregates using a desalting column, CIEX and SEC (GE Healthcare Life Sciences AKTA pure, mobile phase: Histidine 5.2/150 mM NaCl/5% Trehalose, column: GE Healthcare Life Sciences SUPERDEX™ 200 increase 3.2/300, flow rate: 0.5 mL/min).

The purity and identity of the antibody-IL-18 polypeptide immunocytokine is confirmed by RP-HPLC (HPLC: ThermoFisher Scientific UHPLC Ultimate 3000, column: Waters BEH C-4 300A, 3.0 µm, 4.6 mm, 250 mm, mobile phase A: 0.05% TFA in Water, mobile phase B: 0.05% TFA in mixture of ACN:IPA:ETOH:H2O (5:1.5:2:1.5), flow rate: 0.5 mL/min, injection amount: µg (10 µL Injection of 1 mg/mL), gradient: 0% to 20% mobile phase B in 50 min) and SDS-PAGE.

Figure 8:
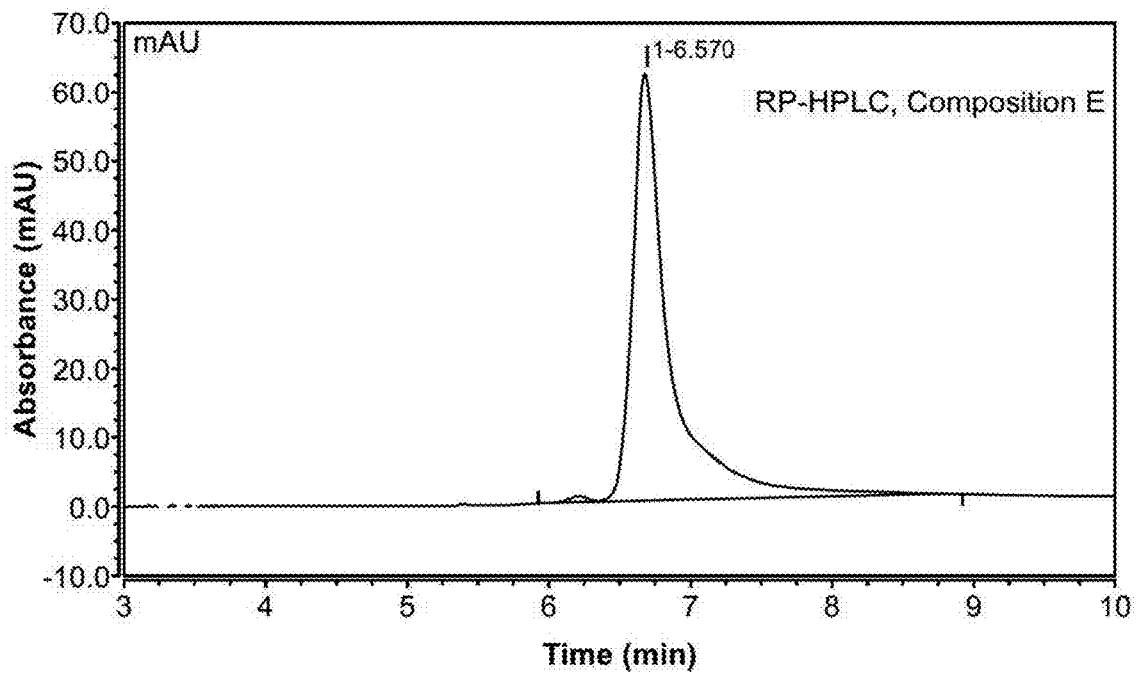
FIG. 8 shows a reverse phase HPLC chromatogram of a purified IL-18/anti-PD-1 antibody (LZM009) as provided herein with a DAR of 1 attached at residue K248 of the Fc region of the antibody (EU numbering).
Figure 9:
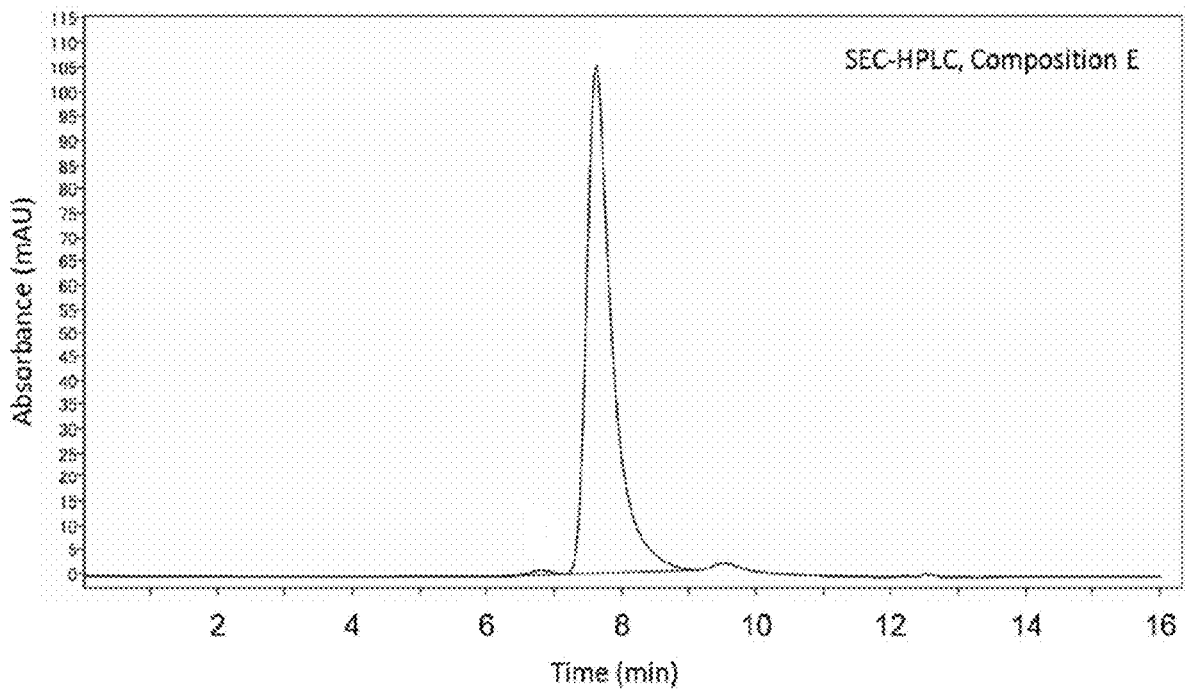
FIG. 9 shows a size exclusion HPLC chromatogram of a purified IL-18/anti-PD-1 antibody (LZM009) as provided herein with a DAR of 1 attached at residue K248 of the Fc region of the antibody (EU numbering).
Figure 10:
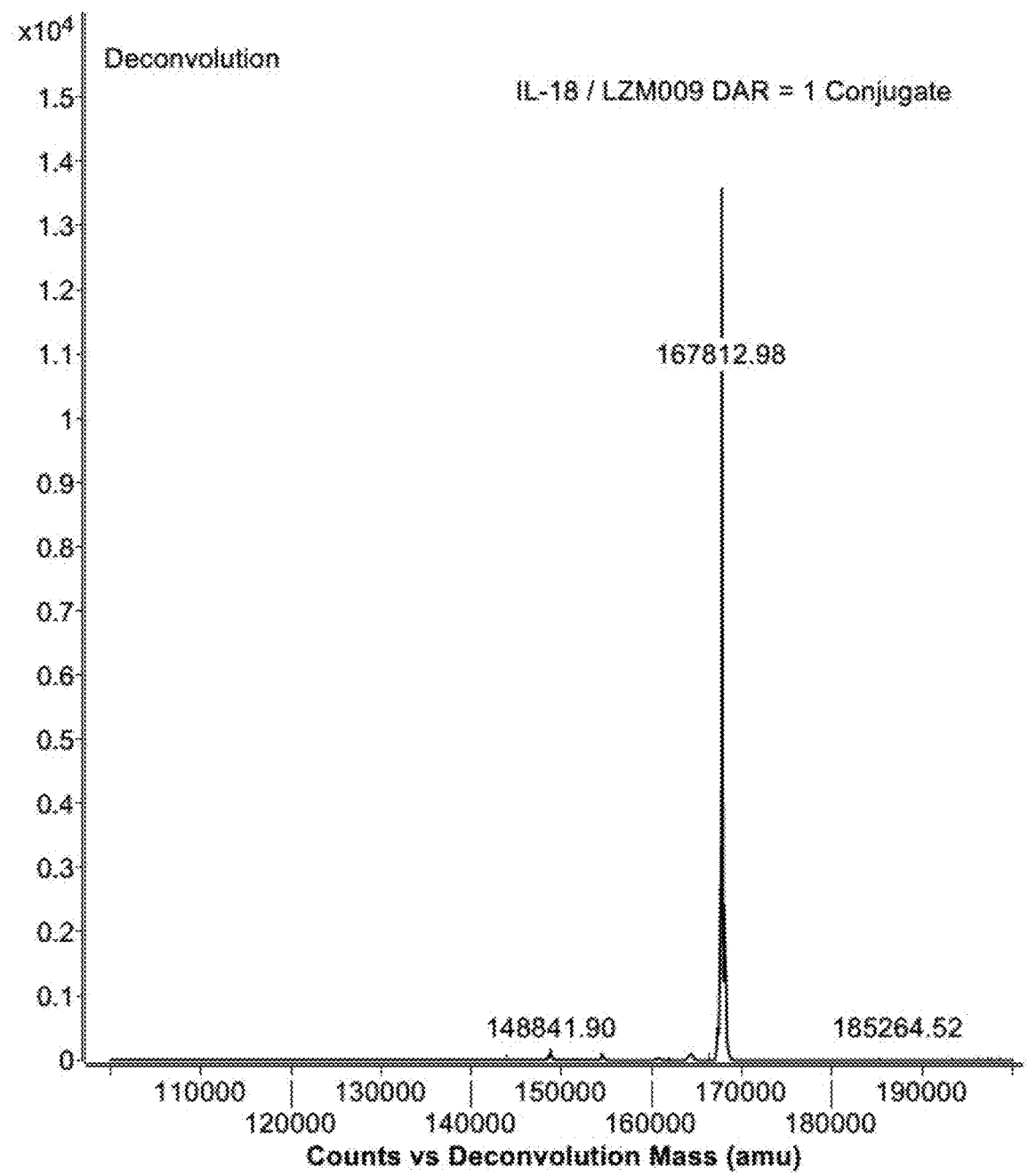
FIG. 10 shows a mass spectrometry trace (Q-TOF) of a purified IL-18/anti-PD-1 antibody (LZM009) as provided herein with a DAR of 1 attached at residue K248 of the Fc region of the antibody (EU numbering).

Exemplary chromatograms and analytical characterization of DAR1 immunocytokines of an IL-18 of SEQ ID NO: 60 conjugated via residue C68 and an anti-PD-1 antibody (LZM-009) prepared according to the described methods are shown in FIGS. 8-10.

Figure 11:
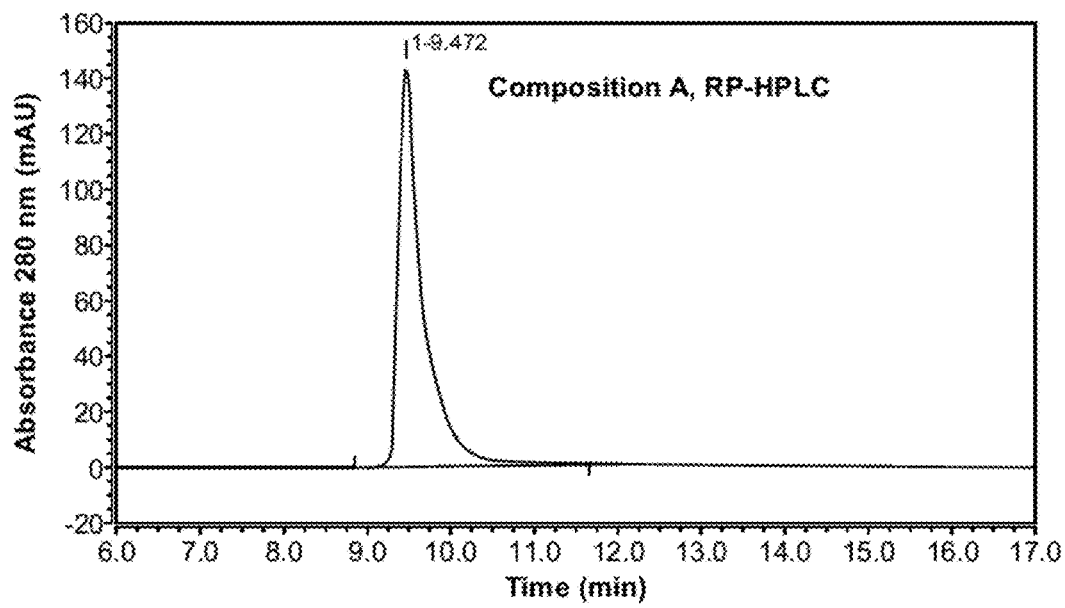
FIG. 11 shows the RP-HPLC chromatograms of purified composition A (detection: 280 nm).
Figure 12:
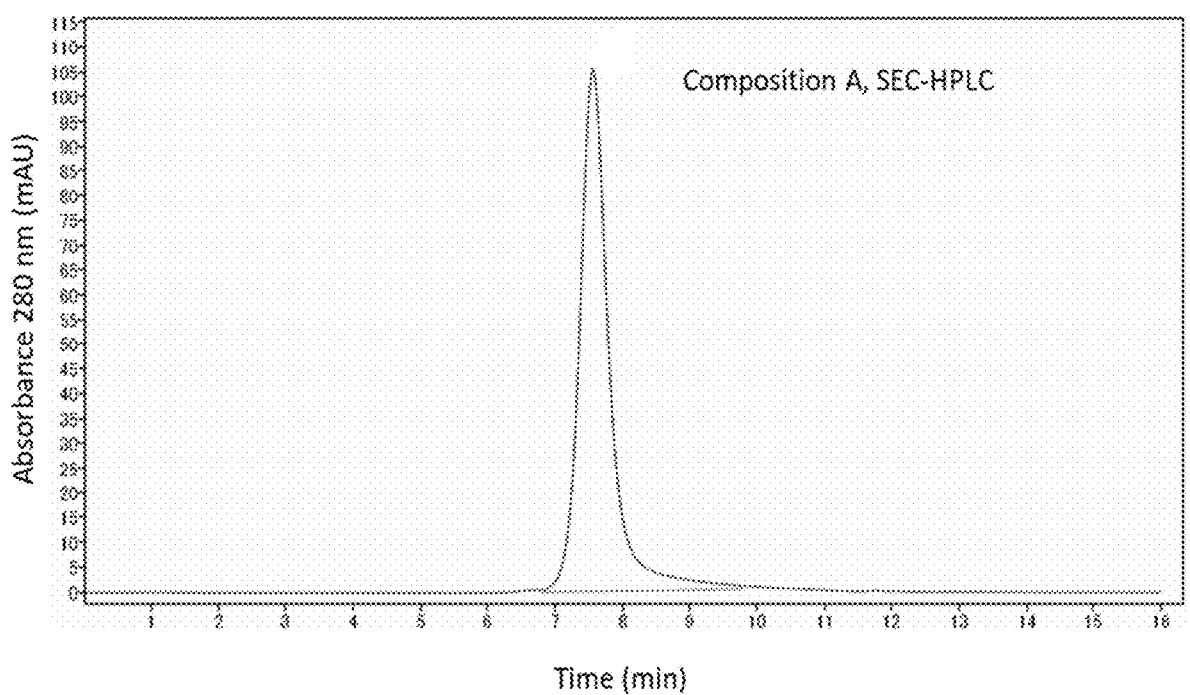
FIG. 12 shows the Analytical SEC-HPLC chromatograms of purified composition A (detection: 280 nm).
Figure 13:
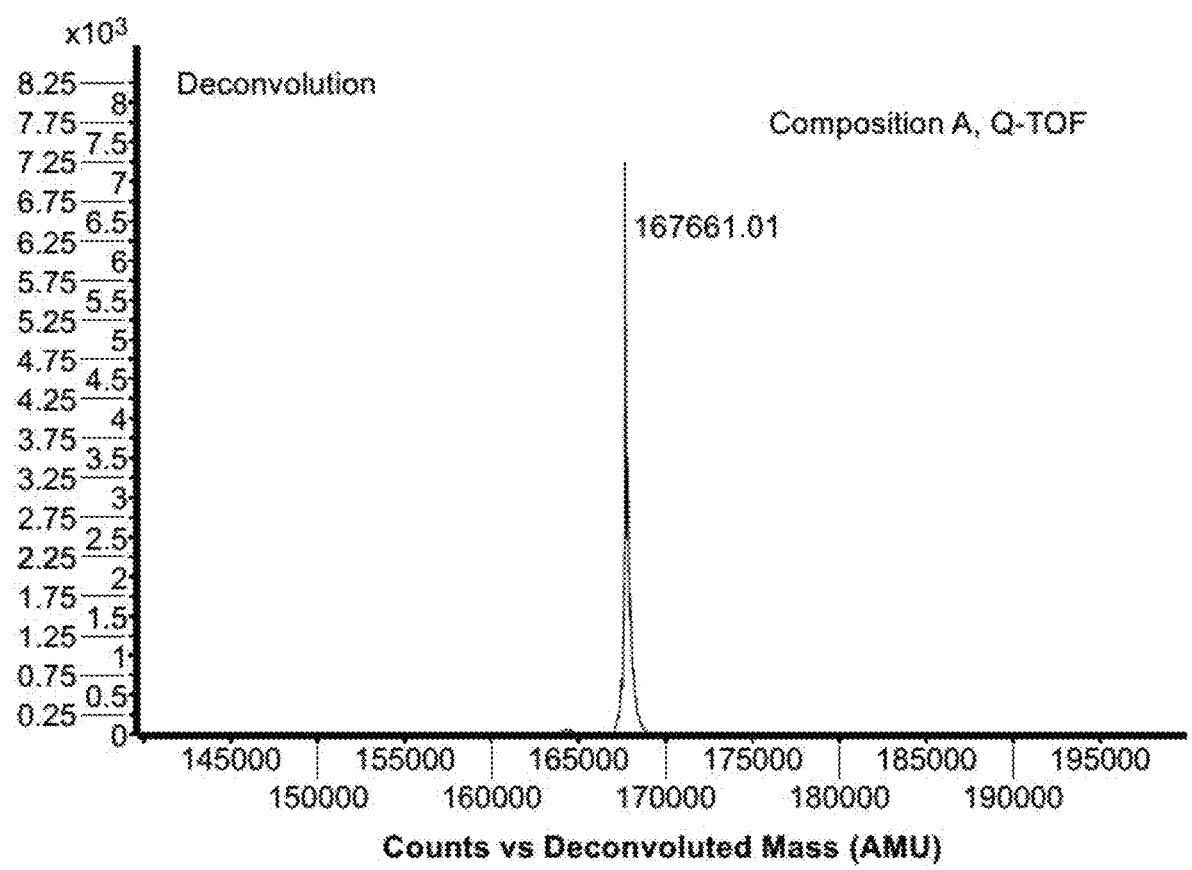
FIG. 13 shows the Q-TOF mass spectrometry deconvolution chromatogram of purified composition A.

Additional exemplary chromatograms and analytical characterization of a DAR1 immunocytokine of an IL-18 of SEQ ID NO: 30 conjugated via residue C68 to Fc residue K248 of the anti-PD-1 antibody LZM-009 are shown in FIG. 11 (RP HPLC), FIG. 12 (SEC-HPLC), and FIG. 13 (Q-TOF Mass Spectrometry). The immunocytokine shown is Composition A.

Example 4—Characterization of Immunocytokine IL-18 Activity

The ability of the immunocytokine to perform various IL-18 activities is measured as provided below, as well as relevant comparisons to non-conjugated IL-18 polypeptides.

Surface Plasmon Resonance

The interaction of immunocytokines, wild type IL-18, and of modified IL-18 polypeptides with human IL-18 receptor subunits are measured with Surface Plasmon Resonance (SPR) technology. Anti-human IgG antibodies are bound by amine coupling onto a CM5 chip to capture 6 g/mL of Fc fused human IL-18Rα, 6 g/mL of Fc fused human IL-18Rβ, or 2 g/mL of Fc fused human IL-18BP isoform a (IL-18BPa) for 30 min before capture. In other settings, 6 g/mL of alpha and beta IL-18 receptors are mixed and pre-incubated for 30 min before capture of the alpha/beta heterodimer IL-18 receptor.

The kinetic binding of the IL-18 analytes and immunocytokines are measured with a Biacore 8K instrument in two-fold serial dilutions starting at 1 µM down to 0.98 nM. Regeneration of the surface back to amine coupled anti IgG antibody is done after every concentration of analyte. To measure the protein association to the receptors, the samples are injected with a flow rate of 50 L/min for 60 s, followed by 300 s buffer only to detect the dissociation. The used running buffer is 1×PBS with 0.05% Tween20. The relative response units (RU, Y-axis) are plotted against time (s, X-axis) and analyzed in a kinetic 1:1 binding model for the monomer receptor binding and for the binding to the IL-18BP. A kinetic heterogenous ligand fit model is applied for the alpha/beta heterodimer binding.

IL-18BP Binding alphaLISA Assay

A human IL-18BP AlphaLISA Assay Kit is used to determine the binding affinity of each immunocytokine and IL-18 variant for IL-18BP, which detected the presence of free form IL-18BP.

Sixteen three-fold serial dilutions of IL-18 analytes are prepared in aMEM medium supplemented with 20% FCS, Glutamax, and 25 µM β-mercaptoethanol in the presence of 5 ng/mL of His-tagged human IL-18BP. Final IL-18 analytes concentration range from 2778 nM to 0.2 pM.

After 1 hr incubation at room temperature, free IL-18BP levels are measured using a Human IFNγ AlphaLISA Assay Kit. In a 384 well OPTIplate, 5 µL of 5× Anti-IL-18BP acceptor beads are added to 7.5 µL of an IL-18/IL-18BP mix. After 30 min incubation at room temperature with shaking, 5 µL of biotinylated Anti-IL-18BP antibodies are added to each well. The plate is incubated further for 1 hr at room temperature. Under subdued light, 12.5 µL of 2× streptavidin (SA) donor beads are pipetted into each well, and the wells are incubated with shaking for an additional 30 min at room temperature. The AlphaLisa signal is then measured on an Enspire plate reader with 680 and 615 nm as excitation and emission wavelengths, respectively. The dissociation constant ($K_D$) is calculated based on a variable slope, four parameter analysis using GraphPad PRISM software.

IFNγ Induction Cellular Assay

The ability of immunocytokines and IL-18 polypeptides provided herein are assessed for ability to induce IFNγ in a cellular assay according to the protocol below.

The NK cell line NK-92 derived from a patient with lymphoma (ATCC® CRL-2407™) is cultured in aMEM medium supplemented with 20% FCS, Glutamax, 25 μM β-mercaptoethanol, and 100 IU/mL of recombinant human IL-2.

On the day of experiment, cells are harvested and washed with aMEM medium without IL-2 and containing 1 ng/mL of recombinant human IL-12. After counting, cells are seeded at 100,000 cells/well in a 384 well titer plate and incubated at 37° C./5% $CO_2$. Sixteen 4-fold serial dilutions of IL-18 analytes are prepared in aMEM medium, and 1 ng/mL of IL-12 were added to the NK-92 cells. Final IL-18 analyte concentrations range from 56 nM to $5×10^{-5}$ pM.

After incubating the cells for 16-20 hr at 37° C./5% $CO_2$, 5 μL of supernatant is carefully transferred to a 384 microwell OptiPlate. IFNγ levels are measured using a human IFNγ AlphaLISA Assay Kit. Briefly, 10 μL of 2.5× AlphaLISA Anti-IFNγ acceptor beads and biotinylated antibody anti-IFNγ mix are added to the 5 μL of NK-92 supernatants. The mixtures are incubated for 1 hr at room temperature with shaking. Under subdued light, 2.5 μL of 2× streptavidin (SA) donor beads are pipetted into each well, and the wells are incubated for 30 min at room temperature with shaking. AlphaLISA signals are then measured on an EnSpire™ plate reader using 680 nm and 615 nm as excitation and emission wavelengths, respectively. Half maximal effective concentrations ($EC_{50}$) are calculated based on a variable slope and four parameter analysis using GraphPad PRISM software.

IL-18 Binding Protein Inhibition Cellular Assay

The NK cell line NK-92 derived from a patient with lymphoma (ATCC® CRL-2407™) is cultured in aMEM medium supplemented with 20% FCS-Glutamax, 25 μM β-mercaptoethanol, and 100 IU/mL of recombinant human IL-2.

On the day of experiment, cells are harvested and washed with aMEM medium without IL-2 and containing 1 ng/mL of recombinant human IL-12. After counting, the cells are seeded at 100,000 cells/well in a 384 well titer plate and incubated at 37° C./5% $CO_2$. Sixteen 2-fold serial dilutions of Fc-fused human IL-18 binding protein isoform a (IL-18BPa) are prepared in aMEM medium. 1 ng/mL of IL-12 containing 2 nM of each modified IL-18 polypeptide variant is added to the NK-92 cells. The final IL-18 analyte concentration is 1 nM, and the final IL-18BPa concentration ranged from 566 nM to 17 pM.

After incubating the cells for 16-20 hr at 37° C./5% $CO_2$, 5 μL of the supernatant is carefully transferred to a 384 microwell OptiPlate. IFNγ levels are measured using a human IFNγ AlphaLISA Assay Kit. Briefly, 10 μL of 2.5× AlphaLISA anti-IFNγ acceptor beads and biotinylated antibody anti-IFNγ mix are added to 5 μL of NK-92 supernatants. The mixtures are incubated for 1 hr at room temperature with shaking. Under subdued light, 2.5 μL of 2×SA donor beads are pipetted in each well and incubated for 30 min at room temperature with shaking. AlphaLISA signals are then measured on an EnSpire™ plate reader using 680 nm and 615 nm as excitation and emission wavelengths, respectively. Half maximal inhibitory concentrations ($IC_{50}$) are calculated based on a variable slope and four parameter analysis using GraphPad PRISM software.

IFNγ Induction on Primary Human Cells

Ability of IL-18 variants to stimulate Human peripheral blood mononuclear cells (PBMCs) was assessed according to the following protocol.

Isolation of lymphocytes: Blood from Buffy Coats of healthy volunteers was diluted with equal volume of PBS and slowly poured on top of SepMate tube prefilled with 15 mL Histopaque-1077. Tubes were centrifuged for 10 minutes at 1200 g, the top layer was collected and washed 3 times with PBS containing 2% of Fetal Bovine Serum. PBMCs were counted and cryopreserved as aliquots of $20×10^6$ cells.

Cryopreserved PBMCs were thawed and seeded at 150 000 cells/well in a 96w round bottom 96 well plate. PBMCs were stimulated with a gradient of human IL-18 variants ranging from 0.2 pg/mL to 3600 ng/mL. All stimulations were performed in the presence of hIL-12 (1 ng/ml, Sino Biological, #CT011-H08H) for 24 hrs in RPMI containing 10% Fetal Bovine Serum.

Cytokine production after 24 hr stimulation were measured using Legendplex bead-based cytokine assay (Biolegend #740930) according to manufacturer protocol. Half maximal effective concentrations ($EC_{50}$) of IFNg released in culture supernatant were calculated based on a variable slope and four parameter analysis using GraphPad PRISM software.

IFNγ Induction on Primary Mouse Cells

Ability of IL-18 variants to stimulate murine splenocytes was assessed according to the following protocol.

Cryopreserved splenocytes isolated from BALB/c and C57BL6 mice were purchased from IQ Biosciences (Berkeley, CA, USA).

Cryopreserved splenocytes were thawed, treated with DNAseI, and seeded at 200 000 cells/well in a 96w round bottom 96 well plate. Splenocytes were stimulated with a gradient of human IL-18 variants ranging from 0.2 pg/mL to 3600 ng/mL. All stimulations were performed in the presence of mIL-12 (1 ng/ml, Peprotech, cat #210-12) for 24 hrs in RPMI containing 10% Fetal Bovine Serum.

Cytokine production after 24 hr stimulation were measured using Legendplex bead-based cytokine assay (Biolegend #740622) according to manufacturer protocol. Half maximal effective concentrations ($EC_{50}$) of IFNg released in culture supernatant were calculated based on a variable slope and four parameter analysis using GraphPad PRISM software.

Example 5—Immune Cell Associated Antigen Binding ELISA Assay (FIG. 14A, FIG. 14B, FIG. 15A, and FIG. 15B)

The interaction of the unmodified antibodies and corresponding IL-18 immunocytokines with relevant immune cell associated antigen are measured by ELISA assay. For these studies, Corning high-binding half-area plates (Fisher Scientific, Reinach, Switzerland) are coated overnight at 4° C. with 25 μl of unmodified antibodies corresponding IL-18 immunocytokines at 5 μg/ml in PBS. Plates are then washed four times with 100 μl of PBS-0.02% Tween20. Plate surfaces are blocked with 25 μl of PBS-0.02% Tween20-1% BSA at 37° C. during 1 h. Plates are then washed four times with 100 μl of PBS-0.02% Tween20. Twenty-five microliters (25 μl) of recombinant biotinylated human PD-1 (Biotinylated Recombinant Human PD-1/CD279-Fc Chimera, carrier-free, Biolegend #789406) or PD-L1 (Biotinylated Human PD-L1/B7-H1, ACROBiosystems, PD1-H82E5-25UG) protein are added in seven-fold serial dilutions starting at 12 nM down to 0.15 pM into PBS-0.02% Tween20-0.1% BSA and incubated at 37° C. during 2 h. Plates are then washed four times with 100 μl of PBS-0.02% Tween20. Twenty-five microliters of Streptavidin-Horseradish peroxidase (#RABHRP3, Merck, Buchs, Switzerland) diluted at 1:500 into PBS-0.02% Tween20-0.1% BSA are added to each well and incubated at Room Temperature during 30 min. Plates are then washed four times with 100 μl of PBS-0.02% Tween20. Fifty microliters of TMB substrate reagent (#CL07, Merck, Buchs, Switzerland) are added to each well and incubated at 37° C. during 5 min. After 5 min at 37° C., Horseradish peroxidase reaction is stopped by adding 50 μl/well of 0.5M $H_2SO_4$ stop solution. ELISA signal is then measured at 450 nm on an ENSPTRE® plate reader from Perkin Elmer (Schwerzenbach, Switzerland). Results from this experiment are shown in the table below.

KD Values of the Interaction of Immunocytokines with PD-1 and PD-L1 as Measured by ELISA

| Composition | Antibody | IL-18 polypeptide | PD-1 KD (pM) | PD-L1 KD (pM) |
| --- | --- | --- | --- | --- |
| — | Pembrolizumab/Keytruda | — | — | >100000 |
| — | LZM-009 | — | 40.7 | >100000 |
| — | Nivolumab/Opdivo | — | 91.9 | >100000 |
| — | Durvalumab/Imfinzi | — | >100000 | 146 |
| — | Atezolizumab/Tecentriq | — | >100000 | 443 |
| — | Avelumab/Bavencio | — | >100000 | 36 |
| A | LZM-009 | SEQ ID NO: 30 | 46.7 | >100000 |
| B | Atezolizumab/Tecentriq | SEQ ID NO: 30 | >100000 | 473 |

Figure 14A:
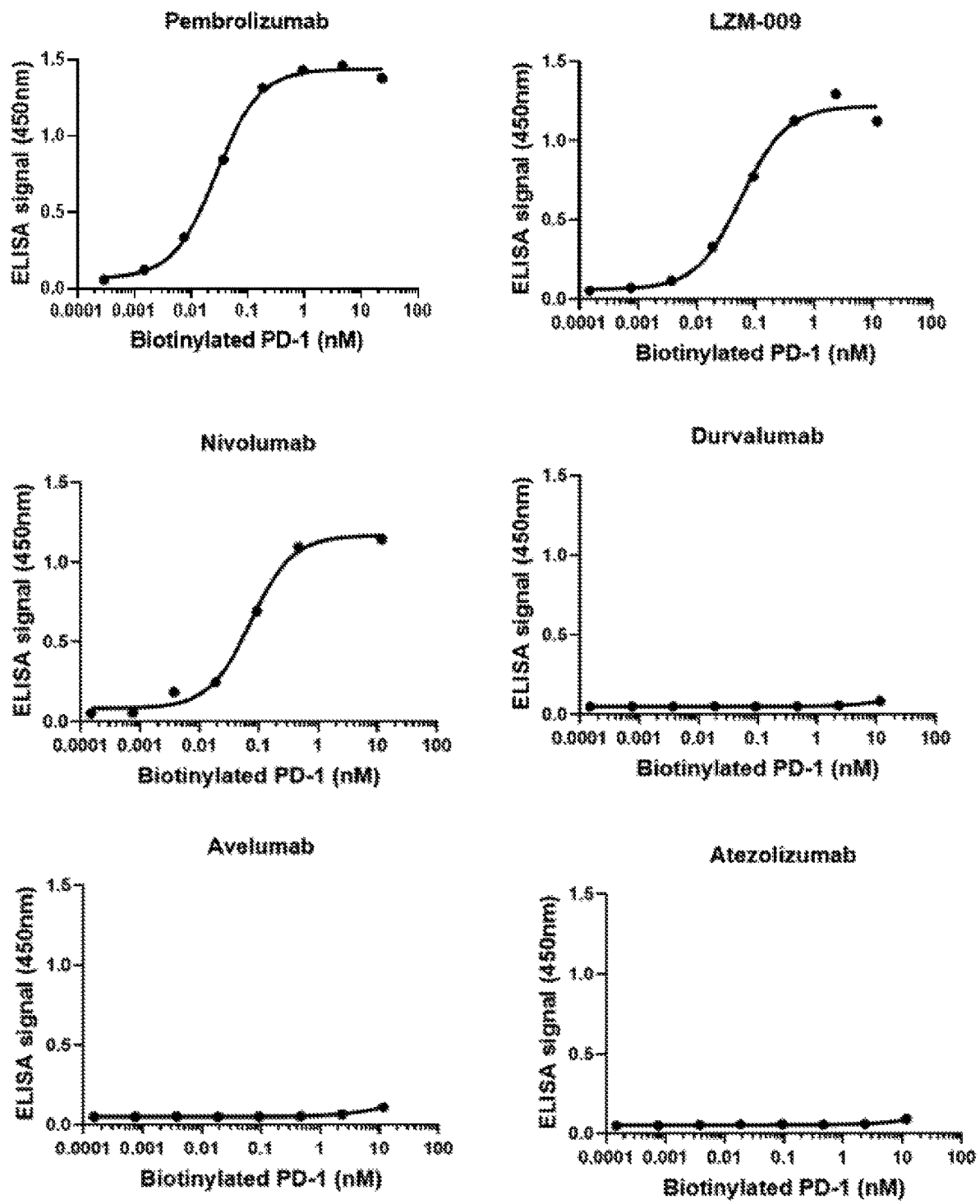
FIG. 14A and FIG. 14B show plots measuring ability of the unmodified and of conjugated anti-PD1 antibodies to bind with human PD1/CD279 ligand, with the figure showing ELISA signal on the y-axis and dosage of the biotinylated PD-1 protein on the x-axis.
Figure 14B:
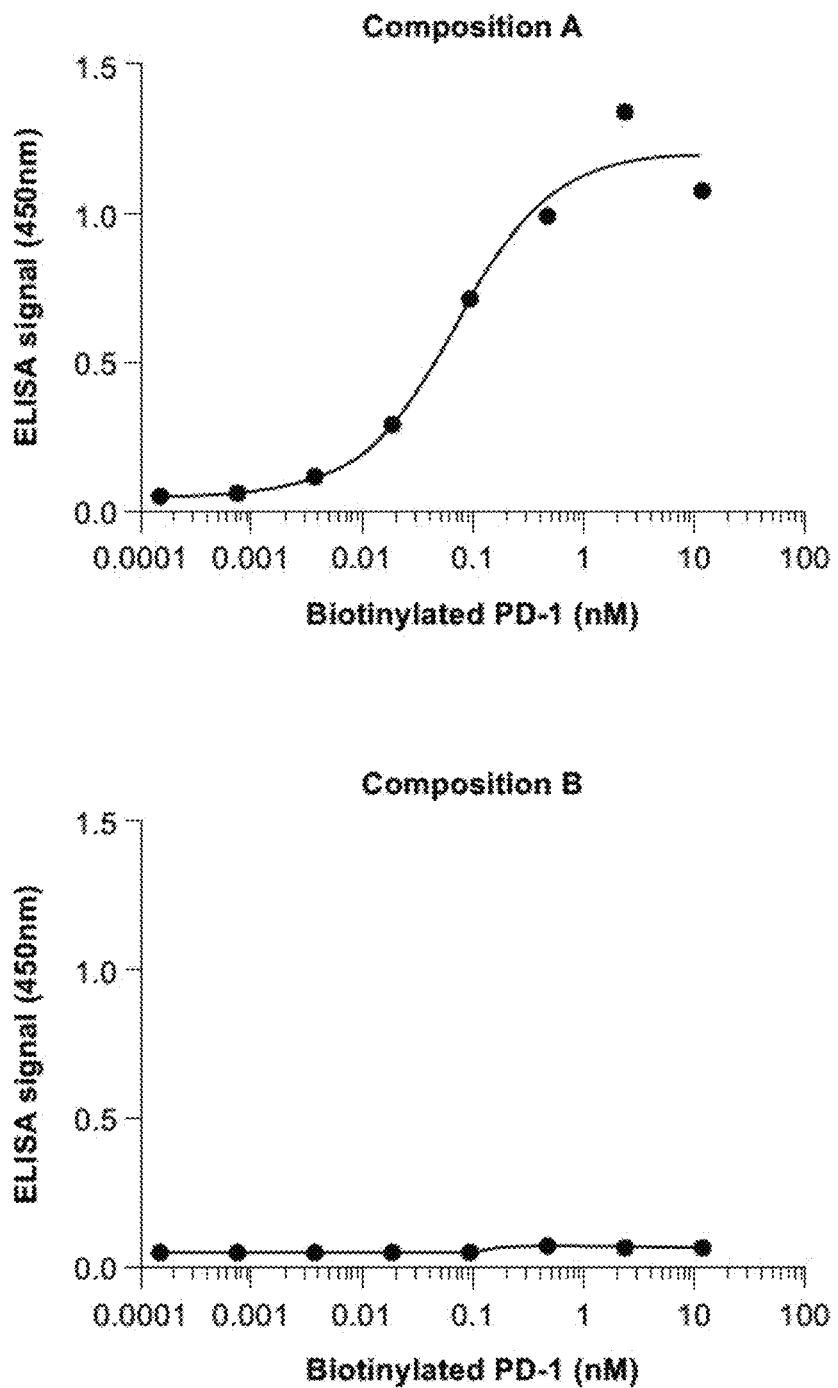

FIG. 14A and FIG. 14B show plots measuring ability of the unmodified and of conjugated anti-PD1 antibodies to bind with human PD1/CD279 ligand, with the figure showing ELISA signal on the y-axis and dosage of the biotinylated PD-1 protein on the x-axis. The unconjugated reference antibodies are Pembrolizumab, LZM-009, Nivolumab, Atezolizumab, Durvalumab, and Avelumab. The conjugated antibodies tested in this figure are compositions A and composition B.

Figure 15A:
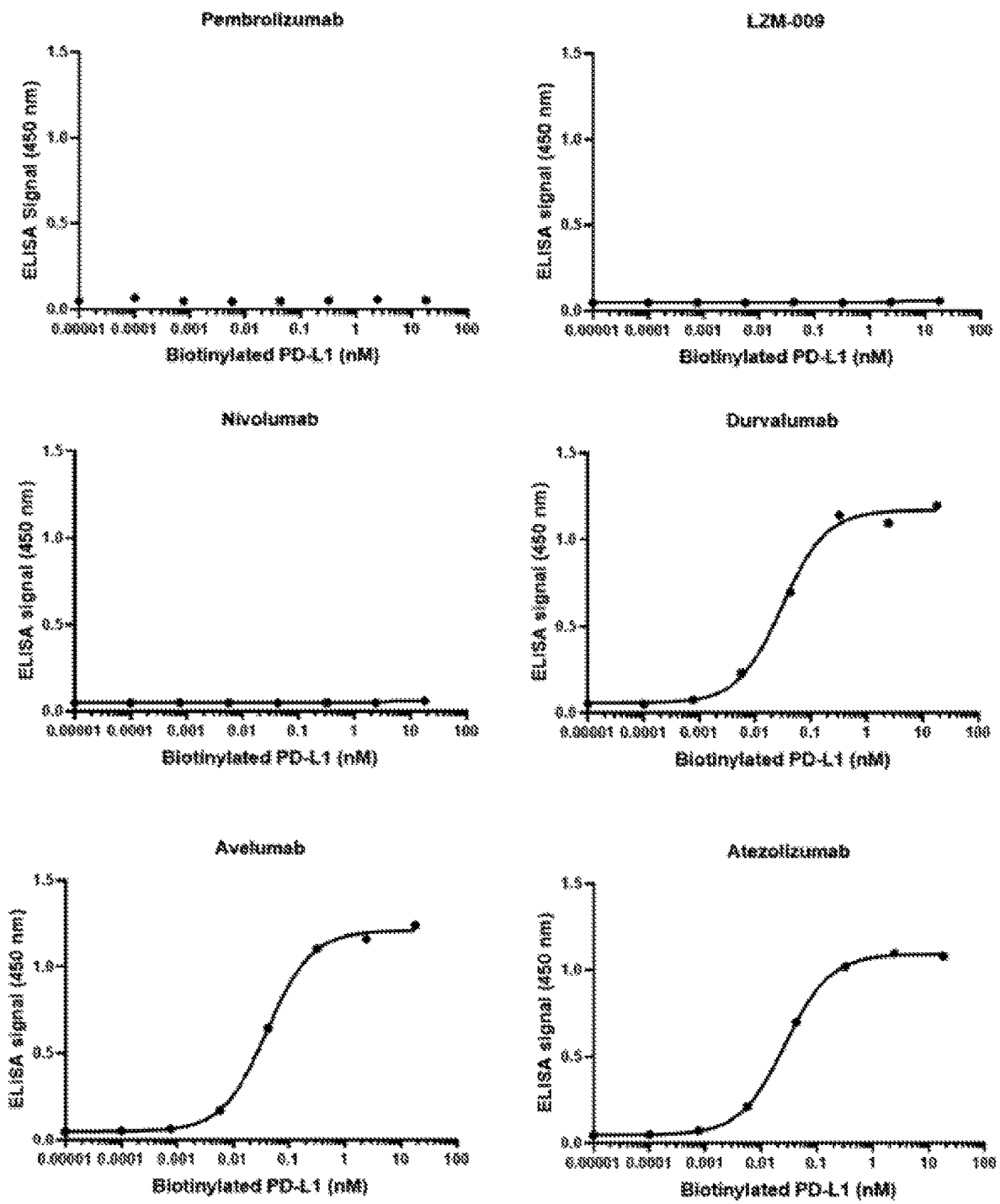
FIG. 15A and FIG. 15B show plots measuring ability of the unmodified and of conjugated antibodies to bind with human PD-L1/B7-H1 ligand, with the figure showing ELISA signal on the y-axis and dosage of the biotinylated PD-L1 protein on the x-axis.
Figure 15B:
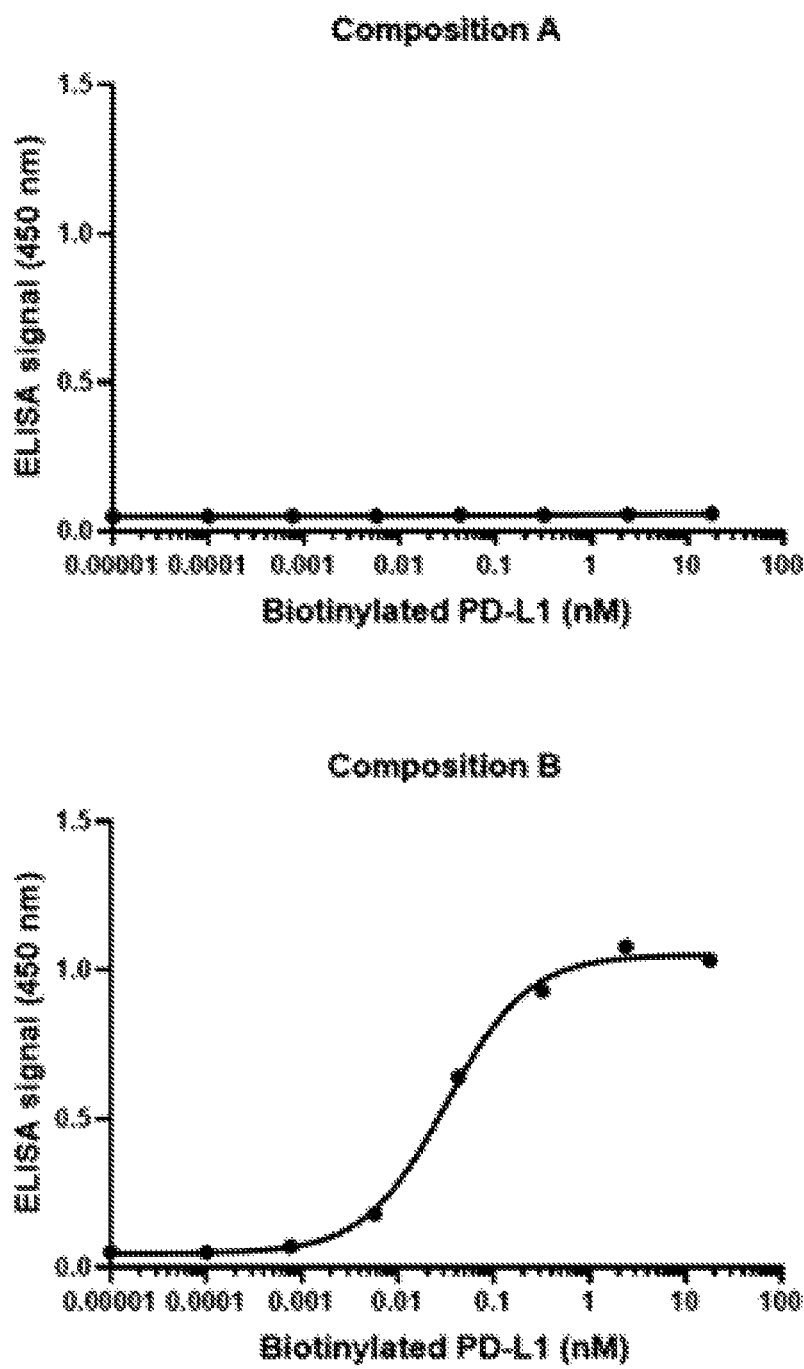

FIG. 15A and FIG. 15B show plots measuring ability of the unmodified and of conjugated antibodies to bind with human PD-L1/B7-H1 ligand, with the figure showing ELISA signal on the y-axis and dosage of the biotinylated PD-L1 protein on the x-axis. The unconjugated reference antibodies are Pembrolizumab, LZM-009, Nivolumab, Atezolizumab, Durvalumab, and Avelumab. The conjugated antibodies tested in this figure are compositions A and composition B.

Figure 16:
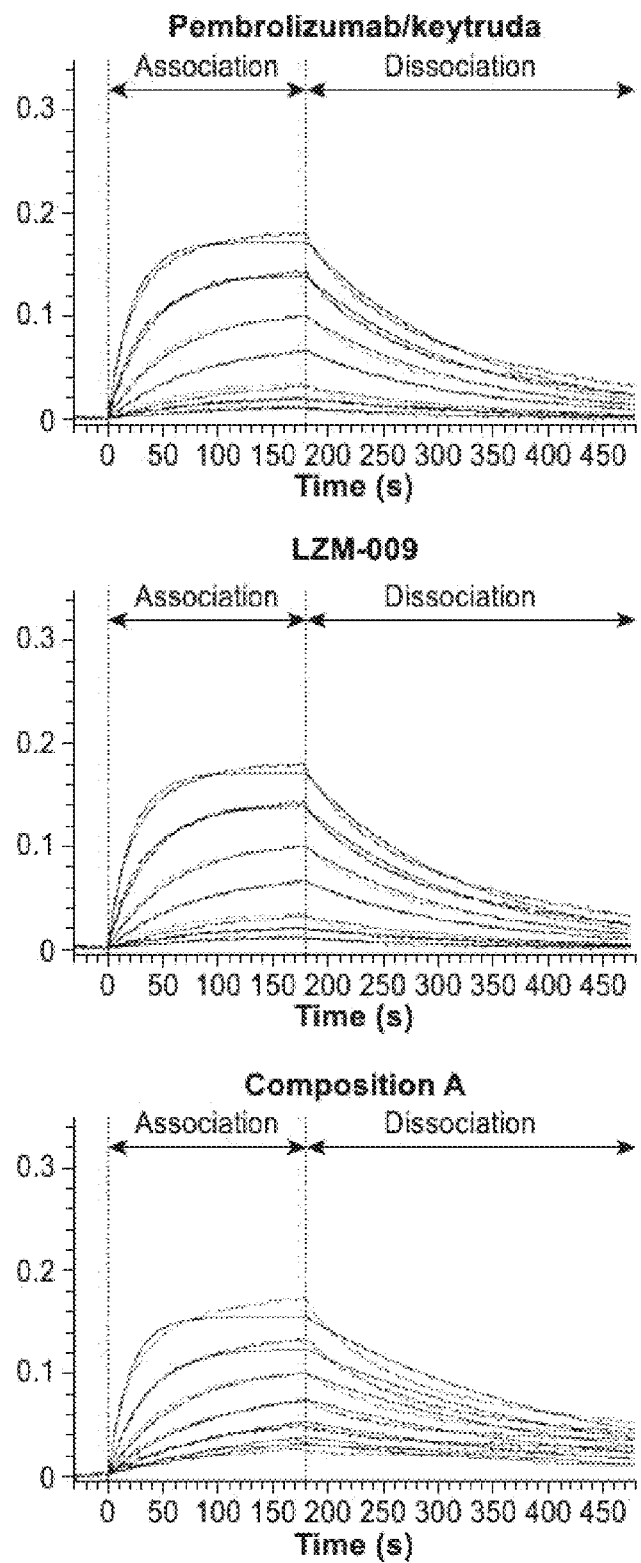
FIG. 16 shows plots measuring ability of the unmodified and of conjugated antibodies to bind to human PD-L1/B7-H1 ligand, with the figure showing net BioLayer interferometry shift in nanometer on the y-axis and time of incubation dosage of the biotinylated PD-L1 protein on the x-axis. The figure shows mean ELISA signal on the y-axis and dosage of the human Fc gamma receptors on the x-axis. The unconjugated reference antibodies are Pembrolizumab and LZM-009. The conjugated antibodies tested is Compositions A.

Example 6—Kinetic Analysis of Binding of Reference Antibodies and Immunocytokines to Immune Cell Associated Antigens (FIG. 16)

Based on Bio-Layer Interferometry (BLI), Octet® BLI systems enable real-time, label-free analysis for the determination of kinetics and affinity of a ligands to its receptor. Here anti-human IgG FC Capture (AHC) sensors are loaded with the test items (ICs). Sensors are first dipped into a kinetic buffer for baseline measurement, then into an analyte solution, here human PD1, to allow association and again into a buffer solution where the analyte is allowed to come off the ligand (dissociation). Several concentrations of analyte are run in parallel and enable the calculation of affinity parameters: Ka, Kd, KD.

Typically, first, the sensors are regenerated by 3 cycles of dipping into 10 mM glycine solution at pH=2 for 20 seconds, followed by 20 second kinetics buffer and a final 60 seconds in kinetics buffer to establish the initial signal (baseline). Second, the loading column will contain the ligand, here the unmodified PD-1 antibodies and of IL-18 polypeptide conjugated PD-1 antibody, at a fixed concentration determined in the loading scout experiment (20 ug/mL). Then another wash/baseline step allows non immobilized proteins to be washed away. The association column will contain the 2-fold dilution series of the analyte (His-tagged human PD1, R&D #8986-PD) including a no analyte control. The highest concentration should be ~10-fold the KD. The dissociation designates the sensors to return to previous baseline column with kinetics buffer. After acquisition, the data is analyzed with Data Analysis Studio software (Sartorius). Data sets are first preprocessed by subtracting references samples and aligning curves on the baseline step. Group fitting is then applied to the data series and kinetics parameters are calculated. Results from this experiment are shown in the table below.

Binding Kinetics of the Interaction of Reference Antibodies and Immunocytokines with PD-1 as Measured by Bio-Layer Interferometry (BLI)

| Composition | Antibody | IL-18 polypeptide | ka (1/Ms) | kd (1/s) | KD (nM) |
| --- | --- | --- | --- | --- | --- |
| — | Pembrolizumab/Keytruda | — | 4.00E+05 | 2.72E−03 | 6.77 |
| — | LZM-009 | — | 3.42E+05 | 7.70E−03 | 23.50 |
| A | LZM-009 | SEQ ID NO: 30 | 4.54E+05 | 4.79E−03 | 11.50 |

FIG. 16 shows plots measuring ability of the unmodified and of conjugated antibodies to bind to human PD-L1/B7-H1 ligand, with the figure showing net BioLayer interferometry shift in nanometer on the y-axis and time of incubation dosage of the biotinylated PD-L1 protein on the x-axis. The figure shows mean ELISA signal on the y-axis and dosage of the human Fc gamma receptors on the x-axis. The unconjugated reference antibodies are Pembrolizumab and LZM-009. The conjugated antibodies tested is Compositions A.

Figure 17A:
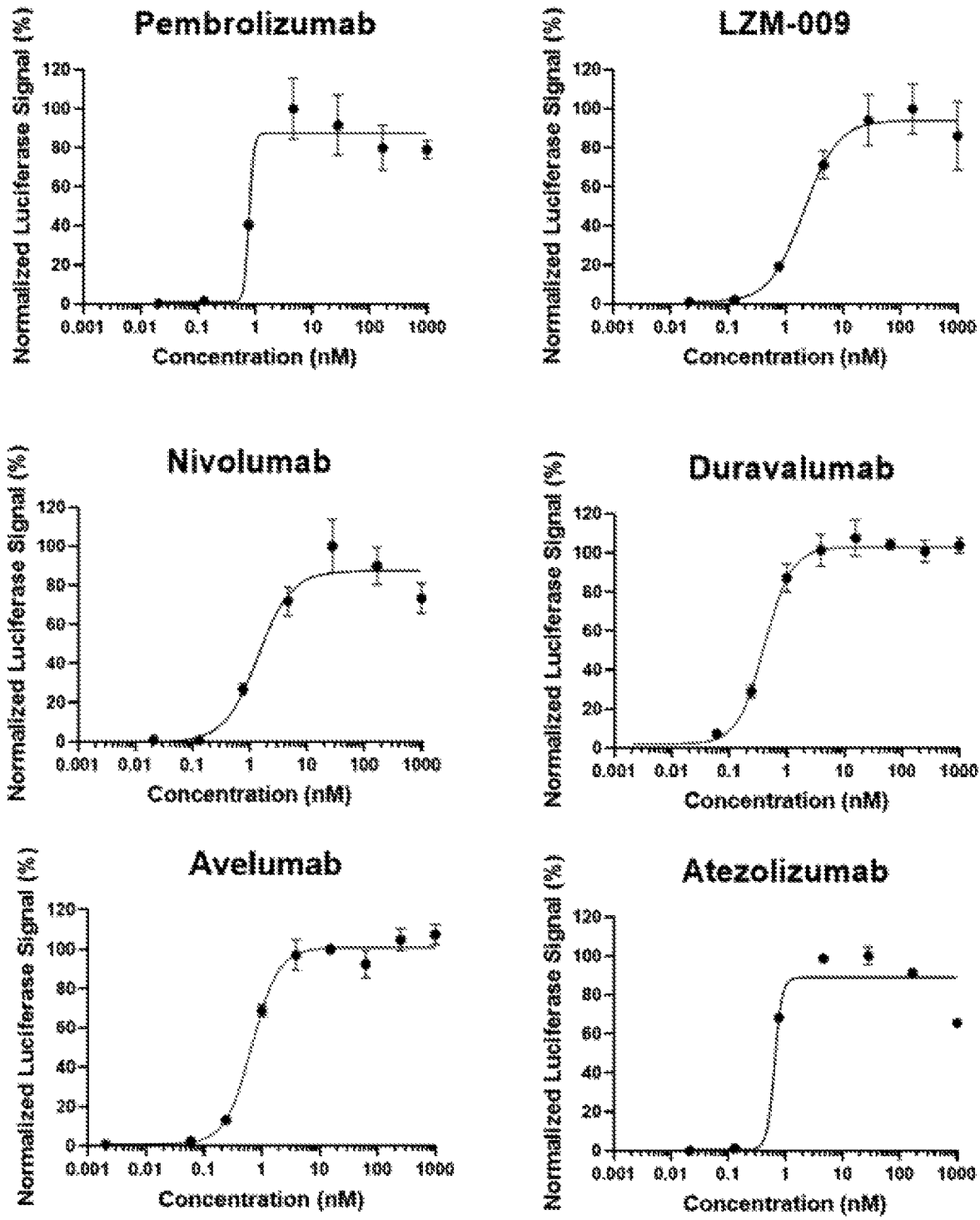
FIG. 17A and FIG. 17B show plots measuring ability of the unmodified and of conjugated anti-PD1 antibodies to interfere with PD1/PDL1 pathway, with the figure showing normalized luminescence intensity of effector cells NFAT-Lucia reporter on the y-axis and dosage of the unmodified and of conjugated anti-PD1 antibodies on the x-axis.
Figure 17B:
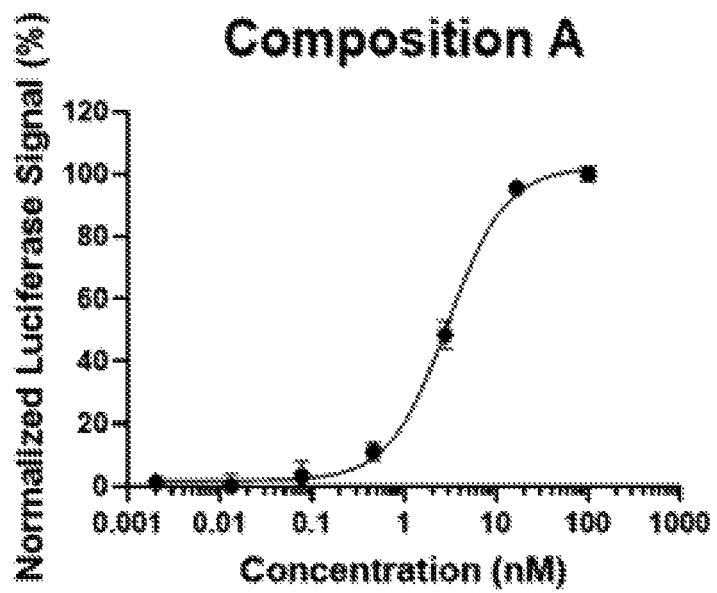
Figure 17B:
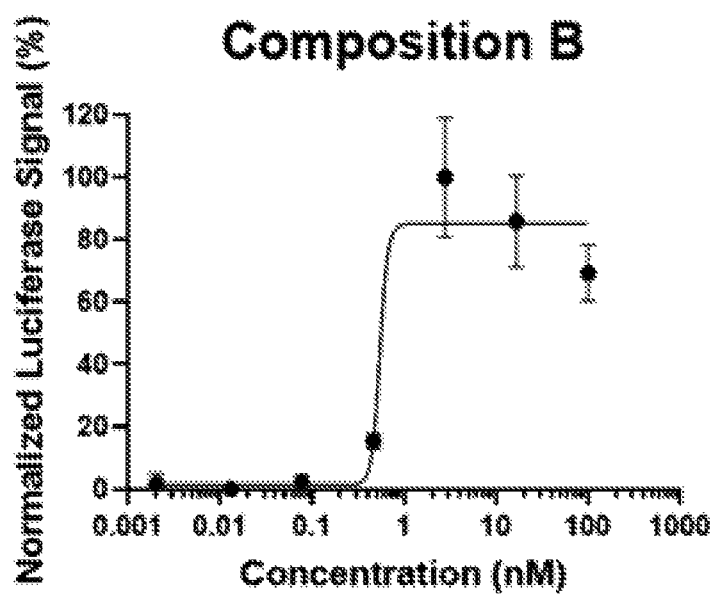

Example 7—PD-1/PD-L1 Blockade Assay (FIGS. 17A and 17B)

For immunocytokine compositions which comprise PD-1 or PD-L1 antibodies or antigen binding fragments, the experiment outlined below is performed to assess the ability of the immunocytokines to interfere with the PD-1/PD-L1 pathway. The assay is the PD-1/PD-L1 Blockade Bioassay from Promega (Cat #J1250, Madison, WI, USA). PD-1/PD-L1 Blockade Bioassay is a bioluminescent cell-based assay based on the co-culture of effector cells with target cells mimicking an immunological synapse. Jurkat T cells expressing human PD-1 and a luciferase reporter driven by a NFAT response element (NFAT-RE) are activated by CHO-K1 cells expressing human PD-L1 and an engineered cell surface protein designed to activate Jurkat cells cognate TCRs. Concurrent interaction PD-1/PD-L1 inhibits TCR signaling and represses NFAT-RE-mediated luminescence. Addition of either an anti-PD-1 or anti-PD-L1 antibody that blocks the PD-1/PD-L1 interaction releases the inhibitory signal, restoring TCR activation and resulting in a gain of signal of NFAT-RE luminescent reporter.

Briefly, PD-L1 aAPC/CHO-K1 Target cells were plated in white tissue culture 96-wells plates and cultured overnight at 37° C./5% $CO_2$. Test molecules were measured in four-fold serial dilutions starting at 1 μM down to 0.002 nM and pre-incubated on target cells for 10 min before the addition of freshly thawed PD-1 Jurkat effector cells. After 6 h at 37° C./5% $CO_2$, activity NFAT-RE luminescent reporter was evaluated by the addition of Bio-Glo reagent and measured on an ENSPTRE® plate reader (1 sec/well) from Perkin Elmer (Schwerzenbach, Switzerland). Results from this experiment are shown in the table below.
Activity of Unconjugated IL-18 Variants and Corresponding IL-18 Immunocytokines in the PD-1/PD-L1 Blockade Cellular Assay

| Composition | Antibody | IL-18 polypeptide | KD FcRn (nM) |
|---|---|---|---|
| — | Pembrolizumab/Keytruda | — | 0.757 |
| — | LZM-009 | — | 5.799 |
| — | Durvalumab/Imfinzi | — | 0.330 |
| — | Atezolizumab/Tecentriq | — | 0.664 |
| — | Avelumab/Bavencio | — | 0.676 |
| — | Trastuzumab/Herceptin | — | >10000 |
| A | LZM-009 | SEQ ID NO: 30 | 4.075 |
| B | Atezolizumab/Tecentriq | SEQ ID NO: 30 | 0.573 |
| C | Trastuzumab/Herceptin | SEQ ID NO: 30 | NT |

FIGS. 17A and 17B shows plots measuring ability of the unmodified and of conjugated anti-PD1 antibodies to interfere with PD1/PDL1 pathway, with the figure showing normalized luminescence intensity of effector cells NFAT-Lucia reporter on the y-axis and dosage of the unmodified and of conjugated anti-PD1 antibodies on the x-axis. The unconjugated reference antibodies are Pembrolizumab, LZM-009, Nivolumab, Atezolizumab, Durvalumab, and Avelumab. The conjugated antibodies tested in this figure are compositions A and composition B.

Figure 18A:
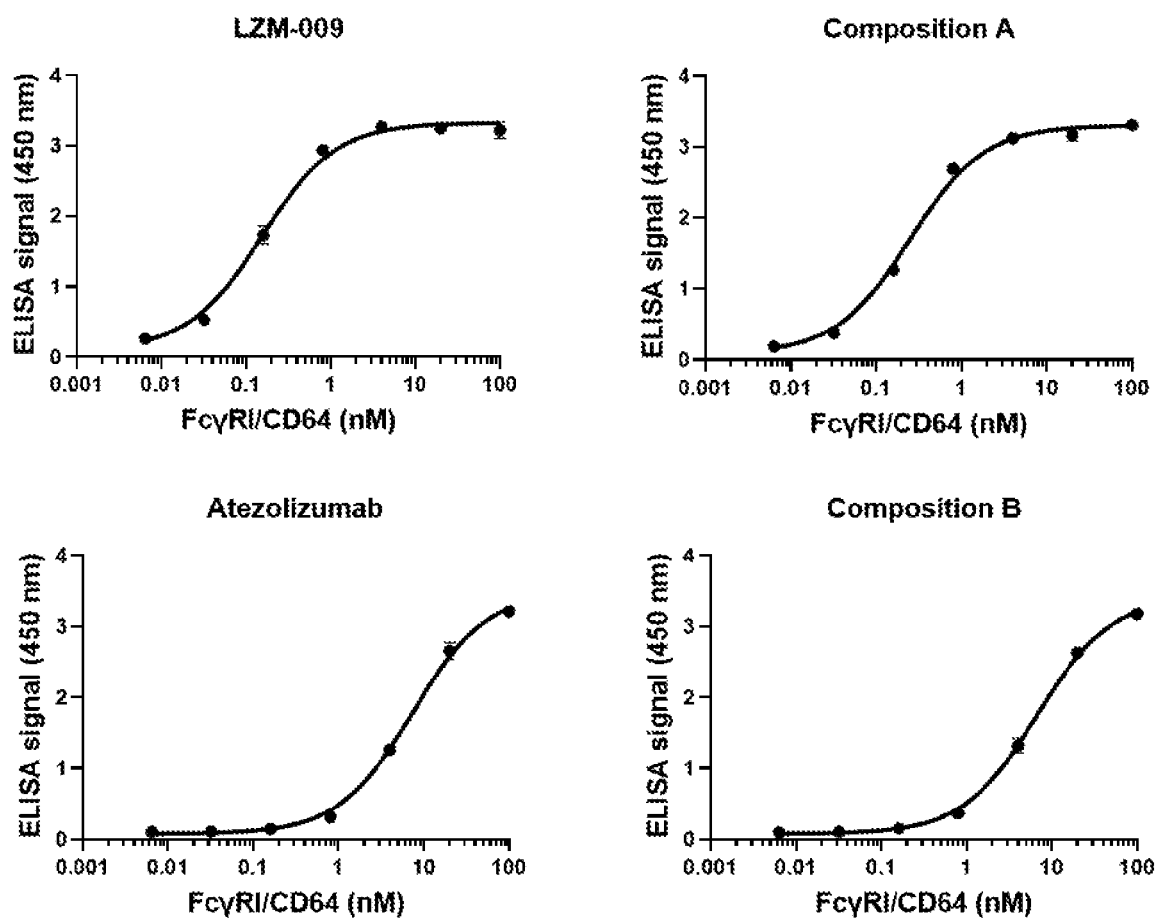
FIG. 18A shows plots measuring ability of the unmodified and of conjugated antibodies to bind to human Fc gamma receptor I (CD64). The figure shows mean ELISA signal on the y-axis and dosage of the human Fc gamma receptors on the x-axis. The unconjugated reference antibodies are LZM-009 and Atezolizumab. The conjugated antibodies tested are Compositions A and B.
Figure 18B:
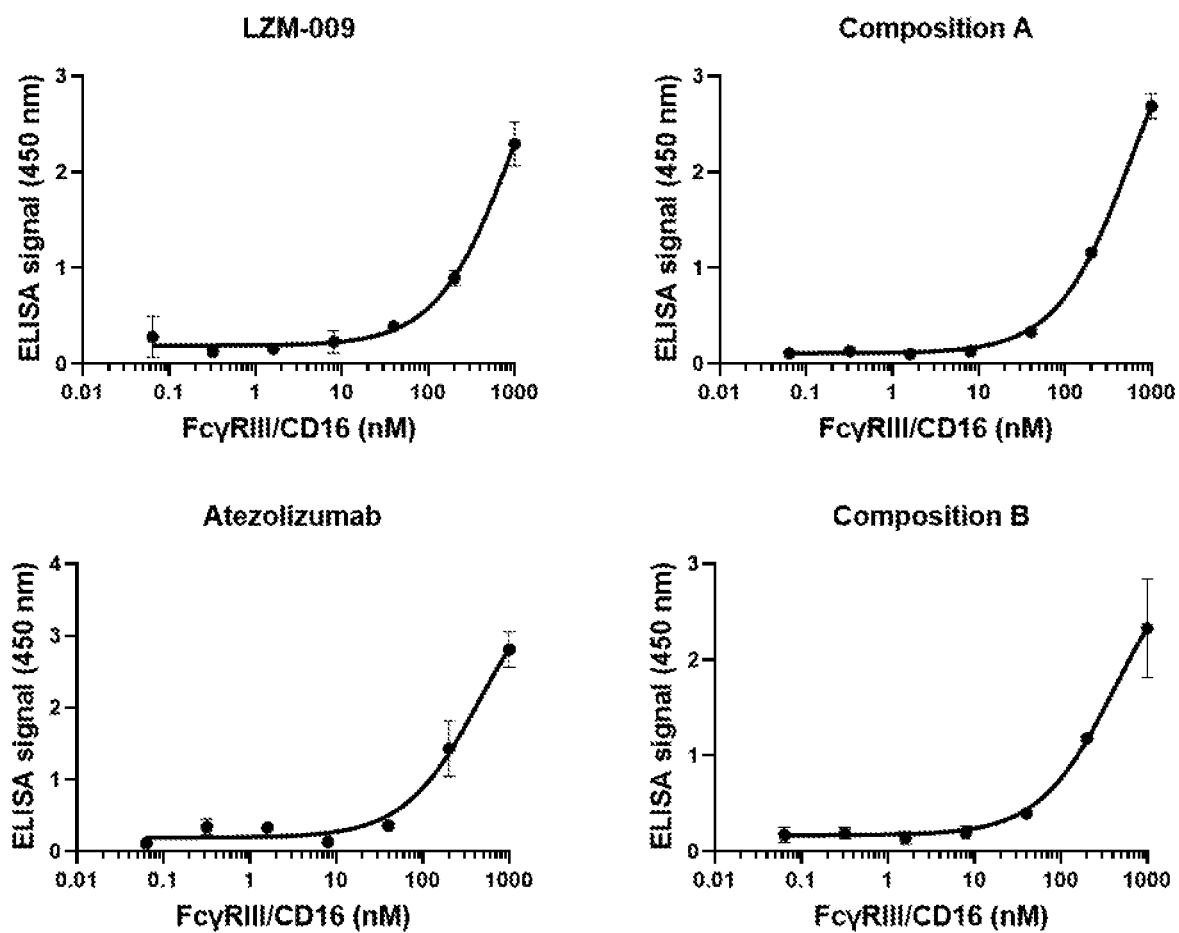
FIG. 18B shows plots measuring ability of the unmodified and of conjugated antibodies to bind to human Fc gamma receptor IIIa (CD16). The figure shows mean ELISA signal on the y-axis and dosage of the human Fc gamma receptors on the x-axis. The unconjugated reference antibodies are LZM-009 and Atezolizumab. The conjugated antibodies tested are Compositions A and B.

Example 8—Human FcγR Binding Assay (FIG. 18A and FIG. 18B)

The interaction of the unmodified and of conjugated antibodies with human Fc gamma receptors I (FcγRI/CD64), with human Fc gamma receptors IIa (FcγRIIa/CD32a), with inhibitory human Fc gamma receptors IIb (FcγRIIb/CD32b), and with human Fc gamma receptors III FcγRIIIa/CD16 were measured by ELISA.

Briefly, Corning high-binding half-area plates (Fisher Scientific, Reinach, Switzerland) were coated overnight at 4° C. with 25 μl of unmodified and of conjugated anti-PD1 antibodies at 2.5 μg/ml in PBS. Plates were then washed four times with 100 μl of PBS-0.02% Tween20. Plates surfaces were blocked with 25 μl of PBS-0.02% Tween20-1% BSA at 37° C. during 1 h. Plates were then washed four times with 100 μl of PBS-0.02% Tween20. Then twenty-five microliters of either recombinant Human Fc gamma RI/CD64 Protein (R&D systems, 1257-FC-050, CF), recombinant Human Fc gamma RIIA/CD32a (H167) Protein (R&D systems, 9595-CD-050, CF), recombinant Human Fc gamma RIIB/CD32b Avi-tag Protein (R&D systems, AVI1875-050, CF), or recombinant Human Fc gamma RIIIA/CD16a Protein (R&D systems, 4325-FC-050; CF) were added in five-fold serial dilutions ranging from 1000 nM to 0.001 nM into PBS-0.02% Tween20-0.1% BSA and incubated at 37° C. during 2 h. Plates were then washed four times with 100 μl of PBS-0.02% Tween20. Twenty-five microliters of a 1/500 HRP-anti-His antibody in PBS—0.02% Tween20-0.1% BSA (R&D systems, anti-HIS—HRP Ab, #MAB050H) were added to each well and plates were incubated at Room Temperature during 1 h. Plates were then washed four times with 100 μl of PBS-0.02% Tween20. Fifty microliters of TMB substrate reagent (#CL07, Merck, Buchs, Switzerland) were added to each well and incubated at 37° C. during 5 min. After 5 min at 37° C., Horseradish peroxidase reaction was stopped by adding 50 μl/well of 0.5M H2SO4 stop solution. ELISA signal was then measured at 450 nm on an EnSpire plate reader from Perkin Elmer (Schwerzenbach, Switzerland). Results from this experiment are shown in the table below.
Binding Affinity of Reference Antibodies and Immunocytokines with Human Fc Gamma Receptors as Measured by ELISA

| Composition | Antibody | IL-18 polypeptide | FcγRI/ (CD64) nM | FcγRIIa (CD32a) nM | FcγRIIIa (CD16) nM | FcγRIIb (CD32b) nM |
|---|---|---|---|---|---|---|
| — | Pembrolizumab/Keytruda | — | 0.5932 | 3358 | 1660 | >10000 |
| — | LZM-009 | — | 0.3150 | 1348 | 1707 | 2627 |
| — | Durvalumab/Imfinzi | — | 2.34 | 160 | 234 | 233 |
| — | Atezolizumab/Tecentriq | — | 9.17 | 1370 | 356 | >10000 |
| — | Trastuzumab/Herceptin | — | 0.0785 | 350 | 807 | 360 |
| A | LZM-009 | SEQ ID NO: 30 | 0.25 | 1892 | 598 | 436 |
| B | Atezolizumab/Tecentriq | SEQ ID NO: 30 | 10.85 | 1740 | 492 | >10000 |
| C | Trastuzumab/Herceptin | SEQ ID NO: 30 | | | 3299 | |

NT: Not Tested

FIG. 18A and FIG. 18B show plots measuring ability of the unmodified and of conjugated antibodies to bind to human Fc gamma receptor I (CD64) on top panels, and to human Fc gamma receptor IIIa (CD16) on lower panels. The figure shows mean ELISA signal on the y-axis and dosage of the human Fc gamma receptors on the x-axis. The unconjugated reference antibodies are LZM-009 and Atezolizumab. The conjugated antibodies tested are Compositions A and B.

Figure 19:
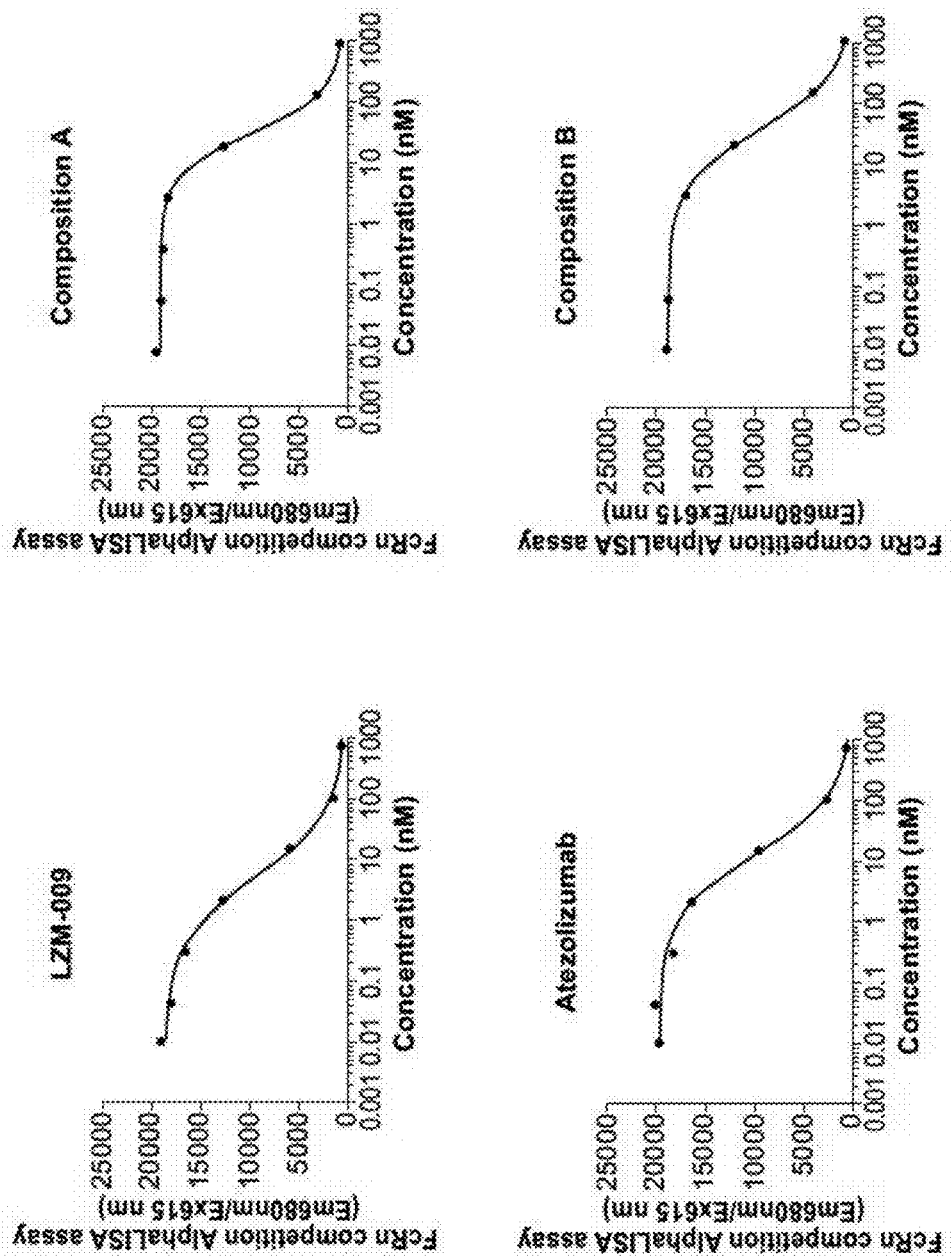
FIG. 19 shows plots measuring ability of the unmodified and of conjugated antibodies to bind to human Fc neonatal receptor. The figure shows mean AlphaLISA signal on the y-axis and dosage of the human Fc neonatal receptor (FcRn) on the x-axis. The unconjugated reference antibodies are LZM-009 and Atezolizumab. The conjugated antibodies tested are Compositions A and B.

Example 9—Human FcRn Binding Assay (FIG. 19)

The interaction of the unmodified and of conjugated anti-PD1 antibodies with the human neonatal Fc receptor (FcRn) at pH 6 was measured using the AlphaLISA® Human FcRn Binding Kit (AL3095C) from Perkin Elmer (Schwerzenbach, Switzerland). The AlphaLISA® detection of FcRn and IgG binding uses IgG coated AlphaLISA® acceptor beads to interact with biotinylated human FcRn captured on Streptavidin-coated donor beads. When reference IgG binds to FcRn, donor and acceptor beads come into proximity enabling the transfer of singlet oxygen that trigger a cascade of energy transfer reactions in the acceptor beads, resulting in a sharp peak of light emission at 615 nm. Addition of a free IgG antibodies into the AlphaLISA® mixture creates a competition for the binding of FcRn to the reference antibody resulting in a loss of signal.

Briefly, test molecules were measured in serial dilutions starting at 5 uM down to 64 pM and incubated with AlphaLISA® reaction mixture consisting of 800 nM of recombinant biotinylated human FcRn, 40 µg/ml of human IgG conjugated Acceptor beads, and 40 µg/ml of Streptavidin coated Donor beads in pH 6 MES buffer. After 90 min at 23° C. in the dark, AlphaLISA® signal was measured on an EnSpire plate reader (Excitation at 680 nm, Emission at 615 nm) from Perkin Elmer (Schwerzenbach, Switzerland). Results from this experiment are shown in the table below.
Binding Affinity of Reference Antibodies and Immunocytokines with the Human Neonatal Fc Receptor as Measured by AlphaLISA

| Composition | Antibody | IL-18 polypeptide | KD FcRn (nM) |
|---|---|---|---|
| — | Pembrolizumab/Keytruda | — | 7.45 |
| — | LZM-009 | — | 6.00 |
| — | Durvalumab/Imfinzi | — | 8.31 |
| — | Atezolizumab/Tecentriq | — | 6.40 |
| — | Avelumab/Bavencio | — | 5.36 |
| — | Trastuzumab/Herceptin | — | 6.55 |
| A | LZM-009 | SEQ ID NO: 30 | 33.45 |
| B | Atezolizumab/Tecentriq | SEQ ID NO: 30 | 36.68 |
| C | Trastuzumab/Herceptin | SEQ ID NO: 30 | 25.12 |

FIG. 19 shows plots measuring ability of the unmodified and of conjugate antibodies to bind to human Fc neonatal receptor. The figure shows mean AlphaLISA signal on the y-axis and dosage of the human Fc neonatal receptor (FcRn) on the x-axis. The unconjugated reference antibodies are LZM-009 and Atezolizumab. The conjugated antibodies tested are Compositions A and B.

Figure 20:
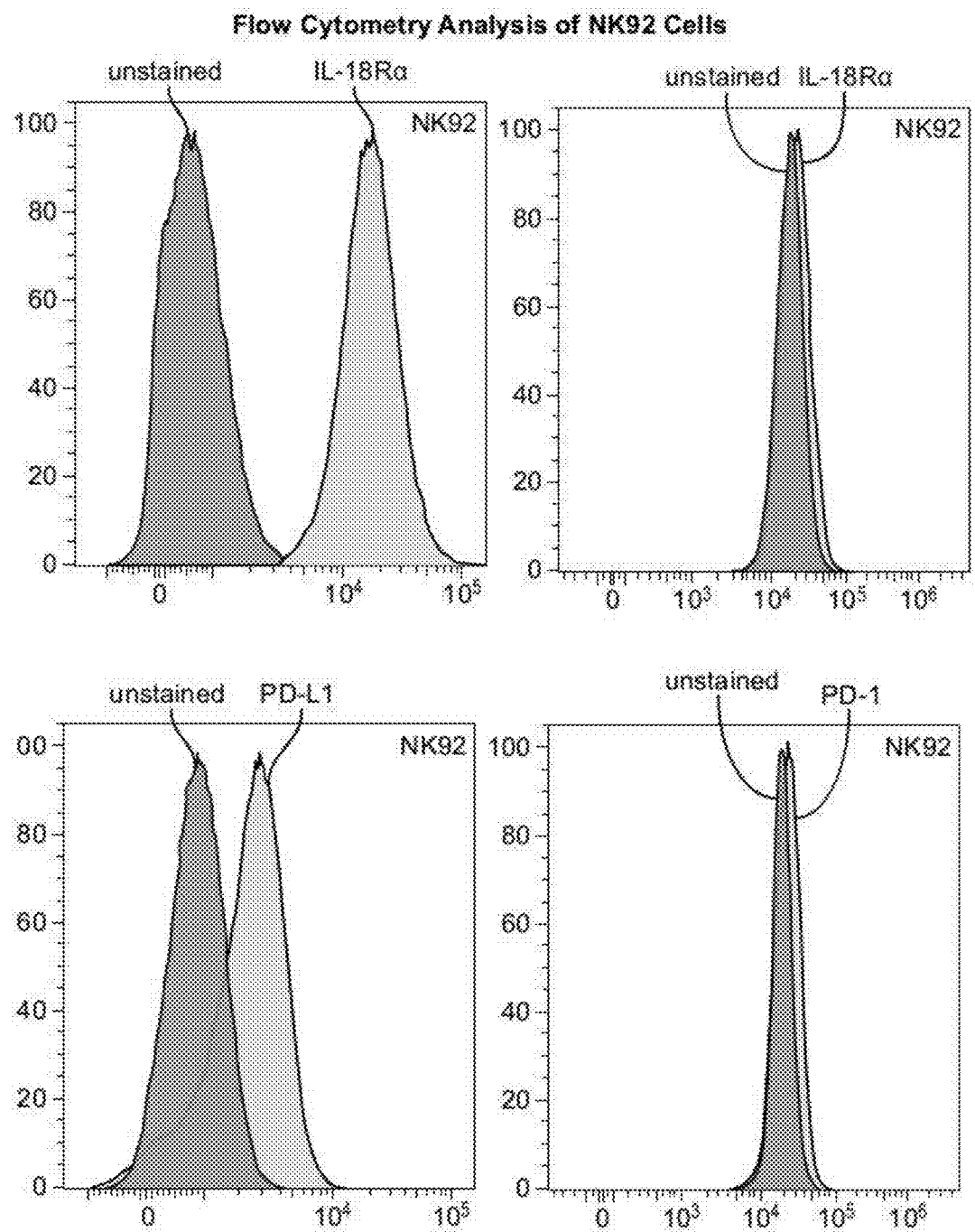
FIG. 20 shows plots measuring the levels PD-1 and PD-L1 surface expression on NK92 cells.
Figure 21:
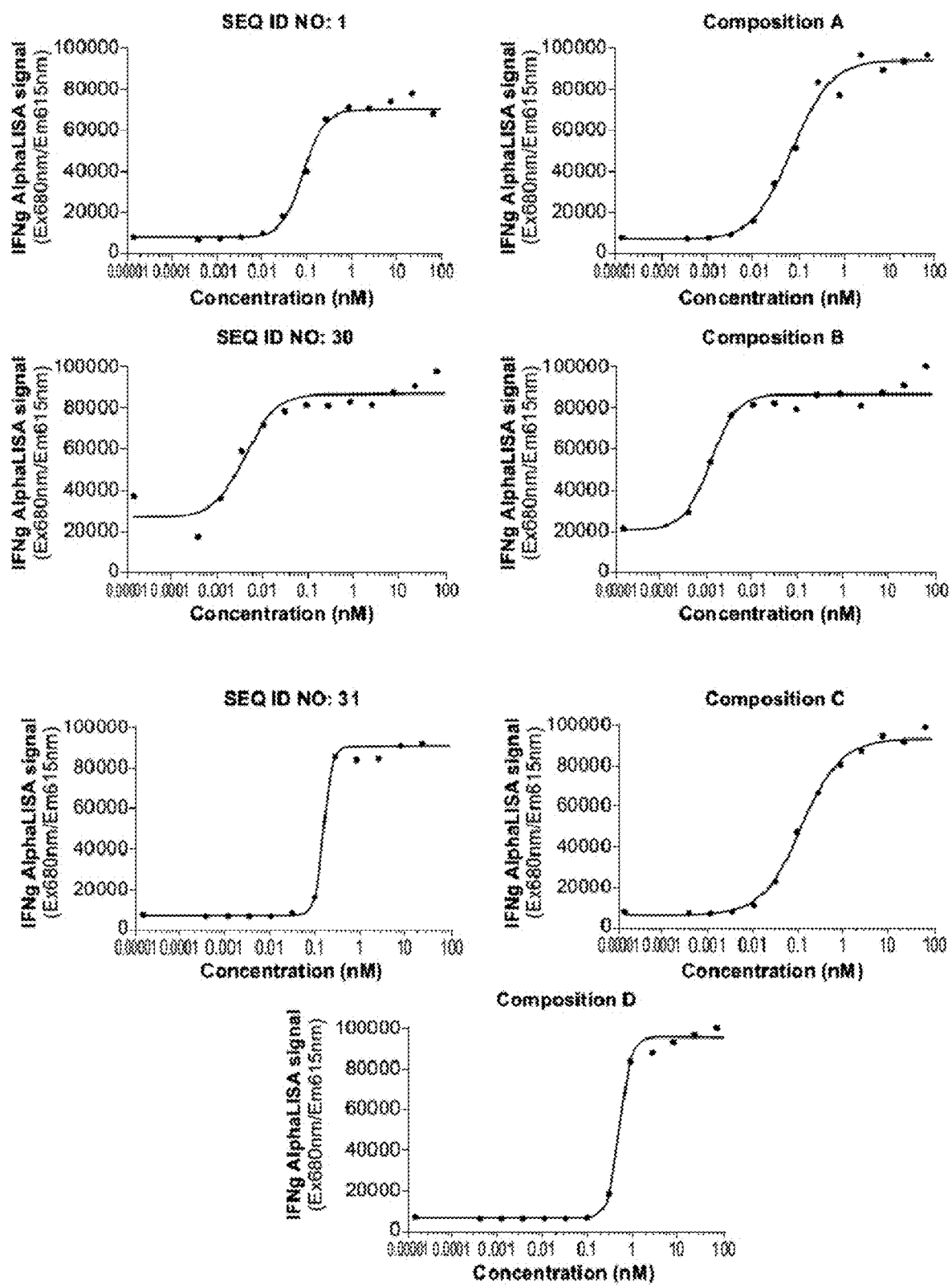
FIG. 21 shows plots measuring ability of the unconjugated IL-18 variants and corresponding IL-18 immunocytokines to stimulate the secretion of IFNgamma by NK92 cells. The figure shows mean IFNg alphaLISA signal on the y-axis and dosage of the unconjugated IL-18 variants and corresponding IL-18 immunocytokines on the x-axis. The unconjugated IL-18 variants are native IL-18 wild-type (SEQ ID NO: 1), SEQ ID NO: 30, and SEQ ID NO: 31. Corresponding IL-18 immunocytokines tested are Compositions A, B, C, and D.

Example 10—IFN Gamma Secretion Assay in NK92 Cells (FIGS. 20 & 21)

The IFNγ-secretion stimulating activity of the unconjugated IL-18 variants and corresponding IL-18 immunocytokines was evaluated on NK92 cell line. The NIK cell line NK-92 derived from a patient with lymphoma (ATCC, Cat #CRL-2407) was cultured in aMIEM medium supplemented with 12.5% FCS, 12.5% horse serum (HS), 50 uM B-mercaptoEthanol, and 2 ng/ml of recombinant Human Interleukin-2 (IL-2).

On the day of experiment, cells were harvested and washed with aNMEM medium without IL-2 and resuspended in medium (w/o IL-2) containing 1 ng/ml of recombinant human Interleukin-12 (Sinofliologicals, Cat #CT011-H08H). After counting, cells were seeded at 100 000 cells/well in a 384 well titer plate and incubated at 37° C./5% $CO_2$. Sixteen 4-fold serial dilutions of IL-18 analytes were prepared in aMIEM medium-1 ng/ml IL-12 and were added to the NK-92 cells. Final IL-18 analytes concentration ranged from to 200 nM down to 0.01 pM.

After 16-20 h incubation at 37° C./5% $CO_2$, 5 µl of supernatant were carefully transferred to a 384 microwells OPTIPlate (Perkin Elmer; Cat #6007270) and Interferongamma (IFNγ) levels measured using the Human IFNγ AlphaLISA Assay Kit (Perkin Elmer, Cat #AL217C). Briefly, 10 µl of 2.5× AlphaLISA Anti-IFNγ acceptor beads and biotinylated Antibody Anti-IFNγ mix were added to the 5 µl of NK-92 supernatants and incubated for 1 h at room temperature under shaking. Under subdued light, 2.5 µl of 2× streptavidin (SA) donor beads were pipetted in each well and incubated for 30 min at room temperature under shaking. AlphaLisa signal was then measured on an Enspire plate reader (Perkin Elmer) using 680 and 615 nm as excitation and emission wavelengths respectively. Half maximal effective concentration (EC50) was calculated based on a variable slope, four parameter analysis using GraphPad PRISM software. Results from this experiment are shown in the table below.
Activity of Unconjugated IL-18 Variants and Corresponding IL-18 Immunocytokines in the IFNγ Secretion NK92 Assay

| Composition | Antibody | IL-18 polypeptide | $EC_{50}$ (nM) |
|---|---|---|---|
| — | — | SEQ ID NO: 1 | 0.374 |
| — | — | SEQ ID NO: 30 | 0.002 |
| — | — | SEQ ID NO: 31 | 0.103 |
| — | — | SEQ ID NO: 60 | 0.008 |
| A | LZM-009 | SEQ ID NO: 30 | 0.073 |
| B | Atezolizumab/Tecentriq | SEQ ID NO: 30 | 0.001 |
| C | Trastuzumab/Herceptin | SEQ ID NO: 30 | 0.027 |
| D | LZM-009 | SEQ ID NO: 31 | 0.471 |
| E | LZM-009 | SEQ ID NO: 60 | 0.056 |
| F | Trastuzumab/Herceptin | SEQ ID NO: 60 | 0.064 |

FIG. 20 shows plots measuring the levels PD-1 and PD-L1 surface expression on NK92 cells FIG. 21 shows plots measuring ability of the unconjugated IL-18 variants and corresponding IL-18 immunocytokines to stimulate the secretion of IFNgamma by NK92 cells. The figure shows mean IFNg alphaLISA signal on the y-axis and dosage of the unconjugated IL-18 variants and corresponding IL-18 immunocytokines on the x-axis. The unconjugated IL-18 variants are native IL-18 wild-type (SEQ ID NO:1), SEQ ID NO: 30, and SEQ ID NO: 31. Corresponding IL-18 immunocytokines tested are Compositions A, B, C, and D.

Figure 22:
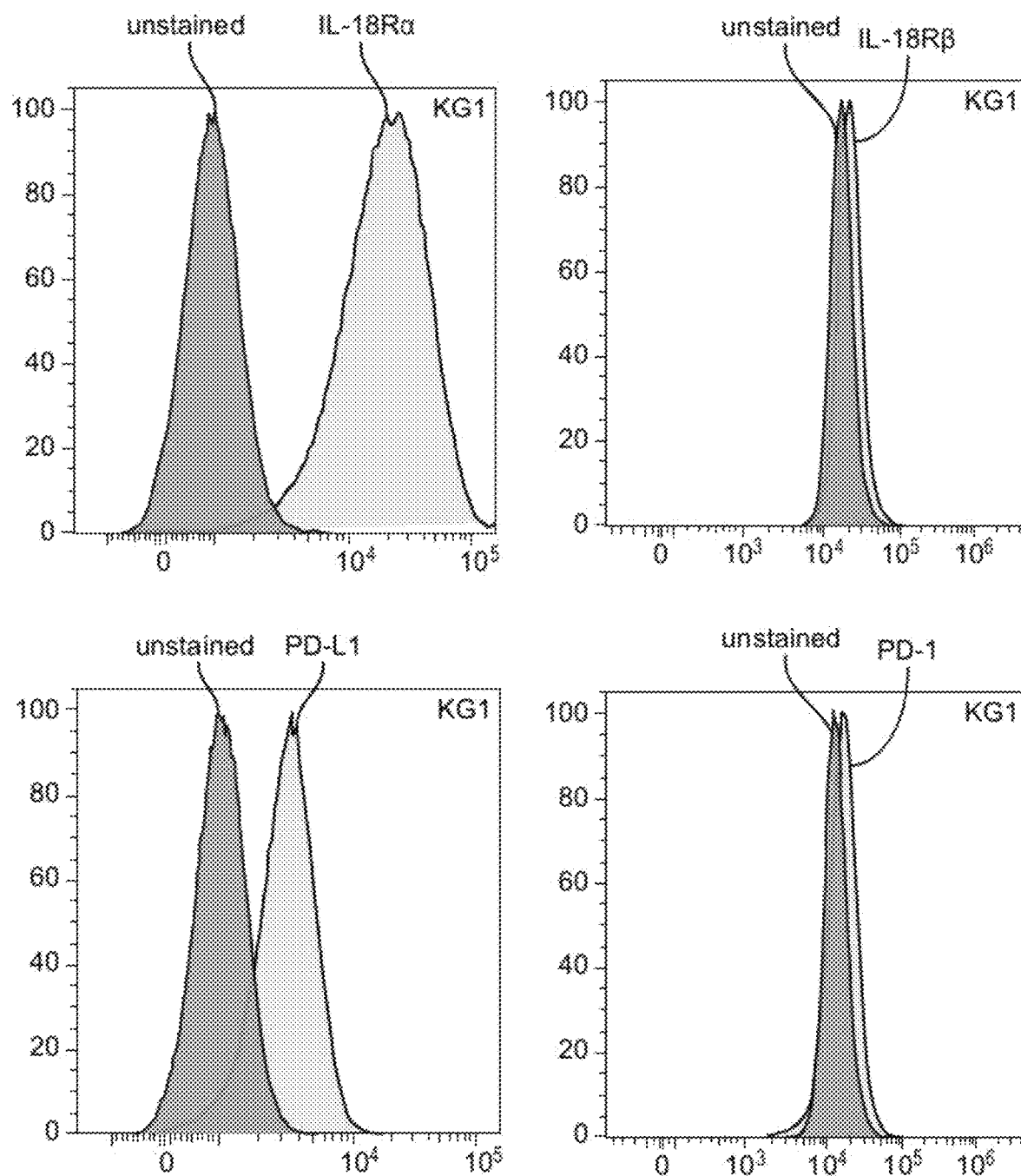
FIG. 22 shows plots measuring the levels PD-1 and PD-L1 surface expression on KG-1 cells.
Figure 23:
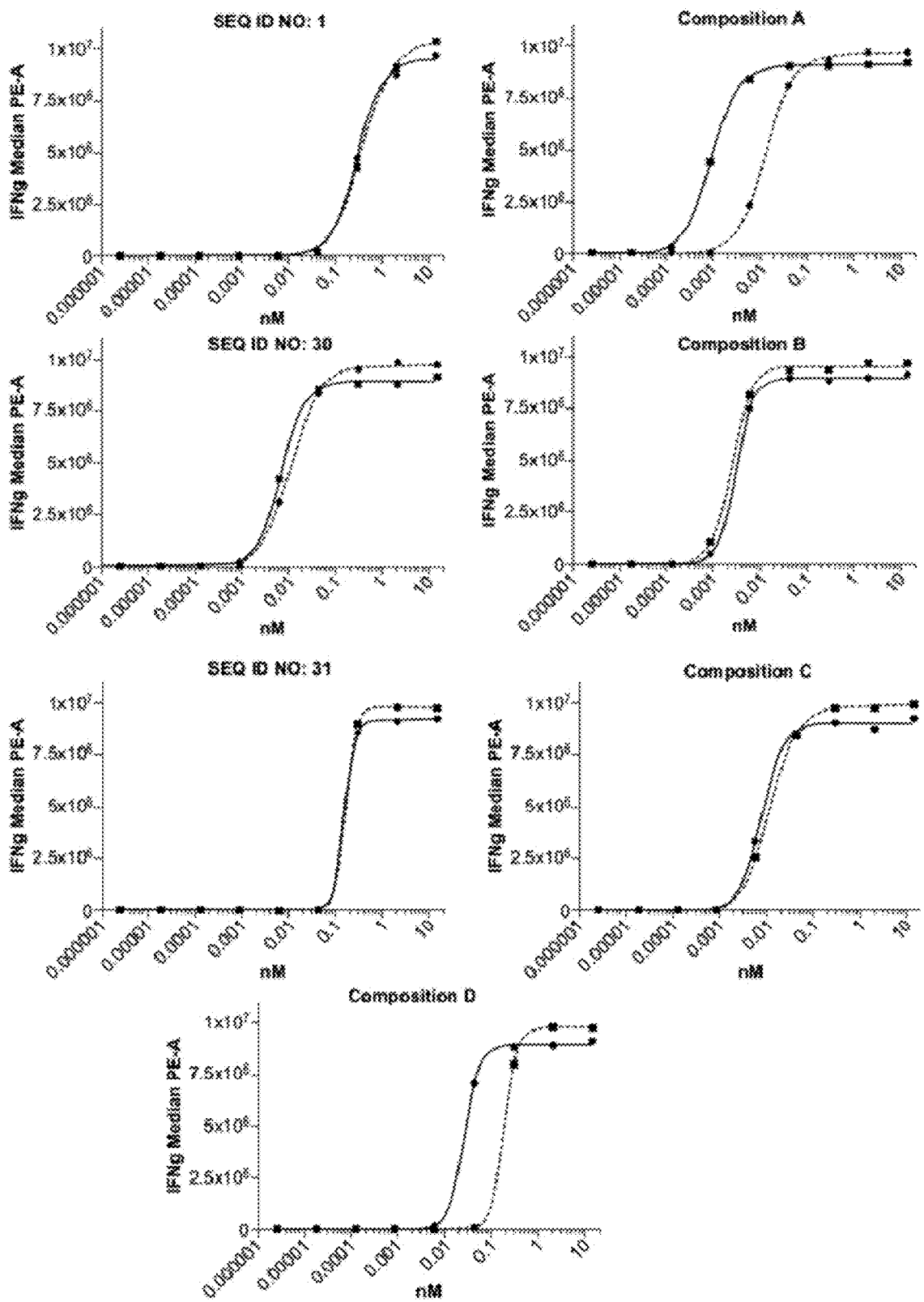
FIG. 23 shows plots measuring the ability of the unconjugated IL-18 variants and corresponding IL-18 immunocytokines to stimulate the secretion of IFNgamma by parental PD-1$^{negative}$ and by engineered PD-1$^{positive}$ KG-1 cells. The figure shows mean IFNg legendplex signal on the y-axis and dosage of the unconjugated IL-18 variants and corresponding IL-18 immunocytokines on the x-axis. The unconjugated IL-18 variants are native IL-18 wild-type (SEQ ID NO: 1), SEQ ID NO: 30, and SEQ ID NO: 31. Corresponding IL-18 immunocytokines tested are Compositions A, B, C, and D.
Figure 24:
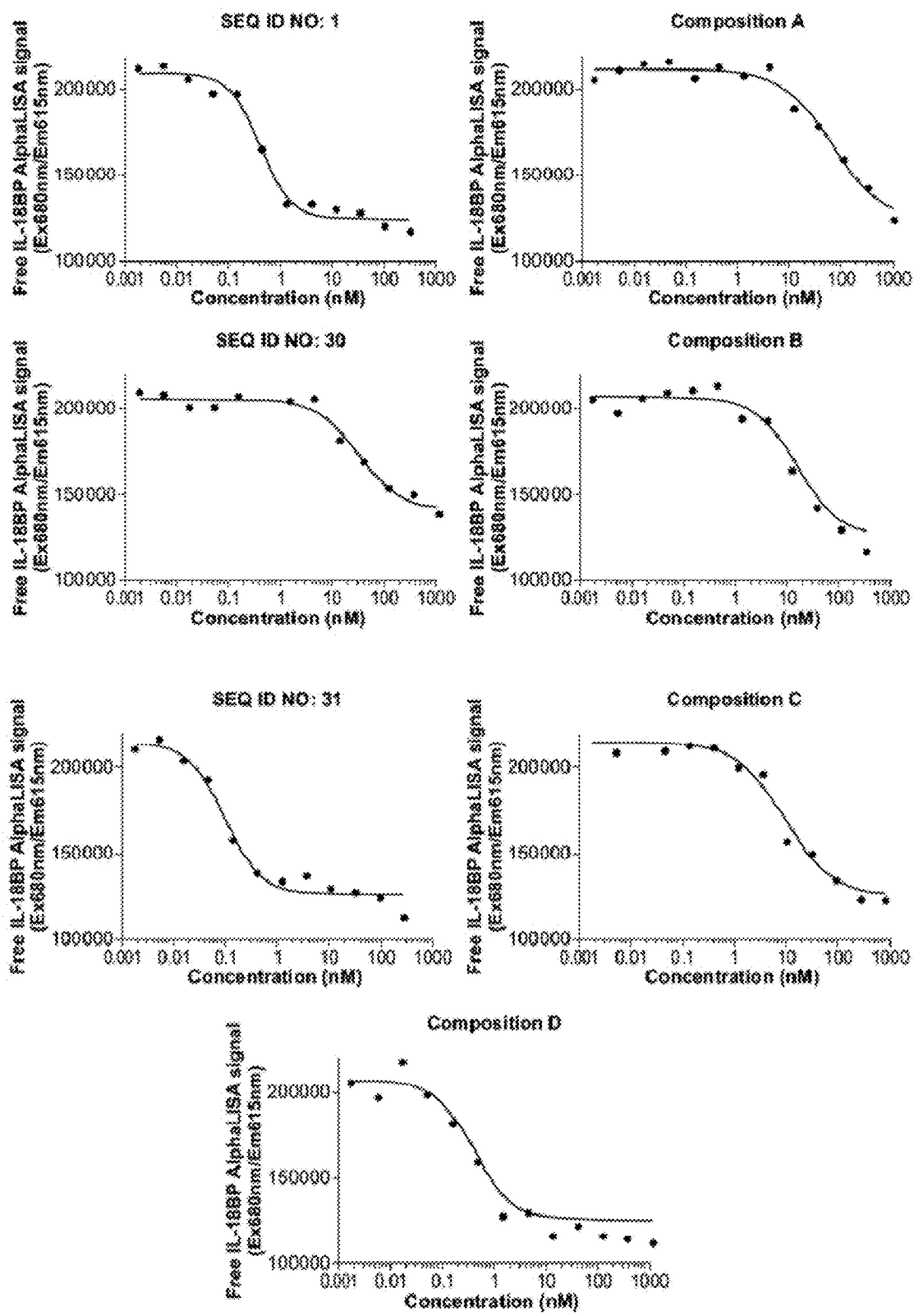
FIG. 24 shows plots measuring the ability of the unconjugated IL-18 variants and corresponding IL-18 immunocytokines to bind to the human IL-18 Binding Protein (IL-18BP). The figure shows mean free IL-18BP AlphaLISA signal on the y-axis and dosage of the unconjugated IL-18 variants and corresponding IL-18 immunocytokines on the x-axis. The unconjugated IL-18 variants are native IL-18 wild-type (SEQ ID NO: 1), SEQ ID NO: 30, and SEQ ID NO: 31. Corresponding IL-18 immunocytokines tested are Compositions A, B, C, and D.

Example 11—IFN Gamma Secretion Assay in KG-1 Cells (FIG. 22-24)

The IL-18 responsive AML cell line KG-1 shows high expression of IL-18Rα and moderate levels of IL18Rβ, respectively. The KG-1 cell line was used to generate a PD-1 expressing cell line and furthermore, to measure IFNγ release upon incubation with TL-18 variants and corresponding TL-18 immunocytokines.

PD-1 expressing cell line generation: Briefly, KG-1 cells were transduced using lentiviral particles carrying the human PD-1 gene (PDCD1 NM_005018; Origene, CAT #: RC210364L3V) at a MOI (Multiplicity of Infection) of 30. Spinfection was performed at 1260 g during 90 min at 37° C. in the presence of 5 µg/ml of Polybrene and 10 mM of HEPES in complete culture media (RPMI, 10% FBS, 1% L-Glutamine). Five days after transduction, puromycin at a final concentration of 1 µg/ml was added to select for PD-1 positive cells. For culture maintenance, puromycin concentration was decreased to 0.5 µg/ml. Stable and homogenous expression of PD-1 was verified by surface staining (BD Pharmingen, #557860).

IFNγ release was assessed in PD-1 positive (transduced) KG-1 cells, as well as in the parental PD-1 negative cells. $0.5 \times 10^5$ cells were seeded into a 96-well U-bottom plate in culture media (RPMI, 10% FBS, 100 L-Glutamine) and stimulated with IL-18 variants/ICs for 20-24 h. The test items were diluted to 100 nM in culture medium, followed by 7 10-fold serial dilutions. The lowest concentration assessed was 0.05 fM. After incubation, IFNγ release was measured using the LEGENDplex custom human mix and match KIT (Biolegend LEGENDplex™ Human IFN-γ Capture Bead B5, 13×#740942, LEGENDplex™ P 1 Essential Immune Response Panel Detection Abs, #740931, LEGENDplex™ Buffer Set A #740368). To this end, cell culture supernatant was collected and diluted 1:1 with Assay Buffer. Fluorescence measurements were done with a Quanteon Flow Cytometer from Acea Biosciences. For analysis, MFI values (median fluorescence intensity) were exported and plotted against concentrations used. The $EC_{50}$ values (half maximal effective concentration) were calculated based on a variable slope and four parameter analysis using GraphPad PRISM software version 9. Results from this experiment are shown in the table below.

Stimulation of IFNγ Secretion by Unconjugated IL-18 Variants and Corresponding IL-18 Immunocytokines in Parental and PD-1 Transduced KG-1 Cells

| Composition | Antibody | IL-18 polypeptide | Parental KG-1 $EC_{50}$ (nM) | PD-1 positive KG-1 $EC_{50}$ (nM) | PD-$1^{pos}$/PD-$1^{neg}$ $EC_{50}$ ratio |
|---|---|---|---|---|---|
| — | — | SEQ ID NO: 1 | 0.387 | 0.297 | 1.298 |
| — | — | SEQ ID NO: 30 | 0.012 | 0.008 | 1.336 |
| — | — | SEQ ID NO: 31 | 0.1485 | 0.1354 | 1.2 |
| A | LZM-009 | SEQ ID NO: 30 | 0.0110 | 0.0012 | 10.9 |
| B | Atezolizumab/Tecentriq | SEQ ID NO: 30 | 0.0016 | 0.0036 | 0.6 |
| C | Trastuzumab/Herceptin | SEQ ID NO: 30 | 0.0166 | 0.0096 | 1.7 |
| D | LZM-009 | SEQ ID NO: 31 | 0.2033 | 0.0225 | 9.3 |

FIG. 22 shows plots measuring the levels PD-1 and PD-L1 surface expression on KG-1 cells FIG. 23 shows plots measuring the ability of the unconjugated IL-18 variants and corresponding IL-18 immunocytokines to stimulate the secretion of IFNgamma by parental PD-$1^{negative}$ and by engineered PD-$1^{positive}$ KG-1 cells. The figure shows mean IFNg legendplex signal on the y-axis and dosage of the unconjugated IL-18 variants and corresponding IL-18 immunocytokines on the x-axis. The unconjugated IL-18 variants are native IL-18 wild-type (SEQ ID NO:1), SEQ TD NO: 30, and SEQ TD NO: 31. Corresponding IL-18 immunocytokines tested are Compositions A, B, C, and D.

Example 12—IL-18 Binding Protein alphaLISA Assay (FIG. 24)

Wild type or modified IL-18 polypeptides samples were diluted at 5.6 µM in a solution of 1× alphaLISA Immunoassay Buffer provided in the alphaLISA IFNγ Detection kit and were diluted applying 3-fold serial dilutions down to 1.7 pM in 384 deep well plates. A solution of 10 ng/ml of human IL-18BP-His was prepared with 1× alphaLISA Immunoassay Buffer. IL-18/IL-18BP complex formation was performed incubating 30 µl of IL-18BP solution to IL-18 sample titrations for 1 h at 20° C. IL-18BP standard was prediluted from stock solution supplied in alphaLISA IFNγ Detection kit at 100 ng/ml with 1× alphaLISA Buffer and titration prepared from applying 2-fold serial dilutions. The following solutions were prepared: a 50 µg/ml solution of anti-IL-18BP alphaLISA Acceptor beads, a 5 nM solution of biotinylated anti-IL18BP antibody and a 80 µg/ml light-protected solution of Streptavidin Donor beads in 1× alphaLISA Immunoassay Buffer. To detect unbound IL-18BP in IL-18/IL-18P complex samples, 5 µl of premixed Acceptor beads solution was transferred on top on 7.5 µL of samples in 384-well Optiplates, followed by a short centrifugation step at 150 g, and incubated for 30 minutes at 20° C. under shaking at 750 rpm.

5 µl of Biotinylated anti-IL-18BP antibody were added, followed by a short centrifugation step at 150 g, and incubated for 60 minutes at 20° C. under shaking at 750 rpm. Under subdued light, 12.5 µl of pre-mixed Donor beads were added, followed by a short centrifugation step at 150 g, and incubated for 30 minutes at 20° C. under shaking at 750 rpm with no light. AlphaLisa signal was then measured on an Enspire plate reader (Perkin Elmer) using 680 and 615 nm as excitation and emission wavelengths respectively. Unbound IL-18BP concentration interpolated from the standard signal-concentration curve using GraphPad Prism. Results from this experiment are shown in the table below.

Binding Affinity of Reference Antibodies and Immunocytokines with the Human IL-18 Binding Protein as Measured by AlphaLISA

| Composition | Antibody | IL-18 polypeptide | IL-18BP KD (nM) |
|---|---|---|---|
| — | — | SEQ ID NO: 1 | 0.411 |
| — | — | SEQ ID NO: 30 | 24.600 |
| — | — | SEQ ID NO: 31 | 0.103 |
| A | LZM-009 | SEQ ID NO: 30 | 10.930 |
| B | Atezolizumab/Tecentriq | SEQ ID NO: 30 | 6.382 |
| C | Trastuzumab/Herceptin | SEQ ID NO: 30 | 10.496 |
| D | LZM-009 | SEQ ID NO: 31 | 15.263 |

FIG. 24 shows plots measuring the ability of the unconjugated IL-18 variants and corresponding IL-18 immunocytokines to bind to the human IL-18 Binding Protein (IL-18BP). The figure shows mean free IL-18BP AlphaLISA signal on the y-axis and dosage of the unconjugated IL-18 variants and corresponding IL-18 immunocytokines on the x-axis. The unconjugated IL-18 variants are native IL-18 wild-type (SEQ ID NO: 1), SEQ ID NO: 30, and SEQ ID NO: 31. Corresponding IL-18 immunocytokines tested are Compositions A, B, C, and D.

Figure 25:
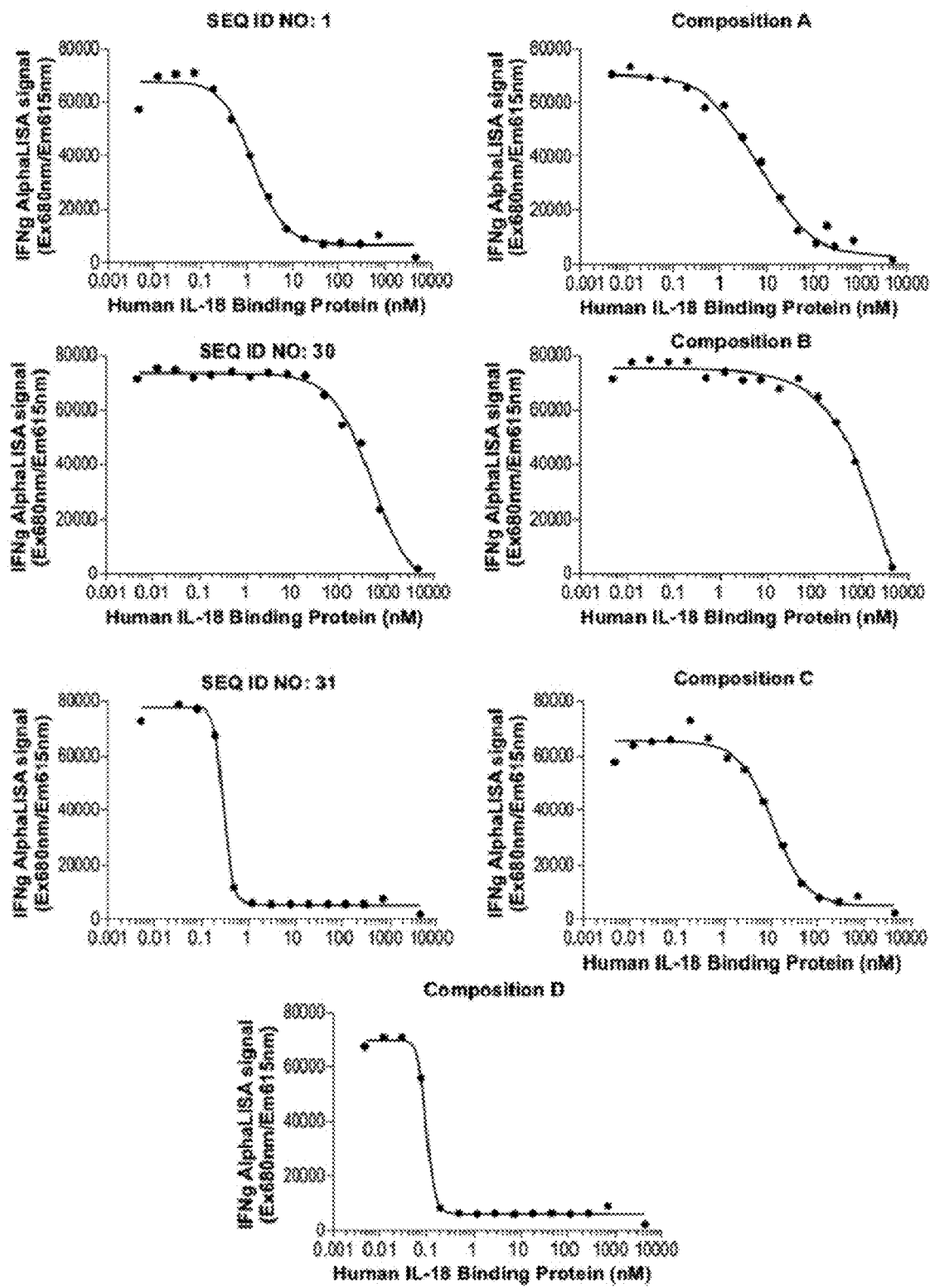
FIG. 25 shows plots measuring the ability of the human IL-18 Binding Protein to inhibit the secretion of IFNgamma by NK92 cells stimulated with 2 nM of unconjugated IL-18 variants and corresponding IL-18 immunocytokines. The figure shows mean IFNg alphaLISA signal on the y-axis and dosage of the human IL-18 Binding Protein on the x-axis. The unconjugated IL-18 variants are native IL-18 wild-type (SEQ ID NO: 1), SEQ ID NO: 30, and SEQ ID NO: 31. Corresponding IL-18 immunocytokines tested are Compositions A, B, C, and D.

Example 13—Cellular IL-18 Binding protein resistance assay (FIG. 25)

The NK cell line NK-92 derived from a patient with lymphoma (ATCC, Cat #CRL-2407) was cultured in aMEM medium supplemented with 20% FCS-Glutamax, 25 µM B-mercaptoEthanol, and 100 IU/ml of recombinant Human Interleukin-2 (TL-2). On the day of experiment, cells were harvested and washed with aMEM medium without IL-2. After counting, cells were seeded at 100 000 cells/well in a 384 well titer plate and incubated at 37° C./5% CO2. Sixteen 2-fold serial dilutions of Fc fused human IL-18 binding protein isoform a (IL-18BPa; R&D systems, Cat #119-BP) were prepared in aMEM medium-1 ng/ml IL-12 containing 2 nM of each IL-18 variants and were added to the NK-92 cells. Final IL-18 analytes concentration was 1 nM and final IL-18BPa concentrations ranged from to 566 nM down to 17 pM.

After 16-20 h incubation at 37° C./5% CO2, 5 µl of supernatant were carefully transferred to a 384 microwells OPTIplate (Perkin Elmer; Cat #6007270) and Interferon-gamma (IFNγ) levels measured using the Human IFNγ AlphaLISA Assay Kit (Perkin Elmer, Cat #AL217C). Briefly, 10 µl of 2.5× AlphaLISA Anti-IFNγ acceptor beads and biotinylated Antibody Anti-IFNγ mix were added to the 5 µl of NK-92 supernatants and incubated for 1 h at room temperature under shaking. Under subdued light, 2.5 µl of 2× streptavidin (SA) donor beads were pipetted in each well and incubated for 30 min at room temperature under shaking. AlphaLisa signal was then measured on an Enspire plate reader (Perkin Elmer) using 680 and 615 nm as excitation and emission wavelengths respectively. Half maximal inhibitory concentration (IC50) was calculated based on a variable slope, four parameter analysis using GraphPad PRISM software. Results from this experiment are shown in the table below.

IL-18BP-Mediated Inhibition of IFNγ Secretion by NK92 Cells Stimulated with Unconjugated IL-18 Variants and Corresponding IL-18 Immunocytokines

| Composition | Antibody | IL-18 polypeptide | IC$_{50}$ (nM) |
|---|---|---|---|
| — | — | SEQ ID NO: 1 | 0.781 |
| — | — | SEQ ID NO: 30 | 487.8 |
| — | — | SEQ ID NO: 31 | 0.282 |
| A | LZM-009 | SEQ ID NO: 30 | 6.87 |
| B | Atezolizumab/Tecentriq | SEQ ID NO: 30 | >1000 |
| C | Trastuzumab/Herceptin | SEQ ID NO: 30 | 21.44 |
| D | LZM-009 | SEQ ID NO: 31 | 0.098 |

FIG. 25 shows plots measuring the ability of the human IL-18 Binding Protein to inhibit the secretion of IFNgamma by NK92 cells stimulated with 2 nM of unconjugated IL-18 variants and corresponding IL-18 immunocytokines. The figure shows mean IFNg alphaLISA signal on the y-axis and dosage of the human IL-18 Binding Protein on the x-axis. The unconjugated IL-18 variants are native IL-18 wild-type (SEQ TD NO: 1), SEQ TD NO: 30, and SEQ TD NO: 31. Corresponding IL-18 immunocytokines tested are Compositions A, B, C, and D.

Example 14—In Vivo Antitumor Activity in MC38 Colon Carcinoma Model (FIG. 26-28)

An in vivo efficacy study was performed in mice. Naïve, 6-8 weeks old, C57BL/6-hPD1 female mice (GemPharmatech Co, Ltd, Nanjing, China) were inoculated subcutaneously at the right upper flank with MC38 tumor cells (3×10$^5$) in 0.1 mL of PBS for tumor development. The animals were randomized (using an Excel-based randomization software performing stratified randomization based upon tumor volumes), and treatment started when the average tumor volume reached approximately 120 mm$^3$. Animals treated with unmodified antibodies received two weekly 10 mL/kg bolus intraperitoneal (i.p.) injections. Animals treated with modified IL-18 polypeptide conjugated antibodies received two weekly 10 mL/kg bolus intravenous (i.v.) injections. After inoculation, the animals were checked daily for morbidity and mortality. At the time, animals were checked for effects on tumor growth and normal behavior such as mobility, food and water consumption, body weight gain/loss (body weights were measured twice weekly), eye/hair matting and any other abnormal effect. The major endpoints were delayed tumor growth or complete tumor regression. Tumor sizes were measured three times a week in two dimensions using a caliper, and the volume was expressed in mm$^3$ using the formula: $V=0.5 \, a \times b^2$ where a and b are the long and short diameters of the tumor, respectively. Death and observed clinical signs were recorded on the basis of the numbers of animals within each subset.

Figure 26A:
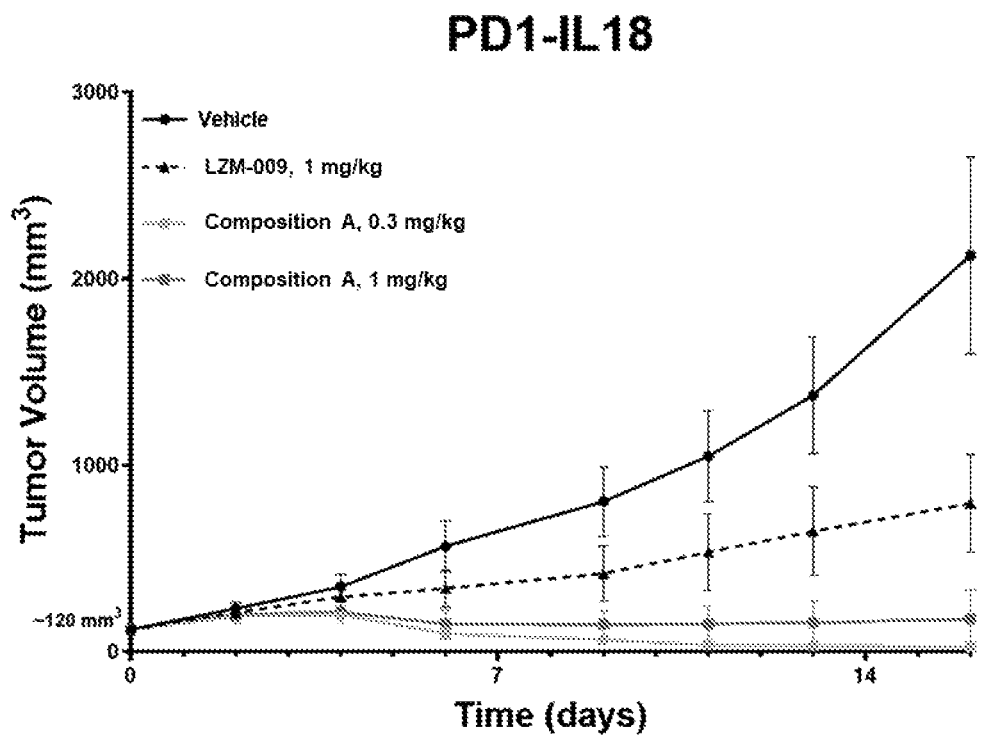
FIG. 26A shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows mean tumor volume on the y-axis and time on the x-axis. The immunocytokine tested in this figure is Composition A tested as a single agent at 0.3 and 1 mg/kg as two weekly i.v. injections. (n=9; mean±SEM).

FIG. 26A shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows mean tumor volume on the y-axis and time on the x-axis. The immunocytokine tested in this figure is Composition A tested as a single agent at 0.3 and 1 mg/kg as two weekly i.v. injections. (n=9; mean±SEM).

Figure 26B:
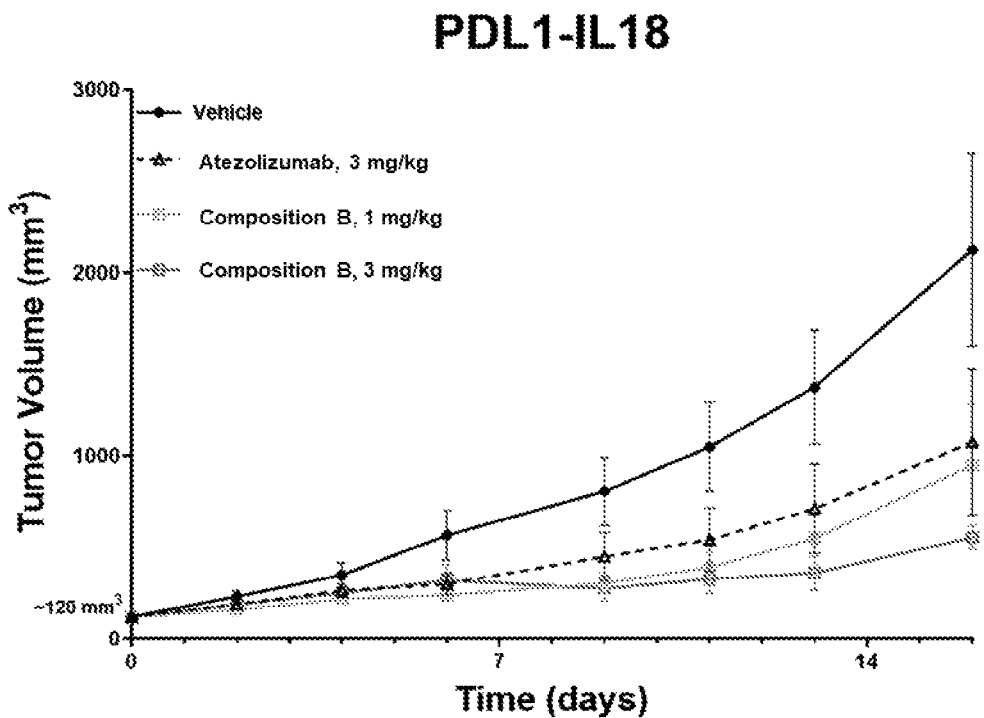
FIG. 26B shows a plot describing the effect of unmodified PD-L1 antibodies and of IL-18 polypeptide conjugated PD-L1 antibody on the growth of MC38 syngeneic colon carcinoma tumors in hPD1 C57BL/6 mice. The figure shows mean tumor volume on the y-axis and time on the x-axis. The immunocytokine tested in this figure is Composition B tested as a single agent at 1 and 3 mg/kg as two weekly i.v. injections. (n=9; mean±SEM).

FIG. 26B shows a plot describing the effect of unmodified PD-L1 antibodies and of IL-18 polypeptide conjugated PD-L1 antibody on the growth of MC38 syngeneic colon carcinoma tumors in hPD1 C57BL/6 mice. The figure shows mean tumor volume on the y-axis and time on the x-axis. The immunocytokine tested in this figure is Composition B tested as a single agent at 1 and 3 mg/kg as two weekly i.v. injections. (n=9; mean±SEM).

Figure 27A:
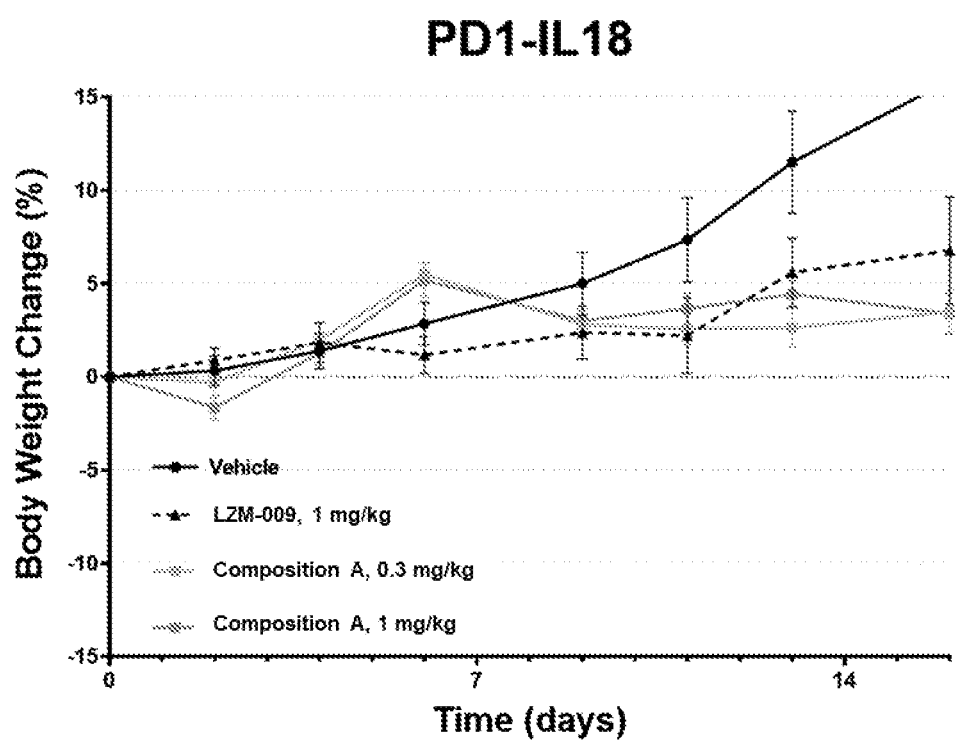
FIG. 27A shows a plot describing the effect of unmodified PD-1 antibodies and of IL-18 polypeptide conjugated PD-1 antibody on the body weight of MC38 syngeneic colon carcinoma tumor-bearing hPD1 C57BL/6 mice. The figure shows mean body weight change on the y-axis and time on the x-axis. The immunocytokine tested in this figure is Composition A tested as a single agent at 0.3 and 1 mg/kg as two weekly i.v. injections. (n=9; mean±SEM).

FIG. 27A shows a plot describing the effect of unmodified PD-1 antibodies and of IL-18 polypeptide conjugated PD-1 antibody on the body weight of MC38 syngeneic colon carcinoma tumor-bearing hPD1 C57BL/6 mice. The figure shows mean body weight change on the y-axis and time on the x-axis. The immunocytokine tested in this figure is Composition A tested as a single agent at 0.3 and 1 mg/kg as two weekly i.v. injections. (n=9; mean±SEM).

Figure 27B:
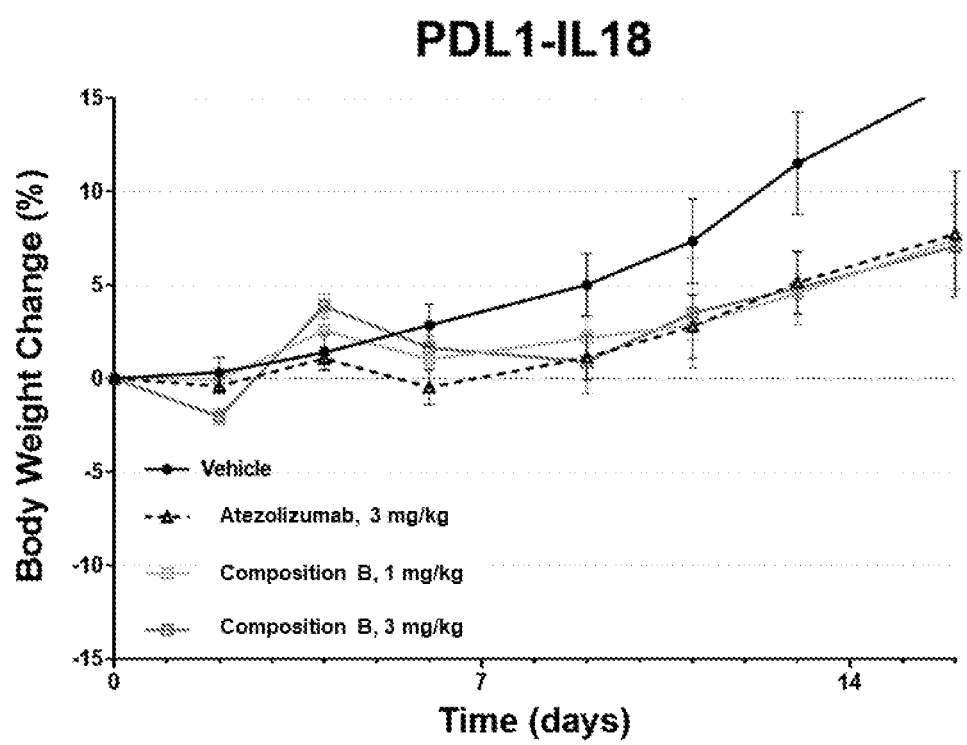
FIG. 27B shows a plot describing the effect of unmodified PD-L1 antibodies and of IL-18 polypeptide conjugated PD-L1 antibody on the body weight of MC38 syngeneic colon carcinoma tumor-bearing hPD1 C57BL/6 mice. The figure shows mean body weight change on the y-axis and time on the x-axis. The immunocytokine tested in this figure is Composition B tested as a single agent at 1 and 3 mg/kg as two weekly i.v. injections. (n=9; mean±SEM).

FIG. 27B shows a plot describing the effect of unmodified PD-L1 antibodies and of IL-18 polypeptide conjugated PD-L1 antibody on the body weight of MC38 syngeneic colon carcinoma tumor-bearing hPD1 C57BL/6 mice. The figure shows mean body weight change on the y-axis and time on the x-axis. The immunocytokine tested in this figure is Composition B tested as a single agent at 1 and 3 mg/kg as two weekly i.v. injections. (n=9; mean±SEM).

Example 15—In Vivo Antitumor Activity in MC38 Colon Carcinoma Model (FIG. 28-31)

An in vivo efficacy study was performed in mice. Naïve, 6-8 weeks old, C57BL/6-hPD1 female mice (GemPharmatech Co, Ltd, Nanjing, China) were inoculated subcutaneously at the right upper flank with MC38 tumor cells ($3 \times 10^5$) in 0.1 mL of PBS for tumor development. The animals were randomized (using an Excel-based randomization software performing stratified randomization based upon tumor volumes), and treatment started when the average tumor volume reached approximately 110 mm$^3$. Animals treated with unmodified antibodies received two weekly 10 mL/kg bolus intraperitoneal (i.p.) injections. Animals treated with modified IL-18 polypeptide conjugated antibodies received two weekly 10 mL/kg bolus intravenous (i.v.) injections. After inoculation, the animals were checked daily for morbidity and mortality. At the time, animals were checked for effects on tumor growth and normal behavior such as mobility, food and water consumption, body weight gain/loss (body weights were measured twice weekly), eye/hair matting and any other abnormal effect. The major endpoints were delayed tumor growth or complete tumor regression. Tumor sizes were measured three times a week in two dimensions using a caliper, and the volume was expressed in mm$^3$ using the formula: $V=0.5 \text{ a} \times b^2$ where a and b are the long and short diameters of the tumor, respectively. Death and observed clinical signs were recorded on the basis of the numbers of animals within each subset.

Figure 28A:
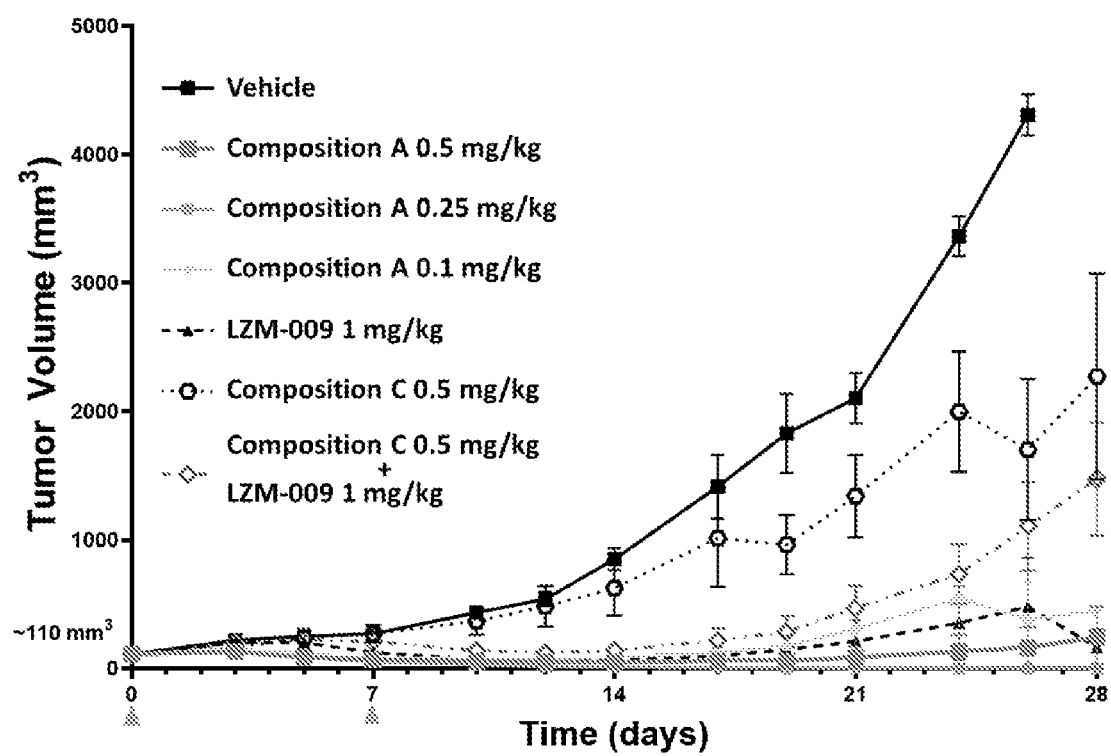
FIG. 28A shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows mean tumor volume on the y-axis and time on the x-axis. The immunocytokine tested in this figure are composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM).

FIG. 28A shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows mean tumor volume on the y-axis and time on the x-axis. The immunocytokine tested in this figure are composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM).

Figure 28B:
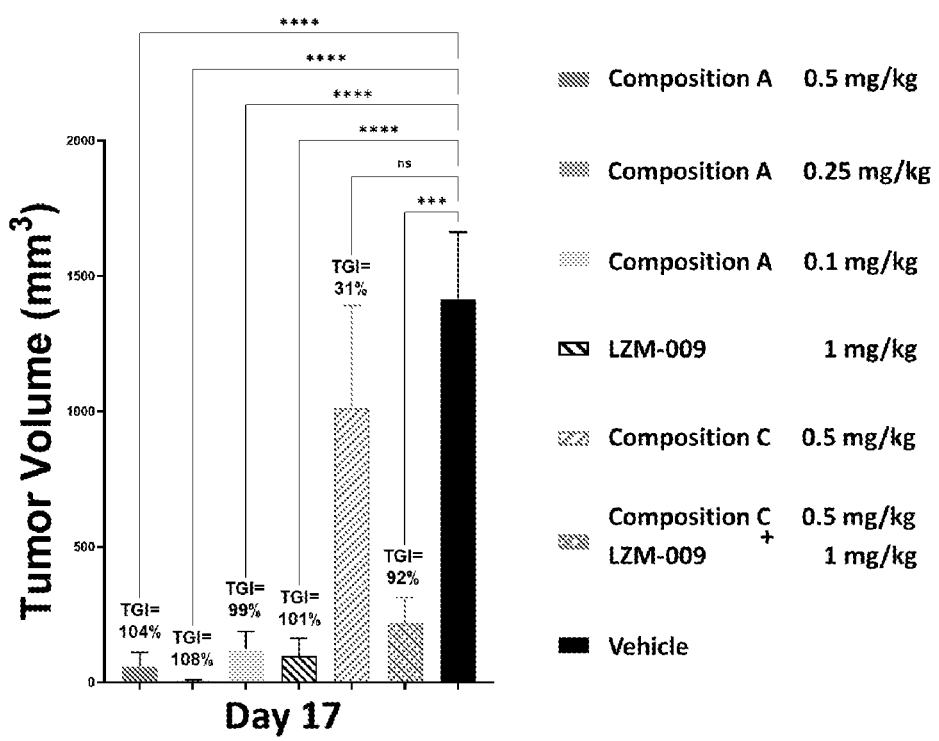
FIG. 28B shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows the mean tumor volume on day 17 post treatment initiation on the y-axis. The immunocytokine tested in this figure are composition A tested as a single agent at 0.1, 0.25, and 0.5 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; One-way Anova test *P-value<0.001, P-value<0.01, *P-value<0.1, ns not significant, TGI: Tumor Growth Inhibition).

FIG. 28B shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows the mean tumor volume on day 17 post treatment initiation on the y-axis. The immunocytokine tested in this figure are composition A tested as a single agent at 0.1, 0.25, and 0.5 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; One-way Anova test *P-value<0.001, P-value<0.01, *P-value<0.1, ns not significant, TGI: Tumor Growth Inhibition).

Figure 28C:
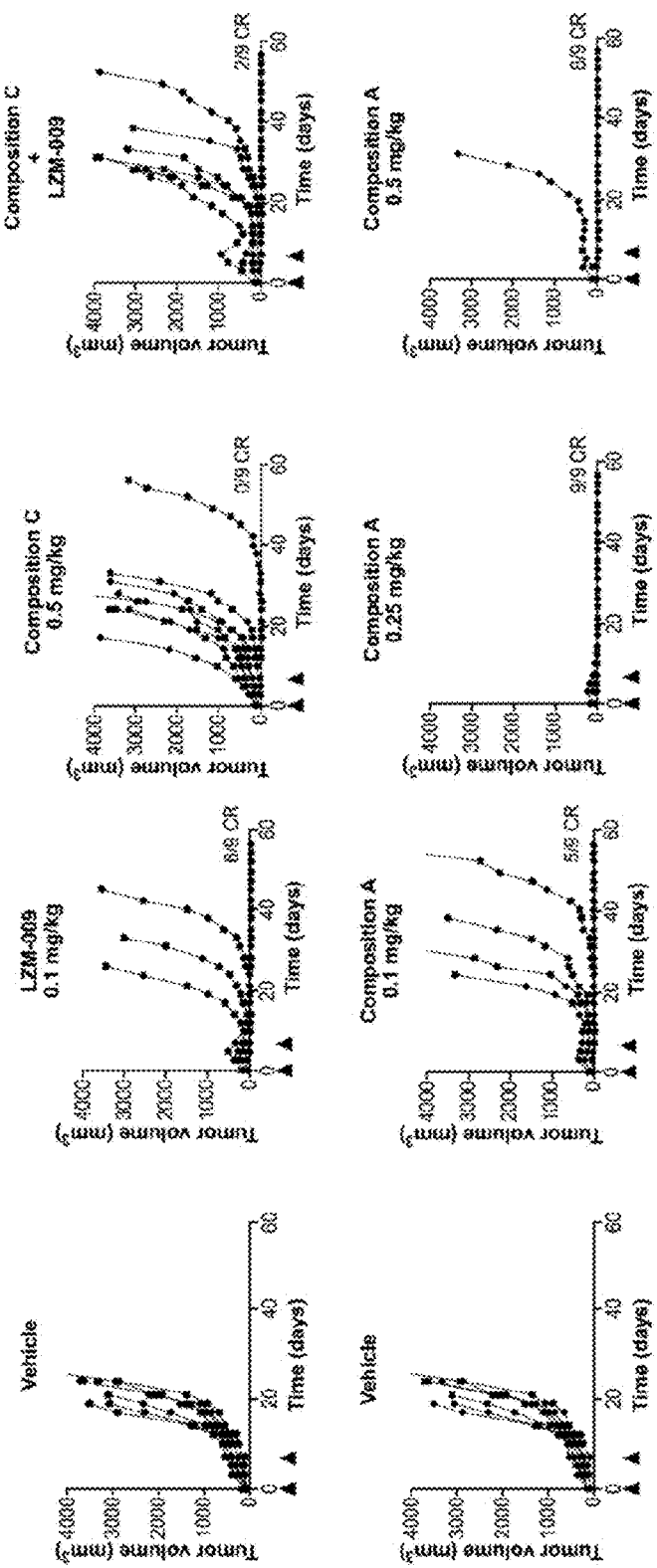
FIG. 28C shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows the tumor volume of each individual animal on the y-axis and time on the x-axis. The immunocytokine tested in this figure are composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; CR: Complete Response).

FIG. 28C shows a plot describing the effect of unmodified PD-1 antibodies and of IL-18 polypeptide conjugated PD-1 antibody on the growth of MC38 syngeneic colon carcinoma tumors in hPD1 C57BL/6 mice. The figure shows the tumor volume of each individual animal on the y-axis and time on the x-axis. The immunocytokine tested in this figure are composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; CR: Complete Response).

Figure 29:
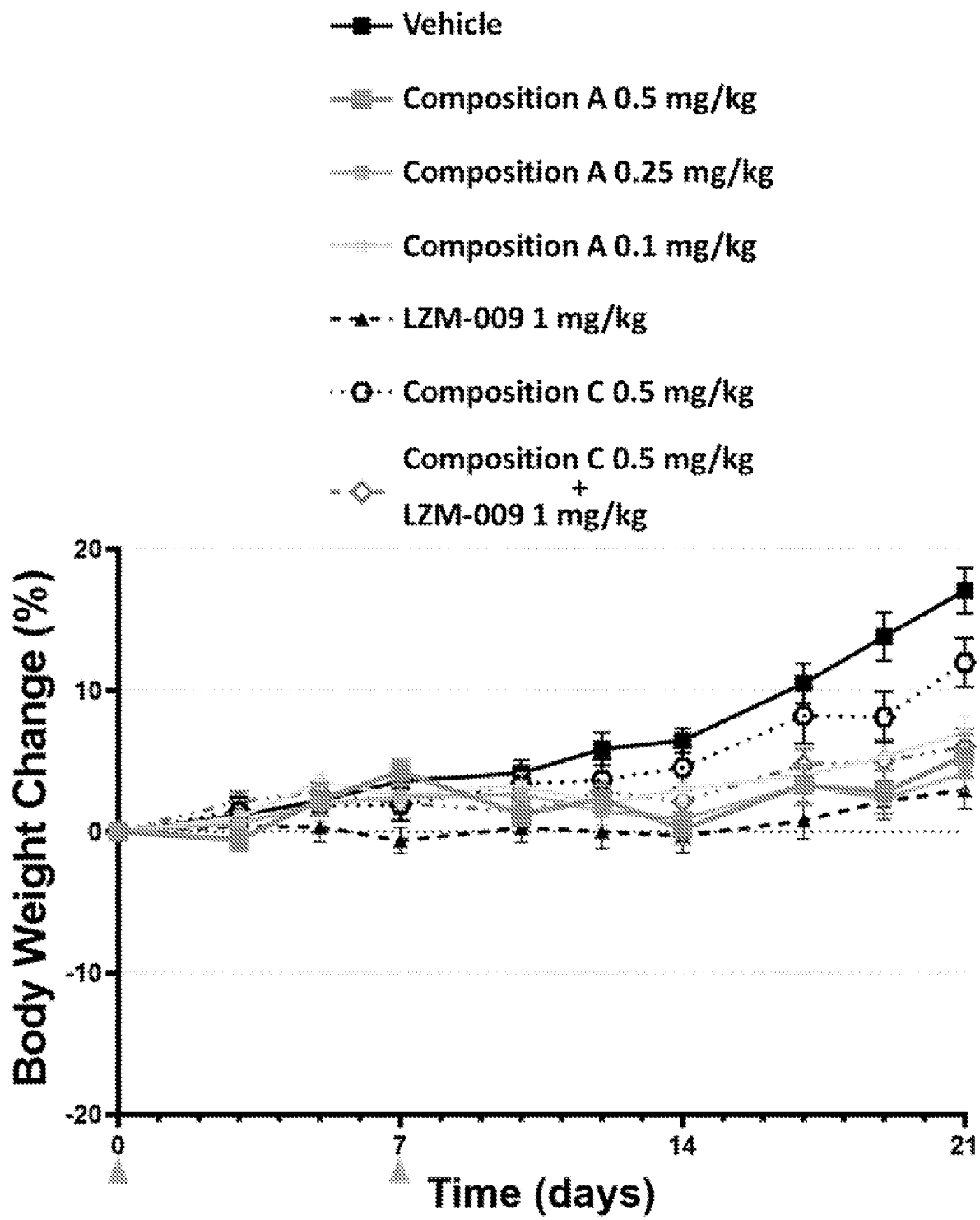
FIG. 29 shows a plot describing the effect of unmodified PD-L1 antibodies and of IL-18 polypeptide conjugated PD-1 antibody on the on the body weight of MC38 syngeneic colon carcinoma tumor-bearing hPD1 C57BL/6 mice. The figure shows mean body weight change on the y-axis and time on the x-axis. The immunocytokine tested in this figure are Composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM).

FIG. 29 shows a plot describing the effect of unmodified PD-L1 antibodies and of IL-18 polypeptide conjugated PD-1 antibody on the on the body weight of MC38 syngeneic colon carcinoma tumor-bearing hPD1 C57BL/6 mice. The figure shows mean body weight change on the y-axis and time on the x-axis. The immunocytokine tested in this figure are Composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM).

Figure 30:
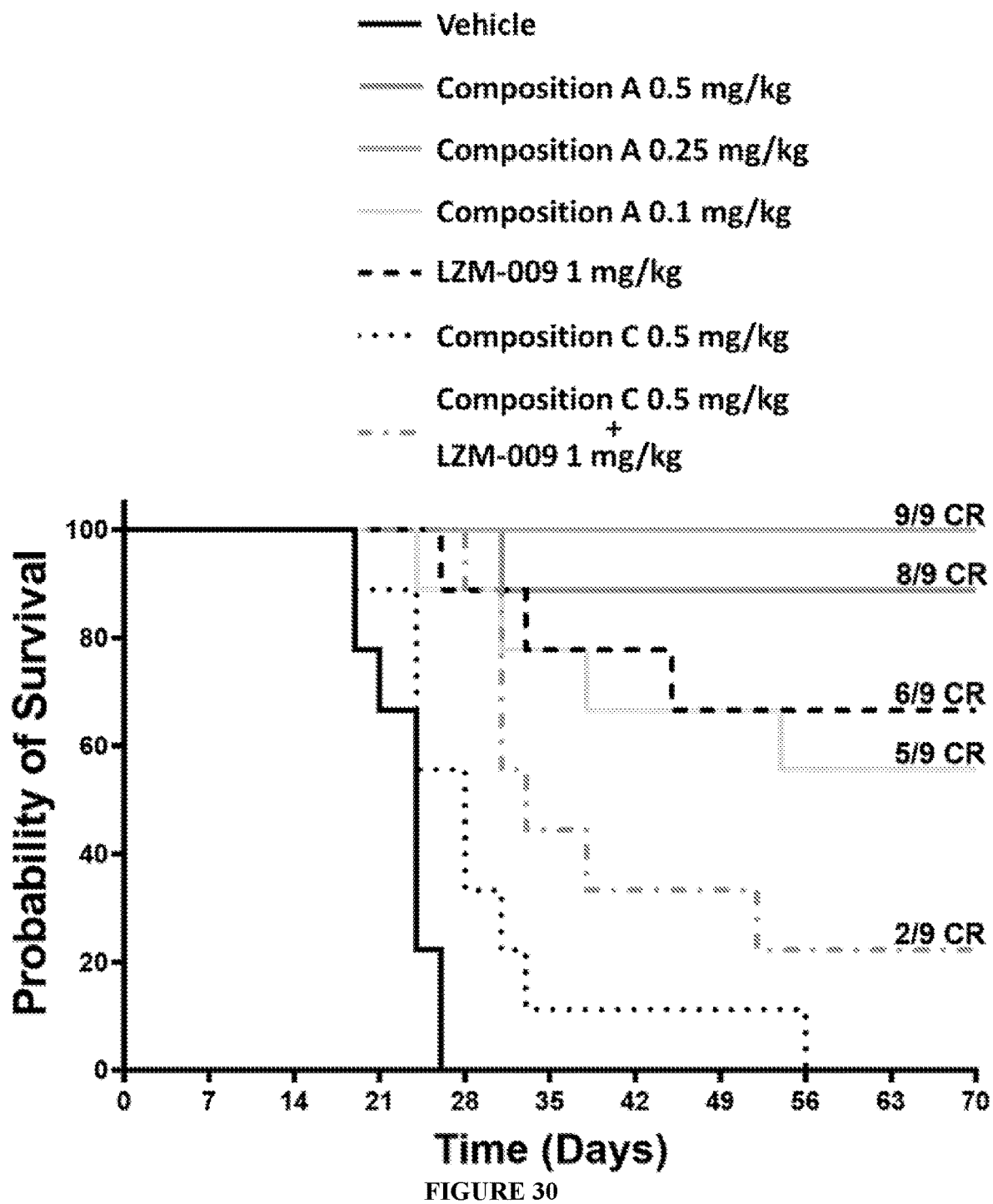
FIG. 30 shows a plot describing the effect of unmodified PD-L1 antibodies and of IL-18 polypeptide conjugated PD-1 antibody on the survival of MC38 syngeneic colon carcinoma tumor-bearing hPD1 C57BL/6 mice. The immunocytokine tested in this figure are Composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM; CR: Complete response).

FIG. 30 shows a plot describing the effect of unmodified PD-L1 antibodies and of IL-18 polypeptide conjugated PD-1 antibody on the survival of MC38 syngeneic colon carcinoma tumor-bearing hPD1 C57BL/6 mice. The immunocytokine tested in this figure are Composition A tested as a single agent at 0.1, 0.25, and 0.5 mg/kg as two weekly i.v. injections. As a control, Her2-targeted immunocytokine composition C was applied at 0.5 mg/kg as a single agent and in combination with LZM-009 anti-PD-1 antibody at 1 mg/kg (n=9; mean±SEM; CR: Complete response).

Example 16—In Vivo Antitumor Activity in B16F10 Melanoma Model (FIG. 31-34)

An in vivo efficacy study was performed in mice. Naïve, 6-8 weeks old, C57BL/6-hPD1 female mice (GemPharmatech Co, Ltd, Nanjing, China) were inoculated subcutaneously at the right upper flank with B16F10 tumor cells ($5 \times 10^4$; 1:1 with Matrigel®) in 0.1 mL of PBS for tumor development. The animals were randomized (using an Excel-based randomization software performing stratified randomization based upon tumor volumes), and treatment started when the average tumor volume reached approximately 70 mm$^3$. Animals treated with unmodified antibodies received two weekly 10 mL/kg bolus intraperitoneal (i.p.) injections. Animals treated with modified IL-18 polypeptide conjugated antibodies received two weekly 10 mL/kg bolus intravenous (i.v.) injections. After inoculation, the animals were checked daily for morbidity and mortality. At the time, animals were checked for effects on tumor growth and normal behavior such as mobility, food and water consumption, body weight gain/loss (body weights were measured twice weekly), eye/hair matting and any other abnormal effect. The major endpoints were delayed tumor growth or complete tumor regression. Tumor sizes were measured three times a week in two dimensions using a caliper, and the volume was expressed in mm$^3$ using the formula: $V=0.5 \text{ a} \times b^2$ where a and b are the long and short diameters of the tumor, respectively. Death and observed clinical signs were recorded on the basis of the numbers of animals within each subset.

Figure 31A:
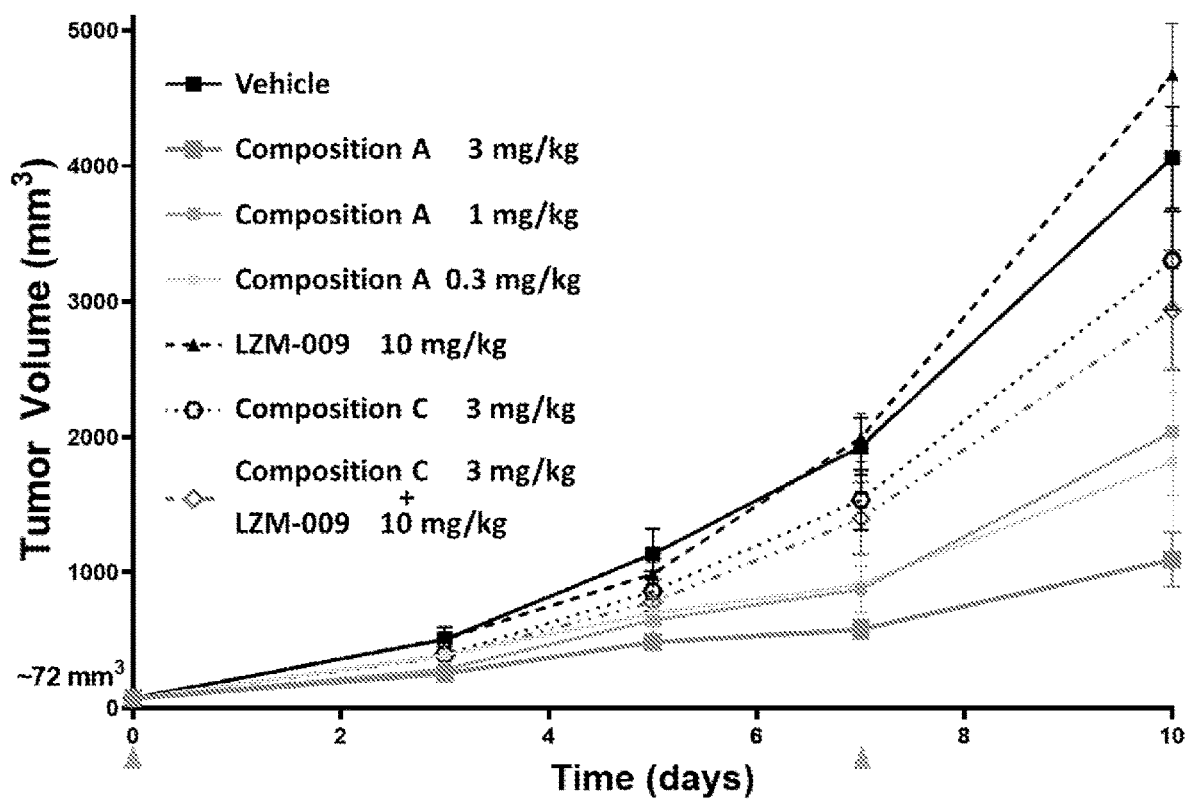
FIG. 31A shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows mean tumor volume on the y-axis and time on the x-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM).

FIG. 31A shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows mean tumor volume on the y-axis and time on the x-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM).

Figure 31B:
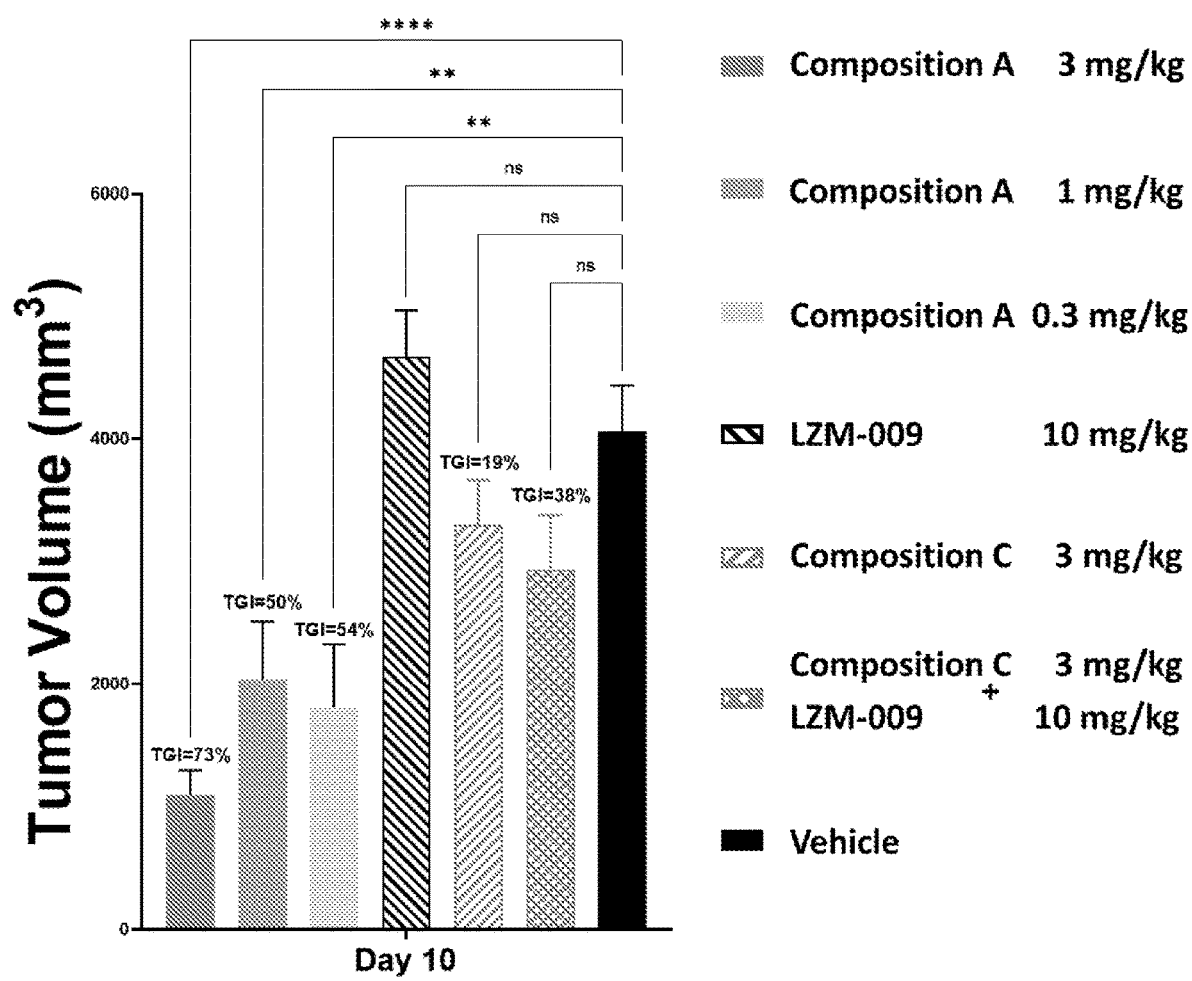
FIG. 31B shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows the mean tumor volume on day 10 post treatment initiation on the y-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; TGI: Tumor Growth Inhibition).

FIG. 31B shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows the mean tumor volume on day 10 post treatment initiation on the y-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; TGI: Tumor Growth Inhibition).

Figure 31C:
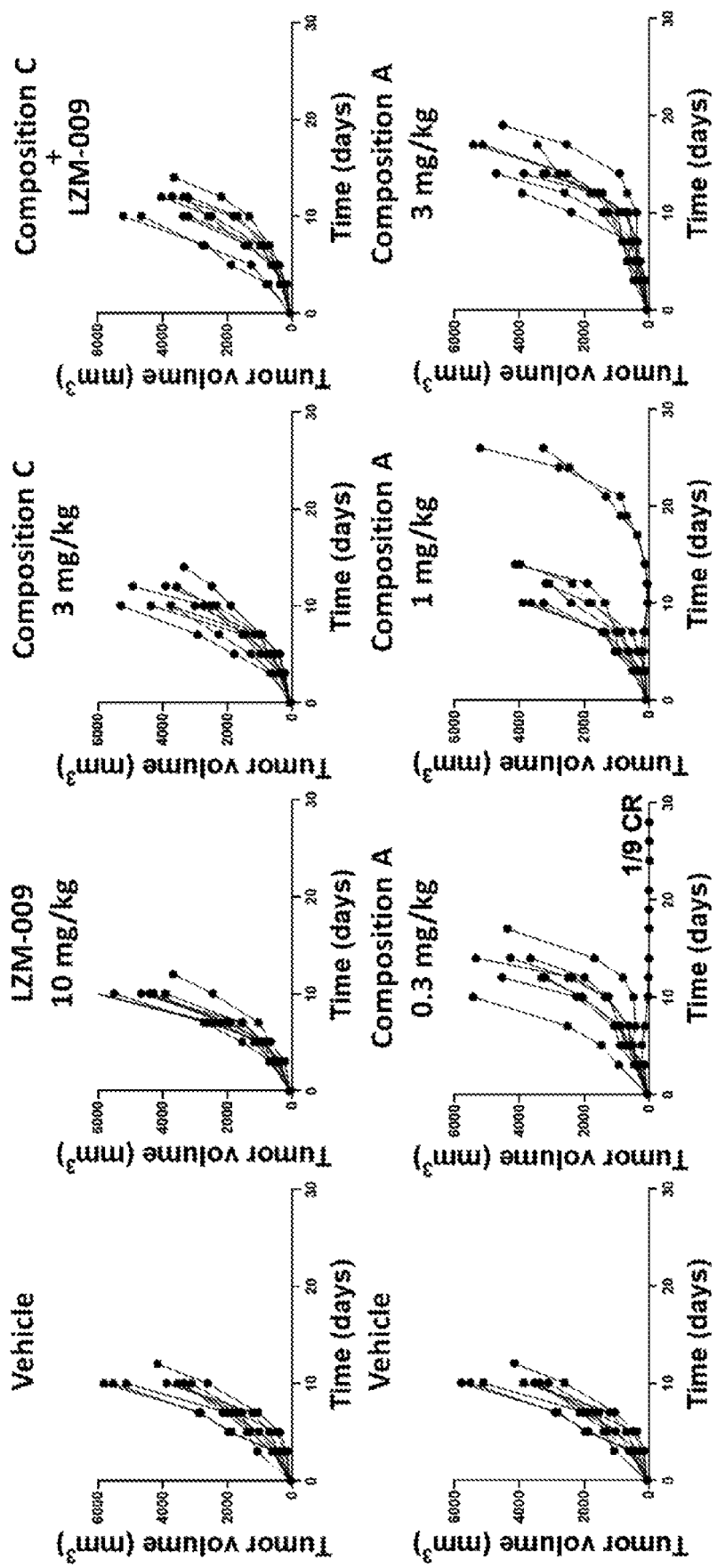
FIG. 31C shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows the tumor volume of each individual animal on the y-axis and time on the x-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; CR: Complete Response).

FIG. 31C shows a plot describing the effect of unmodified PD-1 antibodies and of IL-18 polypeptide conjugated PD-1 antibody on the growth of B16F10 syngeneic melanoma tumors in hPD1 C57BL/6 mice. The figure shows the tumor volume of each individual animal on the y-axis and time on the x-axis. The immunocytokine tested in this figure are composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; CR: Complete Response).

Figure 32:
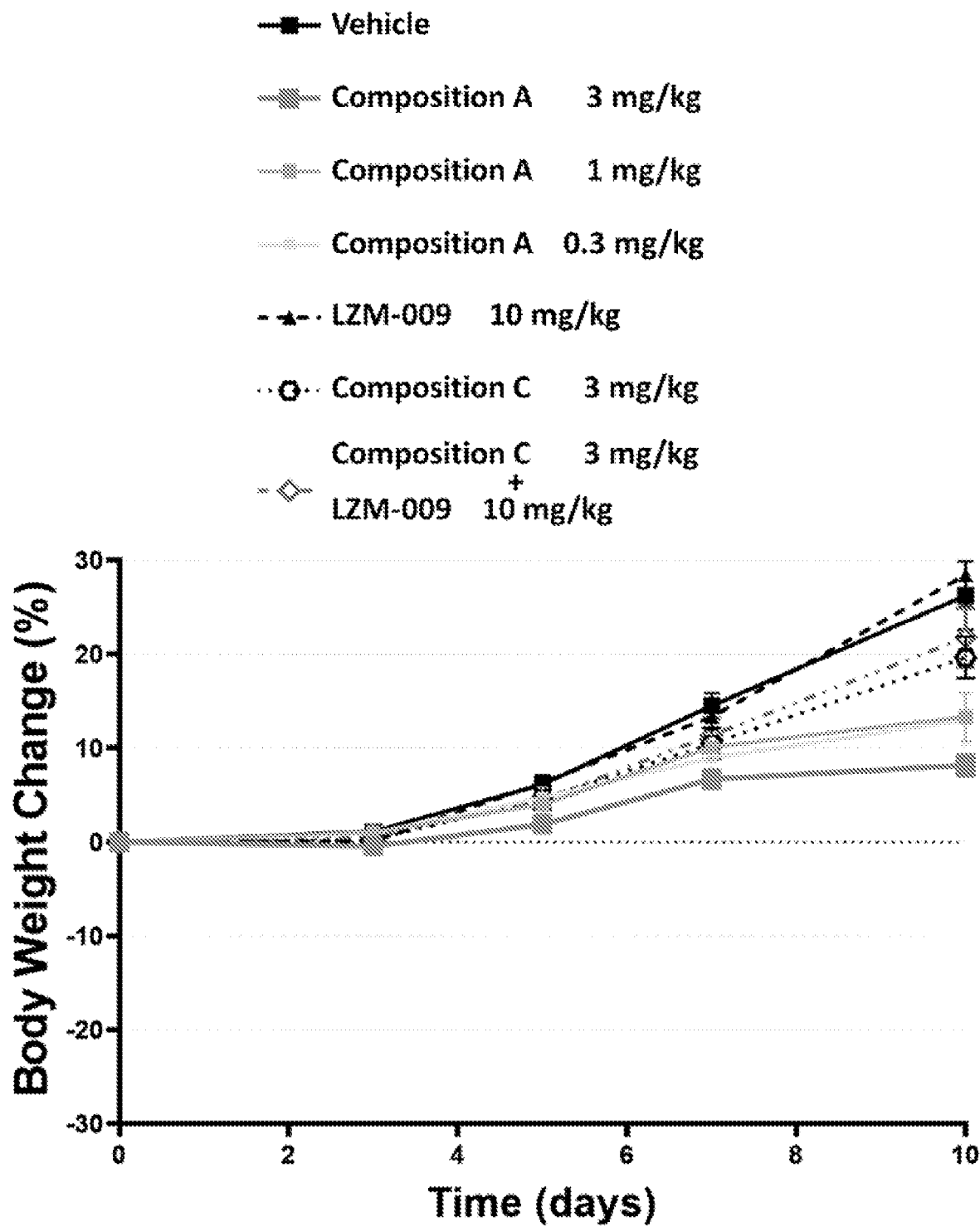
FIG. 32 shows a plot describing the effect of unmodified PD-L1 antibodies and of IL-18 polypeptide conjugated PD-1 antibody on the body weight of B16F10 syngeneic melanoma tumor-bearing hPD1 C57BL/6 mice. The figure shows mean body weight change on the y-axis and time on the x-axis. The immunocytokine tested in this figure are Composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM).

FIG. 32 shows a plot describing the effect of unmodified PD-L1 antibodies and of IL-18 polypeptide conjugated PD-1 antibody on the body weight of B16F10 syngeneic melanoma tumor-bearing hPD1 C57BL/6 mice. The figure shows mean body weight change on the y-axis and time on the x-axis. The immunocytokine tested in this figure are Composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM).

Figure 33:
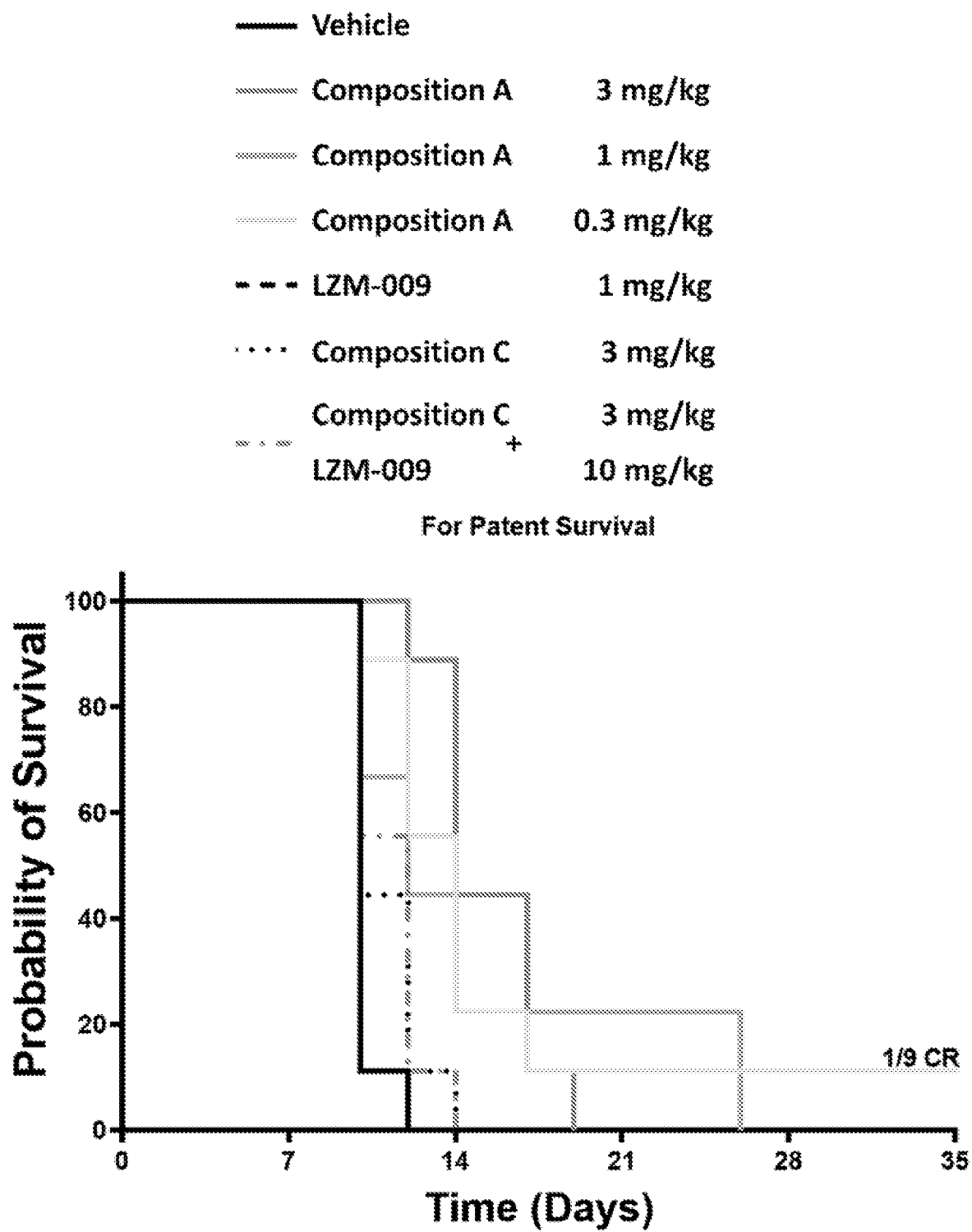
FIG. 33 shows a plot describing the effect of unmodified PD-L1 antibodies and of IL-18 polypeptide conjugated PD-1 antibody on the survival of B16F10 syngeneic melanoma tumor-bearing hPD1 C57BL/6 mice. The immunocytokine tested in this figure are Composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM; CR: Complete response).

FIG. 33 shows a plot describing the effect of unmodified PD-L1 antibodies and of IL-18 polypeptide conjugated PD-1 antibody on the survival of B16F10 syngeneic melanoma tumor-bearing hPD1 C57BL/6 mice. The immunocytokine tested in this figure are Composition A tested as a single agent at 0.3, 1, and 3 mg/kg as two weekly i.v. injections. As a control, Her2-targeted immunocytokine composition C was applied at 3 mg/kg as a single agent and in combination with LZM-009 anti-PD-1 antibody at 10 mg/kg (n=9; mean±SEM; CR: Complete response).

Example 17: Characteristics of Additional IL-18 Polypeptides

17A—HEK-Blue Reporter Assay—An IL-18R positive HEK-Blue reporter cell line is used to determine binding of IL-18 variants to IL-18R and subsequent downstream signaling. The general protocol is outlined below.

$5 \times 10^4$ cells HEK-Blue IL18R reporter cells (InvivoGen, #hkb-hmi118) are seeded into each well of a 96 well plate and stimulated with 0-100 nM of IL-18 polypeptide variants at 37° C. and 5% CO2. After 20 h incubation, 20 µL of cell culture supernatant is then taken from each well and mixed with 180 µL QUANTI-Blue media in a 96 well plate, incubated for 1 hour at 37° C. and 5% CO2. The absorbance signal at 620 nm is then measured on an Enspire plate reader with 680 and 615 nm as excitation and emission wavelengths, respectively. Half Maximal Effective dose (EC50) is calculated based on a variable slope, four parameter analysis using GraphPad PRISM software.

The HEK-Blue IL-18R reporter assay described above was performed on additional IL-18 polypeptides which can be incorporated into immunocytokine compositions provided herein. It is expected that the IL-18 polypeptides provided below would behave similarly to C086 (SEQ ID NO: 30) when incorporated into an immunocytokine composition as those otherwise provided herein.

| SEQ ID NO: or Composition ID | Sequence modifications | $EC_{50}$ (pM) |
|---|---|---|
| 1 | Native sequence | 3.33 |
| 34 | E6K, K53A, S55A | 272.5 |
| 39 | E6K, K53A | 0.72 |
| 42 | E6K, K53A, S55A, T63A | 0.79 |
| 50 | E6K, K53A, T63A | 1.77 |
| 54 | E6K, C38S, K53A, C68S, K70C, C76S, C127S | 9.12 |
| 56 | E6K, K53A, C38S, C76S, C127S | 3.73 |
| 57 | E6K, C38S, K53A | 0.86 |
| 30 | E6K, V11I, C38A, K53A, T63A, C76A, C127A | 0.034 |
| 62 | E6K, C38A, K53A, C127A | 0.17 |
| 60 | E6K, C38Q, K53A | 0.203 |
| 59 | E6K, C38A, K53A | 0.268 |
| 57 | E6K, C38S, K53A | 0.53 |
| C143 | V11I, C38A, K53A, C76A, C127A | 0.98 |
| C144 | V11I, C38A, K53A, T63A, C76A, C127A | 0.17 |
| C145 | V11I, C38A, K53A, S55A, C76A, C127A | 3.63 |
| C146 | V11I, C38A, M51G, K53A, C76A, C127A | 0.8 |
| C147 | V11I, C38A, K53A, D54A, C76A, C127A | 1 |
| C148 | F2A, V11I, C38A, K53A, C76A, C127A | 7.28 |
| C149 | V11I, E31A, C38A, K53A, C76A, C127A | 6.6 |
| C150 | V11I, T34A, C38A, K53A, C76A, C127A | 0.7 |
| C151 | V11I, D35A, C38A, K53A, C76A, C127A | 13.12 |
| C152 | V11I, S36A, C38A, K53A, C76A, C127A | 0.25 |
| C153 | V11I, D37A, C38A, K53A, C76A, C127A | 14.12 |
| C154 | V11I, E31A, D37A, C38A, K53A, C76A, C127A | 11.95 |
| C155 | V11I, C38A, D40A, K53A, C76A, C127A | 0.52 |
| C156 | V11I, C38A, N41A, K53A, C76A, C127A | 11.7 |
| C157 | V11I, C38A, K53A, C76A, C127A, D132A | 1.95 |
| C158 | V11I, C38A, K53A, C76A, G108A, C127A | 15.56 |
| C159 | V11I, C38A, K53A, C76A, H109A, C127A | 19.5 |
| C160 | V11I, C38A, K53A, C76A, D110A, C127A | 2.02 |
| C161 | K8R, V11I, C38A, C76A, Q103E, C127A | 2.01 |
| C162 | K8E, V11I, C38A, C76A, Q103R, C127A | 2.3 |
| C163 | V11I, C38A, C76A, Q103K, C127A | 1.5 |
| C164 | V11I, C38A, S55H, C76A, C127A | 3.14 |
| C165 | V11I, C38A, S55R, C76A, C127A | 1.91 |
| C166 | V11I, C38A, S55T, C76A, C127A | 4.73 |
| C167 | V11I, C38A, C76A, S105I, C127A | 5.37 |
| C168 | V11I, C38A, C76A, S105K, C127A | 7.73 |
| C174 | K8L, E6K, V11I, C38A, K53A, T63A, C76A, C127A | 0.29 |
| C176 | E6K, V11I, C38A, I49M, K53A, T63A, C76A, C127A | 0.07 |
| C177 | E6K, V11I, C38A, I49R, K53A, T63A, C76A, C127A | 0.04 |
| C178 | E6K, V11I, C38A, K53A, T63A, C76A, Q103R, C127A | 0.26 |
| C179 | E6K, K8E, V11I, C38A, K53A, T63A, C76A, Q103R, C127A | 0.4 |
| C181 | E6K, V11I, C38A, K53A, T63A, C76A, C127A, V153E | 0.1 |
| C182 | E6K, V11I, C38A, K53A, T63A, C76A, C127A, V153Y | 0.08 |
| C183 | E6K, V11I, C38A, M51G, K53A, T63A, C76A, C127A | 0.1 |
| C184 | E6R, V11I, C38A, K53A, T63A, C76A, C127A | 0.04 |
| C140 | E6K, V11I, C38A, K53A, T63A, C76A, C127A | 2.5 |
| C141 | E6K, V11I, C38A, K53A, T63A, C76A, C127A | 1.68 |
| C142 | Y1M, E6K, V11I, C38A, K53A, T63A, C76A, C127A | 0.02 |
| C192 | E6K, V11I, C38A, M51G, K53A, T63A, C76A, C127A | 13.99 |

17B—IL-18 BP AlphaLISA assay—An IL-18 binding protein AlphaLISA experiment substantially as described in Example 4 was performed on IL-18 polypeptide which can be incorporated into immunocytokine compositions as provided herein to assess ability to bind to IL-18BP. Results are shown in the Table below.

| SEQ ID NO: or Composition ID | Sequence modifications | KD (nM) |
|---|---|---|
| 1 | Native Sequence | 0.67 |
| 34 | E06K, K53A, S55A | >1500 |
| 35 | Y01G, F02A, E06K, M51G, K53A, D54A, S55A, T63A | 969.0 |
| 36 | K53A | 513.8 |
| 37 | S55A | 10.7 |
| 38 | E06K | 0.13 |
| 39 | E06K, K53A | 130.3 |
| 40 | E06K, S55A | 12.3 |
| 41 | K53A, S55A | 500.0 |
| 42 | E06K, K53A, S55A, T63A | 822.0 |
| 43 | E06K, K53A, S55A, Y01G | |
| 44 | E06K, K53A, S55A, F02A | >1000 |
| 45 | E06K, K53A, S55A, D54A | >1000 |
| 46 | E06K, K53A, S55A, M51G | >1000 |
| 47 | C38S, C68S, C76S, C127S | 0.03 |
| 48 | C38S, C68S, C76S, C127S, K70C | 0.21 |
| 49 | E06K, K53A, S55A, C38S, C68S, C76S, C127S, K70C | >1000 |
| 50 | E06K, K53A, T63A | 339.8 |
| 51 | T63A | 2.59 |
| 52 | E06K, T63A | 0.83 |
| 53 | K53A, T63A | 198 |
| 54 | E06K, K53A, C38S, C68S, C76S, C127S, K70C | 446.0 |
| 55 | K53A, T63A, C38S, C68S, C76S, C127S, K70C | 913 |
| 56 | E6K, K53A, C38S, C76S, C127S | 435.5 |
| 57 | E6K, K53A, C38S | 50.2 |
| C143 | V11I, C38A, K53A, C76A, C127A | 8.86 |
| C144 | V11I, C38A, K53A, T63A, C76A, C127A | 0.66 |
| C145 | V11I, C38A, K53A, S55A, C76A, C127A | 9.74 |
| C146 | V11I, C38A, M51G, K53A, C76A, C127A | 373.30 |
| C147 | V11I, C38A, K53A, D54A, C76A, C127A | 25.77 |
| C148 | F2A, V11I, C38A, K53A, C76A, C127A | 57.21 |
| C149 | V11I, E31A, C38A, K53A, C76A, C127A | 0.64 |
| C150 | V11I, T34A, C38A, K53A, C76A, C127A | 1.24 |
| C151 | V11I, D35A, C38A, K53A, C76A, C127A | 2.88 |
| C152 | V11I, S36A, C38A, K53A, C76A, C127A | 1.12 |
| C153 | V11I, D37A, C38A, K53A, C76A, C127A | 4.55 |
| C154 | V11I, E31A, D37A, C38A, K53A, C76A, C127A | 2.12 |
| C155 | V11I, C38A, D40A, K53A, C76A, C127A | 0.74 |
| C156 | V11I, C38A, N41A, K53A, C76A, C127A | 18.47 |
| C157 | V11I, C38A, K53A, C76A, C127A, D132A | 13.70 |
| C158 | V11I, C38A, K53A, C76A, G108A, C127A | 1.24 |
| C159 | V11I, C38A, K53A, C76A, H109A, C127A | 0.55 |
| C160 | V11I, C38A, K53A, C76A, D110A, C127A | 0.71 |
| C161 | K8R, V11I, C38A, C76A, Q103E, C127A | 0.06 |
| C162 | K8E, V11I, C38A, C76A, Q103R, C127A | 0.85 |
| C163 | V11I, C38A, C76A, Q103K, C127A | 0.05 |
| C164 | V11I, C38A, S55H, C76A, C127A | 0.08 |
| C165 | V11I, C38A, S55R, C76A, C127A | 0.15 |
| C166 | V11I, C38A, S55T, C76A, C127A | 0.02 |
| C167 | V11I, C38A, C76A, S105I, C127A | 0.04 |
| C168 | V11I, C38A, C76A, S105K, C127A | 0.05 |
| C174 | K8L, E6K, V11I, C38A, K53A, T63A, C76A, C127A | 0.14 |
| C176 | E6K, V11I, C38A, I49M, K53A, T63A, C76A, C127A | 25.84 |
| C177 | E6K, V11I, C38A, I49R, K53A, T63A, C76A, C127A | >2800 |
| C178 | E6K, V11I, C38A, K53A, T63A, C76A, Q103R, C127A | >2800 |
| C179 | E6K, K8E, V11I, C38A, K53A, T63A, C76A, Q103R, C127A | >2800 |
| C180 | E6K, V11I, C38A, K53A, T63A, C76A, C127A, V153R | |
| C181 | E6K, V11I, C38A, K53A, T63A, C76A, C127A, V153E | >2800 |
| C182 | E6K, V11I, C38A, K53A, T63A, C76A, C127A, V153Y | >2800 |
| C183 | E6K, V11I, C38A, M51G, K53A, T63A, C76A, C127A | >2800 |
| C184 | E6R, V11I, C38A, K53A, T63A, C76A, C127A | 5.46 |
| C140 | E6K, V11I, C38A, K53A, T63A, C76A, C127A | >2800 |
| C141 | E6K, V11I, C38A, K53A, T63A, C76A, C127A | >2800 |
| C142 | Y1M, E6K, V11I, C38A, K53A, T63A, C76A, C127A | 2.25 |
| C192 | E6K, V11I, C38A, M51G, K53A, T63A, C76A, C127A | >2800 |
| 62 | E6K, C38A, K53A, C127A | 69.62 |
| 60 | E6K, C38Q, K53A | 24.8 |
| 59 | E6K, C38A, K53A | 35.95 |

17C—IFNγ Stimulation and IL-18BP Inhibition Assay—The experiments described in Example 4 for determination of IFNg stimulation in NK92 cells (and inhibition by IL-18 BP) were performed substantially as described on modified IL-18 polypeptides in order to assess their activities and their suitability for incorporation into immunocytokine compositions. Results are shown in the table below.

| SEQ ID NO: or Composition ID | Sequence modifications | IC$_{50}$ (nM) | EC$_{50}$ (nM) |
|---|---|---|---|
| 1 | Native sequence | 1.47 | 0.276 |
| 34 | E06K, K53A, S55A | 229 | 0.824 |
| 35 | Y01G, F02A, E06K, M51G, K53A, D54A, S55A, T63A | >55.0 | >55.0 |
| 36 | K53A | 27.3 | 0.444 |
| 37 | S55A | 4.46 | 0.108 |
| 38 | E06K | 7.79 | 0.0567 |
| 39 | E06K, K53A | >703 | 0.0192 |
| 40 | E06K, S55A | 15 | 0.067 |
| 41 | K53A, S55A | 37.3 | 1.58 |
| 42 | E06K, K53A, S55A, T63A | 1060 | 0.144 |
| 43 | E06K, K53A, S55A, Y01G | 27.8 | 6.12 |
| 44 | E06K, K53A, S55A, F02A | NT | >1000 |
| 45 | E06K, K53A, S55A, D54A | NT | 30 |
| 46 | E06K, K53A, S55A, M51G | 0.189 | 7.4 |
| 47 | C38S, C68S, C76S, C127S | 0.444 | 0.115 |
| 48 | C38S, C68S, C76S, C127S, K70C | 0.114 | 0.488 |
| 49 | E06K, K53A, S55A, C38S, C68S, C76S, C127S, K70C | NT | 58.5 |
| 50 | E06K, K53A, T63A | >1000 | 0.0268 |
| 51 | T63A | 0.239 | 0.449 |
| 52 | E06K, T63A | 47.1 | 0.011 |
| 53 | K53A, T63A | 18.2 | 0.155 |
| 54 | E06K, K53A, C38S, C68S, C76S, C127S, K70C | 23.5 | 0.962 |

-continued

| SEQ ID NO: or Composition ID | Sequence modifications | IC$_{50}$ (nM) | EC$_{50}$ (nM) |
|---|---|---|---|
| 55 | K53A, T63A, C38S, C68S, C76S, C127S, K70C | >1000 | 17.2 |
| 6 | E6K, V11I, C38A, K53A, T63A, C68A, C76A, C127A, D98C | 5.847 | 1.366 |
| 5 | E6K, V11I, C38A, K53A, T63A, C68A, C76A, C127A, M86C | 62.37 | 0.075 |
| 9 | E6K, C38A, K53A, C68A, D98C | 960.8 | 0.069 |
| 4 | E6K, C38A, K53A, C68A, M86C | 396.3 | 0.022 |
| 62 | E6K, C38A, K53A, C127A | 283.6 | 0.026 |
| 60 | E6K, C38Q, K53A | 780.5 | 0.006 |
| 59 | E6K, C38A, K53A | 653.5 | 0.015 |
| 57 | E6K, C38S, K53A | 146.2 | 0.045 |
| C143 | V11I, C38A, K53A, C76A, C127A | 1.625 | 0.138 |
| C144 | V11I, C38A, K53A, T63A, C76A, C127A | 7.522 | 0.012 |
| C145 | V11I, C38A, K53A, S55A, C76A, C127A | 10.24 | 0.087 |
| C146 | V11I, C38A, M51G, K53A, C76A, C127A | 732.9 | 0.037 |
| C147 | V11I, C38A, K53A, D54A, C76A, C127A | 47.63 | 0.079 |
| C148 | F2A, V11I, C38A, K53A, C76A, C127A | 5.055 | 0.256 |
| C149 | V11I, E31A, C38A, K53A, C76A, C127A | 1.167 | 0.187 |
| C150 | V11I, T34A, C38A, K53A, C76A, C127A | 21.27 | 0.015 |
| C151 | V11I, D35A, C38A, K53A, C76A, C127A | 3.622 | 0.061 |
| C152 | V11I, S36A, C38A, K53A, C76A, C127A | 7.85 | 0.033 |
| C153 | V11I, D37A, C38A, K53A, C76A, C127A | 2.222 | 0.175 |
| C154 | V11I, E31A, D37A, C38A, K53A, C76A, C127A | 3.709 | 0.062 |
| C155 | V11I, C38A, D40A, K53A, C76A, C127A | 3.233 | 0.067 |
| C156 | V11I, C38A, N41A, K53A, C76A, C127A | 0.681 | 0.558 |
| C157 | V11I, C38A, K53A, C76A, C127A, D132A | 6.082 | 0.056 |
| C158 | V11I, C38A, K53A, C76A, G108A, C127A | 3.981 | 0.073 |
| C159 | V11I, C38A, K53A, C76A, H109A, C127A | 1.807 | 0.123 |
| C160 | V11I, C38A, K53A, C76A, D110A, C127A | 3.181 | 0.028 |
| C161 | K8R, V11I, C38A, C76A, Q103E, C127A | 1.073 | 0.057 |
| C162 | K8E, V11I, C38A, C76A, Q103R, C127A | 7.292 | 0.061 |
| C163 | V11I, C38A, C76A, Q103K, C127A | 0.823 | 0.093 |
| C164 | V11I, C38A, S55H, C76A, C127A | 0.456 | 0.414 |
| C165 | V11I, C38A, S55R, C76A, C127A | 0.885 | 0.176 |
| C166 | V11I, C38A, S55T, C76A, C127A | 0.44 | 0.098 |
| C167 | V11I, C38A, C76A, S105I, C127A | 0.809 | 0.103 |
| C168 | V11I, C38A, C76A, S105K, C127A | 0.176 | 0.098 |

Although the present disclosure and its advantages have been described in detail, it should be understood that various changes, substitutions and alterations can be made herein without departing from the spirit and scope of the disclosure as defined in the appended claims.

What is claimed is:

1. An immunocytokine composition, comprising:
   an IL-18 polypeptide, wherein the IL-18 polypeptide comprises the amino acid sequence set forth in SEQ ID NO: 30; and
   an antibody or an antigen binding fragment thereof specific for an immune cell associated antigen; and
   a linker, wherein the linker comprises:
      a first point of attachment to the IL-18 polypeptide; and
      a second point of attachment to the antibody or antigen binding fragment thereof.

2. The immunocytokine composition of claim 1, wherein the linker comprises a polymer.

3. The immunocytokine composition of claim 1, wherein the first point of attachment is at a residue which is not the N-terminus or the C-terminus of the IL-18 polypeptide.

4. The immunocytokine composition of claim 1, wherein the first point of attachment is at residue 68 of the IL-18 polypeptide.

5. The immunocytokine composition of claim 1, wherein the second point of attachment is at an amino acid residue in an Fc region of the antibody or antigen binding fragment.

6. The immunocytokine composition of claim 5, wherein the linker is covalently attached at Lys 248 of the Fc region of the antibody, wherein amino acid residue position number is based on EU numbering.

7. The immunocytokine composition of claim 1, wherein the IL-18 polypeptide displays reduced binding to IL-18 binding protein (IL-18BP) compared to the wild type IL-18 polypeptide of SEQ ID NO: 1.

8. The immunocytokine composition of claim 1, wherein the antibody or antigen binding fragment thereof is a monoclonal antibody.

9. The immunocytokine composition of claim 1, wherein the antibody or antigen binding fragment thereof comprises an IgG1 or an IgG4.

10. The immunocytokine composition of claim 1, wherein the immune cell associated antigen is programmed cell death protein 1 (PD-1).

11. The immunocytokine composition of claim 10, wherein the antibody or antigen binding fragment thereof comprises nivolumab, pembrolizumab, LZM-009, or cemiplimab.

12. The immunocytokine composition of claim 1, wherein the immune cell associated antigen is programmed death-ligand 1 (PD-L1).

13. The immunocytokine composition of claim 12, wherein the antibody is durvalumab, atezolizumab, or avelumab.

14. An immunocytokine composition, comprising:
   an IL-18 polypeptide having the amino acid sequence set forth in SEQ ID NO: 30;
   an antibody or an antigen binding fragment thereof comprising an Fc region and having a heavy chain variable region (VH) comprising the amino acid sequence set forth in SEQ ID NO: 376 and a light chain variable region (VL) comprising the amino acid sequence set forth in SEQ ID NO: 377; and
   a linker, wherein the linker comprises:
      a first point of attachment to residue C68 of the IL-18 polypeptide; and a second point of attachment to the antibody or antigen binding fragment thereof at Lys 248 of the Fc region, wherein amino acid residue position number is based on EU numbering.

15. The immunocytokine composition of claim 14, wherein the antibody or antigen binding fragment thereof is LZM-009.

16. The immunocytokine composition of claim 14, wherein the linker comprises polyethylene glycol.

17. An immunocytokine composition, comprising:
   an IL-18 polypeptide having the amino acid sequence set forth in SEQ ID NO: 30;
   an antibody or an antigen binding fragment thereof specific for programmed cell death protein 1 (PD-1) or programmed death-ligand 1 (PD-L1); and
   a linker, wherein the linker comprises:
      a first point of attachment to residue C68 the IL-18 polypeptide; and
      a second point of attachment to the antibody or antigen binding fragment thereof.

18. The immunocytokine composition of claim 17, wherein the antibody or antigen binding fragment thereof is specific for PD-1.

19. The immunocytokine composition of claim 18, wherein the antibody or antigen binding fragment thereof comprises an Fc region, and wherein the second point of attachment to the antibody or antigen binding fragment thereof is Lys 248 of the Fc region, wherein amino acid residue position number is based on EU numbering.

20. The immunocytokine composition of claim 19, wherein the antibody or antigen binding fragment thereof comprises an IgG1 or an IgG4.

* * * * *

```
                        SEQUENCE LISTING

Sequence total quantity: 408
SEQ ID NO: 1              moltype = AA   length = 157
FEATURE                   Location/Qualifiers
source                    1..157
                          mol_type = protein
                          organism = Homo sapiens
SEQUENCE: 1
YFGKLESKLS VIRNLNDQVL FIDQGNRPLF EDMTDSDCRD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 2              moltype = AA   length = 157
FEATURE                   Location/Qualifiers
source                    1..157
                          mol_type = protein
                          organism = synthetic construct
SEQUENCE: 2
YFGKLKSKLS VIRNLNDQVL FIDQGNRPLF EDMTDSDARD NAPRTIFIIS MYADSQPRGM   60
AVTISVKAEK ISTLSCENKI ISFKCMNPPD NIKDTKSDII FFQRSVPGHD NKMQFESSSY  120
EGYFLACEKE RDLFKLILKK EDELGDRSIM FTVQNED                           157

SEQ ID NO: 3              moltype = AA   length = 157
FEATURE                   Location/Qualifiers
source                    1..157
                          mol_type = protein
                          organism = synthetic construct
SEQUENCE: 3
YFGKLKSKLS IIRNLNDQVL FIDQGNRPLF EDMTDSDARD NAPRTIFIIS MYADSQPRGM   60
```

```
AVAISVKAEK ISTLSAENKI ISFKCMNPPD NIKDTKSDII FFQRSVPGHD NKMQFESSSY    120
EGYFLAAEKE RDLFKLILKK EDELGDRSIM FTVQNED                             157

SEQ ID NO: 4              moltype = AA  length = 157
FEATURE                   Location/Qualifiers
source                    1..157
                          mol_type = protein
                          organism = synthetic construct
SEQUENCE: 4
YFGKLKSKLS VIRNLNDQVL FIDQGNRPLF EDMTDSDARD NAPRTIFIIS MYADSQPRGM    60
AVTISVKAEK ISTLSCENKI ISFKECNPPD NIKDTKSDII FFQRSVPGHD NKMQFESSSY    120
EGYFLACEKE RDLFKLILKK EDELGDRSIM FTVQNED                             157

SEQ ID NO: 5              moltype = AA  length = 157
FEATURE                   Location/Qualifiers
source                    1..157
                          mol_type = protein
                          organism = synthetic construct
SEQUENCE: 5
YFGKLKSKLS IIRNLNDQVL FIDQGNRPLF EDMTDSDARD NAPRTIFIIS MYADSQPRGM    60
AVAISVKAEK ISTLSAENKI ISFKECNPPD NIKDTKSDII FFQRSVPGHD NKMQFESSSY    120
EGYFLAAEKE RDLFKLILKK EDELGDRSIM FTVQNED                             157

SEQ ID NO: 6              moltype = AA  length = 157
FEATURE                   Location/Qualifiers
source                    1..157
                          mol_type = protein
                          organism = synthetic construct
SEQUENCE: 6
YFGKLKSKLS IIRNLNDQVL FIDQGNRPLF EDMTDSDARD NAPRTIFIIS MYADSQPRGM    60
AVAISVKAEK ISTLSAENKI ISFKEMNPPD NIKDTKSCII FFQRSVPGHD NKMQFESSSY    120
EGYFLAAEKE RDLFKLILKK EDELGDRSIM FTVQNED                             157

SEQ ID NO: 7              moltype = AA  length = 157
FEATURE                   Location/Qualifiers
source                    1..157
                          mol_type = protein
                          organism = synthetic construct
SEQUENCE: 7
YFGKLKSKLS VIRNLNDQVL FIDQGNRPLF EDMTDSDARD NAPRTIFIIS MYADSQPRGM    60
AVTISVKAEK ISTLSAENKI ISFKECNPPD NIKDTKSDII FFQRSVPGHD NKMQFESSSY    120
EGYFLAAEKE RDLFKLILKK EDELGDRSIM FTVQNED                             157

SEQ ID NO: 8              moltype = AA  length = 157
FEATURE                   Location/Qualifiers
source                    1..157
                          mol_type = protein
                          organism = synthetic construct
SEQUENCE: 8
YFGKLKSKLS IIRNLNDQVL FIDQGNRPLF EDMTDSDARD NAPRTIFIIS MYADSQPRGM    60
AVAISVKAEK ISTLSAENKI ISFKEMNPPD NIKDCKSDII FFQRSVPGHD NKMQFESSSY    120
EGYFLAAEKE RDLFKLILKK EDELGDRSIM FTVQNED                             157

SEQ ID NO: 9              moltype = AA  length = 157
FEATURE                   Location/Qualifiers
source                    1..157
                          mol_type = protein
                          organism = synthetic construct
SEQUENCE: 9
YFGKLKSKLS VIRNLNDQVL FIDQGNRPLF EDMTDSDARD NAPRTIFIIS MYADSQPRGM    60
AVTISVKAEK ISTLSCENKI ISFKEMNPPD NIKDTKSCII FFQRSVPGHD NKMQFESSSY    120
EGYFLACEKE RDLFKLILKK EDELGDRSIM FTVQNED                             157

SEQ ID NO: 10             moltype = AA  length = 157
FEATURE                   Location/Qualifiers
source                    1..157
                          mol_type = protein
                          organism = synthetic construct
SEQUENCE: 10
YFGKLKSKLS VIRNLNDQVL FIDQGNRPLF EDMTDSDARD NAPRTIFIIS MYADSQPRGM    60
AVTISVKAEK ISTLSAENKI ISFKEMNPPD NIKDTKSCII FFQRSVPGHD NKMQFESSSY    120
EGYFLAAEKE RDLFKLILKK EDELGDRSIM FTVQNED                             157

SEQ ID NO: 11             moltype = AA  length = 157
FEATURE                   Location/Qualifiers
source                    1..157
                          mol_type = protein
                          organism = synthetic construct
SEQUENCE: 11
```

```
YFGKLKSKLS IIRNLNDQVL FIDQGNRPLF EDMTDSDARD NAPRTIFIIS MYADSQPRGM   60
AVTISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 12           moltype = AA   length = 157
FEATURE                 Location/Qualifiers
source                  1..157
                        mol_type = protein
                        organism = synthetic construct
SEQUENCE: 12
YFGKLKSKLS VIRNLNDQVL FIDQGNRPLF EDMTDSDARD NAPRTIFIIS MYADSQPRGM   60
AVAISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 13           moltype = AA   length = 157
FEATURE                 Location/Qualifiers
source                  1..157
                        mol_type = protein
                        organism = synthetic construct
SEQUENCE: 13
YFGKLKSKLS VIRNLNDQVL FIDQGNRPLF EDMTDSDCRD NAPRTIFIIS MYADSQPRGM   60
AVNISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 14           moltype = AA   length = 157
FEATURE                 Location/Qualifiers
source                  1..157
                        mol_type = protein
                        organism = synthetic construct
SEQUENCE: 14
YFGKLKSKLS VIRNLNDQVL FIDQGNRPLF EDMTDSDCRD NAPRTIFIIA MYADSQPRGM   60
AVNISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 15           moltype = AA   length = 157
FEATURE                 Location/Qualifiers
source                  1..157
                        mol_type = protein
                        organism = synthetic construct
SEQUENCE: 15
YFGKLKSKLS VIRNLNDQVL FIDQGNRPLF EDMTDSDCRD NAPRTIFIIH MYADSQPRGM   60
AVNISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 16           moltype = AA   length = 157
FEATURE                 Location/Qualifiers
source                  1..157
                        mol_type = protein
                        organism = synthetic construct
SEQUENCE: 16
YFGKLKSKLS VIRNLNDQVL FIDQGNRPLF EDMTDSDCRD NAPRTIFIIS MYADSQPRGM   60
AVNIAVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 17           moltype = AA   length = 157
FEATURE                 Location/Qualifiers
source                  1..157
                        mol_type = protein
                        organism = synthetic construct
SEQUENCE: 17
YFGKLKSKLS VIRNLNDQVL FIDQGNRPLF EDMTDSDCRD NAPRTIFIIH MYADSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 18           moltype = AA   length = 157
FEATURE                 Location/Qualifiers
source                  1..157
                        mol_type = protein
                        organism = synthetic construct
SEQUENCE: 18
YFGKLKSKLS VIRNLNDQVL FIDQGNRPLF EDMTDSDARD NAPRTIFIIS MYADSQPRGM   60
AVTISVKAEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 19           moltype = AA   length = 157
FEATURE                 Location/Qualifiers
source                  1..157
                        mol_type = protein
                        organism = synthetic construct
```

```
SEQUENCE: 19
YFGKLKSKLS VIRNLNDQVL FIDQGNRPLF EDMTDSDCRD NAPRTIFIIS MYADSQPRGM    60
AVTISVKCEK ISTLSCENAI ISFKEMNPPD NIKDTKSDII FFQRSVPGHD NKMQFESSSY   120
EGYFLACEKE RDLFKLILKK EDELGDRSIM FTVQNED                            157

SEQ ID NO: 20          moltype = AA   length = 157
FEATURE                Location/Qualifiers
source                 1..157
                       mol_type = protein
                       organism = synthetic construct
SEQUENCE: 20
YFGKLKSKLS VIRNLNDQVL FIDQGNRPLF EDMTDSDCRD NAPRTIFIIS MYADSQPRGM    60
AVTISVKCEK ISTLSCENAI ISFKEMNPPD NIKDTKSDII FFQRSVPGHD NKMQFESSSY   120
EGYFLACEKE RDLFKLILKK EDELGDRSIM FTVQNED                            157

SEQ ID NO: 21          moltype = AA   length = 157
FEATURE                Location/Qualifiers
source                 1..157
                       mol_type = protein
                       organism = synthetic construct
SEQUENCE: 21
YFGKLKSKLS VIRNLNDQVL FIDQGNRPLF EDMTDSDCRD NAPRTIFIIS MYADSQPRGM    60
AVTISVKCEK ISTLSCENKI ISFKEMNPPD NIKDTKSDII FFQRSVPAHD NKMQFESSSY   120
EGYFLACEKE RDLFKLILKK EDELGDRSIM FTVQNED                            157

SEQ ID NO: 22          moltype = AA   length = 157
FEATURE                Location/Qualifiers
source                 1..157
                       mol_type = protein
                       organism = synthetic construct
SEQUENCE: 22
YFGKLKSKLS VIRNLNDQVL FIDQGNRPLF EDMTDSDCRD NAPRTIFIIS MYADSQPRGM    60
AVTISVKCEK ISTLSCENKI ISFKEMNPPD NIKDTKSDII FFQRSVPGAD NKMQFESSSY   120
EGYFLACEKE RDLFKLILKK EDELGDRSIM FTVQNED                            157

SEQ ID NO: 23          moltype = AA   length = 157
FEATURE                Location/Qualifiers
source                 1..157
                       mol_type = protein
                       organism = synthetic construct
SEQUENCE: 23
YFGKLKSKLS VIRNLNDQVL FIDQGNRPLF EDMTDSDCRD NAPRTIFIIS MYADSQPRGM    60
AVTISVKCEK ISTLSCENKI ISFKEMNPPD NIKDTKSDII FFQRSVPGHD NAMQFESSSY   120
EGYFLACEKE RDLFKLILKK EDELGDRSIM FTVQNED                            157

SEQ ID NO: 24          moltype = AA   length = 157
FEATURE                Location/Qualifiers
source                 1..157
                       mol_type = protein
                       organism = synthetic construct
SEQUENCE: 24
YFGKLKSKLS VIRNLNDQVL FIDQGNRPLF EDMTDSDARD NAPRTIFIIS MYADSQPRGM    60
AVAISVKCEK ISTLSAENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 25          moltype = AA   length = 157
FEATURE                Location/Qualifiers
source                 1..157
                       mol_type = protein
                       organism = synthetic construct
SEQUENCE: 25
YFGKLKSKLS VIRNLNDQVL FIDQGNRPLF EDMTDSDQRD NAPRTIFIIS MYADSQPRGM    60
AVAISVKCEK ISTLSAENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 26          moltype = AA   length = 157
FEATURE                Location/Qualifiers
source                 1..157
                       mol_type = protein
                       organism = synthetic construct
SEQUENCE: 26
YFGKLKSKLS VIRNLNDQVL FIDQGNRPLF EDMTDSDARD NAPRTIFIIS MYADSQPRGM    60
AVAISVKCEK ISTLSCENKI ISFKEMNPPD NIKDTKSDII FFQRSVPGHD NKMQFESSSY   120
EGYFLAAEKE RDLFKLILKK EDELGDRSIM FTVQNED                            157

SEQ ID NO: 27          moltype = AA   length = 157
FEATURE                Location/Qualifiers
source                 1..157
                       mol_type = protein
```

```
                        organism = synthetic construct
SEQUENCE: 27
YFGKLKSKLS VIRNLNDQVL FIDQGNRPLF EDMTDSDQRD NAPRTIFIIS MYADSQPRGM   60
AVAISVKCEK ISTLSCENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 28           moltype = AA   length = 157
FEATURE                 Location/Qualifiers
source                  1..157
                        mol_type = protein
                        organism = synthetic construct
SEQUENCE: 28
YFGKLKSKLS VIRNLNDQVL FIDQGNRPLF EDMTDSDARD NAPRTIFIIS MYADSQPRGM   60
AVAISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 29           moltype = AA   length = 157
FEATURE                 Location/Qualifiers
source                  1..157
                        mol_type = protein
                        organism = synthetic construct
SEQUENCE: 29
YFGKLKSKLS IIRNLNDQVL FIDQGNRPLF EDMTDSDARD NAPRTIFIIS MYADSQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 30           moltype = AA   length = 157
FEATURE                 Location/Qualifiers
source                  1..157
                        mol_type = protein
                        organism = synthetic construct
SEQUENCE: 30
YFGKLKSKLS IIRNLNDQVL FIDQGNRPLF EDMTDSDARD NAPRTIFIIS MYADSQPRGM   60
AVAISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 31           moltype = AA   length = 157
FEATURE                 Location/Qualifiers
source                  1..157
                        mol_type = protein
                        organism = synthetic construct
SEQUENCE: 31
YFGKLESKLS VIRNLNDQVL FIDQGNRPLF EDMTDSDARD NAPRTIFIIS MYKDSQPRGM   60
AVTISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                          157

SEQ ID NO: 32           moltype = AA   length = 157
FEATURE                 Location/Qualifiers
source                  1..157
                        mol_type = protein
                        organism = synthetic construct
SEQUENCE: 32
YFGKLESKLS VIRNLNDQVL FIDQGNRPLF EDMTDSDARD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 33           moltype = AA   length = 157
FEATURE                 Location/Qualifiers
source                  1..157
                        mol_type = protein
                        organism = synthetic construct
SEQUENCE: 33
YFGKLKSKLS VIRNLNDQVL FIDQGNRPLF EDMTDSDARD NAPRTIFIIS MYADSQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 34           moltype = AA   length = 157
FEATURE                 Location/Qualifiers
source                  1..157
                        mol_type = protein
                        organism = synthetic construct
SEQUENCE: 34
YFGKLKSKLS VIRNLNDQVL FIDQGNRPLF EDMTDSDCRD NAPRTIFIIS MYADAQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 35           moltype = AA   length = 157
FEATURE                 Location/Qualifiers
source                  1..157
```

```
                    mol_type = protein
                    organism = synthetic construct
SEQUENCE: 35
GAGKLKSKLS VIRNLNDQVL FIDQGNRPLF EDMTDSDCRD NAPRTIFIIS GYAAAQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 36            moltype = AA  length = 157
FEATURE                  Location/Qualifiers
source                   1..157
                    mol_type = protein
                    organism = synthetic construct
SEQUENCE: 36
YFGKLESKLS VIRNLNDQVL FIDQGNRPLF EDMTDSDCRD NAPRTIFIIS MYADSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 37            moltype = AA  length = 157
FEATURE                  Location/Qualifiers
source                   1..157
                    mol_type = protein
                    organism = synthetic construct
SEQUENCE: 37
YFGKLESKLS VIRNLNDQVL FIDQGNRPLF EDMTDSDCRD NAPRTIFIIS MYKDAQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 38            moltype = AA  length = 157
FEATURE                  Location/Qualifiers
source                   1..157
                    mol_type = protein
                    organism = synthetic construct
SEQUENCE: 38
YFGKLKSKLS VIRNLNDQVL FIDQGNRPLF EDMTDSDCRD NAPRTIFIIS MYKDSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 39            moltype = AA  length = 157
FEATURE                  Location/Qualifiers
source                   1..157
                    mol_type = protein
                    organism = synthetic construct
SEQUENCE: 39
YFGKLKSKLS VIRNLNDQVL FIDQGNRPLF EDMTDSDCRD NAPRTIFIIS MYADSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 40            moltype = AA  length = 157
FEATURE                  Location/Qualifiers
source                   1..157
                    mol_type = protein
                    organism = synthetic construct
SEQUENCE: 40
YFGKLKSKLS VIRNLNDQVL FIDQGNRPLF EDMTDSDCRD NAPRTIFIIS MYKDAQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 41            moltype = AA  length = 157
FEATURE                  Location/Qualifiers
source                   1..157
                    mol_type = protein
                    organism = synthetic construct
SEQUENCE: 41
YFGKLESKLS VIRNLNDQVL FIDQGNRPLF EDMTDSDCRD NAPRTIFIIS MYADAQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 42            moltype = AA  length = 157
FEATURE                  Location/Qualifiers
source                   1..157
                    mol_type = protein
                    organism = synthetic construct
SEQUENCE: 42
YFGKLKSKLS VIRNLNDQVL FIDQGNRPLF EDMTDSDCRD NAPRTIFIIS MYADAQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 43            moltype = AA  length = 157
FEATURE                  Location/Qualifiers
```

```
source                      1..157
                            mol_type = protein
                            organism = synthetic construct
SEQUENCE: 43
GFGKLKSKLS VIRNLNDQVL FIDQGNRPLF EDMTDSDCRD NAPRTIFIIS MYADAQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 44               moltype = AA  length = 157
FEATURE                     Location/Qualifiers
source                      1..157
                            mol_type = protein
                            organism = synthetic construct
SEQUENCE: 44
YAGKLKSKLS VIRNLNDQVL FIDQGNRPLF EDMTDSDCRD NAPRTIFIIS MYADAQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 45               moltype = AA  length = 157
FEATURE                     Location/Qualifiers
source                      1..157
                            mol_type = protein
                            organism = synthetic construct
SEQUENCE: 45
YFGKLKSKLS VIRNLNDQVL FIDQGNRPLF EDMTDSDCRD NAPRTIFIIS MYAAAQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 46               moltype = AA  length = 157
FEATURE                     Location/Qualifiers
source                      1..157
                            mol_type = protein
                            organism = synthetic construct
SEQUENCE: 46
YFGKLKSKLS VIRNLNDQVL FIDQGNRPLF EDMTDSDCRD NAPRTIFIIS GYADAQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 47               moltype = AA  length = 157
FEATURE                     Location/Qualifiers
source                      1..157
                            mol_type = protein
                            organism = synthetic construct
SEQUENCE: 47
YFGKLESKLS VIRNLNDQVL FIDQGNRPLF EDMTDSDSRD NAPRTIFIIS MYKDSQPRGM    60
AVTISVKSEK ISTLSSENKI ISFKEMNPPD NIKDTKSDII FFQRSVPGHD NKMQFESSSY   120
EGYFLASEKE RDLFKLILKK EDELGDRSIM FTVQNED                            157

SEQ ID NO: 48               moltype = AA  length = 157
FEATURE                     Location/Qualifiers
source                      1..157
                            mol_type = protein
                            organism = synthetic construct
SEQUENCE: 48
YFGKLESKLS VIRNLNDQVL FIDQGNRPLF EDMTDSDSRD NAPRTIFIIS MYKDSQPRGM    60
AVTISVKSEC ISTLSSENKI ISFKEMNPPD NIKDTKSDII FFQRSVPGHD NKMQFESSSY   120
EGYFLASEKE RDLFKLILKK EDELGDRSIM FTVQNED                            157

SEQ ID NO: 49               moltype = AA  length = 157
FEATURE                     Location/Qualifiers
source                      1..157
                            mol_type = protein
                            organism = synthetic construct
SEQUENCE: 49
YFGKLKSKLS VIRNLNDQVL FIDQGNRPLF EDMTDSDSRD NAPRTIFIIS MYADAQPRGM    60
AVTISVKSEC ISTLSSENKI ISFKEMNPPD NIKDTKSDII FFQRSVPGHD NKMQFESSSY   120
EGYFLASEKE RDLFKLILKK EDELGDRSIM FTVQNED                            157

SEQ ID NO: 50               moltype = AA  length = 157
FEATURE                     Location/Qualifiers
source                      1..157
                            mol_type = protein
                            organism = synthetic construct
SEQUENCE: 50
YFGKLKSKLS VIRNLNDQVL FIDQGNRPLF EDMTDSDCRD NAPRTIFIIS MYADSQPRGM    60
AVAISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 51               moltype = AA  length = 157
```

```
FEATURE              Location/Qualifiers
source               1..157
                     mol_type = protein
                     organism = synthetic construct
SEQUENCE: 51
YFGKLESKLS VIRNLNDQVL FIDQGNRPLF EDMTDSDCRD NAPRTIFIIS MYKDSQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 52        moltype = AA  length = 157
FEATURE              Location/Qualifiers
source               1..157
                     mol_type = protein
                     organism = synthetic construct
SEQUENCE: 52
YFGKLKSKLS VIRNLNDQVL FIDQGNRPLF EDMTDSDCRD NAPRTIFIIS MYKDSQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 53        moltype = AA  length = 157
FEATURE              Location/Qualifiers
source               1..157
                     mol_type = protein
                     organism = synthetic construct
SEQUENCE: 53
YFGKLESKLS VIRNLNDQVL FIDQGNRPLF EDMTDSDCRD NAPRTIFIIS MYADSQPRGM   60
AVAISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 54        moltype = AA  length = 157
FEATURE              Location/Qualifiers
source               1..157
                     mol_type = protein
                     organism = synthetic construct
SEQUENCE: 54
YFGKLKSKLS VIRNLNDQVL FIDQGNRPLF EDMTDSDSRD NAPRTIFIIS MYADSQPRGM   60
AVTISVKSEC ISTLSSENKI ISFKEMNPPD NIKDTKSDII FFQRSVPGHD NKMQFESSSY  120
EGYFLASEKE RDLFKLILKK EDELGDRSIM FTVQNED                          157

SEQ ID NO: 55        moltype = AA  length = 157
FEATURE              Location/Qualifiers
source               1..157
                     mol_type = protein
                     organism = synthetic construct
SEQUENCE: 55
YFGKLESKLS VIRNLNDQVL FIDQGNRPLF EDMTDSDSRD NAPRTIFIIS MYADSQPRGM   60
AVAISVKSEC ISTLSSENKI ISFKEMNPPD NIKDTKSDII FFQRSVPGHD NKMQFESSSY  120
EGYFLASEKE RDLFKLILKK EDELGDRSIM FTVQNED                          157

SEQ ID NO: 56        moltype = AA  length = 157
FEATURE              Location/Qualifiers
source               1..157
                     mol_type = protein
                     organism = synthetic construct
SEQUENCE: 56
YFGKLKSKLS VIRNLNDQVL FIDQGNRPLF EDMTDSDSRD NAPRTIFIIS MYADSQPRGM   60
AVTISVKCEK ISTLSSENKI ISFKEMNPPD NIKDTKSDII FFQRSVPGHD NKMQFESSSY  120
EGYFLASEKE RDLFKLILKK EDELGDRSIM FTVQNED                          157

SEQ ID NO: 57        moltype = AA  length = 157
FEATURE              Location/Qualifiers
source               1..157
                     mol_type = protein
                     organism = synthetic construct
SEQUENCE: 57
YFGKLKSKLS VIRNLNDQVL FIDQGNRPLF EDMTDSDSRD NAPRTIFIIS MYADSQPRGM   60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                          157

SEQ ID NO: 58        moltype = AA  length = 157
FEATURE              Location/Qualifiers
source               1..157
                     mol_type = protein
                     organism = synthetic construct
SEQUENCE: 58
YFGKLKSKLS VIRNLNDQVL FIDQGNRPLF EDMTDSDSRD NAPRTIFIIS MYADSQPRGM   60
AVTISVKSEC ISTLSSENKI ISFKEMNPPD NIKDTKSDII FFQRSVPGHD NKMQFESSSY  120
EGYFLASEKE RDLFKLILKK EDELGDRSIM FTVQNED                          157
```

```
SEQ ID NO: 59            moltype = AA   length = 157
FEATURE                  Location/Qualifiers
source                   1..157
                         mol_type = protein
                         organism = synthetic construct
SEQUENCE: 59
YFGKLKSKLS VIRNLNDQVL FIDQGNRPLF EDMTDSDARD NAPRTIFIIS MYADSQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 60            moltype = AA   length = 157
FEATURE                  Location/Qualifiers
source                   1..157
                         mol_type = protein
                         organism = synthetic construct
SEQUENCE: 60
YFGKLKSKLS VIRNLNDQVL FIDQGNRPLF EDMTDSDQRD NAPRTIFIIS MYADSQPRGM    60
AVTISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 61            moltype = AA   length = 157
FEATURE                  Location/Qualifiers
source                   1..157
                         mol_type = protein
                         organism = synthetic construct
SEQUENCE: 61
YFGKLKSKLS VIRNLNDQVL FIDQGNRPLF EDMTDSDARD NAPRTIFIIS MYADSQPRGM    60
AVTISVKCEK ISTLSAENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 62            moltype = AA   length = 157
FEATURE                  Location/Qualifiers
source                   1..157
                         mol_type = protein
                         organism = synthetic construct
SEQUENCE: 62
YFGKLKSKLS VIRNLNDQVL FIDQGNRPLF EDMTDSDARD NAPRTIFIIS MYADSQPRGM    60
AVTISVKCEK ISTLSCENKI ISFKEMNPPD NIKDTKSDII FFQRSVPGHD NKMQFESSSY   120
EGYFLAAEKE RDLFKLILKK EDELGDRSIM FTVQNED                            157

SEQ ID NO: 63            moltype = AA   length = 157
FEATURE                  Location/Qualifiers
source                   1..157
                         mol_type = protein
                         organism = synthetic construct
SEQUENCE: 63
YFGKLKSKLS VIRNLNDQVL FIDQGNRPLF EDMTDSDARD NAPRTIFIIS MYADSQPRGM    60
AVTISVKCEK ISTLSAENKI ISFKEMNPPD NIKDTKSDII FFQRSVPGHD NKMQFESSSY   120
EGYFLAAEKE RDLFKLILKK EDELGDRSIM FTVQNED                            157

SEQ ID NO: 64            moltype = AA   length = 157
FEATURE                  Location/Qualifiers
source                   1..157
                         mol_type = protein
                         organism = synthetic construct
SEQUENCE: 64
YFGKLKSKLS VIRNLNDQVL FIDQGNRPLF EDMTDSDARD NAPRTIFIIS MYADAQPRGM    60
AVAISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 65            moltype = AA   length = 157
FEATURE                  Location/Qualifiers
source                   1..157
                         mol_type = protein
                         organism = synthetic construct
SEQUENCE: 65
YFGKLKSKLS VIRNLNDQVL FIDQGNRPLF EDMTDSDQRD NAPRTIFIIS MYADAQPRGM    60
AVAISVKCEK ISTLSCENKI ISFKEMNPPD NIKDTKSDII FFQRSVPGHD NKMQFESSSY   120
EGYFLACEKE RDLFKLILKK EDELGDRSIM FTVQNED                            157

SEQ ID NO: 66            moltype = AA   length = 157
FEATURE                  Location/Qualifiers
source                   1..157
                         mol_type = protein
                         organism = synthetic construct
SEQUENCE: 66
YFGKLKSKLS VIRNLNDQVL FIDQGNRPLF EDMTDSDCRD NAPRTIFIIS MYADSQPRGM    60
AVTISVKCEK ISTLSCENKI ISFAEMNPPD NIKDTKSDII FFQRSVPGHD NKMQFESSSY   120
EGYFLACEKE RDLFKLILKK EDELGDRSIM FTVQNED                            157
```

```
SEQ ID NO: 67           moltype = AA  length = 157
FEATURE                 Location/Qualifiers
source                  1..157
                        mol_type = protein
                        organism = synthetic construct
SEQUENCE: 67
YFGKLKSKLS VIRNLNDQVL FIDQGNRPLF EDMTDSDCRD NAPRTIFIIS MYADSQPRGM   60
AVTISVKCEK ISTLSCENKI ISFKEMNPPD NIKDTKSAII FFQRSVPGHD NKMQFESSSY  120
EGYFLACEKE RDLFKLILKK EDELGDRSIM FTVQNED                           157

SEQ ID NO: 68           moltype = AA  length = 157
FEATURE                 Location/Qualifiers
source                  1..157
                        mol_type = protein
                        organism = synthetic construct
SEQUENCE: 68
YFGKLESKLS IIRNLNDQVL FIDQGNRPLF EDMTDSDARD NAPRTIFIIS GYADSQPRGM   60
AVTISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                           157

SEQ ID NO: 69           moltype = AA  length = 157
FEATURE                 Location/Qualifiers
source                  1..157
                        mol_type = protein
                        organism = synthetic construct
SEQUENCE: 69
YFGKLKSKLS IIRNLNDQVL FIDQGNRPLF EDMTDSDARD NAPRTIFIIS GYADSQPRGM   60
AVAISVKCEK ISTLSAENKI ISFKEMNPPD NIKDTKSDII FFQRSVPGHD NKMQFESSSY  120
EGYFLAAEKE RDLFKLILKK EDELGDRSIM FTVQNED                           157

SEQ ID NO: 70           moltype = AA  length = 158
FEATURE                 Location/Qualifiers
source                  1..158
                        mol_type = protein
                        organism = synthetic construct
SEQUENCE: 70
GYFGKLKSKL SIIRNLNDQV LFIDQGNRPL FEDMTDSDAR DNAPRTIFII SGYADSQPRG   60
MAVAISVKCE KISTLSAENK IISFKEMNPP DNIKDTKSDI IFFQRSVPGH DNKMQFESSS  120
YEGYFLAAEK ERDLFKLILK KEDELGDRSI MFTVQNED                          158

SEQ ID NO: 71           moltype = AA  length = 158
FEATURE                 Location/Qualifiers
source                  1..158
                        mol_type = protein
                        organism = synthetic construct
SEQUENCE: 71
GYFGKLKSKL SIIRNLNDQV LFIDQGNRPL FEDMTDSDAR DNAPRTIFII SMYADSQPRG   60
MAVAISVKCE KISTLSAENK IISFKEMNPP DNIKDTKSDI IFFQRSVPGH DNKMQFESSS  120
YEGYFLAAEK ERDLFKLILK KEDELGDRSI MFTVQNED                          158

SEQ ID NO: 72           moltype = AA  length = 161
FEATURE                 Location/Qualifiers
source                  1..161
                        mol_type = protein
                        organism = synthetic construct
SEQUENCE: 72
GGGGYFGKLK SKLSIIRNLN DQVLFIDQGN RPLFEDMTDS DARDNAPRTI FIISMYADSQ   60
PRGMAVAISV KCEKISTLSA ENKIISFKEM NPPDNIKDTK SDIIFFQRSV PGHDNKMQFE  120
SSSYEGYFLA AEKERDLFKL ILKKEDELGD RSIMFTVQNE D                      161

SEQ ID NO: 73           moltype =     length =
SEQUENCE: 73
000

SEQ ID NO: 74           moltype =     length =
SEQUENCE: 74
000

SEQ ID NO: 75           moltype =     length =
SEQUENCE: 75
000

SEQ ID NO: 76           moltype =     length =
SEQUENCE: 76
000

SEQ ID NO: 77           moltype =     length =
SEQUENCE: 77
```

000

SEQ ID NO: 78          moltype =     length =
SEQUENCE: 78
000

SEQ ID NO: 79          moltype =     length =
SEQUENCE: 79
000

SEQ ID NO: 80          moltype =     length =
SEQUENCE: 80
000

SEQ ID NO: 81          moltype =     length =
SEQUENCE: 81
000

SEQ ID NO: 82          moltype =     length =
SEQUENCE: 82
000

SEQ ID NO: 83          moltype =     length =
SEQUENCE: 83
000

SEQ ID NO: 84          moltype =     length =
SEQUENCE: 84
000

SEQ ID NO: 85          moltype =     length =
SEQUENCE: 85
000

SEQ ID NO: 86          moltype =     length =
SEQUENCE: 86
000

SEQ ID NO: 87          moltype =     length =
SEQUENCE: 87
000

SEQ ID NO: 88          moltype =     length =
SEQUENCE: 88
000

SEQ ID NO: 89          moltype =     length =
SEQUENCE: 89
000

SEQ ID NO: 90          moltype =     length =
SEQUENCE: 90
000

SEQ ID NO: 91          moltype =     length =
SEQUENCE: 91
000

SEQ ID NO: 92          moltype =     length =
SEQUENCE: 92
000

SEQ ID NO: 93          moltype =     length =
SEQUENCE: 93
000

SEQ ID NO: 94          moltype =     length =
SEQUENCE: 94
000

SEQ ID NO: 95          moltype =     length =
SEQUENCE: 95
000

SEQ ID NO: 96          moltype =     length =
SEQUENCE: 96
000

SEQ ID NO: 97          moltype =     length =

| | | |
|---|---|---|
| SEQUENCE: 97 000 | | |
| SEQ ID NO: 98 SEQUENCE: 98 000 | moltype = | length = |
| SEQ ID NO: 99 SEQUENCE: 99 000 | moltype = | length = |
| SEQ ID NO: 100 SEQUENCE: 100 000 | moltype = | length = |
| SEQ ID NO: 101 SEQUENCE: 101 000 | moltype = | length = |
| SEQ ID NO: 102 SEQUENCE: 102 000 | moltype = | length = |
| SEQ ID NO: 103 SEQUENCE: 103 000 | moltype = | length = |
| SEQ ID NO: 104 SEQUENCE: 104 000 | moltype = | length = |
| SEQ ID NO: 105 SEQUENCE: 105 000 | moltype = | length = |
| SEQ ID NO: 106 SEQUENCE: 106 000 | moltype = | length = |
| SEQ ID NO: 107 SEQUENCE: 107 000 | moltype = | length = |
| SEQ ID NO: 108 SEQUENCE: 108 000 | moltype = | length = |
| SEQ ID NO: 109 SEQUENCE: 109 000 | moltype = | length = |
| SEQ ID NO: 110 SEQUENCE: 110 000 | moltype = | length = |
| SEQ ID NO: 111 SEQUENCE: 111 000 | moltype = | length = |
| SEQ ID NO: 112 SEQUENCE: 112 000 | moltype = | length = |
| SEQ ID NO: 113 SEQUENCE: 113 000 | moltype = | length = |
| SEQ ID NO: 114 SEQUENCE: 114 000 | moltype = | length = |
| SEQ ID NO: 115 SEQUENCE: 115 000 | moltype = | length = |
| SEQ ID NO: 116 SEQUENCE: 116 000 | moltype = | length = |

-continued

| | | |
|---|---|---|
| SEQ ID NO: 117<br>SEQUENCE: 117<br>000 | moltype = | length = |
| SEQ ID NO: 118<br>SEQUENCE: 118<br>000 | moltype = | length = |
| SEQ ID NO: 119<br>SEQUENCE: 119<br>000 | moltype = | length = |
| SEQ ID NO: 120<br>SEQUENCE: 120<br>000 | moltype = | length = |
| SEQ ID NO: 121<br>SEQUENCE: 121<br>000 | moltype = | length = |
| SEQ ID NO: 122<br>SEQUENCE: 122<br>000 | moltype = | length = |
| SEQ ID NO: 123<br>SEQUENCE: 123<br>000 | moltype = | length = |
| SEQ ID NO: 124<br>SEQUENCE: 124<br>000 | moltype = | length = |
| SEQ ID NO: 125<br>SEQUENCE: 125<br>000 | moltype = | length = |
| SEQ ID NO: 126<br>SEQUENCE: 126<br>000 | moltype = | length = |
| SEQ ID NO: 127<br>SEQUENCE: 127<br>000 | moltype = | length = |
| SEQ ID NO: 128<br>SEQUENCE: 128<br>000 | moltype = | length = |
| SEQ ID NO: 129<br>SEQUENCE: 129<br>000 | moltype = | length = |
| SEQ ID NO: 130<br>SEQUENCE: 130<br>000 | moltype = | length = |
| SEQ ID NO: 131<br>SEQUENCE: 131<br>000 | moltype = | length = |
| SEQ ID NO: 132<br>SEQUENCE: 132<br>000 | moltype = | length = |
| SEQ ID NO: 133<br>SEQUENCE: 133<br>000 | moltype = | length = |
| SEQ ID NO: 134<br>SEQUENCE: 134<br>000 | moltype = | length = |
| SEQ ID NO: 135<br>SEQUENCE: 135<br>000 | moltype = | length = |
| SEQ ID NO: 136<br>SEQUENCE: 136<br>000 | moltype = | length = |

| | | |
|---|---|---|
| SEQ ID NO: 137 SEQUENCE: 137 000 | moltype = | length = |
| SEQ ID NO: 138 SEQUENCE: 138 000 | moltype = | length = |
| SEQ ID NO: 139 SEQUENCE: 139 000 | moltype = | length = |
| SEQ ID NO: 140 SEQUENCE: 140 000 | moltype = | length = |
| SEQ ID NO: 141 SEQUENCE: 141 000 | moltype = | length = |
| SEQ ID NO: 142 SEQUENCE: 142 000 | moltype = | length = |
| SEQ ID NO: 143 SEQUENCE: 143 000 | moltype = | length = |
| SEQ ID NO: 144 SEQUENCE: 144 000 | moltype = | length = |
| SEQ ID NO: 145 SEQUENCE: 145 000 | moltype = | length = |
| SEQ ID NO: 146 SEQUENCE: 146 000 | moltype = | length = |
| SEQ ID NO: 147 SEQUENCE: 147 000 | moltype = | length = |
| SEQ ID NO: 148 SEQUENCE: 148 000 | moltype = | length = |
| SEQ ID NO: 149 SEQUENCE: 149 000 | moltype = | length = |
| SEQ ID NO: 150 SEQUENCE: 150 000 | moltype = | length = |
| SEQ ID NO: 151 SEQUENCE: 151 000 | moltype = | length = |
| SEQ ID NO: 152 SEQUENCE: 152 000 | moltype = | length = |
| SEQ ID NO: 153 SEQUENCE: 153 000 | moltype = | length = |
| SEQ ID NO: 154 SEQUENCE: 154 000 | moltype = | length = |
| SEQ ID NO: 155 SEQUENCE: 155 000 | moltype = | length = |
| SEQ ID NO: 156 SEQUENCE: 156 | moltype = | length = |

| | | |
|---|---|---|
| SEQ ID NO: 157<br>SEQUENCE: 157<br>000 | moltype = | length = |
| SEQ ID NO: 158<br>SEQUENCE: 158<br>000 | moltype = | length = |
| SEQ ID NO: 159<br>SEQUENCE: 159<br>000 | moltype = | length = |
| SEQ ID NO: 160<br>SEQUENCE: 160<br>000 | moltype = | length = |
| SEQ ID NO: 161<br>SEQUENCE: 161<br>000 | moltype = | length = |
| SEQ ID NO: 162<br>SEQUENCE: 162<br>000 | moltype = | length = |
| SEQ ID NO: 163<br>SEQUENCE: 163<br>000 | moltype = | length = |
| SEQ ID NO: 164<br>SEQUENCE: 164<br>000 | moltype = | length = |
| SEQ ID NO: 165<br>SEQUENCE: 165<br>000 | moltype = | length = |
| SEQ ID NO: 166<br>SEQUENCE: 166<br>000 | moltype = | length = |
| SEQ ID NO: 167<br>SEQUENCE: 167<br>000 | moltype = | length = |
| SEQ ID NO: 168<br>SEQUENCE: 168<br>000 | moltype = | length = |
| SEQ ID NO: 169<br>SEQUENCE: 169<br>000 | moltype = | length = |
| SEQ ID NO: 170<br>SEQUENCE: 170<br>000 | moltype = | length = |
| SEQ ID NO: 171<br>SEQUENCE: 171<br>000 | moltype = | length = |
| SEQ ID NO: 172<br>SEQUENCE: 172<br>000 | moltype = | length = |
| SEQ ID NO: 173<br>SEQUENCE: 173<br>000 | moltype = | length = |
| SEQ ID NO: 174<br>SEQUENCE: 174<br>000 | moltype = | length = |
| SEQ ID NO: 175<br>SEQUENCE: 175<br>000 | moltype = | length = |
| SEQ ID NO: 176 | moltype = | length = |

| | | |
|---|---|---|
| SEQUENCE: 176 000 | | |
| SEQ ID NO: 177 SEQUENCE: 177 000 | moltype = | length = |
| SEQ ID NO: 178 SEQUENCE: 178 000 | moltype = | length = |
| SEQ ID NO: 179 SEQUENCE: 179 000 | moltype = | length = |
| SEQ ID NO: 180 SEQUENCE: 180 000 | moltype = | length = |
| SEQ ID NO: 181 SEQUENCE: 181 000 | moltype = | length = |
| SEQ ID NO: 182 SEQUENCE: 182 000 | moltype = | length = |
| SEQ ID NO: 183 SEQUENCE: 183 000 | moltype = | length = |
| SEQ ID NO: 184 SEQUENCE: 184 000 | moltype = | length = |
| SEQ ID NO: 185 SEQUENCE: 185 000 | moltype = | length = |
| SEQ ID NO: 186 SEQUENCE: 186 000 | moltype = | length = |
| SEQ ID NO: 187 SEQUENCE: 187 000 | moltype = | length = |
| SEQ ID NO: 188 SEQUENCE: 188 000 | moltype = | length = |
| SEQ ID NO: 189 SEQUENCE: 189 000 | moltype = | length = |
| SEQ ID NO: 190 SEQUENCE: 190 000 | moltype = | length = |
| SEQ ID NO: 191 SEQUENCE: 191 000 | moltype = | length = |
| SEQ ID NO: 192 SEQUENCE: 192 000 | moltype = | length = |
| SEQ ID NO: 193 SEQUENCE: 193 000 | moltype = | length = |
| SEQ ID NO: 194 SEQUENCE: 194 000 | moltype = | length = |
| SEQ ID NO: 195 SEQUENCE: 195 000 | moltype = | length = |

-continued

```
SEQ ID NO: 196          moltype =    length =
SEQUENCE: 196
000

SEQ ID NO: 197          moltype =    length =
SEQUENCE: 197
000

SEQ ID NO: 198          moltype =    length =
SEQUENCE: 198
000

SEQ ID NO: 199          moltype =    length =
SEQUENCE: 199
000

SEQ ID NO: 200          moltype =    length =
SEQUENCE: 200
000

SEQ ID NO: 201          moltype =    length =
SEQUENCE: 201
000

SEQ ID NO: 202          moltype =    length =
SEQUENCE: 202
000

SEQ ID NO: 203          moltype =    length =
SEQUENCE: 203
000

SEQ ID NO: 204          moltype =    length =
SEQUENCE: 204
000

SEQ ID NO: 205          moltype =    length =
SEQUENCE: 205
000

SEQ ID NO: 206          moltype =    length =
SEQUENCE: 206
000

SEQ ID NO: 207          moltype =    length =
SEQUENCE: 207
000

SEQ ID NO: 208          moltype =    length =
SEQUENCE: 208
000

SEQ ID NO: 209          moltype =    length =
SEQUENCE: 209
000

SEQ ID NO: 210          moltype = AA   length = 152
FEATURE                 Location/Qualifiers
source                  1..152
                        mol_type = protein
                        organism = Homo sapiens
SEQUENCE: 210
DCDIEGKDGK QYESVLMVSI DQLLDSMKEI GSNCLNNEFN FFKRHICDAN KEGMFLFRAA    60
RKLRQFLKMN STGDFDLHLL KVSEGTTILL NCTGQVKGRK PAALGEAQPT KSLEENKSLK   120
EQKKLNDLCF LKRLLQEIKT CWNKILMGTK EH                                 152

SEQ ID NO: 211          moltype = AA   length = 133
FEATURE                 Location/Qualifiers
source                  1..133
                        mol_type = protein
                        organism = Homo sapiens
SEQUENCE: 211
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLT                                                      133

SEQ ID NO: 212          moltype =    length =
SEQUENCE: 212
000
```

| | | |
|---|---|---|
| SEQ ID NO: 213 | moltype = length = | |
| SEQUENCE: 213 | | |
| 000 | | |
| | | |
| SEQ ID NO: 214 | moltype = length = | |
| SEQUENCE: 214 | | |
| 000 | | |
| | | |
| SEQ ID NO: 215 | moltype = length = | |
| SEQUENCE: 215 | | |
| 000 | | |
| | | |
| SEQ ID NO: 216 | moltype = length = | |
| SEQUENCE: 216 | | |
| 000 | | |
| | | |
| SEQ ID NO: 217 | moltype = length = | |
| SEQUENCE: 217 | | |
| 000 | | |
| | | |
| SEQ ID NO: 218 | moltype = length = | |
| SEQUENCE: 218 | | |
| 000 | | |
| | | |
| SEQ ID NO: 219 | moltype = length = | |
| SEQUENCE: 219 | | |
| 000 | | |
| | | |
| SEQ ID NO: 220 | moltype = length = | |
| SEQUENCE: 220 | | |
| 000 | | |
| | | |
| SEQ ID NO: 221 | moltype = length = | |
| SEQUENCE: 221 | | |
| 000 | | |
| | | |
| SEQ ID NO: 222 | moltype = length = | |
| SEQUENCE: 222 | | |
| 000 | | |
| | | |
| SEQ ID NO: 223 | moltype = length = | |
| SEQUENCE: 223 | | |
| 000 | | |
| | | |
| SEQ ID NO: 224 | moltype = AA length = 20 | |
| FEATURE | Location/Qualifiers | |
| source | 1..20 | |
| | mol_type = protein | |
| | organism = synthetic construct | |
| VARIANT | 1..20 | |
| | note = This sequence may encompass 1-10 GS repeating units | |
| SEQUENCE: 224 | | |
| GSGSGSGSGS GSGSGSGSGS | | 20 |
| | | |
| SEQ ID NO: 225 | moltype = AA length = 30 | |
| FEATURE | Location/Qualifiers | |
| source | 1..30 | |
| | mol_type = protein | |
| | organism = synthetic construct | |
| VARIANT | 1..30 | |
| | note = This sequence may encompass 1-10 GGS repeating units | |
| SEQUENCE: 225 | | |
| GGSGGSGGSG GSGGSGGSGG SGGSGGSGGS | | 30 |
| | | |
| SEQ ID NO: 226 | moltype = AA length = 40 | |
| FEATURE | Location/Qualifiers | |
| source | 1..40 | |
| | mol_type = protein | |
| | organism = synthetic construct | |
| VARIANT | 1..40 | |
| | note = This sequence may encompass 1-10 GGGS repeating units | |
| SEQUENCE: 226 | | |
| GGGSGGGSGG GSGGGSGGGS GGGSGGGSGG GSGGGSGGGS | | 40 |
| | | |
| SEQ ID NO: 227 | moltype = AA length = 40 | |
| FEATURE | Location/Qualifiers | |
| source | 1..40 | |
| | mol_type = protein | |

```
                        organism = synthetic construct
VARIANT                 1..40
                        note = This sequence may encompass 1-10 GGSG repeating units
SEQUENCE: 227
GGSGGGSGGG SGGGSGGGSG GGSGGGSGGG SGGGSGGGSG                              40

SEQ ID NO: 228          moltype = AA  length = 50
FEATURE                 Location/Qualifiers
source                  1..50
                        mol_type = protein
                        organism = synthetic construct
VARIANT                 1..50
                        note = This sequence may encompass 1-10 GGSGG repeating
                         units
SEQUENCE: 228
GGSGGGGSGG GGSGGGGSGG GGSGGGGSGG GGSGGGGSGG GGSGGGGSGG                   50

SEQ ID NO: 229          moltype = AA  length = 50
FEATURE                 Location/Qualifiers
source                  1..50
                        mol_type = protein
                        organism = synthetic construct
VARIANT                 1..50
                        note = This sequence may encompass 1-10 GGGGS repeating
                         units
SEQUENCE: 229
GGGGSGGGGS GGGGSGGGGS GGGGSGGGGS GGGGSGGGGS GGGGSGGGGS                   50

SEQ ID NO: 230          moltype = AA  length = 15
FEATURE                 Location/Qualifiers
source                  1..15
                        mol_type = protein
                        organism = synthetic construct
SEQUENCE: 230
GGGGSGGGGS GGGGS                                                         15

SEQ ID NO: 231          moltype = AA  length = 20
FEATURE                 Location/Qualifiers
source                  1..20
                        mol_type = protein
                        organism = synthetic construct
SEQUENCE: 231
GGGGSGGGGS GGGGSGGGGS                                                    20

SEQ ID NO: 232          moltype = AA  length = 450
FEATURE                 Location/Qualifiers
source                  1..450
                        mol_type = protein
                        organism = synthetic construct
SEQUENCE: 232
EVQLLESGGG LVQPGGSLRL SCAASGFTFS SYIMMWVRQA PGKGLEWVSS IYPSGGITFY        60
ADTVKGRFTI SRDNSKNTLY LQMNSLRAED TAVYYCARIK LGTVTTVDYW GQGTLVTVSS       120
ASTKGPSVFP LAPSSKSTSG GTAALGCLVK DYFPEPVTVS WNSGALTSGV HTFPAVLQSS       180
GLYSLSSVVT VPSSSLGTQT YICNVNHKPS NTKVDKKVEP KSCDKTHTCP PCPAPELLGG       240
PSVFLFPPKP KDTLMISRTP EVTCVVVDVS HEDPEVKFNW YVDGVEVHNA KTKPREEQYN       300
STYRVVSVLT VLHQDWLNGK EYKCKVSNKA LPAPIEKTIS KAKGQPREPQ VYTLPPSRDE       360
LTKNQVSLTC LVKGFYPSDI AVEWESNGQP ENNYKTTPPV LDSDGSFFLY SKLTVDKSRW       420
QQGNVFSCSV MHEALHNHYT QKSLSLSPGK                                       450

SEQ ID NO: 233          moltype = AA  length = 216
FEATURE                 Location/Qualifiers
source                  1..216
                        mol_type = protein
                        organism = synthetic construct
SEQUENCE: 233
QSALTQPASV SGSPGQSITI SCTGTSSDVG GYNYVSWYQQ HPGKAPKLMI YDVSNRPSGV        60
SNRFSGSKSG NTASLTISGL QAEDEADYYC SSYTSSSTRV FGTGTKVTVL GQPKANPTVT       120
LFPPSSEELQ ANKATLVCLI SDFYPGAVTV AWKADGSPVK AGVETTKPSK QSNNKYAASS       180
YLSLTPEQWK SHRSYSCQVT HEGSTVEKTV APTECS                                216

SEQ ID NO: 234          moltype = AA  length = 451
FEATURE                 Location/Qualifiers
source                  1..451
                        mol_type = protein
                        organism = synthetic construct
SEQUENCE: 234
EVQLVESGGG LVQPGGSLRL SCAASGFTFS RYWMSWVRQA PGKGLEWVAN IKQDGSEKYY        60
VDSVKGRFTI SRDNAKNSLY LQMNSLRAED TAVYYCAREG GWFGELAFDY WGQGTLVTVS       120
SASTKGPSVF PLAPSSKSTS GGTAALGCLV KDYFPEPVTV SWNSGALTSG VHTFPAVLQS       180
```

```
SGLYSLSSVV TVPSSSLGTQ TYICNVNHKP SNTKVDKRVE PKSCDKTHTC PPCPAPEFEG    240
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPASIEKTI SKAKGQPREP QVYTLPPSRE    360
EMTKNQVSLT CLVKGFYPSD IAVEWESNGQ PENNYKTTPP VLDSDGSFFL YSKLTVDKSR    420
WQQGNVFSCS VMHEALHNHY TQKSLSLSPG K                                  451

SEQ ID NO: 235            moltype = AA  length = 215
FEATURE                   Location/Qualifiers
source                    1..215
                          mol_type = protein
                          organism = synthetic construct
SEQUENCE: 235
EIVLTQSPGT LSLSPGERAT LSCRASQRVS SSYLAWYQQK PGQAPRLLIY DASSRATGIP     60
DRFSGSGSGT DFTLTISRLE PEDFAVYYCQ QYGSLPWTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215

SEQ ID NO: 236            moltype = AA  length = 448
FEATURE                   Location/Qualifiers
source                    1..448
                          mol_type = protein
                          organism = synthetic construct
SEQUENCE: 236
EVQLVESGGG LVQPGGSLRL SCAASGFTFS DSWIHWVRQA PGKGLEWVAW ISPYGGSTYY     60
ADSVKGRFTI SADTSKNTAY LQMNSLRAED TAVYYCARRH WPGGFDYWGQ GTLVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPELLGGPS    240
VFLFPPKPKD TLMISRTPEV TCVVVDVSHE DPEVKFNWYV DGVEVHNAKT KPREEQYAST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                      448

SEQ ID NO: 237            moltype = AA  length = 214
FEATURE                   Location/Qualifiers
source                    1..214
                          mol_type = protein
                          organism = synthetic construct
SEQUENCE: 237
DIQMTQSPSS LSASVGDRVT ITCRASQDVS TAVAWYQQKP GKAPKLLIYS ASFLYSGVPS     60
RFSGSGSGTD FTLTISSLQP EDFATYYCQQ YLYHPATFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 238            moltype = AA  length = 448
FEATURE                   Location/Qualifiers
source                    1..448
                          mol_type = protein
                          organism = synthetic construct
SEQUENCE: 238
EVQLLESGGG LVQPGGSLRL SCAASGFTFS SYAMSWVRQA PGKGLEWVSG ISGSGGFTYY     60
ADSVKGRFTI SRDNSKNTLY LQMNSLRAED TAVYYCAKPP RGYNYGPFDY WGQGTLVTVS    120
SASTKGPSVF PLAPCSRSTS ESTAALGCLV KDYFPEPVTV SWNSGALTSG VHTFPAVLQS    180
SGLYSLSSVV TVPSSSLGTK TYTCNVDHKP SNTKVDKRVE SKYGPPCPPC PAPEFLGGPS    240
VFLFPPKPKD TLMISRTPEV TCVVVDVSQE DPEVQFNWYV DGVEVHNAKT KPREEQFNST    300
YRVVSVLTVL HQDWLNGKEY KCKVSNKGLP SSIEKTISKA KGQPREPQVY TLPPSQEEMT    360
KNQVSLTCLV KGFYPSDIAV EWESNGQPEN NYKTTPPVLD SDGSFFLYSR LTVDKSRWQE    420
GNVFSCSVMH EALHNHYTQK SLSLSLGK                                      448

SEQ ID NO: 239            moltype = AA  length = 214
FEATURE                   Location/Qualifiers
source                    1..214
                          mol_type = protein
                          organism = synthetic construct
SEQUENCE: 239
SYVLTQPPSV SVAPGQTARI TCGGNNIGSK SVHWYQQKPG QAPVLVVYDD SDRPSGIPER     60
FSGSNSGNTA TLTISRVEAG DEADYYCQVW DSSSDHVVFG GGTKLTVLGQ PKAAPSVTLF    120
PPSSEELQAN KATLVCLISD FYPGAVTVAW KADSSPVKAG VETTTPSKQS NNKYAASSYL    180
SLTPEQWKSH RSYSCQVTHE GSTVEKTVAP TECS                               214

SEQ ID NO: 240            moltype =    length =
SEQUENCE: 240
000

SEQ ID NO: 241            moltype =    length =
SEQUENCE: 241
000

SEQ ID NO: 242            moltype = AA  length = 118
FEATURE                   Location/Qualifiers
```

```
source                  1..118
                        mol_type = protein
                        organism = synthetic construct
SEQUENCE: 242
QGQLQESGPS LVKPSQTLSL TCTVSGDSIT RGYWNWIRKH PGKGLEYIGY ISYTGSTYSN   60
LSLKSRVTIS RDTSKNQYYL KLSSVTAADT AVYYCATSTG WLDPVDYWGQ GTLVTVSS    118

SEQ ID NO: 243          moltype = AA   length = 107
FEATURE                 Location/Qualifiers
source                  1..107
                        mol_type = protein
                        organism = synthetic construct
SEQUENCE: 243
DIVMTQSPDS LAVSLGERAT INCKASQNVD TSVAWFQQKP GQPPKALIYS ASFRYSGVPD   60
RFSGSGSGTD FTLTISSLQA EDVAVYFCQQ YYGYPFTFGQ GTKLEIK                107

SEQ ID NO: 244          moltype = AA   length = 123
FEATURE                 Location/Qualifiers
source                  1..123
                        mol_type = protein
                        organism = synthetic construct
SEQUENCE: 244
EVQLVQSGGG LVKPGGSLRL SCAASGFTFS SYTMNWVRQA PGKGLEWVSS ISSGSDYLYY   60
ADSVKGRFTI SRDNAKNSLY LQMNSLRAED TAVYYCARNE LRWYPQAGAF DRWGQGTMVT  120
VSS                                                                123

SEQ ID NO: 245          moltype = AA   length = 109
FEATURE                 Location/Qualifiers
source                  1..109
                        mol_type = protein
                        organism = synthetic construct
SEQUENCE: 245
QSVVTQPPSM SAAPGQRVTI SCSGSSSYIE SSYVGWYQQL PGTAPRLLIY DDDMRPSGIP   60
DRFSGSKSGT SATLAITGLQ TGDEADYYCE IWRSGLGGVF GGGTKLTVL              109

SEQ ID NO: 246          moltype =     length =
SEQUENCE: 246
000

SEQ ID NO: 247          moltype =     length =
SEQUENCE: 247
000

SEQ ID NO: 248          moltype = AA   length = 453
FEATURE                 Location/Qualifiers
source                  1..453
                        mol_type = protein
                        organism = synthetic construct
SEQUENCE: 248
QVQLVQSGAE VKKPGSSVKV SCKASGGTFS SYAISWVRQA PGQGLEWMGG IIPIFGTANY   60
AQKFQGRVTI TADKSTSTAY MELSSLRSED TAVYYCARSP DYSPYYYGM  DVWGQGTTVT  120
VSSASTKGPS VFPLAPSSKS TSGGTAALGC LVKDYFPEPV TVSWNSGALT SGVHTFPAVL  180
QSSGLYSLSS VVTVPSSSLG TQTYICNVNH KPSNTKVDKR VEPKSCDKTH TCPPCPAPEA  240
EGAPSVFLFP PKPKDTLMIS RTPEVTCVVV DVSHEDPEVK FNWYVDGVEV HNAKTKPREE  300
QYNSTYRVVS VLTVLHQDWL NGKEYKCKVS NKALPSSIEK TISKAKGQPR EPQVYTLPPS  360
REEMTKNQVS LTCLVKGFYP SDIAVEWESN GQPENNYKTT PPVLDSDGSF FLYSKLTVDK  420
SRWQQGNVFS CSVMHEALHN HYTQKSLSLS PGK                               453

SEQ ID NO: 249          moltype = AA   length = 216
FEATURE                 Location/Qualifiers
source                  1..216
                        mol_type = protein
                        organism = synthetic construct
SEQUENCE: 249
QSVLTQPPSA SGTPGQRVTI SCSGSSSNIG SNTVNWYQQL PGTAPKLLIY GNSNRPSGVP   60
DRFSGSKSGT SASLAISGLQ SEDEADYYCQ SYDSSLSGSV FGGGIKLTVL GQPKAAPSVT  120
LFPPSSEELQ ANKATLVCLI SDFYPGAVTV AWKADSSPVK AGVETTTPSK QSNNKYAASS  180
YLSLTPEQWK SHRSYSCQVT HEGSTVEKTV APAECS                            216

SEQ ID NO: 250          moltype = AA   length = 5
FEATURE                 Location/Qualifiers
source                  1..5
                        mol_type = protein
                        organism = synthetic construct
SEQUENCE: 250
SYTMN                                                                5

SEQ ID NO: 251          moltype = AA   length = 17
FEATURE                 Location/Qualifiers
```

```
source                    1..17
                          mol_type = protein
                          organism = synthetic construct
SEQUENCE: 251
SISSGSDYLY YADSVKG                                                  17

SEQ ID NO: 252            moltype = AA   length = 14
FEATURE                   Location/Qualifiers
source                    1..14
                          mol_type = protein
                          organism = synthetic construct
SEQUENCE: 252
NELRWYPQAG AFDR                                                     14

SEQ ID NO: 253            moltype = AA   length = 13
FEATURE                   Location/Qualifiers
source                    1..13
                          mol_type = protein
                          organism = synthetic construct
SEQUENCE: 253
SGSSSYIESS YVG                                                      13

SEQ ID NO: 254            moltype = AA   length = 7
FEATURE                   Location/Qualifiers
source                    1..7
                          mol_type = protein
                          organism = synthetic construct
SEQUENCE: 254
DDDMRPS                                                             7

SEQ ID NO: 255            moltype = AA   length = 10
FEATURE                   Location/Qualifiers
source                    1..10
                          mol_type = protein
                          organism = synthetic construct
SEQUENCE: 255
EIWRSGLGGV                                                          10

SEQ ID NO: 256            moltype = AA   length = 360
FEATURE                   Location/Qualifiers
source                    1..360
                          mol_type = protein
                          organism = synthetic construct
SEQUENCE: 256
QVQLVESGGG LVQPGGSLRL SCAASGKMSS RRCMAWFRQA PGKERERVAK LLTTSGSTYL   60
ADSVKGRFTI SRDNSKNTVY LQMNSLRAED TAVYYCAADS FEDPTCTLVT SSGAFQYWGQ   120
GTLVTVSSEP KSSDKTHTCP PCPAPELLGG PSVFLFPPKP KDTLMISRTP EVTCVVVAVS   180
HEDPEVKFNW YVDGVEVHNA KTKPREEQYN STYRVVSVLT VLHQDWLNGK EYKCKVSNKA   240
LPAGIEKTIS KAKGQPREPQ VYTLPPSRDE LTKNQVSLTC LVKGFYPSDI AVEWESNGQP   300
ENNYKTTPPV LDSDGSFFLY SKLTVDKSRW QQGNVFSCSV MHEALHNHYT QKSLSLSPGK   360

SEQ ID NO: 257            moltype = AA   length = 759
FEATURE                   Location/Qualifiers
source                    1..759
                          mol_type = protein
                          organism = synthetic construct
SEQUENCE: 257
DIQMTQSPAS LSASVGDRVT ITCQASQSIG TYLAWYQQKP GKPPKLLIYR AFILASGVPS   60
RFSGSGSGTD FTLTISSLQP EDFATYYCQS NFYSDSTTIG PNAFGTGTKV TVLGGGGGSE   120
VQLVESGGGL VQPGGSLRLS CAASGFSFSA NYYPCWVRQA PGKGLEWIGC IYGGSSDITY   180
DANWTKGRFT ISRDNSKNTV YLQMNSLRAE DTAVYYCARS AWYSGWGGDL WGQGTLVTVS   240
SGGGGSGGGG SGGGGSGGGG SIQMTQSPSS LSASVGDRVT ITCQASQSIS NRLAWYQQKP   300
GKAPKLLIYS ASTLASGVPS RFSGSGSGTD FTLTISSLQP EDFATYYCQS TYYGNDGNAF   360
GTGTKVTVLG GGGGSEVQLV ESGGGLVQPG GSLRLSCAAS GFSFNSDYWI YWVRQAPGKG   420
LEWIASIYGG SSGNTQYASW AQGRFTISRD NSKNTVYLQM NSLRAEDTAV YFCARGYVDY   480
GGATDLWGQG TLVTVSSGGG GSGGGGSIQM TQSPSSLSAS VGDRVTITCQ SSESVYSNNQ   540
LSWYQQKPGQ PPKLLIYDAS DLASGVPSRF SGSGSGTDFT LTISSLQPED FATYYCAGGF   600
SSSSDTAFGG GTKLTVLGGG GSGGGGSGG GGSGGGGSEV QLVESGGGLV QPGGSLRLSC   660
AASGFSLSSN AMGWVRQAPG KGLEYIGIIS VGGFTYYASW AKGRFTISRD NSKNTVYLQM   720
NSLRAEDTAT YFCARDRHGG DSSGAFYLWG QGTLVTVSS                         759

SEQ ID NO: 258            moltype = AA   length = 942
FEATURE                   Location/Qualifiers
source                    1..942
                          mol_type = protein
                          organism = synthetic construct
SEQUENCE: 258
QMQLVQSGAE VKKPGSSVKV SCKASGGTFS SYAISWVRQA PGQGLEWMGR IIPILGIANY   60
AQKFQGRVTI TADKSTSTAY MELSSLRSED TAVYYCAKPR DGYNLVAFDI WGQGTMVTVS   120
```

```
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPGGGGSEVQ LQQSGPELVK PGPSMKISCK ASGYSFTGYT MNWVKQSHGK NLEWMGLINP   300
YKGVSTYNQK FKDKATLTVD KSSSTAYMEL LSLTSEDSAV YYCARSGYYG DSDWYFDVWG   360
QGTTLTVFSQ MQLVQSGAEV KKPGSSVKVS CKASGGTFSS YAISWVRQAP GQGLEWMGRI   420
IPILGIANYA QKFQGRVTIT ADKSTSTAYM ELSSLRSEDT AVYYCAKPRD GYNLVAFDIW   480
GQGTMVTVSS ASTKGPSVFP LAPSSKSTSG GTAALGCLVK DYPPEPVTVS WNSGALTSGV   540
HTFPAVLQSS GLYSLSSVVT VPSSSLGTQT YICNVNHKPS NTKVDKKVEP KSCDKTHTCP   600
PCPAPELLGG PGGGGSDIQM TQTTSSLSAS LGDRVTISCR ASQDIRNYLN WYQQKPDGTV   660
KLLIYYTSRL HSGVPSKFSG SGSGTDYSLT ISNLEQEDIA TYFCQQGNTL PWTFAGGTKL   720
EIKRQLVLTQ PPSVSGAPGQ RVTISCTGSS SNIGAGYDVH WYQQLPGAAP KLLIYGDINR   780
PSGVPDRFSG SKSGISASLA ITGLQAEDEA DYYCQSYDSS LSGGVFGGGT KLTVLRTVAA   840
PSVFIFPPSD EQLKSGTASV VCLLNNFYPR EAKVQWKVDN ALQSGNSQES VTEQDSKDST   900
YSLSSTLTLS KADYEKHKVY ACEVTHQGLS SPVTKSFNRG EC                      942

SEQ ID NO: 259          moltype =    length =
SEQUENCE: 259
000

SEQ ID NO: 260          moltype = AA   length = 230
FEATURE                 Location/Qualifiers
source                  1..230
                        mol_type = protein
                        organism = synthetic construct
VARIANT                 18
                        note = Any naturally occurring amino acid
VARIANT                 19
                        note = Any naturally occurring amino acid
VARIANT                 21
                        note = Any naturally occurring amino acid
VARIANT                 140
                        note = Any naturally occurring amino acid
VARIANT                 142
                        note = Any naturally occurring amino acid
VARIANT                 177
                        note = Any naturally occurring amino acid
SEQUENCE: 260
PKSCDKTHTC PPCPAPEXXG XPSVFLFPPK PKDTLMISRT PEVTCVVVDV SHEDPEVKFN    60
WYVDGVEVHN AKTKPREEQY DSTYRVVSVL TVLHQDWLNG KEYKCKVSNK ALPAPIEKTI   120
SKAKGQPREP QVYTLPPSRX EXTKNQVSLT CLVKGFYPSD IAVEWESNGQ PENNYKXTPP   180
VLDSDGSFFL YSKLTVDKSR WQQGNVFSCS VMHEALHNHY TQKSLSLSPG              230

SEQ ID NO: 261          moltype = AA   length = 48
FEATURE                 Location/Qualifiers
source                  1..48
                        mol_type = protein
                        organism = synthetic construct
SEQUENCE: 261
QETNPTENLY FQQKNMQCQR RFYEALHDPN LNEEQRNARI RSIRDDDC                 48

SEQ ID NO: 262          moltype = AA   length = 61
FEATURE                 Location/Qualifiers
source                  1..61
                        mol_type = protein
                        organism = synthetic construct
SEQUENCE: 262
QTADNQKNMQ CQRRFYEALH DPNLNEEQRN ARIRSIRDDC SQSANLLAEA QQLNDAQAPQ    60
A                                                                    61

SEQ ID NO: 263          moltype = AA   length = 38
FEATURE                 Location/Qualifiers
source                  1..38
                        mol_type = protein
                        organism = synthetic construct
SEQUENCE: 263
QETKNMQCQR RFYEALHDPN LNEEQRNARI RSIRDDDC                            38

SEQ ID NO: 264          moltype = AA   length = 38
FEATURE                 Location/Qualifiers
source                  1..38
                        mol_type = protein
                        organism = synthetic construct
SEQUENCE: 264
QETFNKQCQR RFYEALHDPN LNEEQRNARI RSIRDDDC                            38

SEQ ID NO: 265          moltype = AA   length = 38
FEATURE                 Location/Qualifiers
source                  1..38
                        mol_type = protein
```

```
                        organism = synthetic construct
SEQUENCE: 265
QETFNMQCQR RFYEALHDPN LNKEQRNARI RSIRDDDC                                 38

SEQ ID NO: 266          moltype = AA   length = 37
FEATURE                 Location/Qualifiers
source                  1..37
                        mol_type = protein
                        organism = synthetic construct
SEQUENCE: 266
QETFNMQCQR RFYEALHDPN LNEEQRNARI RSIKDDC                                  37

SEQ ID NO: 267          moltype = AA   length = 35
FEATURE                 Location/Qualifiers
source                  1..35
                        mol_type = protein
                        organism = synthetic construct
SEQUENCE: 267
QETMQCQRRF YEALHDPNLN EEQRNARIRS IKDDC                                    35

SEQ ID NO: 268          moltype = AA   length = 34
FEATURE                 Location/Qualifiers
source                  1..34
                        mol_type = protein
                        organism = synthetic construct
SEQUENCE: 268
QETQCQRRFY EALHDPNLNE EQRNARIRSI KDDC                                     34

SEQ ID NO: 269          moltype = AA   length = 33
FEATURE                 Location/Qualifiers
source                  1..33
                        mol_type = protein
                        organism = synthetic construct
SEQUENCE: 269
QETCQRRFYE ALHDPNLNEE QRNARIRSIK DDC                                      33

SEQ ID NO: 270          moltype = AA   length = 20
FEATURE                 Location/Qualifiers
source                  1..20
                        mol_type = protein
                        organism = synthetic construct
SEQUENCE: 270
QETRGNCAYH KGQLVWCTYH                                                     20

SEQ ID NO: 271          moltype = AA   length = 20
FEATURE                 Location/Qualifiers
source                  1..20
                        mol_type = protein
                        organism = synthetic construct
SEQUENCE: 271
QETRGNCAYH KGQIIWCTYH                                                     20

SEQ ID NO: 272          moltype = AA   length = 6
FEATURE                 Location/Qualifiers
source                  1..6
                        mol_type = protein
                        organism = synthetic construct
VARIANT                 6
                        note = A or P
SEQUENCE: 272
LLQGPX                                                                    6

SEQ ID NO: 273          moltype = AA   length = 8
FEATURE                 Location/Qualifiers
source                  1..8
                        mol_type = protein
                        organism = synthetic construct
SEQUENCE: 273
GGLLQGPP                                                                  8

SEQ ID NO: 274          moltype =      length =
SEQUENCE: 274
000

SEQ ID NO: 275          moltype =      length =
SEQUENCE: 275
000

SEQ ID NO: 276          moltype =      length =
```

| | | |
|---|---|---|
| SEQUENCE: 276 000 | | |
| SEQ ID NO: 277 SEQUENCE: 277 000 | moltype = | length = |
| SEQ ID NO: 278 SEQUENCE: 278 000 | moltype = | length = |
| SEQ ID NO: 279 SEQUENCE: 279 000 | moltype = | length = |
| SEQ ID NO: 280 SEQUENCE: 280 000 | moltype = | length = |
| SEQ ID NO: 281 SEQUENCE: 281 000 | moltype = | length = |
| SEQ ID NO: 282 SEQUENCE: 282 000 | moltype = | length = |
| SEQ ID NO: 283 SEQUENCE: 283 000 | moltype = | length = |
| SEQ ID NO: 284 SEQUENCE: 284 000 | moltype = | length = |
| SEQ ID NO: 285 SEQUENCE: 285 000 | moltype = | length = |
| SEQ ID NO: 286 SEQUENCE: 286 000 | moltype = | length = |
| SEQ ID NO: 287 SEQUENCE: 287 000 | moltype = | length = |
| SEQ ID NO: 288 SEQUENCE: 288 000 | moltype = | length = |
| SEQ ID NO: 289 SEQUENCE: 289 000 | moltype = | length = |
| SEQ ID NO: 290 SEQUENCE: 290 000 | moltype = | length = |
| SEQ ID NO: 291 SEQUENCE: 291 000 | moltype = | length = |
| SEQ ID NO: 292 SEQUENCE: 292 000 | moltype = | length = |
| SEQ ID NO: 293 SEQUENCE: 293 000 | moltype = | length = |
| SEQ ID NO: 294 SEQUENCE: 294 000 | moltype = | length = |
| SEQ ID NO: 295 SEQUENCE: 295 000 | moltype = | length = |

| | | |
|---|---|---|
| SEQ ID NO: 296<br>SEQUENCE: 296<br>000 | moltype = | length = |
| SEQ ID NO: 297<br>SEQUENCE: 297<br>000 | moltype = | length = |
| SEQ ID NO: 298<br>SEQUENCE: 298<br>000 | moltype = | length = |
| SEQ ID NO: 299<br>SEQUENCE: 299<br>000 | moltype = | length = |
| SEQ ID NO: 300<br>SEQUENCE: 300<br>000 | moltype = | length = |
| SEQ ID NO: 301<br>SEQUENCE: 301<br>000 | moltype = | length = |
| SEQ ID NO: 302<br>SEQUENCE: 302<br>000 | moltype = | length = |
| SEQ ID NO: 303<br>SEQUENCE: 303<br>000 | moltype = | length = |
| SEQ ID NO: 304<br>SEQUENCE: 304<br>000 | moltype = | length = |
| SEQ ID NO: 305<br>SEQUENCE: 305<br>000 | moltype = | length = |
| SEQ ID NO: 306<br>SEQUENCE: 306<br>000 | moltype = | length = |
| SEQ ID NO: 307<br>SEQUENCE: 307<br>000 | moltype = | length = |
| SEQ ID NO: 308<br>SEQUENCE: 308<br>000 | moltype = | length = |
| SEQ ID NO: 309<br>SEQUENCE: 309<br>000 | moltype = | length = |
| SEQ ID NO: 310<br>SEQUENCE: 310<br>000 | moltype = | length = |
| SEQ ID NO: 311<br>SEQUENCE: 311<br>000 | moltype = | length = |
| SEQ ID NO: 312<br>SEQUENCE: 312<br>000 | moltype = | length = |
| SEQ ID NO: 313<br>SEQUENCE: 313<br>000 | moltype = | length = |
| SEQ ID NO: 314<br>SEQUENCE: 314<br>000 | moltype = | length = |
| SEQ ID NO: 315<br>SEQUENCE: 315<br>000 | moltype = | length = |

```
SEQ ID NO: 316          moltype =    length =
SEQUENCE: 316
000

SEQ ID NO: 317          moltype =    length =
SEQUENCE: 317
000

SEQ ID NO: 318          moltype =    length =
SEQUENCE: 318
000

SEQ ID NO: 319          moltype =    length =
SEQUENCE: 319
000

SEQ ID NO: 320          moltype =    length =
SEQUENCE: 320
000

SEQ ID NO: 321          moltype =    length =
SEQUENCE: 321
000

SEQ ID NO: 322          moltype =    length =
SEQUENCE: 322
000

SEQ ID NO: 323          moltype =    length =
SEQUENCE: 323
000

SEQ ID NO: 324          moltype =    length =
SEQUENCE: 324
000

SEQ ID NO: 325          moltype =    length =
SEQUENCE: 325
000

SEQ ID NO: 326          moltype =    length =
SEQUENCE: 326
000

SEQ ID NO: 327          moltype =    length =
SEQUENCE: 327
000

SEQ ID NO: 328          moltype =    length =
SEQUENCE: 328
000

SEQ ID NO: 329          moltype =    length =
SEQUENCE: 329
000

SEQ ID NO: 330          moltype = AA   length = 290
FEATURE                 Location/Qualifiers
source                  1..290
                        mol_type = protein
                        organism = Homo sapiens
SEQUENCE: 330
MRIFAVFIFM TYWHLLNAFT VTVPKDLYVV EYGSNMTIEC KFPVEKQLDL AALIVYWEME    60
DKNIIQFVHG EEDLKVQHSS YRQRARLLKD QLSLGNAALQ ITDVKLQDAG VYRCMISYGG   120
ADYKRITVKV NAPYNKINQR ILVVDPVTSE HELTCQAEGY PKAEVIWTSS DHQVLSGKTT   180
TTNSKREEKL FNVTSTLRIN TTTNEIFYCT FRRLDPEENH TAELVIPELP LAHPPNERTH   240
LVILGAILLC LGVALTFIFR LRKGRMMDVK KCGIQDTNSK KQSDTHLEET             290

SEQ ID NO: 331          moltype = AA   length = 288
FEATURE                 Location/Qualifiers
source                  1..288
                        mol_type = protein
                        organism = Homo sapiens
SEQUENCE: 331
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
```

```
CVPEQTEYAT IVFPSGMGTS SPARRGSADG PRSAQPLRPE DGHCSWPL            288

SEQ ID NO: 332          moltype = AA   length = 445
FEATURE                 Location/Qualifiers
source                  1..445
                        mol_type = protein
                        organism = synthetic construct
SEQUENCE: 332
QVQLQESGPG LVKPSETLSL TCTVSGFSLT SYGVHWIRQP PGKGLEWIGV IYADGSTNYN    60
PSLKSRVTIS KDTSKNQVSL KLSSVTAADT AVYYCARAYG NYWYIDVWGQ GTTVTVSSAS   120
TKGPSVFPLA PCSRSTSEST AALGCLVKDY FPEPVTVSWN SGALTSGVHT FPAVLQSSGL   180
YSLSSVVTVP SSSLGTKTYT CNVDHKPSNT KVDKRVESKY GPPCPPCPAP PVAGGPSVFL   240
FPPKPKDTLM ISRTPEVTCV VVAVSQEDPE VQFNWYVDGV EVHNAKTKPR EEQFNSTYRV   300
VSVLTVVHQD WLNGKEYKCK VSNKGLPSSI EKTISKAKGQ PREPQVYTLP PSQEEMTKNQ   360
VSLTCLVKGF YPSDIAVEWE SNGQPENNYK TTPPVLDSDG SFFLYSKLTV DKSRWQEGNV   420
FSCSVMHEAL HNHYTQKSLS LSLGK                                        445

SEQ ID NO: 333          moltype = AA   length = 214
FEATURE                 Location/Qualifiers
source                  1..214
                        mol_type = protein
                        organism = synthetic construct
SEQUENCE: 333
DIVMTQSPDS LAVSLGERAT INCKSSESVS NDVAWYQQKP GQPPKLLINY AFHRFTGVPD    60
RFSGSGYGTD FTLTISSLQA EDVAVYYCHQ AYSSPYTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 334          moltype = AA   length = 447
FEATURE                 Location/Qualifiers
source                  1..447
                        mol_type = protein
                        organism = synthetic construct
SEQUENCE: 334
QVQLVQSGAE VKKPGSSVKV SCKASGGTFS SYAISWVRQA PGQGLEWMGL IIPMFDTAGY    60
AQKFQGRVAI TVDESTSTAY MELSSLRSED TAVYYCARAE HSSTGTFDYW GQGTLVTVSS   120
ASTKGPSVFP LAPCSRSTSE STAALGCLVK DYFPEPVTVS WNSGALTSGV HTFPAVLQSS   180
GLYSLSSVVT VPSSSLGTKT YTCNVDHKPS NTKVDKRVES KYGPPCPPCP APEFLGGPSV   240
FLFPPKPKDT LMISRTPEVT CVVVDVSQED PEVQFNWYVD GVEVHNAKTK PREEQFNSTY   300
RVVSVLTVLH QDWLNGKEYK CKVSNKGLPS SIEKTISKAK GQPREPQVYT LPPSQEEMTK   360
NQVSLTCLVK GFYPSDIAVE WESNGQPENN YKTTPPVLDS DGSFFLYSRL TVDKSRWQEG   420
NVFSCSVMHE ALHNHYTQKS LSLSLGK                                      447

SEQ ID NO: 335          moltype = AA   length = 214
FEATURE                 Location/Qualifiers
source                  1..214
                        mol_type = protein
                        organism = synthetic construct
SEQUENCE: 335
DIQMTQSPSS VSASVGDRVT ITCRASQGIS SWLAWYQQKP GKAPKLLISA ASSLQSGVPS    60
RFSGSGSGTD FTLTISSLQP EDFATYYCQQ ANHLPFTGQG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 336          moltype = AA   length = 452
FEATURE                 Location/Qualifiers
source                  1..452
                        mol_type = protein
                        organism = synthetic construct
SEQUENCE: 336
QGQLVQSGAE VKKPGASVKV SCKASGYTFT DYEMHWVRQA PIHGLEWIGV IESETGGTAY    60
NQKFKGRVTI TADKSTSTAY MELSSLRSED TAVYYCAREG ITTVATTYYW YFDVWGQGTT   120
VTVSSASTKG PSVFPLAPCS RSTSESTAAL GCLVKDYFPE PVTVSWNSGA LTSGVHTFPA   180
VLQSSGLYSL SSVVTVPSSS LGTKTYTCNV DHKPSNTKVD KRVESKYGPP CPPCPAPEFL   240
GGPSVFLFPP KPKDTLMISR TPEVTCVVVD VSQEDPEVQF NWYVDGVEVH NAKTKPREEQ   300
FNSTYRVVSV LTVLHQDWLN GKEYKCKVSN KGLPSSIEKT ISKAKGQPRE PQVYTLPPSQ   360
EEMTKNQVSL TCLVKGFYPS DIAVEWESNG QPENNYKTTP PVLDSDGSFF LYSRLTVDKS   420
RWQEGNVFSC SVMHEALHNH YTQKSLSLSL GK                                452

SEQ ID NO: 337          moltype = AA   length = 219
FEATURE                 Location/Qualifiers
source                  1..219
                        mol_type = protein
                        organism = synthetic construct
SEQUENCE: 337
DVVMTQSPLS LPVTLGQPAS ISCRSSQSIV HSNGNTYLEW YLQKPGQSPQ LLIYKVSNRF    60
SGVPDRFSGS GSGTDFTLKI SRVEAEDVGV YYCFQGSHVP LTFGQGTKLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                         219
```

```
SEQ ID NO: 338          moltype = AA  length = 443
FEATURE                 Location/Qualifiers
source                  1..443
                        mol_type = protein
                        organism = synthetic construct
SEQUENCE: 338
EVQLVESGGG LVQPGGSLRL SCAASGFTFS SYMMSWVRQA PGKGLEWVAT ISGGGANTYY    60
PDSVKGRFTI SRDNAKNSLY LQMNSLRAED TAVYYCARQL YYFDYWGQGT TVTVSSASTK   120
GPSVFPLAPC SRSTSESTAA LGCLVKDYFP EPVTVSWNSG ALTSGVHTFP AVLQSSGLYS   180
LSSVVTVPSS SLGTKTYTCN VDHKPSNTKV DKRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPS QEEMTKNQVS   360
LTCLVKGFYP SDIAVEWESN GQPENNYKTT PPVLDSDGSF FLYSRLTVDK SRWQEGNVFS   420
CSVMHEALHN HYTQKSLSLS LGK                                          443

SEQ ID NO: 339          moltype = AA  length = 214
FEATURE                 Location/Qualifiers
source                  1..214
                        mol_type = protein
                        organism = synthetic construct
SEQUENCE: 339
DIQMTQSPSS LSASVGDRVT ITCLASQTIG TWLTWYQQKP GKAPKLLIYT ATSLADGVPS    60
RFSGSGSGTD FTLTISSLQP EDFATYYCQQ VYSIPWTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 340          moltype = AA  length = 444
FEATURE                 Location/Qualifiers
source                  1..444
                        mol_type = protein
                        organism = synthetic construct
SEQUENCE: 340
EVQLLESGGV LVQPGGSLRL SCAASGFTFS NFGMTWVRQA PGKGLEWVSG ISGGGRDTYF    60
ADSVKGRFTI SRDNSKNTLY LQMNSLKGED TAVYYCVKWG NIYFDYWGQG TLVTVSSAST   120
KGPSVFPLAP CSRSTSESTA ALGCLVKDYF PEPVTVSWNS GALTSGVHTF PAVLQSSGLY   180
SLSSVVTVPS SSLGTKTYTC NVDHKPSNTK VDKRVESKYG PPCPPCPAPE FLGGPSVFLF   240
PPKPKDTLMI SRTPEVTCVV VDVSQEDPEV QFNWYVDGVE VHNAKTKPRE EQFNSTYRVV   300
SVLTVLHQDW LNGKEYKCKV SNKGLPSSIE KTISKAKGQP REPQVYTLPP SQEEMTKNQV   360
SLTCLVKGFY PSDIAVEWES NGQPENNYKT TPPVLDSDGS FFLYSRLTVD KSRWQEGNVF   420
SCSVMHEALH NHYTQKSLSL SLGK                                         444

SEQ ID NO: 341          moltype = AA  length = 261
FEATURE                 Location/Qualifiers
source                  1..261
                        mol_type = protein
                        organism = synthetic construct
SEQUENCE: 341
DIQMTQSPSS LSASVGDSIT ITCRASLSIN TFLNWYQQKP GKAPNLLIYA ASSLHGGVPS    60
RFSGSGSGTD FTLTIRTLQP EDFATYYCQQ SSNTPFTFGP GTVVDFRRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECDISULF IDEBRIDGEH HHLHHHHHHH   240
HHHHHHLHHH HHHLLLLLLL L                                            261

SEQ ID NO: 342          moltype =    length =
SEQUENCE: 342
000

SEQ ID NO: 343          moltype =    length =
SEQUENCE: 343
000

SEQ ID NO: 344          moltype =    length =
SEQUENCE: 344
000

SEQ ID NO: 345          moltype =    length =
SEQUENCE: 345
000

SEQ ID NO: 346          moltype = AA  length = 447
FEATURE                 Location/Qualifiers
source                  1..447
                        mol_type = protein
                        organism = synthetic construct
SEQUENCE: 346
QVQLVQSGVE VKKPGASVKV SCKASGYTFT NYYMYWVRQA PGQGLEWMGG INPSNGGTNF    60
NEKFKNRVTL TTDSSTTTAY MELKSLQFDD TAVYYCARRD YRFDMGFDYW GQGTTVTVSS   120
ASTKGPSVFP LAPCSRSTSE STAALGCLVK DYFPEPVTVS WNSGALTSGV HTFPAVLQSS   180
```

```
GLYSLSSVVT VPSSSLGTKT YTCNVDHKPS NTKVDKRVES KYGPPCPPCP APEFLGGPSV    240
FLFPPKPKDT LMISRTPEVT CVVVDVSQED PEVQFNWYVD GVEVHNAKTK PREEQFNSTY    300
RVVSVLTVLH QDWLNGKEYK CKVSNKGLPS SIEKTISKAK GQPREPQVYT LPPSQEEMTK    360
NQVSLTCLVK GFYPSDIAVE WESNGQPENN YKTTPPVLDS DGSFFLYSRL TVDKSRWQEG    420
NVFSCSVMHE ALHNHYTQKS LSLSLGK                                        447

SEQ ID NO: 347          moltype = AA   length = 218
FEATURE                 Location/Qualifiers
source                  1..218
                        mol_type = protein
                        organism = synthetic construct
SEQUENCE: 347
EIVLTQSPAT LSLSPGERAT LSCRASKGVS TSGYSYLHWY QQKPGQAPRL LIYLASYLES     60
GVPARFSGSG SGTDFTLTIS SLEPEDFAVY YCQHSRDLPL TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 348          moltype = AA   length = 166
FEATURE                 Location/Qualifiers
source                  1..166
                        mol_type = protein
                        organism = synthetic construct
SEQUENCE: 348
QVQLVQSGVE VKKPGASVKV SCKASGYTFT NYYMYWVRQA PGQGLEWMGG FPSNGGTNFN     60
EKFKNRVTLT TDSSTTTAYM ELKSLQFDDT AVYYCARRDY RFDMGFDYWG QGTTVTVSSD    120
ISULFIDEBR IDGEHHHLHH HHHHHHHHHH HLHHHHHHLL LLLLLL                   166

SEQ ID NO: 349          moltype = AA   length = 111
FEATURE                 Location/Qualifiers
source                  1..111
                        mol_type = protein
                        organism = synthetic construct
SEQUENCE: 349
EIVLTQSPAT LSLSPGERAT LSCRASKGVS TSGYSYLHWY QQKPGQAPRL LIYLASYLES     60
GVPARFSGSG SGTDFTLTIS SLEPEDFAVY YCQHSRDLPL TFGGGTKVEI K             111

SEQ ID NO: 350          moltype = AA   length = 113
FEATURE                 Location/Qualifiers
source                  1..113
                        mol_type = protein
                        organism = synthetic construct
SEQUENCE: 350
QVQLVESGGG VVQPGRSLRL DCKASGITFS NSGMHWVRQA PGKGLEWVAV IWYDGSKRYY     60
ADSVKGRFTI SRDNSKNTLF LQMNSLRAED TAVYYCATND DYWGQGTLVT VSS           113

SEQ ID NO: 351          moltype = AA   length = 154
FEATURE                 Location/Qualifiers
source                  1..154
                        mol_type = protein
                        organism = synthetic construct
SEQUENCE: 351
EIVLTQSPAT LSLSPGERAT LSCRASQSVS SYLAWYQQKP GQAPRLLIYD ASNRATGIPA     60
RFSGSGSGTD FTLTISSLEP EDFAVYYCQQ SSNWPRTFGQ GTKVEIKDIS ULFIDEBRID    120
GEHHHLHHHH HHHHHHHHHL HHHHHHLLLL LLLL                                154

SEQ ID NO: 352          moltype = AA   length = 459
FEATURE                 Location/Qualifiers
source                  1..459
                        mol_type = protein
                        organism = synthetic construct
SEQUENCE: 352
QVQLVQSGGG LVQPGGSLRL SCAASGFTFS SYWMYWVRQV PGKGLEWVSA IDTGGGRTYY     60
ADSVKGRFAI SRVNAKNTMY LQMNSLRAED TAVYYCARDE GGGTGWGVLK DWPYGLDAWG    120
QGTLVTVSSA STKGPSVFPL APSSKSTSGG TAALGCLVKD YFPEPVTVSW NSGALTSGVH    180
TFPAVLQSSG LYSLSSVVTV PSSSLGTQTY ICNVNHKPSN TKVDKRVEPK SCDKTHTCPP    240
CPAPEAGGPS SVFLFPPKPK DTLMISRTPE VTCVVVDVSH EDPEVKFNWY VDGVEVHNAK    300
TKPREEQYNS TYRVVSVLTV LHQDWLNGKE YKCKVSNKAL PAPIEKTISK AKGQPREPQV    360
YTLPPSREEM TKNQVSLTCL VKGFYPSDIA VEWESNGQPE NNYKTTPPVL DSDGSFFLYS    420
KLTVDKSRWQ QGNVFSCSVM HEALHNHYTQ KSLSLSPGK                           459

SEQ ID NO: 353          moltype = AA   length = 214
FEATURE                 Location/Qualifiers
source                  1..214
                        mol_type = protein
                        organism = synthetic construct
SEQUENCE: 353
QPVLTQPLSV SVALGQTARI TCGGNNIGSK NVHWYQQKPG QAPVLVIYRD SNRPSGIPER     60
FSGSNSGNTA TLTISRAQAG DEADYYCQVW DSSTAVFGTG TKLTVLQRTV AAPSVFIFPP    120
SDEQLKSGTA SVVCLLNNFY PREAKVQWKV DNALQSGNSQ ESVTEQDSKD STYSLSSTLT    180
```

```
LSKADYEKHK VYACEVTHQG LSSPVTKSFN RGEC                        214

SEQ ID NO: 354          moltype = AA  length = 439
FEATURE                 Location/Qualifiers
source                  1..439
                        mol_type = protein
                        organism = synthetic construct
SEQUENCE: 354
QVQLVESGGG VVQPGRSLRL SCAASGFTFS SYGMHWVRQA PGKGLEWVAV IWYDGSNKYY    60
ADSVKGRFTI SRDNSKNTLY LQMNSLRAED TAVYYCASNG DHWGQGTLVT VSSASTKGPS   120
VFPLAPCSRS TSESTAALGC LVKDYFPEPV TVSWNSGALT SGVHTFPAVL QSSGLYSLSS   180
VVTVPSSSLG TKTYTCNVDH KPSNTKVDKR VESKYGPPCP PCPAPEFLGG PSVFLFPPKP   240
KDTLMISRTP EVTCVVVDVS QEDPEVQFNW YVDGVEVHNA KTKPREEQFN STYRVVSVLT   300
VLHQDWLNGK EYKCKVSNKG LPSSIEKTIS KAKGQPREPQ VYTLPPSQEE MTKNQVSLTC   360
LVKGFYPSDI AVEWESNGQP ENNYKTTPPV LDSDGSFFLY SRLTVDKSRW QEGNVFSCSV   420
MHEALHNHYT QKSLSLSLG                                              439

SEQ ID NO: 355          moltype = AA  length = 214
FEATURE                 Location/Qualifiers
source                  1..214
                        mol_type = protein
                        organism = synthetic construct
SEQUENCE: 355
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YNNWPRTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 356          moltype = AA  length = 443
FEATURE                 Location/Qualifiers
source                  1..443
                        mol_type = protein
                        organism = synthetic construct
SEQUENCE: 356
EVQLLESGGG LVQPGGSLRL SCAASGFTFS SYDMSWVRQA PGKGLEWVST ISGGGSYTYY    60
QDSVKGRFTI SRDNSKNTLY LQMNSLRAED TAVYYCASPY YAMDYWGQGT TVTVSSASTK   120
GPSVFPLAPC SRSTSESTAA LGCLVKDYFP EPVTVSWNSG ALTSGVHTFP AVLQSSGLYS   180
LSSVVTVPSS SLGTKTYTCN VDHKPSNTKV DKRVESKYGP PCPPCPAPEF LGGPSVFLFP   240
PKPKDTLMIS RTPEVTCVVV DVSQEDPEVQ FNWYVDGVEV HNAKTKPREE QFNSTYRVVS   300
VLTVLHQDWL NGKEYKCKVS NKGLPSSIEK TISKAKGQPR EPQVYTLPPS QEEMTKNQVS   360
LTCLVKGFYP SDIAVEWESN GQPENNYKTT PPVLDSDGSF FLYSRLTVDK SRWQEGNVFS   420
CSVMHEALHN HYTQKSLSLS LGK                                          443

SEQ ID NO: 357          moltype = AA  length = 214
FEATURE                 Location/Qualifiers
source                  1..214
                        mol_type = protein
                        organism = synthetic construct
SEQUENCE: 357
DIQLTQSPSF LSAYVGDRVT ITCKASQDVG TAVAWYQQKP GKAPKLLIYW ASTLHTGVPS    60
RFSGSGSGTE FTLTISSLQP EDFATYYCQH YSSYPWTFGQ GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 358          moltype = AA  length = 443
FEATURE                 Location/Qualifiers
source                  1..443
                        mol_type = protein
                        organism = synthetic construct
SEQUENCE: 358
QVQLVESGGG LVKPGGSLRL SCAASGFTFS NYGMSWIRQA PGKGLEWSTI SGGGSNIYYA    60
DSVKGRFTIS RDNAKNSLYL QMNSLRAEDT AVYYCVSYYY GIDFWGQGTS VTVSSASKYG   120
PSVFPLAPCS RSTSESTAAL GCLVKDYFPE PVTVSWNSGA LTSGVHTFPA VLQSSGLYSL   180
SSVVTVPSSS LGTKTYTCNV DHKPSNTKVD KRVESKYGPP CPPCPAPEFL GGPSVFLFPP   240
KPKDTLMISR TPEVTCVVVD VSQEDPEVQF NWYVDGVEVH NAKTKPREEQ FNSTYRVVSV   300
VLTVLHQDWL NGKEYKCKVS NKGLPSSIEK TISKAKGQPR EPQVYTLPPS QEEMTKNQVS   360
LTCLVKGFYP SDIAVEWESN GQPENNYKTT PPVLDSDGSF FLYSRLTVDK SRWQEGNVFS   420
CSVMHEALHN HYTQKSLSLS LGK                                          443

SEQ ID NO: 359          moltype = AA  length = 214
FEATURE                 Location/Qualifiers
source                  1..214
                        mol_type = protein
                        organism = synthetic construct
SEQUENCE: 359
DIQMTQSPSS LSASVGDRVT ITCKASQDVT TAVAWYQQKP GKAPKLLIYW ASTRHTGVPS    60
RFSGSGSGTD FTLTISSLQP EDFATYYCQQ HYTIPWTFGG GTKLEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214
```

```
SEQ ID NO: 360          moltype = AA  length = 445
FEATURE                 Location/Qualifiers
source                  1..445
                        mol_type = protein
                        organism = synthetic construct
SEQUENCE: 360
QVQLVQSGAE VKKPGASVKV SCKASGYSFT SYWMNWVRQA PGQGLEWIGV IHPSDSETWL   60
DQKFKDRVTI TVDKSTSTAY MELSSLRSED TAVYYCAREH YGTSPFAYWG QGTLVTVSSA  120
STKGPSVFPL APCSRSTSES TAALGCLVKD YFPEPVTVSW NSGALTSGVH TFPAVLQSSG  180
LYSLSSVVTV PSSSLGTKTY TCNVDHKPSN TKVDKRVESK YGPPCPPCPA PEFLGGPSVF  240
LFPPKPKDTL MISRTPEVTC VVVDVSQEDP EVQFNWYVDG VEVHNAKTKP REEQFNSTYR  300
VVSVLTVLHQ DWLNGKEYKC KVSNKGLPSS IEKTISKAKG QPREPQVYTL PPSQEEMTKN  360
QVSLTCLVKG FYPSDIAVEW ESNGQPENNY KTTPPVLDSD GSFFLYSRLT VDKSRWQEGN  420
VFSCSVMHEA LHNHYTQKSL SLSLG                                       445

SEQ ID NO: 361          moltype = AA  length = 218
FEATURE                 Location/Qualifiers
source                  1..218
                        mol_type = protein
                        organism = synthetic construct
SEQUENCE: 361
EIVLTQSPAT LSLSPGERAT LSCRASESVD NYGMSFMNWF QQKPGQPPKL LIHAASNQGS   60
GVPSRFSGSG SGTDFTLTIS SLEPEDFAVY FCQQSKEVPY TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 362          moltype = AA  length = 444
FEATURE                 Location/Qualifiers
source                  1..444
                        mol_type = protein
                        organism = synthetic construct
SEQUENCE: 362
QVQLVQSGAE VKKPGASVKV SCKASGYTFT SYWINWVRQA PGQGLEWMGN IYPGSSLTNY   60
NEKFKNRVTM TRDTSTSTVY MELSSLRSED TAVYYCARLS TGTFAYWGQG TLVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLGK                                        444

SEQ ID NO: 363          moltype = AA  length = 220
FEATURE                 Location/Qualifiers
source                  1..220
                        mol_type = protein
                        organism = synthetic construct
SEQUENCE: 363
DIVMTQSPDS LAVSLGERAT INCKSSQSLW DSGNQKNFLT WYQQKPGQPP KLLIYWTSYR   60
ESGVPDRFSG SGSGTDFTLT ISSLQAEDVA VYYCQNDYFY PHTFGGGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220

SEQ ID NO: 364          moltype = AA  length = 443
FEATURE                 Location/Qualifiers
source                  1..443
                        mol_type = protein
                        organism = synthetic construct
SEQUENCE: 364
EVQLVQSGAE VKKPGESLRI SCKGSGYTFT TYWMHWVRQA TGQGLEWMGN IYPGTGGSNF   60
DEKFKNRVTI TADKSTSTAY MELSSLRSED TAVYYCTRWT TGTGAYWGQG TTVTVSSAST  120
KGPSVFPLAP CSRSTSESTA ALGCLVKDYF PEPVTVSWNS GALTSGVHTF PAVLQSSGLY  180
SLSSVVTVPS SSLGTKTYTC NVDHKPSNTK VDKRVESKYG PPCPPCPAPE FLGGPSVFLF  240
PPKPKDTLMI SRTPEVTCVV VDVSQEDPEV QFNWYVDGVE VHNAKTKPRE EQFNSTYRVV  300
SVLTVLHQDW LNGKEYKCKV SNKGLPSSIE KTISKAKGQP REPQVYTLPP SQEEMTKNQV  360
SLTCLVKGFY PSDIAVEWES NGQPENNYKT TPPVLDSDGS FFLYSRLTVD KSRWQEGNVF  420
SCSVMHEALH NHYTQKSLSL SLG                                         443

SEQ ID NO: 365          moltype = AA  length = 220
FEATURE                 Location/Qualifiers
source                  1..220
                        mol_type = protein
                        organism = synthetic construct
SEQUENCE: 365
EIVLTQSPAT LSLSPGERAT LSCKSSQSLL DSGNQKNFLT WYQQKPGQAP RLLIYWASTR   60
ESGVPSRFSG SGSGTDFTFT ISSLEAEDAA TYYCQNDYSY PYTFGQGTKV EIKRTVAAPS  120
VFIFPPSDEQ LKSGTASVVC LLNNFYPREA KVQWKVDNAL QSGNSQESVT EQDSKDSTYS  180
LSSTLTLSKA DYEKHKVYAC EVTHQGLSSP VTKSFNRGEC                       220
```

```
SEQ ID NO: 366           moltype = AA  length = 450
FEATURE                  Location/Qualifiers
source                   1..450
                         mol_type = protein
                         organism = synthetic construct
SEQUENCE: 366
QVQLVQSGAE VKKPGSSVKV SCKASGGTFS SYAISWVRQA PGQGLEWMGG IIPIFDTANY     60
AQKFQGRVTI TADESTSTAY MELSSLRSED TAVYYCARPG LAAAYDTGSL DYWGQGTLVT    120
VSSASTKGPS VFPLAPCSRS TSESTAALGC LVKDYFPEPV TVSWNSGALT SGVHTFPAVL    180
QSSGLYSLSS VVTVPSSSLG TKTYTCNVDH KPSNTKVDKR VESKYGPPCP PCPAPEFLGG    240
PSVFLFPPKP KDTLMISRTP EVTCVVVDVS QEDPEVQFNW YVDGVEVHNA KTKPREEQFN    300
STYRVVSVLT VLHQDWLNGK EYKCKVSNKG LPSSIEKTIS KAKGQPREPQ VYTLPPSQEE    360
MTKNQVSLTC LVKGFYPSDI AVEWESNGQP ENNYKTTPPV LDSDGSFFLY SRLTVDKSRW    420
QEGNVFSCSV MHEALHNHYT QKSLSLSLGK                                    450

SEQ ID NO: 367           moltype = AA  length = 214
FEATURE                  Location/Qualifiers
source                   1..214
                         mol_type = protein
                         organism = synthetic construct
SEQUENCE: 367
EIVLTQSPAT LSLSPGERAT LSCRASQSVR SYLAWYQQKP GQAPRLLIYD ASNRATGIPA     60
RFSGSGSGTD FTLTISSLEP EDFAVYYCQQ RNYWPLTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                               214

SEQ ID NO: 368           moltype = AA  length = 496
FEATURE                  Location/Qualifiers
source                   1..496
                         mol_type = protein
                         organism = synthetic construct
SEQUENCE: 368
DIQMTQSPSS LSASVGDRVT ITCRASQDVS SVVAWYQQKP GKAPKLLIYS ASYRYTGVPS     60
RFSGSGSGTD FTLTISSLQP EDFATYYCQQ HYSTPWTFGQ GTKLEIKGGG SGGGGQVQLV    120
QSGAEVKKPG ASVKVSCKAS GYSFTSYWMN WVRQAPGQGL EWIGVIHPSD SETWLDQKFK    180
DRVTITVDKS TSTAYMELSS LRSEDTAVYY CAREHYGTSP FAYWGQGTLV TVSSGGCGGG    240
EVAACEKEVA ALEKEVAALE KEVAALEKES KYGPPCPPCP APEFLGGPSV FLFPPKPKDT    300
LYITREPEVT CVVVDVSQED PEVQFNWYVD GVEVHNAKTK PREEQFNSTY RVVSVLTVLH    360
QDWLNGKEYK CKVSNKGLPS SIEKTISKAK GQPREPQVYT LPPSQEEMTK NQVSLTCLVK    420
GFYPSDIAVE WESNGQPENN YKTTPPVLDS DGSFFLYSRL TVDKSRWQEG NVFSCSVMHE    480
ALHNHYTQKS LSLSLG                                                   496

SEQ ID NO: 369           moltype = AA  length = 271
FEATURE                  Location/Qualifiers
source                   1..271
                         mol_type = protein
                         organism = synthetic construct
SEQUENCE: 369
EIVLTQSPAT LSLSPGERAT LSCRASESVD NYGMSFMNWF QQKPGQPPKL LIHAASNQGS     60
GVPSRFSGSG SGTDFTLTIS SLEPEDFAVY FCQQSKEVPY TFGGGTKVEI KGGGSGGGGQ    120
VQLVQSGAEV KKPGASVKVS CKASGYTFTD YNMDWVRQAP GQGLEWMGDI NPDNGVTIYN    180
QKFEGRVTMT TDTSTAYMEL RSLRSDDTAV YYCAREAD YFYFDYWGQG TTLTVSSGGC      240
GGGKVAACKE KVAALKEKVA ALKEKVAALK E                                  271

SEQ ID NO: 370           moltype = AA  length = 447
FEATURE                  Location/Qualifiers
source                   1..447
                         mol_type = protein
                         organism = synthetic construct
SEQUENCE: 370
QVQLVQSGSE LKKPGASVKI SCKASGYTFT NYGMNWVRQA PGQGLQWMGW INTDSGESTY     60
AEEFKGRFVF SLDTSVNTAY LQITSLTAED TGMYFCVRVG YDALDYWGQG TLVTVSSAST    120
KGPSVFPLAP SSKSTSGGTA ALGCLVKDYF PEPVTVSWNS GALTSGVHTF PAVLQSSGLY    180
SLSSVVTVPS SSLGTQTYIC NVNHKPSNTK VDKRVEPKSC DKTHTCPPCP APELLGGPSV    240
FLFPPKPKDT LMISRTPEVT CVVVDVSHED PEVKFNWYVD GVEVHNAKTK PREEQYNSTY    300
RVVSVLTVLH QDWLNGKEYK CKVSNKALPA PIEKTISKAK GQPREPQVYT LPPSREEMTK    360
NQVSLTCLVK GFYPSDIAVE WESNGQPENN YKTTPPVLDS DGSFFLYSKL TVDKSRWQQG    420
NVFSCSVMHE ALHNHYTQKS LSLSPGK                                       447

SEQ ID NO: 371           moltype = AA  length = 213
FEATURE                  Location/Qualifiers
source                   1..213
                         mol_type = protein
                         organism = synthetic construct
SEQUENCE: 371
EIVLTQSPSS LSASVGDRVT ITCSARSSVS YMHWFQQKPG KAPKLWIYRT SNLASGVPSR     60
FSGSGSGTSY CLTINSLQPE DFATYYCQQR SSFPLTFGGG TKLEIKRTVA APSVFIFPPS    120
DEQLKSGTAS VVCLLNNFYP REAKVQWKVD NALQSGNSQE SVTEQDSKDS TYSLSSTLTL    180
SKADYEKHKV YACEVTHQGL SSPVTKSFNR GEC                                213
```

```
SEQ ID NO: 372          moltype = AA  length = 113
FEATURE                 Location/Qualifiers
source                  1..113
                        mol_type = protein
                        organism = synthetic construct
SEQUENCE: 372
QVQLVESGGG VVQPGRSLRL TCKASGLTFS SSGMHWVRQA PGKGLEWVAV IWYDGSKRYY    60
ADSVKGRFTI SRDNSKNTLF LQMNSLRAED TAVYYCATNN DYWGQGTLVT VSS           113

SEQ ID NO: 373          moltype = AA  length = 107
FEATURE                 Location/Qualifiers
source                  1..107
                        mol_type = protein
                        organism = synthetic construct
SEQUENCE: 373
EIVLTQSPAT LSLSPGERAT LSCRASQSVS SYLAWYQQKP GQAPRLLIYT ASNRATGIPA    60
RFSGSGSGTD FTLTISSLEP EDFAVYYCQQ YSNWPRTFGQ GTKVEIK                  107

SEQ ID NO: 374          moltype = AA  length = 120
FEATURE                 Location/Qualifiers
source                  1..120
                        mol_type = protein
                        organism = synthetic construct
SEQUENCE: 374
EVQLQQSGPV LVKPGASVKM SCKASGYTFT SYYMYWVKQS HGKSLEWIGG VNPSNGGTNF    60
NEKFKSKATL TVDKSSSTAY MELNSLTSED SAVYYCARRD YRYDMGFDYW GQGTTLTVSS    120

SEQ ID NO: 375          moltype = AA  length = 111
FEATURE                 Location/Qualifiers
source                  1..111
                        mol_type = protein
                        organism = synthetic construct
SEQUENCE: 375
QIVLTQSPAI MSASPGEKVT MTCRASKGVS TSGYSYLHWY QQKPGSSPRL LIYLASYLES    60
GVPVRFSGSG SGTSYSLTIS RMEAEDAATY YCQHSRELPL TFGTGTRLEI K             111

SEQ ID NO: 376          moltype = AA  length = 120
FEATURE                 Location/Qualifiers
source                  1..120
                        mol_type = protein
                        organism = synthetic construct
SEQUENCE: 376
QVQLVQSGAE VKKPGASVKV SCKASGYTFT SYYMYWVRQA PGQGLEWMGG VNPSNGGTNF    60
NEKFKSRVTI TADKSTSTAY MELSSLRSED TAVYYCARRD YRYDMGFDYW GQGTTVTVSS    120

SEQ ID NO: 377          moltype = AA  length = 111
FEATURE                 Location/Qualifiers
source                  1..111
                        mol_type = protein
                        organism = synthetic construct
SEQUENCE: 377
EIVLTQSPAT LSLSPGERAT ISCRASKGVS TSGYSYLHWY QQKPGQAPRL LIYLASYLES    60
GVPARFSGSG SGTDFTLTIS SLEPEDFATY YCQHSRELPL TFGTGTKVEI K             111

SEQ ID NO: 378          moltype = AA  length = 448
FEATURE                 Location/Qualifiers
source                  1..448
                        mol_type = protein
                        organism = synthetic construct
SEQUENCE: 378
EIQLVQSGAE VKKPGSSVKV SCKASGYTFT HYGMNWVRQA PGQGLEWVGW VNTYTGEPTY    60
ADDFKGRLTF TLDTSTSTAY MELSSLRSED TAVYYCTREG EGLGFGDWGQ GTTVTVSSAS    120
TKGPSVFPLA PSSKSTSGGT AALGCLVKDY FPEPVTVSWN SGALTSGVHT FPAVLQSSGL    180
YSLSSVVTVP SSSLGTQTYI CNVNHKPSNT KVDKKVEPKS CDKTHTCPPC PAPEAAGGPS    240
VFLFPPKPKD TLMISRTPEV TCVVVDVSHE DPEVKFNWYV DGVEVHNAKT KPREEQYNST    300
YRVVSVLTVL HQDWLNGKEY KCKVSNKALP APIEKTISKA KGQPREPQVY TLPPSREEMT    360
KNQVSLTCLV KGFYPSDIAV EWESNGQPEN NYKTTPPVLD SDGSFFLYSK LTVDKSRWQQ    420
GNVFSCSVMH EALHNHYTQK SLSLSPGK                                      448

SEQ ID NO: 379          moltype = AA  length = 219
FEATURE                 Location/Qualifiers
source                  1..219
                        mol_type = protein
                        organism = synthetic construct
SEQUENCE: 379
DVVMTQSPLS LPVTPGEPAS ISCRSSQSIV HSHGDTYLEW YLQKPGQSPQ LLIYKVSNRF    60
SGVPDRFSGS GSGTDFTLKI SRVEAEDVGV YYCFQGSHIP VTFGQGTKLE IKRTVAAPSV    120
FIFPPSDEQL KSGTASVVCL LNNFYPREAK VQWKVDNALQ SGNSQESVTE QDSKDSTYSL    180
```

```
SSTLTLSKAD YEKHKVYACE VTHQGLSSPV TKSFNRGEC                                                219

SEQ ID NO: 380            moltype = AA   length = 5
FEATURE                   Location/Qualifiers
source                    1..5
                          mol_type = protein
                          organism = synthetic construct
SEQUENCE: 380
NYYMY                                                                                    5

SEQ ID NO: 381            moltype = AA   length = 17
FEATURE                   Location/Qualifiers
source                    1..17
                          mol_type = protein
                          organism = synthetic construct
SEQUENCE: 381
GINPSNGGTN FNEKFKN                                                                       17

SEQ ID NO: 382            moltype = AA   length = 11
FEATURE                   Location/Qualifiers
source                    1..11
                          mol_type = protein
                          organism = synthetic construct
SEQUENCE: 382
RDYRFDMGFD Y                                                                             11

SEQ ID NO: 383            moltype = AA   length = 15
FEATURE                   Location/Qualifiers
source                    1..15
                          mol_type = protein
                          organism = synthetic construct
SEQUENCE: 383
RASKGVSTSG YSYLH                                                                         15

SEQ ID NO: 384            moltype = AA   length = 7
FEATURE                   Location/Qualifiers
source                    1..7
                          mol_type = protein
                          organism = synthetic construct
SEQUENCE: 384
LASYLES                                                                                  7

SEQ ID NO: 385            moltype = AA   length = 9
FEATURE                   Location/Qualifiers
source                    1..9
                          mol_type = protein
                          organism = synthetic construct
SEQUENCE: 385
QHSRDLPLT                                                                                9

SEQ ID NO: 386            moltype = AA   length = 5
FEATURE                   Location/Qualifiers
source                    1..5
                          mol_type = protein
                          organism = synthetic construct
SEQUENCE: 386
NSGMH                                                                                    5

SEQ ID NO: 387            moltype = AA   length = 17
FEATURE                   Location/Qualifiers
source                    1..17
                          mol_type = protein
                          organism = synthetic construct
SEQUENCE: 387
VIWYDGSKRY YADSVKG                                                                       17

SEQ ID NO: 388            moltype = AA   length = 4
FEATURE                   Location/Qualifiers
source                    1..4
                          mol_type = protein
                          organism = synthetic construct
SEQUENCE: 388
NDDY                                                                                     4

SEQ ID NO: 389            moltype = AA   length = 11
FEATURE                   Location/Qualifiers
source                    1..11
                          mol_type = protein
                          organism = synthetic construct
```

```
SEQUENCE: 389
RASQSVSSYL A                                                                               11

SEQ ID NO: 390          moltype = AA  length = 7
FEATURE                 Location/Qualifiers
source                  1..7
                        mol_type = protein
                        organism = synthetic construct
SEQUENCE: 390
DASNRAT                                                                                    7

SEQ ID NO: 391          moltype = AA  length = 9
FEATURE                 Location/Qualifiers
source                  1..9
                        mol_type = protein
                        organism = synthetic construct
SEQUENCE: 391
QQSSNWPRT                                                                                  9

SEQ ID NO: 392          moltype = AA  length = 9
FEATURE                 Location/Qualifiers
source                  1..9
                        mol_type = protein
                        organism = synthetic construct
SEQUENCE: 392
FTFSNYGMS                                                                                  9

SEQ ID NO: 393          moltype = AA  length = 10
FEATURE                 Location/Qualifiers
source                  1..10
                        mol_type = protein
                        organism = synthetic construct
SEQUENCE: 393
TISGGGSNIY                                                                                10

SEQ ID NO: 394          moltype = AA  length = 9
FEATURE                 Location/Qualifiers
source                  1..9
                        mol_type = protein
                        organism = synthetic construct
SEQUENCE: 394
VSYYYGIDF                                                                                  9

SEQ ID NO: 395          moltype = AA  length = 11
FEATURE                 Location/Qualifiers
source                  1..11
                        mol_type = protein
                        organism = synthetic construct
SEQUENCE: 395
KASQDVTTAV A                                                                              11

SEQ ID NO: 396          moltype = AA  length = 7
FEATURE                 Location/Qualifiers
source                  1..7
                        mol_type = protein
                        organism = synthetic construct
SEQUENCE: 396
WASTRHT                                                                                    7

SEQ ID NO: 397          moltype = AA  length = 9
FEATURE                 Location/Qualifiers
source                  1..9
                        mol_type = protein
                        organism = synthetic construct
SEQUENCE: 397
QQHYTIPWT                                                                                  9

SEQ ID NO: 398          moltype = AA  length = 8
FEATURE                 Location/Qualifiers
source                  1..8
                        mol_type = protein
                        organism = synthetic construct
SEQUENCE: 398
GLTFSSSG                                                                                   8

SEQ ID NO: 399          moltype = AA  length = 8
FEATURE                 Location/Qualifiers
source                  1..8
                        mol_type = protein
```

```
                                -continued
                            organism = synthetic construct
SEQUENCE: 399
IWYDGSKR                                                                    8

SEQ ID NO: 400              moltype = AA  length = 6
FEATURE                     Location/Qualifiers
source                      1..6
                            mol_type = protein
                            organism = synthetic construct
SEQUENCE: 400
ATNNDY                                                                      6

SEQ ID NO: 401              moltype = AA  length = 11
FEATURE                     Location/Qualifiers
source                      1..11
                            mol_type = protein
                            organism = synthetic construct
SEQUENCE: 401
RASQSVSSYL A                                                               11

SEQ ID NO: 402              moltype = AA  length = 7
FEATURE                     Location/Qualifiers
source                      1..7
                            mol_type = protein
                            organism = synthetic construct
SEQUENCE: 402
TASNRAT                                                                     7

SEQ ID NO: 403              moltype = AA  length = 9
FEATURE                     Location/Qualifiers
source                      1..9
                            mol_type = protein
                            organism = synthetic construct
SEQUENCE: 403
QQYSNWPRT                                                                   9

SEQ ID NO: 404              moltype = AA  length = 831
FEATURE                     Location/Qualifiers
source                      1..831
                            mol_type = protein
                            organism = synthetic construct
SEQUENCE: 404
MQIPQAPWPW WAVLQLGWRP GWFLDSPDRP WNPPTFSPAL LVVTEGDNAT FTCSFSNTSE    60
SFVLNWYRMS PSNQTDKLAA FPEDRSQPGQ DCRFRVTQLP NGRDFHMSVV RARRNDSGTY   120
LCGAISLAPK AQIKESLRAE LRVTERRAEV PTAHPSPSPR PAGQFQSKYG PPCPSCPAPE   180
FLGGPSVFLF PPKPKDTLMI SRTPEVTCVV DVSQEDPEVQ FNWYVDGVEV HNAKTKPREE   240
QFNSTYRVVS VLTVLHQDWL SGKEYKCKVS SKGLPSSIEK TISNATGQPR EPQVYTLPPS   300
QEEMTKNQVS LTCLVKGFYP SDIAVEWESN GQPENNYKTT PPVLDSDGSF FLYSRLTVDK   360
SSWQEGNVFS CSVMHEALHN HYTQKSLSLS LGKIEGRMDQ VSHRYPRIQS IKVQFTEYKK   420
EKGFILTSQK EDEIMKVQNN SVIINCDGFY LISLKGYFSQ EVNISLHYQK DEEPLFQLKK   480
VRSVNSLMVA SLTYKDKVYL NVTTDNTSLD DFHVNGGELI LIHQNPGEFC VLMQIPQAPW   540
PWWAVLQLGW RPGWFLDSPD RPWNPPTFSP ALLVVTEGDN ATFTCSFSNT SESFVLNWYR   600
MSPSNQTDKL AAFPEDRSQP GQDCRFRVTQ LPNGRDFHMS VVRARRNDSG TYLCGAISLA   660
PKAQIKESLR AELRVTERRA EVPTAHPSPS RPAGQFQQV SHRYPRIQSI KVQFTEYKKE   720
KGFILTSQKE DEIMKVQNNS VIINCDGFYL ISLKGYFSQE VNISLHYQKD EEPLFQLKKV   780
RSVNSLMVAS LTYKDKVYLN VTTDNTSLDD FHVNGGELIL IHQNPGEFCV L           831

SEQ ID NO: 405              moltype = AA  length = 5
FEATURE                     Location/Qualifiers
source                      1..5
                            mol_type = protein
                            organism = synthetic construct
SEQUENCE: 405
GGGGS                                                                       5

SEQ ID NO: 406              moltype = AA  length = 17
FEATURE                     Location/Qualifiers
source                      1..17
                            mol_type = protein
                            organism = synthetic construct
SITE                        1
                            note = Acetylated residue
SITE                        8
                            note =
                            Lysine-3-((3-((2,5-dioxopyrrolidin-1-yl)oxy)-3-oxopropyl)di
                            sulfaneyl)propanoate
SITE                        17
                            note = Amidated residue
DISULFID                    4..14
```

```
                        note = Intrachain disulfide bridge
SEQUENCE: 406
RGNCAYHKGQ LVWCTYH                                                    17

SEQ ID NO: 407          moltype = AA   length = 17
FEATURE                 Location/Qualifiers
source                  1..17
                        mol_type = protein
                        organism = synthetic construct
SITE                    1
                        note = Acetylated residue
SITE                    8
                        note =
                        N-(4-oxo-4-((3-oxo-3-(phenylthio)propyl)thio)butanoyl)-L-Ly
                         sine
SITE                    17
                        note = Amidated residue
DISULFID                4..14
                        note = Intrachain disulfide bridge
SEQUENCE: 407
RGNCAYHKGQ LVWCTYH                                                    17

SEQ ID NO: 408          moltype = AA   length = 34
FEATURE                 Location/Qualifiers
source                  1..34
                        mol_type = protein
                        organism = synthetic construct
SITE                    1
                        note = Acetylated residue
SITE                    31
                        note =
                        N-(3-(((3-oxo-3-(phenylthio)propyl)thio)carbonyl)benzoyl)-L
                         -Lysine
SITE                    34
                        note = Amidated residue
DISULFID                5..34
                        note = Intrachain disulfide bridge
SEQUENCE: 408
FNMQCQRRFY EALHDPNLNE EQRNARIRSI KDDC                                 34
```